US010640544B2

(12) United States Patent
Macielag et al.

(10) Patent No.: US 10,640,544 B2
(45) Date of Patent: *May 5, 2020

(54) ANTIBODY-COUPLED CYCLIC PEPTIDE TYROSINE TYROSINE COMPOUNDS AS MODULATORS OF NEUROPEPTIDE Y RECEPTORS

(71) Applicant: JANSSEN PHARMACEUTICA NV, Beerse (BE)

(72) Inventors: Mark Macielag, Lower Gwynedd, PA (US); Raymond J Patch, Yardley, PA (US); Rui Zhang, Belle Mead, NJ (US); Martin A Case, San Diego, CA (US); Shamina M Rangwala, Furlong, PA (US); James N Leonard, Ambler, PA (US); Raul C Camacho, Philadelphia, PA (US); Michael J Hunter, Santee, CA (US); Katharine E. D'Aquino, Perkasie, PA (US); Wilson Edwards, Cardiff-by the-Sea, CA (US); Ronald V Swanson, Del Mar, CA (US); Wenying Jian, Princeton, NJ (US); Yue-Mei Zhang, Wellesley, MA (US); Mark Wall, Lansdale, PA (US); Ellen Chi, San Diego, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/794,171

(22) Filed: Oct. 26, 2017

(65) Prior Publication Data

US 2018/0117170 A1 May 3, 2018

Related U.S. Application Data

(60) Provisional application No. 62/413,586, filed on Oct. 27, 2016, provisional application No. 62/413,613, filed on Oct. 27, 2016.

(51) Int. Cl.
*C07K 14/575* (2006.01)
*A61K 47/68* (2017.01)
(Continued)

(52) U.S. Cl.
CPC .......... *C07K 14/575* (2013.01); *A61K 9/0019* (2013.01); *A61K 38/17* (2013.01); *A61K 38/1709* (2013.01); *A61K 38/22* (2013.01); *A61K 38/26* (2013.01); *A61K 45/06* (2013.01); *A61K 47/60* (2017.08); *A61K 47/64* (2017.08); *A61K 47/68* (2017.08); *A61K 47/6811* (2017.08); *A61K 47/6845* (2017.08); *A61K 47/6883* (2017.08); *A61K 49/0032* (2013.01); *A61K 49/0052* (2013.01); *A61K 49/0056* (2013.01); *A61P 3/00* (2018.01); *A61P 3/04* (2018.01); *A61P 3/06* (2018.01); *A61P 3/08* (2018.01); *A61P 3/10* (2018.01); *C07K 1/061* (2013.01); *C07K 1/1072* (2013.01); *C07K 1/12* (2013.01); *C07K 1/18* (2013.01); *C07K 5/0205* (2013.01); *C07K 14/57545* (2013.01); *C07K 16/00* (2013.01); *C07K 16/24* (2013.01); *A61K 38/00* (2013.01); *A61K 2039/505* (2013.01); *C07K 2317/14* (2013.01); *C07K 2317/21* (2013.01); *C07K 2317/24* (2013.01); *C07K 2317/33* (2013.01); *C07K 2317/52* (2013.01); *C07K 2317/55* (2013.01);

(Continued)

(58) Field of Classification Search
CPC ........ A61K 45/06; A61K 38/22; A61K 47/60; A61K 38/00; A61K 47/64; A61K 47/6811; A61K 38/17; A61K 49/0032; A61K 49/0052; A61K 49/0056; A61K 47/68; A61K 47/6883; C07K 2317/24; C07K 2317/565; C07K 5/0205; C07K 2317/55; C07K 2317/92; C07K 2317/94; C07K 2317/567; C07K 16/00; C07K 14/575; C07K 2317/21; C07K 2319/30; C07K 1/12; C07K 2317/52; A61P 3/00; A61P 3/04; A61P 3/06; A61P 3/10; A61P 3/08

See application file for complete search history.

(56) References Cited

U.S. PATENT DOCUMENTS 4,248,890 A  2/1981 Maffrand
5,627,044 A  5/1997 Brown
(Continued)

FOREIGN PATENT DOCUMENTS

WO  2005077094 A2  8/2005
WO  2005080424 A2  9/2005
(Continued)

OTHER PUBLICATIONS

Lecklin et al., "Agonists for neuropeptide Y receptors Y1 and Y5 stimulate different phases of feeding in guinea pigs," Br. J. Pharmacol. 139(8):1433-40 (2003).

(Continued)

*Primary Examiner* — Gregory S Emch
(74) *Attorney, Agent, or Firm* — Ice Miller LLP

(57) ABSTRACT

The present invention comprises conjugates comprising a monoclonal antibody conjugated to a cyclic PYY peptide. The invention also relates to pharmaceutical compositions and methods for use thereof. The novel conjugates are useful for preventing, treating or ameliorating diseases and disorders disclosed herein.

28 Claims, 9 Drawing Sheets

Specification includes a Sequence Listing.

(51) Int. Cl.

| | |
|---|---|
| *C07K 16/24* | (2006.01) |
| *A61K 9/00* | (2006.01) |
| *A61K 38/17* | (2006.01) |
| *A61K 38/26* | (2006.01) |
| *C07K 1/06* | (2006.01) |
| *C07K 1/107* | (2006.01) |
| *A61K 47/64* | (2017.01) |
| *A61P 3/10* | (2006.01) |
| *A61K 49/00* | (2006.01) |
| *C07K 1/12* | (2006.01) |
| *C07K 1/18* | (2006.01) |
| *C07K 5/02* | (2006.01) |
| *A61K 47/60* | (2017.01) |
| *A61P 3/08* | (2006.01) |
| *A61P 3/00* | (2006.01) |
| *A61P 3/04* | (2006.01) |
| *A61P 3/06* | (2006.01) |
| *A61K 38/22* | (2006.01) |
| *A61K 45/06* | (2006.01) |
| *C07K 16/00* | (2006.01) |
| *A61K 38/00* | (2006.01) |
| *A61K 39/00* | (2006.01) |

(52) U.S. Cl.
CPC .... *C07K 2317/56* (2013.01); *C07K 2317/565* (2013.01); *C07K 2317/567* (2013.01); *C07K 2317/71* (2013.01); *C07K 2317/92* (2013.01); *C07K 2317/94* (2013.01); *C07K 2319/30* (2013.01)

(56) References Cited

U.S. PATENT DOCUMENTS

| | | | |
|---|---|---|---|
| 7,166,575 | B2 | 1/2007 | Quay |
| 8,759,295 | B2 | 6/2014 | Ghosh et al. |
| 2006/0094653 | A1 | 5/2006 | Levy et al. |
| 2007/0244041 | A1 | 10/2007 | Larsen et al. |
| 2010/0074886 | A1 | 3/2010 | Das et al. |
| 2010/0130424 | A1 | 5/2010 | Swanson et al. |
| 2010/0292172 | A1 | 11/2010 | Ghosh et al. |
| 2013/0040877 | A1 | 2/2013 | Kofoed et al. |
| 2014/0212440 | A1 | 7/2014 | Jung et al. |
| 2015/0258209 | A1 | 9/2015 | Benz et al. |
| 2016/0108098 | A1 | 4/2016 | Dock et al. |
| 2017/0121420 | A1 | 5/2017 | Heidrich et al. |

FOREIGN PATENT DOCUMENTS

| | | | | |
|---|---|---|---|---|
| WO | WO-2009033743 | A1 * | 3/2009 | ............ C07K 16/18 |
| WO | 2011006497 | A1 | 1/2011 | |
| WO | 2012047583 | A2 | 4/2012 | |
| WO | 2014073842 | A1 | 5/2014 | |
| WO | 2014102299 | A2 | 7/2014 | |
| WO | 2014110368 | A1 | 7/2014 | |

OTHER PUBLICATIONS

Int'l Search Report and Written Opinion dated Feb. 21, 2018 in Int'l Application No. PCT/US2017/058451.
Int'l Search Report and Written Opinion dated Mar. 13, 2018 in Int'l Application No. PCT/US2017/058455.
Altschul et al. "Basic Local Alignment Search Tool" J. Mol. Biol., vol. 215, pp. 403-410, 1990.
Altschul et al., "Gapped Blast and PSI-BLAST: a new generation of protein database search programs" Nucleic Acids Research, vol. 25, No. 17, pp. 3389-3402, 1997.
Andrushchenko et al., "Optimization of the hydrochloric acid concentration used for trifluoroacetate removal from Synthetic peptides" Journal of Peptide Science, vol. 13, pp. 37-43, 2007.
Batterham et al., "Inhibition of Food Intake in Obese Subjects by Peptide YY 3-36", The New England Journal of Medicine, vol. 349, No. 10, Sep. 2003.
Batterham et al., "Gut Hormone PYY3-36 Physiologically Inhibits Food Intake", Nature Publishing Group, vol. 418, pp. 650-654, Aug. 2002.
Challis et al., "Acute effects on PYY3-36 on food intake and hypothalamic neuropeptide expression in the mouse," Biochem Biophys Res Commun 311,vol. No. 4, pp. 915-919, Oct. 2003.
Germain et al., "Analogs of pancreatic polypeptide and peptide YY with a locked PP-fold structure are biologically active," Peptides vol. 39, pp. 6-10, 2013.
Kaiser et al., "Color test for detection of free terminal amino groups in the solid-phase synthesis of peptides," Anal. Biochem. vol. 34, pp. 595-598, 1970.
Le Roux et al., "Gut hormone profiles following bariatric surgery favor an anorectic state, facilitate weight loss, and improve metabolic parameters," Annals Surgery, vol. 243, No. 1, pp. 108-114, 2006.
Palasek et al., "Limiting racemization and aspartimide formation in microwave-enhanced Fmoc solid phase peptide synthesis," Journal of Peptide Science, vol. 13, No. 3, pp. 143-148, 2007.
Pittner et al., "Effects of PYY[3-36] in rodent models of diabetes and obesity," International Journal of Obesity, vol. 28, No. 8, pp. 963-971, 2004.
Toräng et al., "In vivo and in vitro degradation of peptide YY3-36 to inactive peptide YY3-34 in humans," Am. J. Physiol. Regul. Integr. Comp. Physiol., vol. 310, pp. R866-R874, 2016.
Vrang et al., "PYY3-36 reduces food intake and body weight and improves insulin sensitivity in rodent models of diet-induced obesity," Am. J. Physiol Regul. Integr. Comp. Physiol., vol. 291, No. 2, pp. R367-R375, 2006.
Yu et al., "Enhanced coupling efficiency in solid-phase peptide synthesis by microwave irradiation," J. Organic Chem., vol. 57, No. 18, pp. 5781-5784, 1992.
Int'l Search Report and Written Opinion dated Feb. 12, 2018 in Int'l Application No. PCT/US2017/058462.
Dennler et al., "Antibody conjugates: from heterogeneous populations to defined reagents," Antibodies vol. 4, pp. 197-224, 2015.
Teplyakov et al., "Structural diversity in a human antibody germline library," mAbs, vol. 8 No. 6, pp. 1045-1063, 2016.

* cited by examiner

Fig. 1
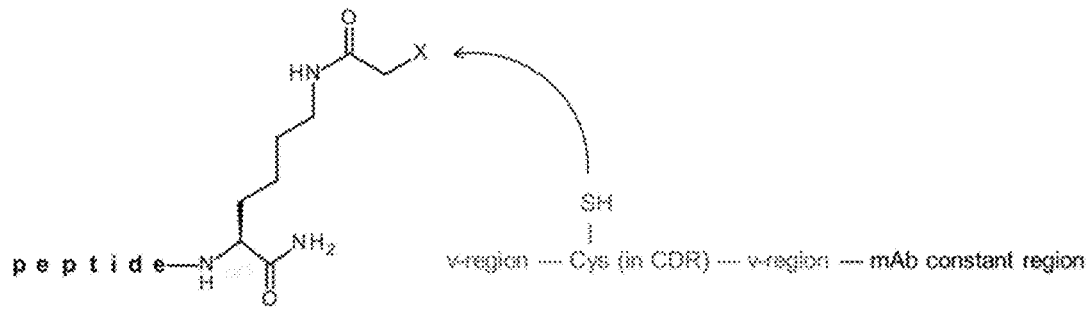
Fig. 2
PH9H5 VH (SEQ ID NO:129)
EVQLLESGGGLVQPGGSLRLSCAASGFTFSSYAMSWVRQAPGKGLEWVSAISGSGGSTYYADSV
KGRFTISRDNSKNTLYLQMNSLRAEDTAVYYCAKYDGIYGELDFWGQGTLVTVSS
PH9L3 VL (SEQ ID NO:128)
EIVLTQSPATLSLSPGERATLSCRASQSVSSYLAWYQQKPGQAPRLLIYDASNRATGIPARFSG
SGSGTDFTLTISSLEPEDFAVYYCQQRSNWPLTFGQGTKVEIK
Fig. 3
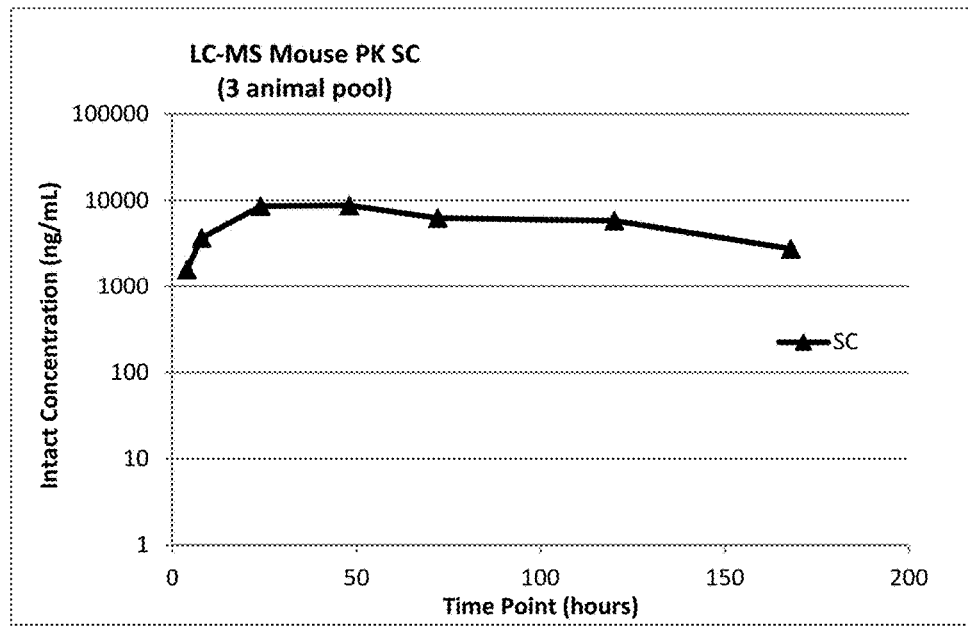

TWO-way RM ANOVA, Tukey's
*p< 0.05 Vehicle vs. all groups
# p< 0.05 Vehicle vs Compound1
1.0, 3.0, and 7.5nmol/kg ANTIBODY-COUPLED CYCLIC PEPTIDE TYROSINE TYROSINE COMPOUNDS AS MODULATORS OF NEUROPEPTIDE Y RECEPTORS

FIELD OF THE INVENTION

The present invention is directed generally to novel antibody coupled cyclic peptide tyrosine tyrosine (PYY) conjugates, which are modulators of the neuropeptide Y2 receptor. The invention also relates to pharmaceutical compositions and methods for use thereof. The novel antibody coupled compounds are useful for preventing, treating or ameliorating diseases and disorders, such as obesity, type 2 diabetes, the metabolic syndrome, insulin resistance, and dyslipidemia, among others.

CROSS-REFERENCE TO RELATED APPLICATIONS

This application claims priority to U.S. Provisional Patent Application No. 62/413,613, filed on Oct. 27, 2016, and U.S. Provisional Patent Application No. 62/413,586 filed on Oct. 27, 2016. Each disclosure is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "PRD3436 Sequence Listing" and a creation date of Oct. 23, 2017, and having a size of 135 kb. The sequence listing submitted via EFS-Web is part of the specification and is herein incorporated by reference in its entirety. In the event of any inconsistency with regard to the structures for SEQ ID NOs: 1-156 between the information described herein and the Sequence Listing submitted electronically via EFS-Web with a file name "PRD3436 Sequence Listing," the information herein will prevail.

BACKGROUND OF THE INVENTION

Neuropeptide Y (NPY) receptors are activated by a closely related group of peptide agonists termed "NPY family" which have differing affinities for each receptor sub-type. NPY, peptide tyrosine-tyrosine (PYY) and pancreatic polypeptide (PP), all 36 amino acids in length, are agonists for the NPY family of receptors. NPY is a neurotransmitter, synthesized, co-stored and released with norepinephrine and epinephrine. NPY is one of the most abundant and widely distributed peptides in the central nervous system (CNS) of humans and rodents and is expressed in areas of the brain related to feeding and stress. In the peripheral nervous system, NPY-containing neurons are predominantly sympathetic. PYY is predominantly synthesized and released by intestinal endocrine cells. Cleavage of NPY and PYY by the endothelial serine-protease, di-peptidyl peptidase IV (DPP-IV), generates $NPY_{3-36}$ and $PYY_{3-36}$ which are selective ligands for Y2 and Y5 sub-types of the NPY receptor family. PP is mainly found in pancreatic islet cells distinct from those storing insulin, glucagon or somatostatin.

Five distinct NPY receptors have been identified to date, four of which are understood as relevant to human physiology. The receptors Y1, Y2 and Y5 preferentially bind NPY and PYY, whereas the Y4 receptor preferentially binds PP. The Y2 and Y5 receptors are also potently activated by $NPY_{3-36}$ and $PYY_{3-36}$. In general, the NPY family of ligands possesses variable selectivity for each of the NPY receptor isoforms, with $PYY_{3-36}$ previously reported to have modest-to-robust selectivity for the Y2 isoform. Each of these receptors is coupled to inhibition of adenylate cyclase via pertussis-toxin sensitive Gαi.

PYY is secreted from endocrine L-cells in response to food, and in particular following fat ingestion. $PYY_{1-36}$ predominates in the fasting state, with $PYY_{3-36}$ being the major form found post-prandially in humans, with plasma concentrations negatively correlated with the number of calories consumed. $PYY_{3-36}$ has been demonstrated to reduce food intake in humans, monkeys, rats, rabbits, and mice (Batterham R L et al. Nature 2002 Aug. 8; 418(6898): 650-4; Batterham R L et al. N Engl J Med 2003 Sep. 4; 349(10):941-8; Challis B G et al., Biochem Biophys Res Commun 2003 Nov. 28; 311(4):915-9). The anorexigenic effects of $PYY_{3-36}$ are believed to be Y2-mediated, based on preferential binding at this receptor and loss of feeding efficacy in Y2-deficient mice (Batterham R L, et al. Nature 2002 Aug. 8; 418(6898):650-4). Intra-arcuate injection of $PYY_{3-36}$ reduces food intake in rats and mice (Batterham et al. Nature 2002 Aug. 8; 418(6898):650-4), suggesting that engagement of hypothalamic Y2 receptors may mediate these effects. Acute effects on feeding have also been shown to translate to dose-dependent effects on body-weight in ob/ob mice, DIO mice and Zucker fa/fa mice (Pittner R A et al. Int J Obes relat Metab Disord 2004 August; 28(8):963-71). In addition, $PYY_{3-36}$ has also been shown to improve insulin-mediated glucose disposal and insulin sensitivity in DIO rodents (Vrang N et al., Am J Physiol Regul Integr Comp Physiol August; 291(2):R367-75). Bariatric surgery results in increased circulating PYY-immunoreactivity (le Roux C W et al., Ann Surg 2006 January; 243(1); 108-14), which appears to play a role in postoperative weight loss.

Given its role in controlling appetite and food intake as well as its anti-secretory and pro-absorptive effects in the gastrointestinal tract in mammals, $PYY_{3-36}$ may be effective in treating obesity and associated conditions as well as in a number of gastrointestinal disorders. However, the therapeutic utility of $PYY_{3-36}$ itself as a treatment agent is limited by its rapid metabolism and resultant short circulating half-life (Torang et al., Am. J. Physiol. Regul. Integr. Comp. Physiol. 310:R866-R874 (2016)).

Thus, it is desirable to obtain a PYY analogue or derivative thereof with an improved metabolic stability and pharmacokinetic profile relative to $PYY_{3-36}$. Such derivatives, with a protracted half-life in vivo, would provide Y2 receptor modulation with greater duration of action, making them suitable as therapeutic agents for subjects in need of such modulation.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In one general aspect, the invention relates to novel antibody coupled cyclic peptide tyrosine tyrosine (PYY) compounds, which are modulators of the neuropeptide Y2 receptor.

Provided herein are conjugates comprising a monoclonal antibody or an antigen binding fragment thereof coupled to a cyclic PYY peptide, wherein the cyclic PYY peptide is represented by Formula I or a derivative or pharmaceutically acceptable salt thereof:

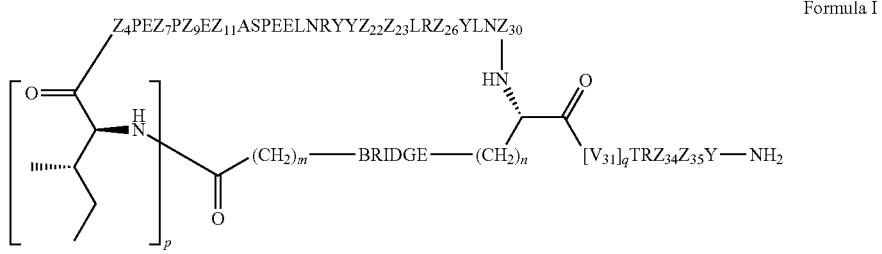

Formula I wherein
p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K;
$Z_9$ is G or K;
$Z_{11}$ is D or K;
$Z_{22}$ is A or K;
$Z_{23}$ is S or K;
$Z_{26}$ is A or H;
$Z_{30}$ is L, W, absent, or K;
provided that $Z_{30}$ is absent only when q is 1;
$Z_{34}$ is

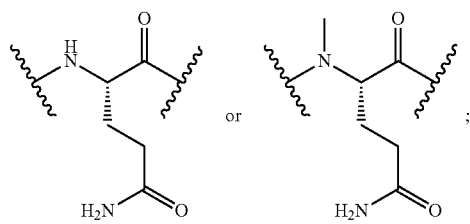 [SMILES: *N[C@@H](CCC(N)=O)C(*)=O ; *C(=O)[C@H](CCC(N)=O)N(*)C]

$Z_{35}$ is

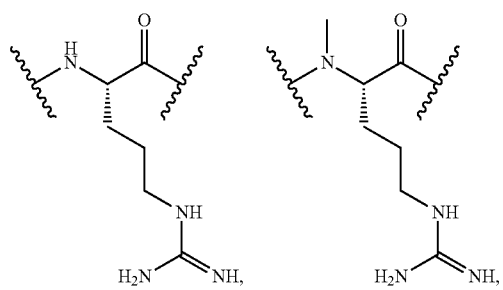

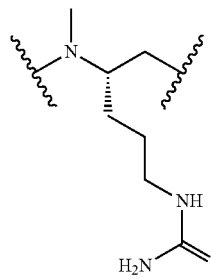
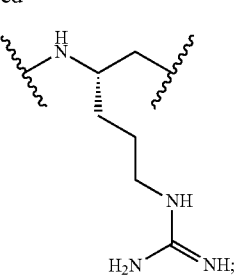

wherein the derivative is the compound of Formula I that is modified by one or more processes selected from the group consisting of amidation, glycosylation, carbamylation, sulfation, phosphorylation, cyclization, lipidation, and pegylation. In certain embodiments, the cyclic PYY peptide is a compound of Formula I or a derivative of the cyclic PYY peptide of Formula I that is modified by one or more processes selected from the group consisting amidation, lipidation, and pegylation, or a pharmaceutically acceptable salt thereof.
In certain embodiments, the cyclic PYY peptide is represented by Formula I or the derivative or pharmaceutically acceptable salt thereof, wherein:
p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K, wherein the amino side chain of said K is optionally substituted with

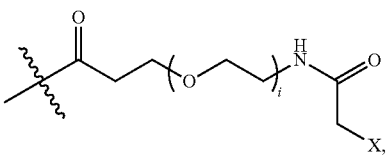

wherein i is an integer of 0 to 24, and X=Br, I or Cl, —C(O)CH$_2$Br, —C(O)CH$_2$I, or —C(O)CH$_2$Cl;
$Z_9$ is G or K, wherein the amino side chain of said K is optionally substituted with

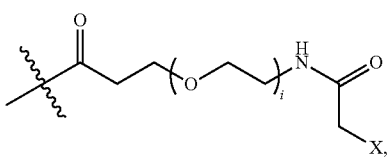

wherein i is an integer of 0 to 24, and X=Br, I or Cl, —C(O)CH$_2$Br, —C(O)CH$_2$I, or —C(O)CH$_2$Cl;

$Z_{11}$ is D or K, wherein the amino side chain of said K is optionally substituted with

wherein i is an integer of 0 to 24, and X=Br, I or Cl, —C(O)CH$_2$Br, —C(O)CH$_2$I, or —C(O)CH$_2$Cl;

$Z_{22}$ is A or K, wherein the amino side chain of said K is optionally substituted with

wherein i is an integer of 0 to 24, and X=Br, I or Cl, —C(O)CH$_2$Br, —C(O)CH$_2$I, or —C(O)CH$_2$Cl;

$Z_{23}$ is S or K, wherein the amino side chain of said K is optionally substituted with

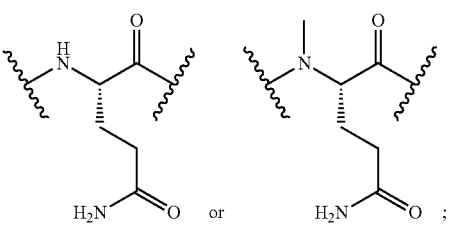

wherein i is an integer of 0 to 24, and X=Br, I or Cl, —C(O)CH$_2$Br, —C(O)CH$_2$I, or —C(O)CH$_2$Cl;

$Z_{26}$ is A or H;

$Z_{30}$ is L or K, wherein the amino side chain of said K is substituted with

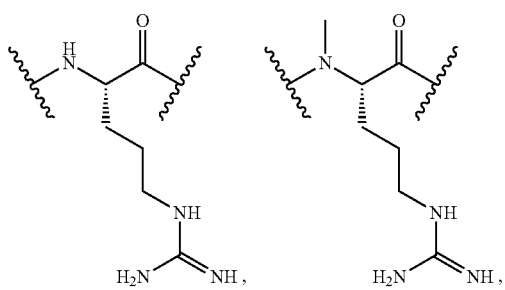

$Z_{34}$ is

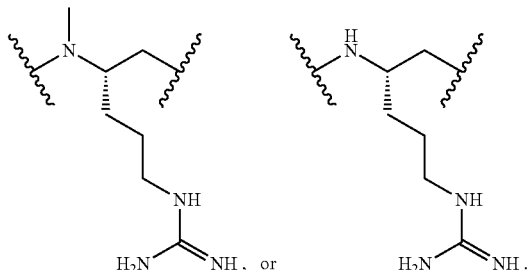

and $Z_{35}$ is

In certain embodiments, the cyclic PYY peptide is represented by Formula I or the derivative or pharmaceutically acceptable salt thereof, wherein:

p is 0 or 1;
m is 0, 1, 2, 3, or 5;
n is 1, 2, or 4;
q is 0 or 1; provided that q may be 1 only when $Z_{30}$ is absent;
BRIDGE is -Ph-CH$_2$—S—, -triazolyl-, —NHC(O)CH$_2$S—, —(OCH$_2$CH$_2$)$_2$NHC(O)CH$_2$S, —NHC(O)—, or —CH$_2$S—;
$Z_4$ is K, A, E, S, or R;
$Z_7$ is A or K, wherein the amino side chain of said K is substituted with $Z_9$ is G or K, $Z_{11}$ is D or K, wherein the amino side chain of said K is substituted with

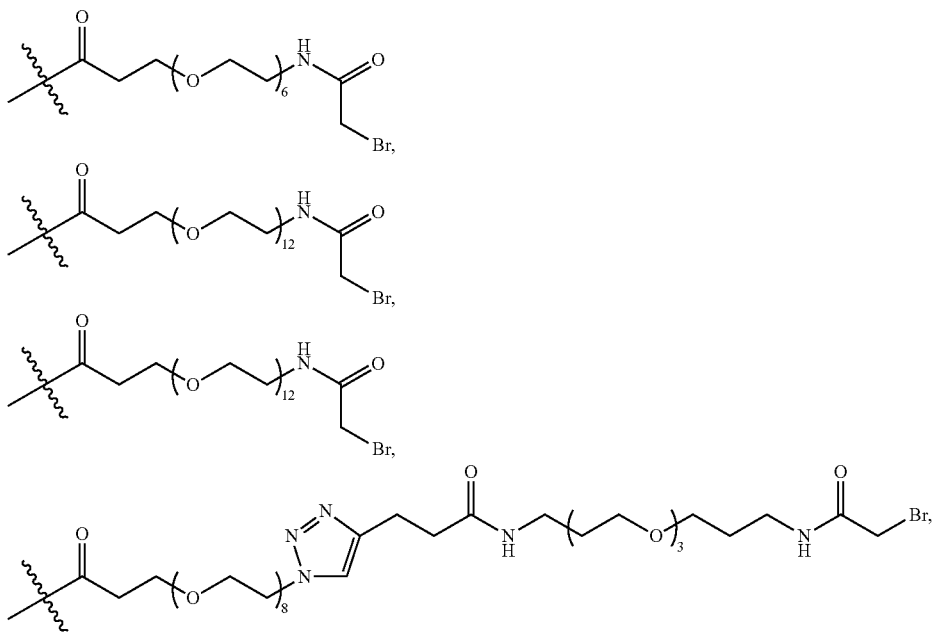
—C(O)CH$_2$Br,
Z$_{22}$ is A or K, wherein the amino side chain of said K is substituted with
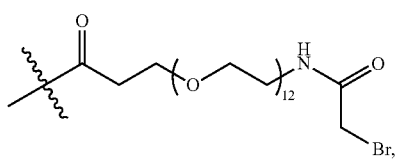
Z$_{23}$ is S or K, wherein the amino side chain of said K is substituted with
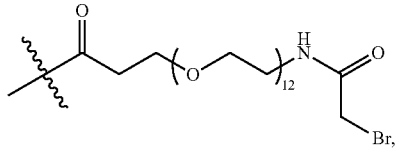
Z$_{26}$ is A or H,
Z$_{30}$ is L or K, wherein the amino side chain of said K is substituted with
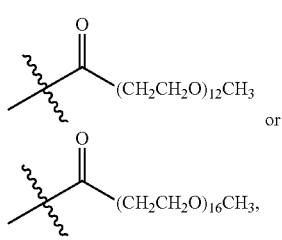
Z$_{34}$ is
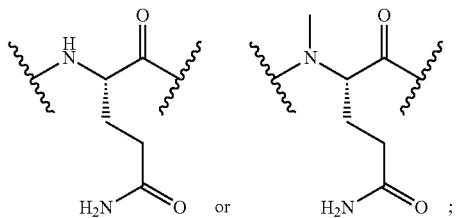 [SMILES: *N[C@@H](CCC(N)=O)C(*)=O ; *C(=O)[C@H](CCC(N)=O)N(*)C]
Z$_{35}$ is
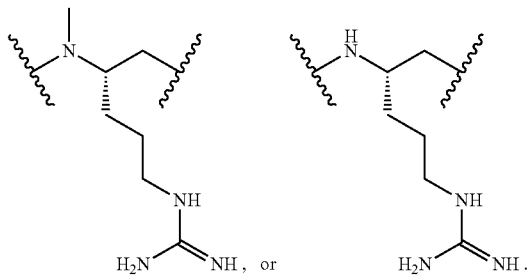

In certain embodiments, the cyclic PYY peptide is selected from the group consisting of SEQ ID NOs:1, 73-100, and 147-156, or a pharmaceutically acceptable salt thereof.

In certain embodiments, the monoclonal antibody or the antigen binding fragment thereof is covalently linked to the cyclic PYY peptide at a lysine residue of the cyclic PYY peptide via a linker. The linker can, for example, comprise a linker selected from the group consisting of polyethylene glycol (PEG)8-triazolyl-CH$_2$CH$_2$CO-PEG4, a PEG chain of 2-24 PEG units, an alkyl chain containing 2-10 carbon atoms, (Gly4Ser)$_j$ wherein j=1-4, (AlaPro)$_u$ wherein u=1-10, and a bond.

In certain embodiments, only one of $Z_7$, $Z_9$, $Z_{11}$, $Z_{22}$ and $Z_{23}$ in Formula I is lysine, and the lysine is covalently linked to an engineered cysteine residue of the monoclonal antibody or the antigen binding fragment thereof via the linker.

Also provided are conjugates comprising a monoclonal antibody or an antigen binding fragment thereof coupled to a cyclic PYY peptide, wherein the conjugate comprises a sequence selected from the group consisting of SEQ ID NOs: 102-127 or a pharmaceutically acceptable salt thereof, wherein mAb represents the monoclonal antibody or the antigen binding fragment thereof, and ]$_2$ represents that 1 or 2 of the cyclic PYY peptide are covalently conjugated to the mAb.

In certain embodiments, the monoclonal antibody or the antigen binding fragment thereof comprises a heavy chain complementarity determining region 1 (HCDR1), HCDR2, HCDR3, and a light chain complementarity determining region 1 (LCDR1), LCDR2, and LCDR3, having the polypeptide sequences of SEQ ID NO: 141, 142, 143, 144, 145, and 146, respectively. In certain embodiments, the isolated monoclonal antibody comprises a heavy chain variable domain (VH) having the polypeptide sequence of SEQ ID NO: 137, and a light chain variable domain (VL) having the polypeptide sequence of SEQ ID NO: 139. In certain embodiments, the isolated monoclonal antibody further comprises a Fc portion. In certain embodiments, the isolated monoclonal antibody comprises a heavy chain (HC) having the polypeptide sequence of SEQ ID NO: 138 and a light chain (LC) having the polypeptide sequence of SEQ ID NO: 140.

Also provided are conjugates comprising a monoclonal antibody or an antigen binding fragment thereof coupled to a cyclic PYY peptide, wherein the monoclonal antibody or the antigen binding fragment thereof comprises a heavy chain complementarity determining region 1 (HCDR1), HCDR2, HCDR3, and a light chain complementarity determining region 1 (LCDR1), LCDR2, and LCDR3, having the polypeptide sequences of SEQ ID NO: 141, 142, 143, 144, 145, and 146, respectively, preferably the monoclonal antibody or antigen binding fragment thereof comprises a heavy chain variable domain (VH) having the polypeptide sequence of SEQ ID NO: 137, and a light chain variable domain (VL) having the polypeptide sequence of SEQ ID NO: 139, and more preferably, the monoclonal antibody a heavy chain (HC) having the polypeptide sequence of SEQ ID NO: 138 and a light chain (LC) having the polypeptide sequence of SEQ ID NO: 140; the cyclic PYY peptide comprises a polypeptide sequence selected from the group consisting of SEQ ID NOs: 1, 73-100, and 147-156, or a pharmaceutically acceptable salt thereof; and the monoclonal antibody or antigen binding fragment thereof is conjugated to the cyclic PYY peptide at residue 7, 9, 11, 22 or 23 of the cyclic PYY peptide, preferably at lysine residue 11 of the cyclic PYY peptide, directly or via a linker.

Also provided are methods of producing the conjugates of the invention. The methods comprise reacting an electrophile, preferably bromoacetamide or maleimide, introduced onto a sidechain of the cyclic PYY peptide, preferably with the sidechain of a lysine residue of the cyclic PYY peptide, with the sulfhydryl group of the cysteine residue of SEQ ID NO: 143 of the monoclonal antibody or antigen-binding fragment thereof, thereby creating a covalent linkage between the cyclic PYY peptide and the monoclonal antibody or antigen-binding fragment thereof.

Also provided are pharmaceutical compositions comprising the conjugates of the invention and a pharmaceutically acceptable carrier.

Also provided are methods for treating or preventing a disease or disorder in a subject in need thereof, wherein said disease or disorder is selected from the group consisting of obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema. The methods comprise administering to the subject in need thereof an effective amount of the pharmaceutical compositions of the invention.

Also provided are methods of reducing food intake in a subject in need thereof. The methods comprise administering to the subject in need thereof an effective amount of the pharmaceutical composition of the invention.

Also provided are methods of modulating Y2 receptor activity in a subject in need thereof. The methods comprise administering to the subject in need thereof an effective amount of the pharmaceutical composition of the invention.

In certain embodiments, the pharmaceutical composition is administered via an injection. In certain embodiments, the pharmaceutical composition is administered in a combination with at least one antidiabetic agent. The antidiabetic agent can, for example, be a glucagon-like-peptide-1 receptor modulator. In certain embodiments, the pharmaceutical composition is administered in combination with liraglutide.

Also provided are kits comprising the conjugates of the invention, preferably further comprising a liraglutide and a device for injection.

Also provided are methods of producing the pharmaceutical compositions of the invention. The methods comprise combining the conjugate with a pharmaceutically acceptable carrier to obtain the pharmaceutical composition.

Further aspects, features and advantages of the present invention will be better appreciated upon a reading of the following detailed description of the invention and claims.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1: Shows a general peptide-mAb conjugation strategy according to an embodiment of the invention. X represents an electrophile introduced onto a sidechain of a therapeutic peptide, such as bromoacetamide or maleimide, that reacts site specifically with the sulfhydryl group of the Cys residue engineered into a CDR of a half-life extending mAb, creating a covalent linkage between peptide and mAb.

FIG. 2: Summary of CDR residues selected for substitution in PH9H5_VH (SEQ ID NO: 129) and in PH9L3_VL (SEQ ID NO: 128). Residues substituted with Cys are bolded and underlined.

FIG. 3: Pharmacokinetics of the compound 1 in Diet-Induced Obese Mice (DIO) mice.

FIG. 11A shows a graph demonstrating the effect of compound 1 monotherapy (PYY) and liraglutide combo therapy (PYY+Lira) on glucose levels. FIG. 11B shows a graph demonstrating the effect of compound 1 monotherapy (PYY) and liraglutide combo therapy (PYY+Lira) on insulin levels. FIG. 11C shows a graph demonstrating the effect of compound 1 monotherapy (PYY) and liraglutide combo therapy (PYY+Lira) on HOMA-IR. FIG. 11D shows a graph demonstrating the effect of compound 1 monotherapy (PYY) and liraglutide combo therapy (PYY+Lira) on triglycerides levels.

FIG. 12A shows a graph demonstrating the effect of compound 1 monotherapy (PYY) and liraglutide combo therapy (PYY+Lira) on cholesterol levels. FIG. 12B shows a graph demonstrating the effect of compound 1 monotherapy (PYY) and liraglutide combo therapy (PYY+Lira) on HDL levels. FIG. 12C shows a graph demonstrating the effect of compound 1 monotherapy (PYY) and liraglutide combo therapy (PYY+Lira) on ALT levels. FIG. 12D shows a graph demonstrating the effect of compound 1 monotherapy (PYY) and liraglutide combo therapy (PYY+Lira) on AST levels.

DETAILED DESCRIPTION OF THE INVENTION

Figure 4:
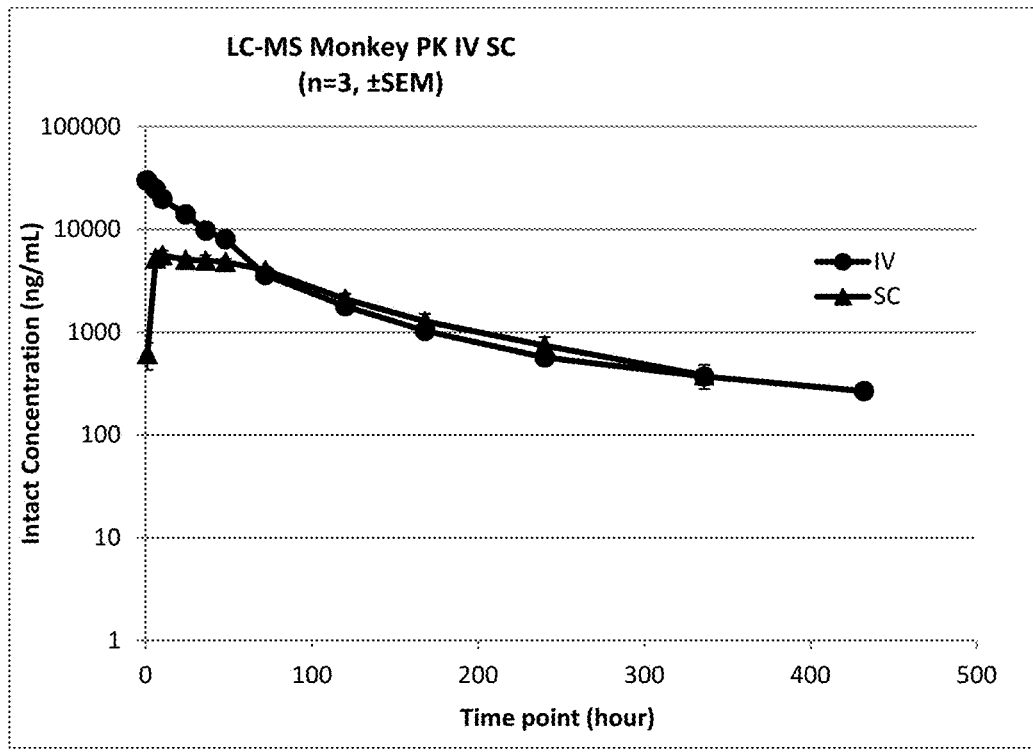
FIG. 4: Pharmacokinetics of the compound 1 in cynomolgus monkeys.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., cyclic $PYY_{3-36}$ polypeptide sequences, antibody light chain or heavy chain sequences), refer to two or more sequences or subsequences that are the same or have a specified percentage of amino acid residues or nucleotides that are the same, when compared and aligned for maximum correspondence, as measured using one of the following sequence comparison algorithms or by visual inspection using methods known in the art in view of the present disclosure.

For sequence comparison, typically one sequence acts as a reference sequence, to which test sequences are compared.

When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The term "administering" with respect to the methods of the invention, means a method for therapeutically or prophylactically preventing, treating or ameliorating a syndrome, disorder or disease as described herein by using a conjugate of the invention or a form, composition or medicament thereof. Such methods include administering an effective amount of said conjugate, a form, composition or medicament thereof at different times during the course of a therapy or concurrently in a combination form. The methods of the invention are to be understood as embracing all known therapeutic treatment regimens.

The term "effective amount" means that amount of active conjugate or pharmaceutical agent that elicits the biological or medicinal response in a tissue system, animal or human, that is being sought by a researcher, veterinarian, medical doctor, or other clinician, which includes preventing, treating or ameliorating a syndrome, disorder, or disease being treated, or the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

As used herein the term "coupled" refers to the joining or connection of two or more objects together. When referring to chemical or biological compounds, coupled can refer to a covalent connection between the two or more chemical or biological compounds. By way of a non-limiting example, an antibody of the invention can be coupled with a peptide of interest to form an antibody coupled peptide. An antibody coupled peptide can be formed through specific chemical reactions designed to conjugate the antibody to the peptide. In certain embodiments, an antibody of the invention can be covalently coupled with a peptide of the invention through a linker. The linker can, for example, be first covalently connected to the antibody or the peptide, then covalently connected to the peptide or the antibody.

As used herein, the term "linker" refers to a chemical module comprising a covalent or atomic chain that covalently attaches an antibody to the peptide. The linker can, for example, include, but is not limited to, a peptide linker, a hydrocarbon linker, a polyethylene glycol (PEG) linker, a polypropylene glycol (PPG) linker, a polysaccharide linker, a polyester linker, a hybrid linker consisting of PEG and an embedded heterocycle, and a hydrocarbon chain.

As used herein, the term "conjugate" refers to an antibody or a fragment thereof covalently coupled to a pharmaceutically active moiety. The term "conjugated to" refers to an antibody or a fragment thereof of invention covalently linked to or covalently connected to a pharmaceutically active moiety, preferably a therapeutic peptide, directly or indirectly via a linker. By way of a non-limiting example, the antibody can be a monoclonal antibody of the invention and the pharmaceutically active moiety can be a therapeutic peptide, such as a cyclic PYY peptide of interest.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Antibodies

In one general aspect, the invention relates to a novel antibody, which has been engineered to be non-targeting and to contain a cysteine residue capable of being used to chemically conjugate (i.e., couple) a pharmaceutically active moiety, such as a therapeutic peptide (e.g., a cyclic PYY peptide), in a site-specific manner, such that the antibody coupled peptide has an extended/increased half-life compared to the peptide alone. As used herein, the term "non-targeting" in the context of an antibody refers to an antibody that does not specifically bind to any target in vivo. As used herein, an antibody that "specifically binds to a target" refers to an antibody that binds to a target antigen, with a KD of $1\times10^{-8}$ M or less, preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as a Octet RED96 system. The smaller the value of the KD of an antibody, the higher affinity that the antibody binds to a target antigen.

Monoclonal antibodies, complete or a fragment thereof, can be used as a half-life extending moiety. Monoclonal antibodies are well-studied proteins that have been utilized and characterized for uses in vivo, and as such, the mechanisms that enable their protracted half-life in vivo and the mechanisms for their elimination in vivo are well understood. Additionally, the spatial separation and presentation of the two "arms" of the monoclonal antibody can be advantageous for effective bivalent presentation of a therapeutic moiety (i.e., a therapeutic peptide). Therapeutics in which toxins or other small molecule drugs are chemically linked to a monoclonal antibody have been developed but typically utilize a monoclonal antibody that binds to a specific antigen and targets the antibody-drug conjugate to a tissue/cell of interest, which preferentially expressed the antigen, and typically the drug/small molecule is attached to the antibody in a manner that does not impact antigen binding of the antibody.

For therapeutic peptide-mAb conjugates, antigen specific binding by the half-life extending monoclonal antibody is not desired. Because of this, a heavy chain (HC) and light chain (LC) variable (V) domain pair not expected to specifically bind any target are used for preparing the coupling-enabled, non-targeting monoclonal antibody of the invention. To obtain a coupling-enabled, non-targeting monoclonal antibody, a cysteine residue is engineered into one of the complementarity determining regions (CDRs) of a selected non-targeting antibody. The pharmaceutically active moiety (e.g., therapeutic peptide/compound) can contain the appropriate chemical moiety to allow for the conjugation of the pharmaceutically active moiety to the engineered cysteine residue of the non-targeting monoclonal antibody. A peptide-monoclonal antibody general conjugation strategy according to an embodiment of the invention is shown in FIG. 1.

The term "antibodies" as used herein is meant in a broad sense and includes non-human (e.g., murine, rat), human, human-adapted, humanized and chimeric monoclonal antibodies, antibody fragments, bispecific or multispecific antibodies, dimeric, tetrameric or multimeric antibodies, and single chain antibodies.

Antibody light chains of any vertebrate species can be assigned to one of two clearly distinct types, namely kappa (κ) and lambda (k), based on the amino acid sequences of their constant domains. Accordingly, the antibodies of the invention can contain a kappa or lambda light chain constant domain. According to particular embodiments, the antibodies of the invention include heavy and/or light chain constant regions from mouse or human antibodies. In addition to the heavy and light constant domains, antibodies contain an antigen-binding region that is made up of a light chain variable region and a heavy chain variable region, each of which contains three domains (i.e., complementarity determining regions 1-3; (CDR1, CDR2, and CDR3)). The light chain variable region domains are alternatively referred to as LCDR1, LCDR2, and LCRD3, and the heavy chain variable region domains are alternatively referred to as HCDR1, HCRD2, and HCDR3.

Immunoglobulins can be assigned to five major classes, namely IgA, IgD, IgE, IgG and IgM, depending on the heavy chain constant domain amino acid sequence. IgG is the most stable of the five types of immunoglobulins, having a serum half-life in humans of about 23 days. IgA and IgG are further sub-classified as the isotypes $IgA_1$, $IgA_2$, $IgG_1$, $IgG_2$, $IgG_3$ and $IgG_4$. Each of the four IgG subclasses has different biological functions known as effector functions. These effector functions are generally mediated through interaction with the Fc receptor (FcγR) or by binding C1q and fixing complement. Binding to FcγR can lead to antibody dependent cell mediated cytolysis, whereas binding to complement factors can lead to complement mediated cell lysis. An antibody of the invention utilized for its ability to extend half-life of a therapeutic peptide has no or minimal effector function, but retains its ability to bind FcRn, the binding of which can be a primary means by which antibodies have an extended in vivo half-life.

In one embodiment, the invention relates to an isolated antibody or antigen binding fragment thereof comprising a light chain variable region having completely human Ig germline V gene sequences, and a heavy chain variable region having completely human Ig germline V gene sequences except HCDR3 having the amino acid sequence of SEQ ID NO: 143, wherein the antibody or antigen binding fragment thereof does not specifically bind to any human antigen in vivo. In certain embodiments, the invention relates to a conjugate comprising an isolated antibody or antigen binding fragment thereof comprising a light chain variable region having completely human Ig germline V gene sequences, and a heavy chain variable region having completely human Ig germline V gene sequences except HCDR3 having the amino acid sequence of SEQ ID NO: 143 and a pharmaceutically active moiety (e.g., a cyclic PYY peptide of the invention) conjugated thereto, wherein the antibody or antigen binding fragment thereof does not specifically bind to any human antigen in vivo. In the present disclosure, with respect to an antibody or antigen binding fragment thereof according to an embodiment of the invention, the phrase "a conjugate comprising an antibody or antigen binding fragment thereof and a pharmaceutically active moiety conjugated thereto" is used interchangeably with the phrase "an antibody or antigen binding fragment thereof conjugated to a pharmaceutically active moiety."

As used herein, the term "antigen-binding fragment" refers to an antibody fragment such as, for example, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment (i.e., portion of the heavy chain which is included in the Fab fragment). According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids.

As used herein, the term "single domain antibody" refers to a conventional single domain antibody in the field, which comprises a heavy chain variable region and a heavy chain constant region or which comprises only a heavy chain variable region.

The phrase "isolated antibody or antibody fragment" refers to an antibody or antibody fragment that is substantially free of other antibodies having different antigenic specificities (e.g., an isolated antibody specifically binding a target antigen is substantially free of antibodies that specifically do not bind the target antigen). Moreover, an isolated antibody or antibody fragment can be substantially free of other cellular material and/or chemicals.

An antibody variable region consists of a "framework" region interrupted by three "antigen binding sites". The antigen binding sites are defined using various terms: (i) Complementarity Determining Regions (CDRs), three in the VH (HCDR1, HCDR2, HCDR3), and three in the VL (LCDR1, LCDR2, LCDR3), are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991). (ii) "Hypervariable regions," "HVR," or "HV," three in the VH (H1, H2, H3) and three in the VL (L1, L2, L3), refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro Mol Recognit 17:132-43, 2004). The International ImMunoGeneTics (IMGT) database (http://www_mgt_org) provides a standardized numbering and definition of antigen-binding sites. The correspondence between CDRs, HVs and IMGT delineations is described in Lefranc et al., Dev Comparat Immunol 27:55-77, 2003.

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

In one embodiment of the invention, an isolated antibody or antigen binding fragment thereof comprises a light chain variable region having the LCDR1, LCDR2 and LCDR3 of the amino acid sequence of SEQ ID NO: 144, SEQ ID NO: 145 and SEQ ID NO: 146, respectively, and a heavy chain variable region having the HCDR1, HCDR2 and HCDR3 of the amino acid sequences of SEQ ID NO: 141, SEQ ID NO: 142 and SEQ ID NO: 143, respectively.

In another embodiment, the isolated antibody further comprises a Fc region derived from human IgG4 Fc region. Human IgG4 Fc region has reduced ability to bind FcγR and complement factors compared to other IgG sub-types. Preferably, the Fc region contains human IgG4 Fc region having substitutions that eliminate effector function. Thus, an isolated antibody further comprises a Fc region having a modified human IgG4 Fc region containing one or more of the following substitutions: substitution of proline for glutamate at residue 233, alanine or valine for phenylalanine at residue 234 and alanine or glutamate for leucine at residue 235 (EU numbering, Kabat, E. A. et al. (1991) *Sequences of Proteins of Immunological Interest*, 5th Ed. U.S. Dept. of Health and Human Services, Bethesda, Md., NIH Publication no. 91-3242). Removing the N-linked glycosylation site in the IgG4 Fc region by substituting Ala for Asn at residue 297 (EU numbering) is another way to ensure that residual effector activity is eliminated.

Preferably, an antibody of the invention exists as dimers joined together by disulfide bonds and various non-covalent interactions. Thus, the Fc portion useful for the antibody of the invention can be human IgG4 Fc region containing a substitution, such as serine to proline at position at 228 (EU numbering), that stabilizes heavy chain dimer formation and prevents the formation of half-IgG4 Fc chains.

In another embodiment, the C-terminal Lys residue in the heavy chain is removed, as commonly seen in recombinantly produced monoclonal antibodies.

"Human antibody" refers to an antibody having heavy and light chain variable regions in which both the framework and the antigen binding sites are derived from sequences of human origin. If the antibody contains a constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. "Human antibody" may contain amino acid differences when compared to the human germline or rearranged immunoglobulin sequences due to for example naturally occurring somatic mutations or intentional introduction of substitutions in the framework or antigen binding sites. Typically, "human antibody" is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of "human antibody".

Isolated humanized antibodies may be synthetic. Human antibodies, while derived from human immunoglobulin sequences, may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

The term "recombinant antibody" as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange.

The term "monoclonal antibody" as used herein refers to a preparation of antibody molecules of a single molecular composition. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

In certain embodiments, the term "mAb" refers to a monoclonal antibody having a variable heavy chain (VH) sequence comprising SEQ ID NO: 137 and a variable light chain (VL) sequence comprising SEQ ID NO: 139. In certain embodiments the mAb is a fully human monoclonal antibody having a heavy chain (HC) sequence comprising SEQ ID NO:138 and a light chain (LC) sequence comprising SEQ ID NO:140. In certain embodiments, the lysine residue at position 446 of SEQ ID NO: 138 is optionally missing.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope or comprises germline sequences lacking any known binding specificity and a second immunoglobulin variable domain sequence of the plurality has binding specificity for a second epitope or comprises germline sequences lacking any known binding specificity, and wherein the first and/or second immunoglobulin variable domain optionally include a conjugated pharmaceutically active moiety (e.g., a therapeutic peptide). In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, the first and second immunoglobulin variable domains include the same conjugated pharmaceutically active moiety. In an embodiment, the first and second immunoglobulin variable domains include different pharmaceutically active moieties. In an embodiment, only the first immunoglobulin variable domain includes a conjugated pharmaceutically active moiety. In an embodiment, only the second immunoglobulin variable domain includes a conjugated pharmaceutically active moiety. In an embodiment, a multispecific antibody comprises a third, fourth, or fifth immunoglobulin variable domain. In an embodiment, a multispecific antibody is a bispecific antibody molecule, a trispecific antibody, or a tetraspecific antibody molecule.

As used herein, the term "bispecific antibody" refers to a multispecific antibody that binds no more than two epitopes or two antigens and/or comprises two conjugated pharmaceutically active moieties (e.g., the same or different pharmaceutically active moiety). A bispecific antibody is characterized by a first immunoglobulin variable domain sequence which has binding specificity for a first epitope or comprises germline sequences lacking any known binding specificity and a second immunoglobulin variable domain sequence that has binding specificity for a second epitope or comprises germline sequences lacking any known binding specificity, and wherein the first and/or second immunoglobulin variable domain optionally include a conjugated pharmaceutically active moiety. In an embodiment, the first and second epitopes are on the same antigen, e.g., the same protein (or subunit of a multimeric protein). In an embodiment, the first and second epitopes overlap or substantially overlap. In an embodiment the first and second epitopes are on different antigens, e.g., the different proteins (or different subunits of a multimeric protein). In an embodiment, the first and second immunoglobulin variable domains include the same conjugated pharmaceutically active moiety. In an embodiment, the first and second immunoglobulin variable domains include different pharmaceutically active moieties. In an embodiment, only the first immunoglobulin variable domains includes a conjugated pharmaceutically active moiety. In an embodiment, only the second immunoglobulin variable domain includes a conjugated pharmaceutically active moiety. In an embodiment a bispecific antibody comprises a first heavy chain variable domain sequence and light chain variable domain sequence which have binding specificity for a first epitope or comprise germline sequences lacking any known binding specificity and a second heavy chain variable domain sequence and light chain variable domain sequence which have binding specificity for a second epitope or comprise germline sequences lacking any known binding specificity, and wherein the first and/or second heavy chain variable domains optionally include a conjugated pharmaceutically active moiety. In an embodiment, the first and second heavy chain variable domains include the same conjugated pharmaceutically active moiety. In an embodiment, the first and second heavy chain variable domains include different conjugated pharmaceutically active moieties. In an embodiment, only the first heavy chain variable domain includes a conjugated pharmaceutically active moiety. In an embodiment, only the second heavy chain variable domain includes a conjugated pharmaceutically active moiety.

"Full length antibody" as used herein refers to an antibody having two full length antibody heavy chains and two full length antibody light chains. A full length antibody heavy chain (HC) consists of well known heavy chain variable and constant domains VH, CH1, CH2, and CH3. A full length antibody light chain (LC) consists of well known light chain variable and constant domains VL and CL. The full length antibody may be lacking the C-terminal lysine (K) in either one or both heavy chains.

The term "Fab-arm" or "half molecule" refers to one heavy chain-light chain pair that specifically binds an antigen.

Full length bispecific antibodies can be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent monospecific antibodies are reduced. The resulting free cysteines of one of the parent monospecific antibodies form an inter heavy-chain disulfide bond with cysteine residues of a second parent monospecific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each can bind a distinct epitope.

"Homodimerization" as used herein, with respect to the antibodies, refers to an interaction of two heavy chains having identical CH3 amino acid sequences. "Homodimer" as used herein, with respect to the antibodies, refers to an antibody having two heavy chains with identical CH3 amino acid sequences.

"Heterodimerization" as used herein, with respect to the antibodies, refers to an interaction of two heavy chains having non-identical CH3 amino acid sequences. "Heterodimer" as used herein, with respect to the antibodies, refers to an antibody having two heavy chains with non-identical CH3 amino acid sequences.

The "knob-in-hole" strategy (see, e.g., PCT Intl. Publ. No. WO 2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by following substitutions (expressed as modified position in the first CH$_3$ domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Pat. Publ. No. US2012/0149876 or U.S. Pat. Publ. No. US2013/0195849.

In addition to methods described above, bispecific antibodies can be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody and the second monospecific bivalent antibody are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

The numbering of amino acid residues in the antibody constant region throughout the specification is performed according to the EU index as described in Kabat et al., Sequences of Proteins of Immunological Interest, 5th Ed. Public Health Service, National Institutes of Health, Bethesda, Md. (1991), unless otherwise explicitly stated.

Conjugates

In another general aspect, the invention relates to a conjugate comprising an antibody of the invention covalently conjugated to a pharmaceutically active moiety, such as a synthetic therapeutic peptide (e.g., a cyclic PYY peptide), in a site-specific manner, such that the antibody coupled peptide has an extended/increased half-life compared to the peptide alone. The invention also relates to pharmaceutical compositions and methods for use thereof. The conjugates are useful for preventing, treating, or ameliorating diseases or disorders, such as obesity, type 2 diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, among others.

In certain embodiments, the antibody of the invention is modified to comprise at least one cysteine residue substitution that is capable of being conjugated to the pharmaceutically active moiety to extend/increase the half-life of the pharmaceutically active moiety. In certain embodiments, the at least one cysteine residue substitution is comprised in a complementarity determining region of the antibody. In certain embodiments, the at least one cysteine residue substitution is in a heavy chain complementarity determining region (HCDR). In certain embodiments, the at least one cysteine residue substitution is in an HCDR3, wherein the HCDR3 comprises an amino acid sequence of SEQ ID NO:143. In certain embodiments, the antibody comprising an HCDR3 comprising an amino acid sequence of SEQ ID NO: 143 has at least one additional cysteine substitution that is capable of being conjugated to a pharmaceutically active moiety.

In certain embodiments the pharmaceutically active moiety can comprise a linker. The linker can be modified chemically to allow for the conjugation of the antibody to the pharmaceutically active moiety. The linker can, for example, include, but is not limited to, a peptide linker, a hydrocarbon linker, a polyethylene glycol (PEG) linker, a polypropylene glycol (PPG) linker, a polysaccharide linker, a polyester linker, a hybrid linker consisting of PEG and an embedded heterocycle, or a hydrocarbon chain. The PEG linkers can, for example, comprise 2-24 PEG units.

In certain embodiments, a monoclonal antibody of the invention is conjugated to one, two, three, four, five, or six pharmaceutically active moieties (e.g., therapeutic peptide(s)) of interest. In preferred embodiments, the non-targeting monoclonal antibody is conjugated to two pharmaceutically active moieties of interest. In certain embodiments where the monoclonal antibody is conjugated to at least two pharmaceutically active moieties of interest, the pharmaceutically active moieties of interest can be the same pharmaceutically active moiety or can be different pharmaceutically active moieties.

Methods of conjugating antibodies of the invention with the pharmaceutically active moieties of the invention are known in the art. Briefly, the antibodies of the invention can be reduced with a reducing agent (e.g., TCEP (tris(2-carboxyethyl) phosphine), purified (e.g., by protein A adsorption or gel filtration), and conjugated with the pharmaceutically active moiety (e.g., by providing a lyophilized peptide to the reduced antibody under conditions that allow for conjugation). After the conjugation reaction, the conjugate can be purified by ion exchange chromatography or hydrophobic interaction chromatography (HIC) with a final purification step of protein A adsorption. In certain embodiments, the antibodies of the invention can be purified prior to being reduced utilizing HIC methods. For more detailed description of the conjugation methods, see, e.g., Example 103 and Dennler et al., Antibodies 4:197-224 (2015).

Provided herein are conjugates comprising a monoclonal antibody or an antigen binding fragment thereof coupled to a cyclic PYY peptide, wherein the cyclic PYY peptide is represented by Formula I or a derivative or pharmaceutically acceptable salt thereof:

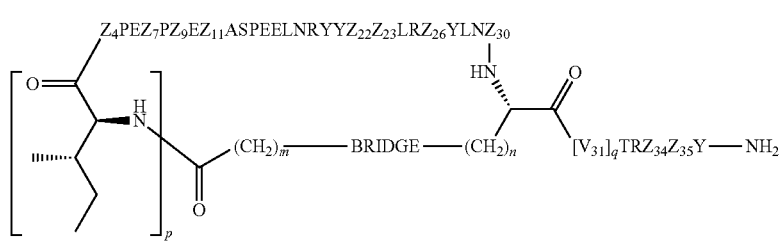

Formula I wherein p is 0 or 1;

m is 0, 1, 2, 3, 4, or 5;

n is 1, 2, 3, or 4;

q is 0 or 1; provided that q is 1 only when $Z_{30}$ is absent;

BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;

$Z_4$ is K, A, E, S, or R;

$Z_7$ is A or K;

$Z_9$ is G or K;

$Z_{11}$ is D or K;

$Z_{22}$ is A or K;

$Z_{23}$ is S or K;

$Z_{26}$ is A or H;

$Z_{30}$ is L, W, absent, or K;

provided that $Z_{30}$ is absent only when q is 1;

$Z_{34}$ is

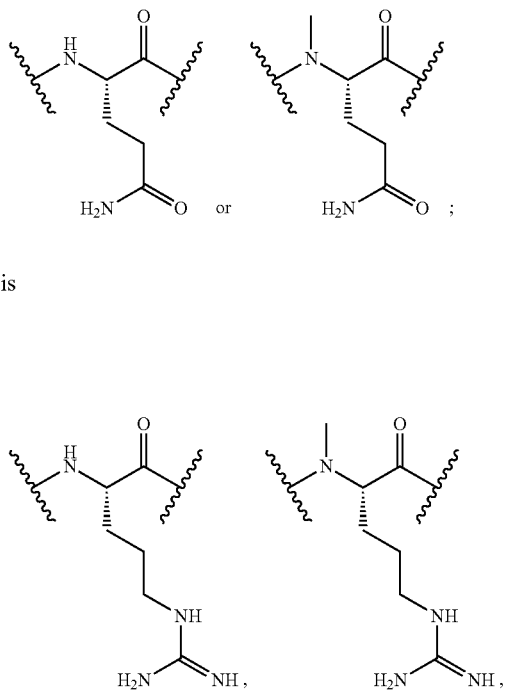

$Z_{35}$ is

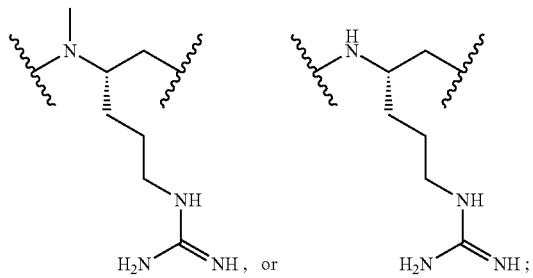

wherein the derivative is the compound of Formula I that is modified by one or more processes selected from the group consisting of amidation, glycosylation, carbamylation, sulfation, phosphorylation, cyclization, lipidation, and pegylation.

In certain embodiments, the cyclic PYY peptide is a derivative of the cyclic PYY peptide of Formula I that is modified by one or more processes selected from the group consisting amidation, lipidation, and pegylation, or a pharmaceutically acceptable salt thereof.

In certain embodiments, the cyclic PYY peptide is represented by Formula I or the derivative or pharmaceutically acceptable salt thereof, wherein:

p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K, wherein the amino side chain of said K is optionally substituted with

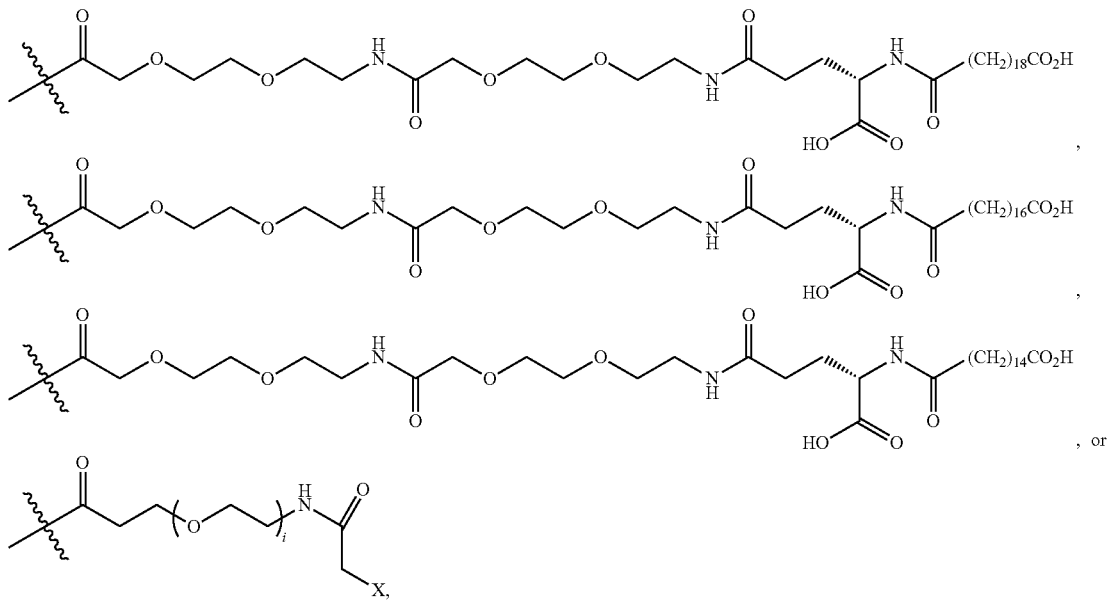

wherein i is an integer of 0 to 24, and X=Br, I or Cl, —C(O)CH$_2$Br, —C(O)CH$_2$I, or —C(O)CH$_2$Cl; $Z_9$ is G or K, wherein the amino side chain of said K is optionally substituted with

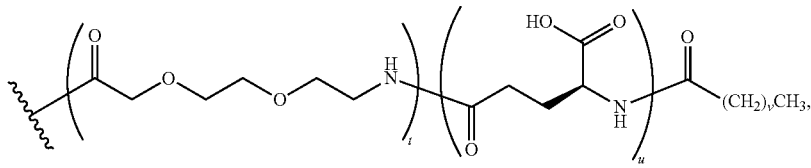

wherein t is 0, 1, or 2;
u is 0 or 1; and
v is 14, 16, or 18;

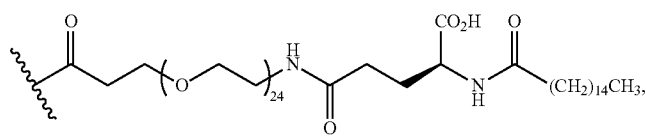

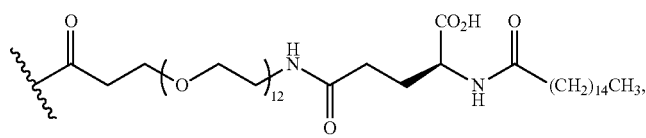

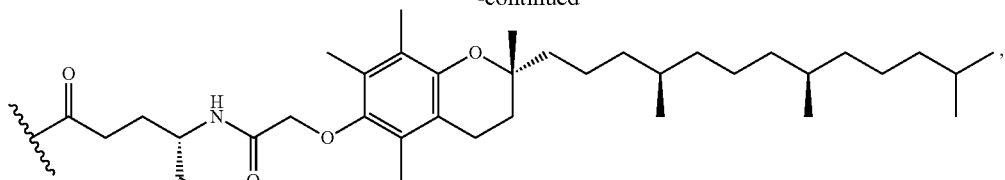
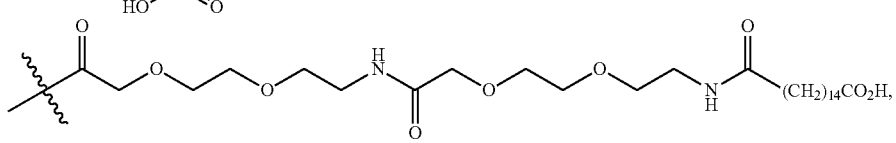
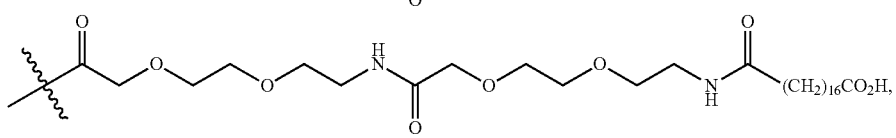
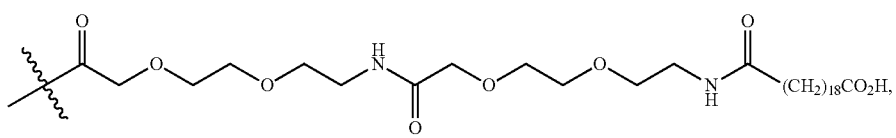
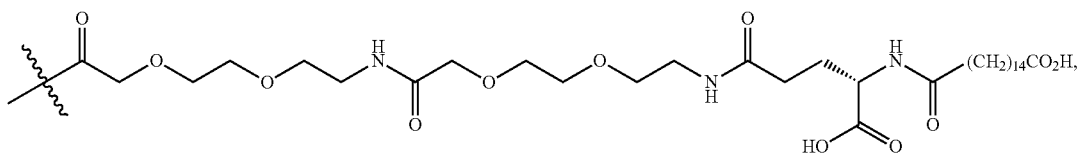
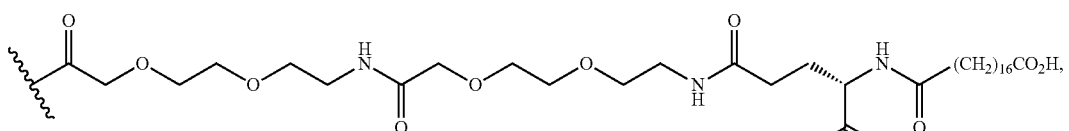
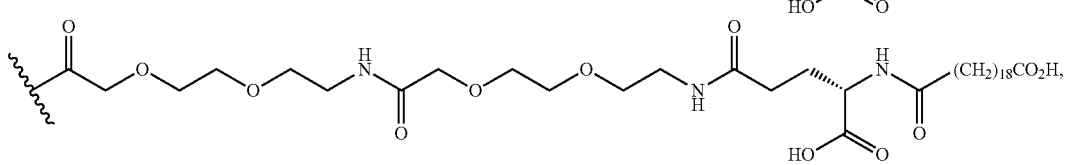
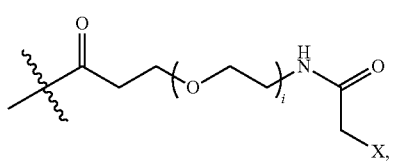
wherein i is an integer of 0 to 24, and X=Br, I or Cl, —C(O)CH$_2$Br, —C(O)CH$_2$I, or —C(O)CH$_2$Cl;
$Z_{11}$ is D or K, wherein the amino side chain of said K is optionally substituted with
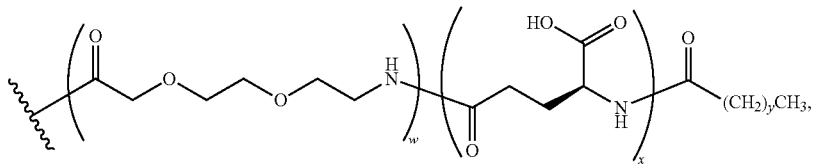

wherein w is 0, 1, 2, or 4;
x is 0 or 1; and
y is 14, 16, or 18;
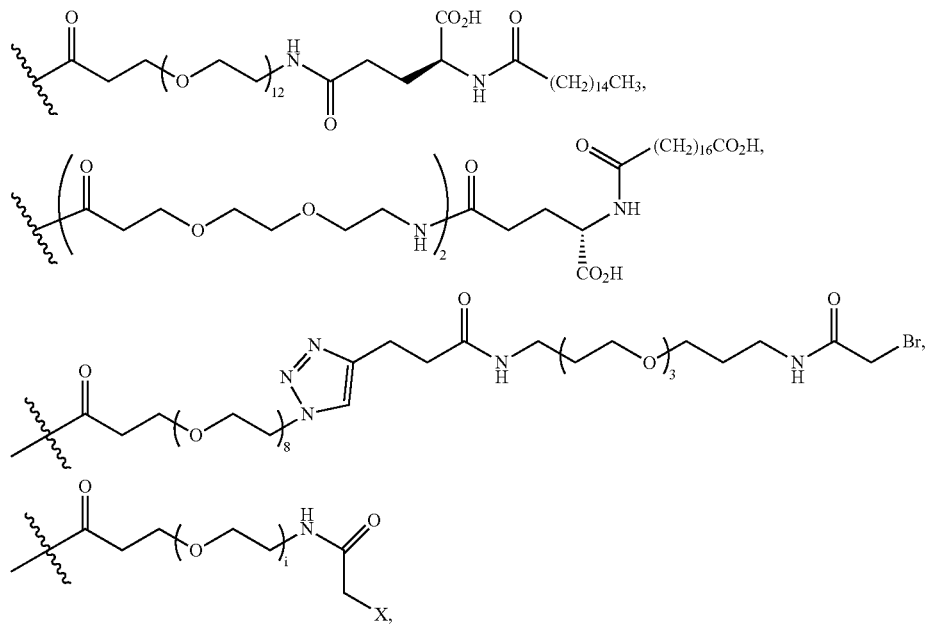
wherein i is an integer of 0 to 24, and X=Br, I or Cl,
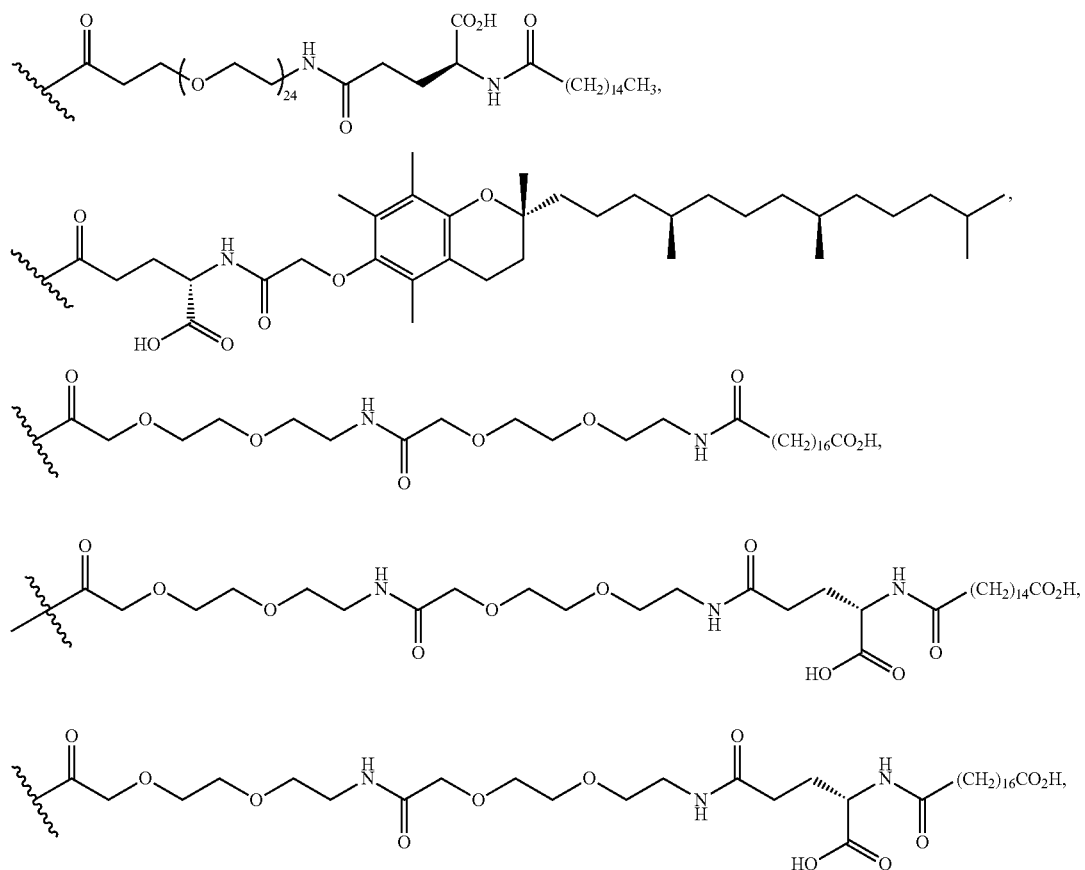

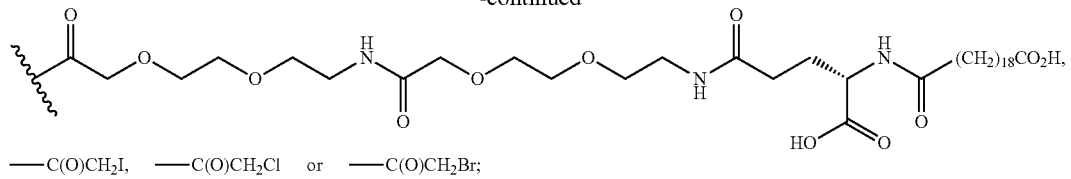
—C(O)CH$_2$I, —C(O)CH$_2$Cl or —C(O)CH$_2$Br;
$Z_{22}$ is A or K, wherein the amino side chain of said K is optionally substituted with
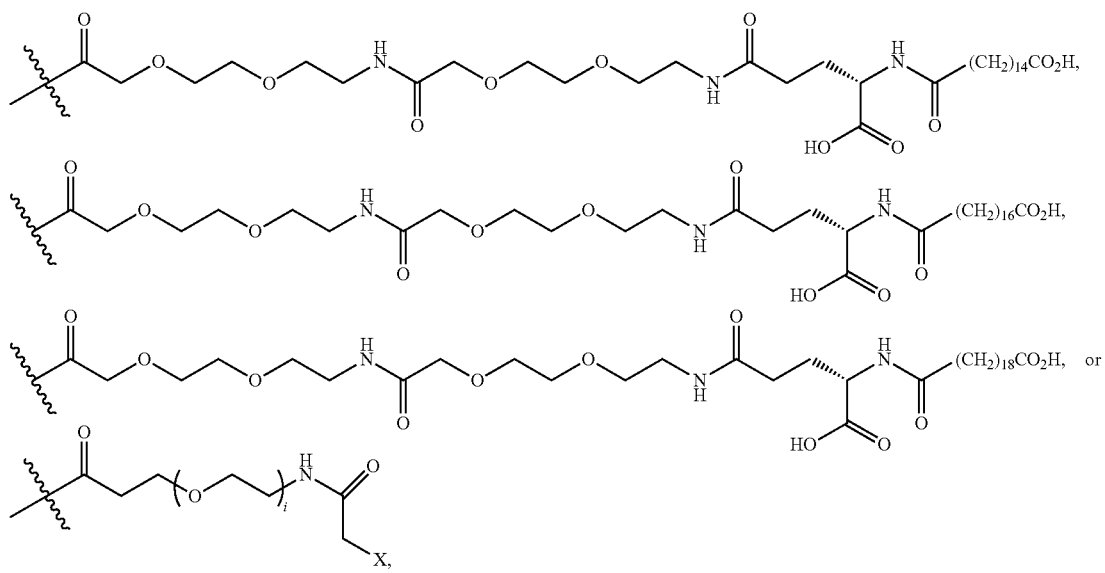
wherein i is an integer of 0 to 24, and X=Br, I or Cl, —C(O)CH$_2$Br, —C(O)CH$_2$I, or —C(O)CH$_2$Cl;
$Z_{23}$ is S or K; wherein the amino side chain of said K is optionally substituted with
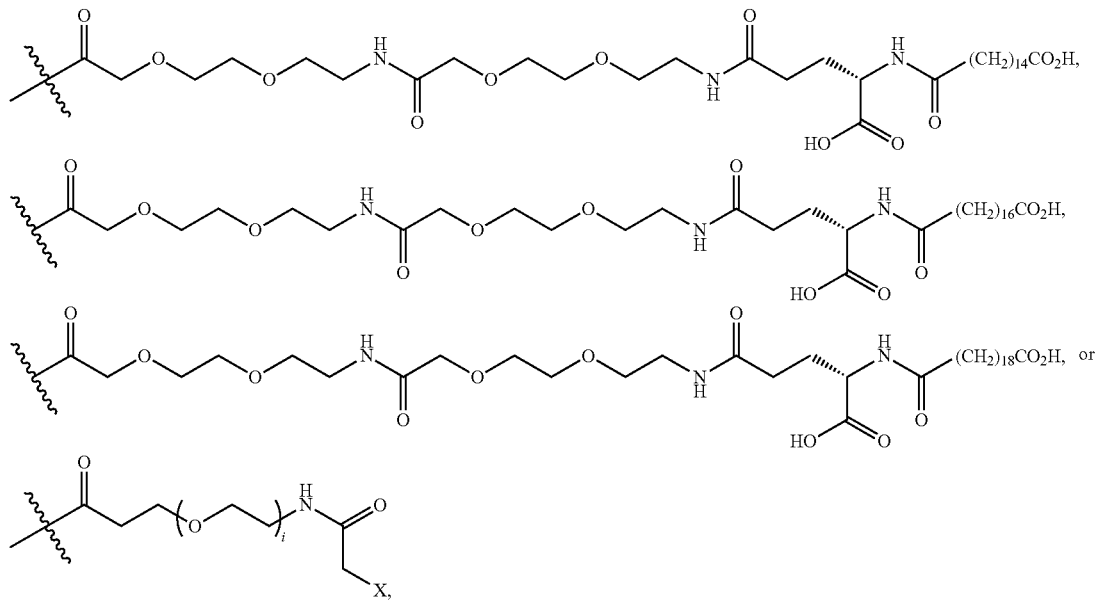

wherein i is an integer of 0 to 24, and X=Br, I or Cl, —C(O)CH$_2$Br, —C(O)CH$_2$I, or —C(O)CH$_2$Cl;
$Z_{26}$ is A or H;
$Z_{30}$ is L, W, absent, or K, provided that $Z_{30}$ is absent only when q is 1, wherein the amino side chain of said K is optionally substituted with
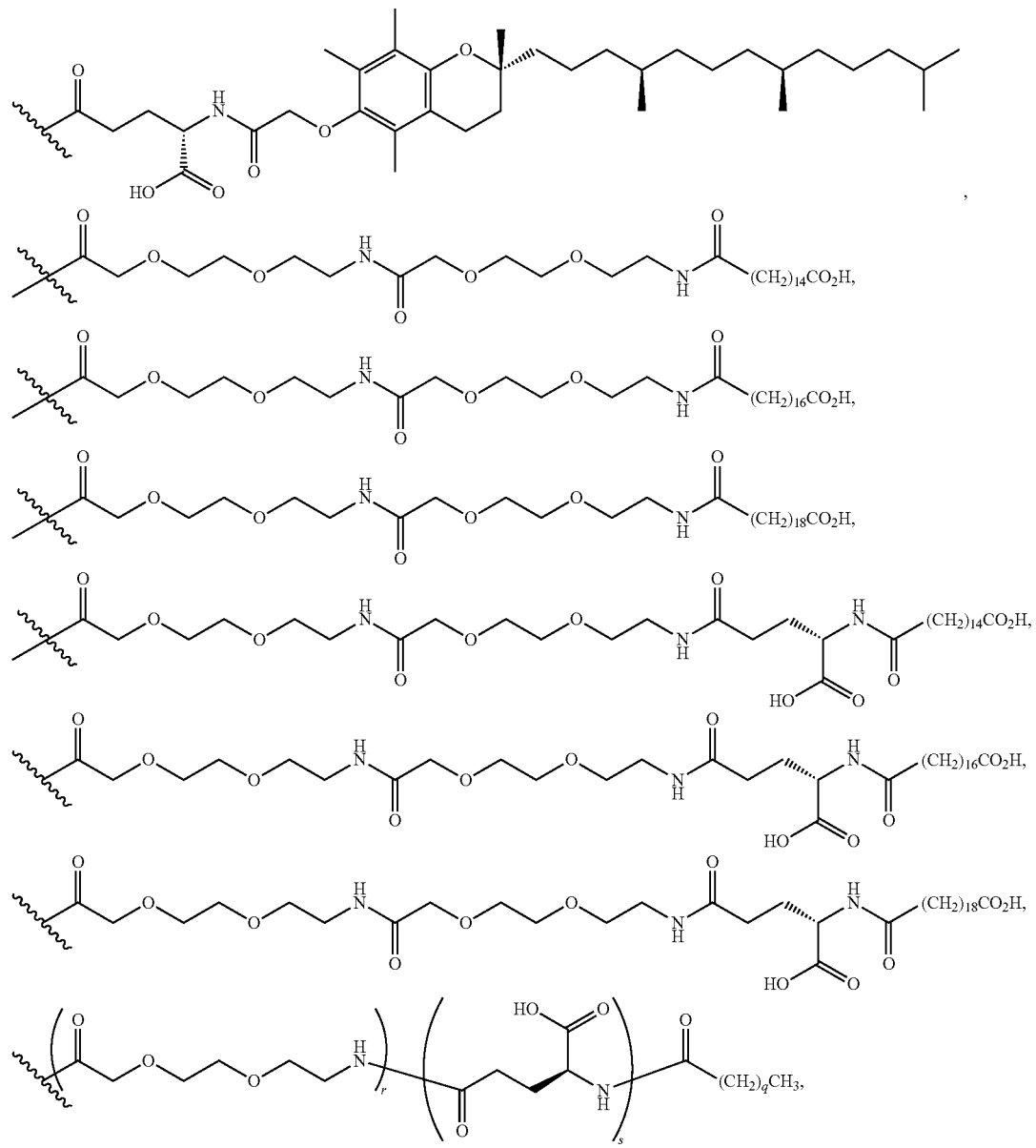
wherein r is 0, 1, or 2;
s is 0 or 1; and
q is 14, 16, or 18; or
-continued
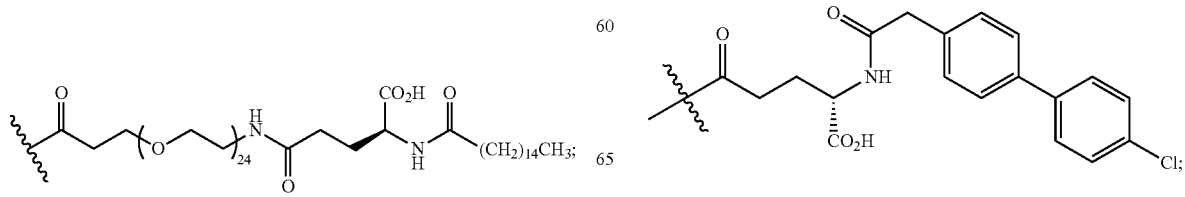

35
-continued
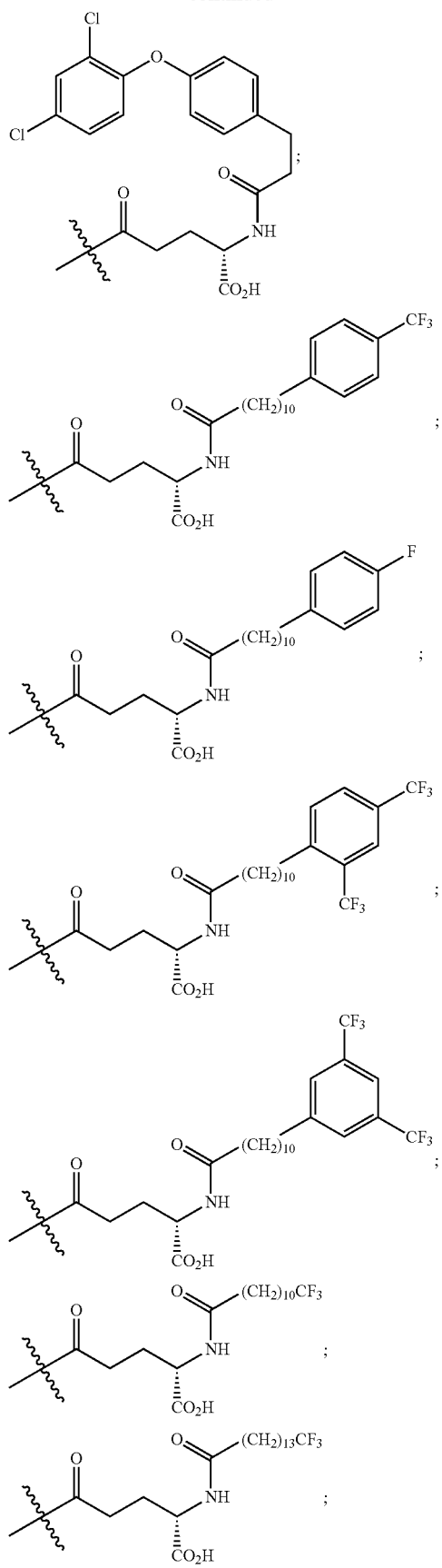
36
-continued
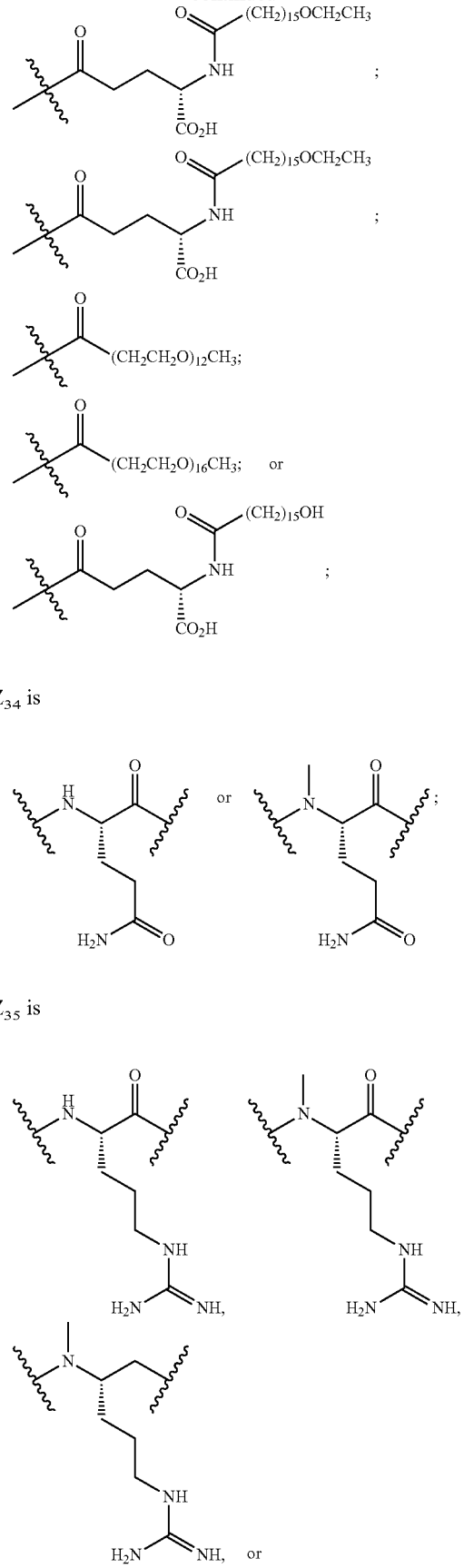
$Z_{34}$ is
$Z_{35}$ is

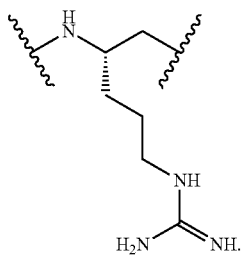

In certain embodiments, the cyclic PYY peptide is represented by Formula I or the derivative or pharmaceutically acceptable salt thereof, wherein:
p is 0 or 1;
m is 0, 1, 2, 3, or 5;
n is 1, 2, or 4;
q is 0 or 1; provided that q is 1 only when $Z_{30}$ is absent;
BRIDGE is -Ph-CH$_2$—S—, -triazolyl-, —NHC(O)CH$_2$S—, —SCH$_2$C(O)NH—, —(OCH$_2$CH$_2$)$_2$NHC(O)CH$_2$S, —NHC(O)—, or —CH$_2$S—;
$Z_4$ is K, A, E, S, or R;
$Z_7$ is A or K, wherein the amino side chain of said K is substituted with

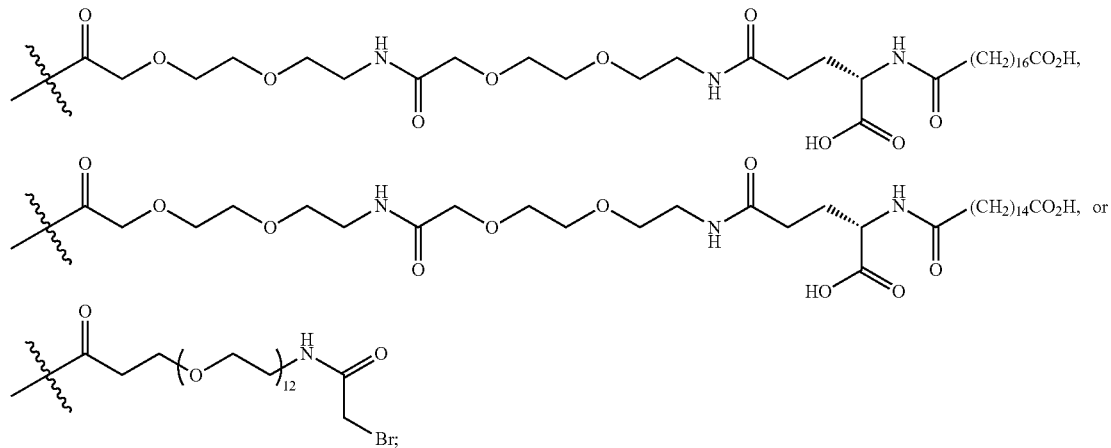

$Z_9$ is G or K, wherein the amino side chain of said K is substituted with $Z_{11}$ is D or K, wherein the amino side chain of said K is optionally substituted with

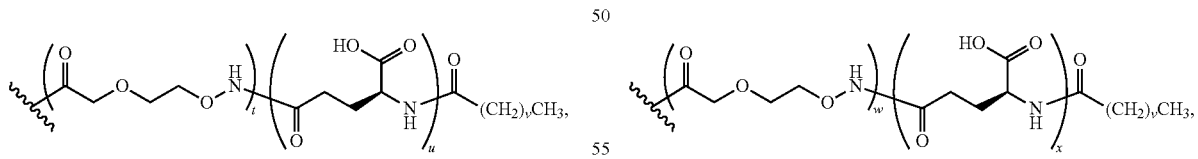

wherein t is 0;
u is 1; and
v is 14;

wherein w is 0, or 4;
x is 1; and
y is 14;

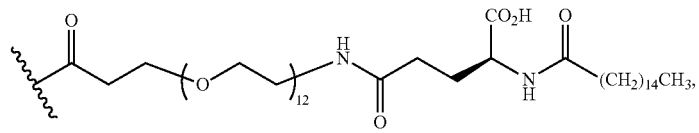

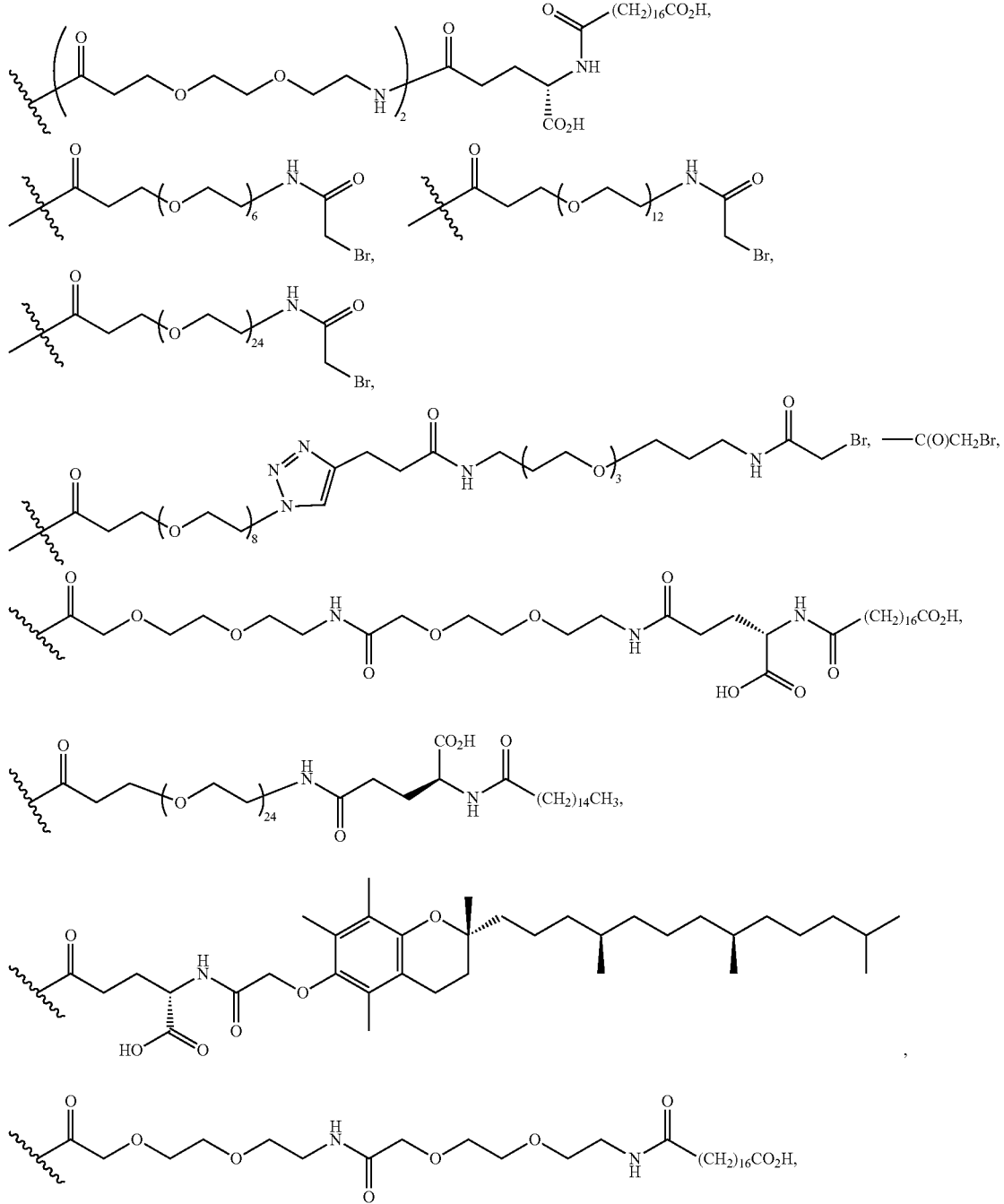
or
Z$_{22}$ is A or K, wherein the amino side chain of said K is substituted with
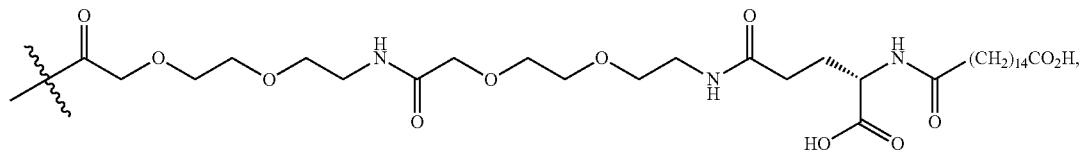

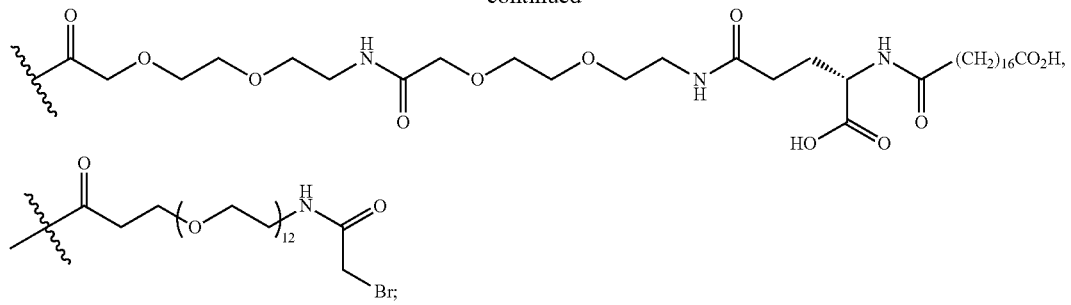
$Z_{23}$ is S or K, wherein the amino side chain of said K is substituted with
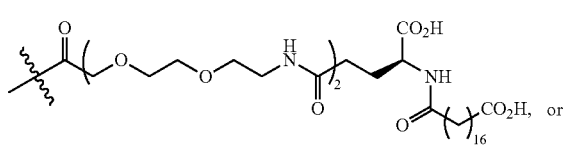 or
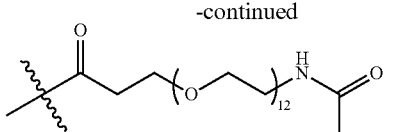
$Z_{26}$ is A or H;
$Z_{30}$ is L or K, wherein the amino side chain of said K is substituted with
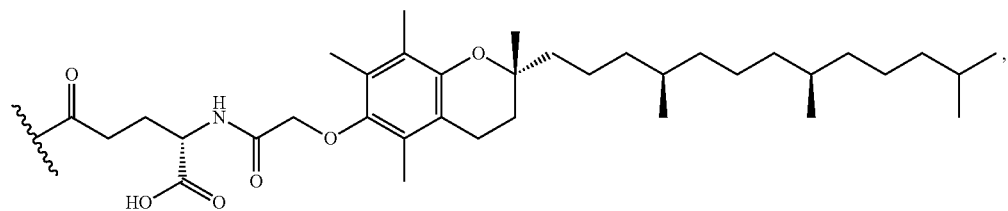
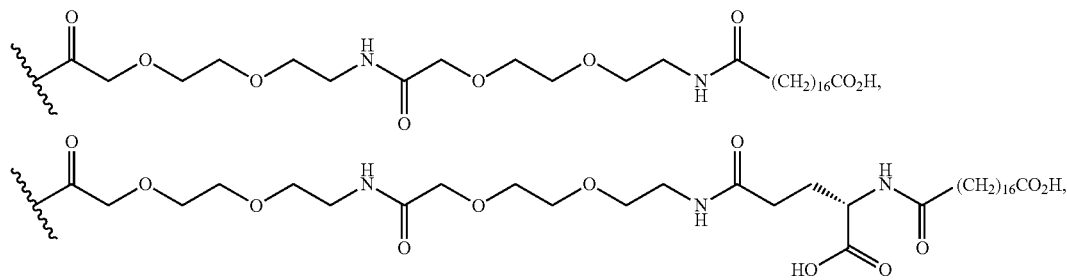
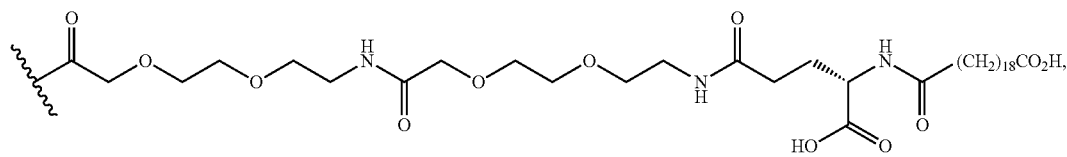
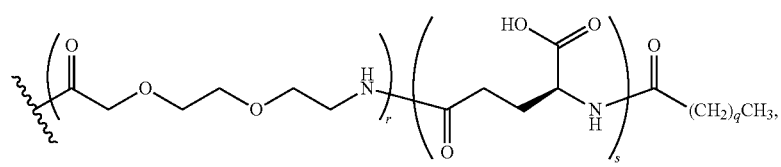

wherein r is 0, or 2;
s is 1; and
q is 14, 16, or 18; or
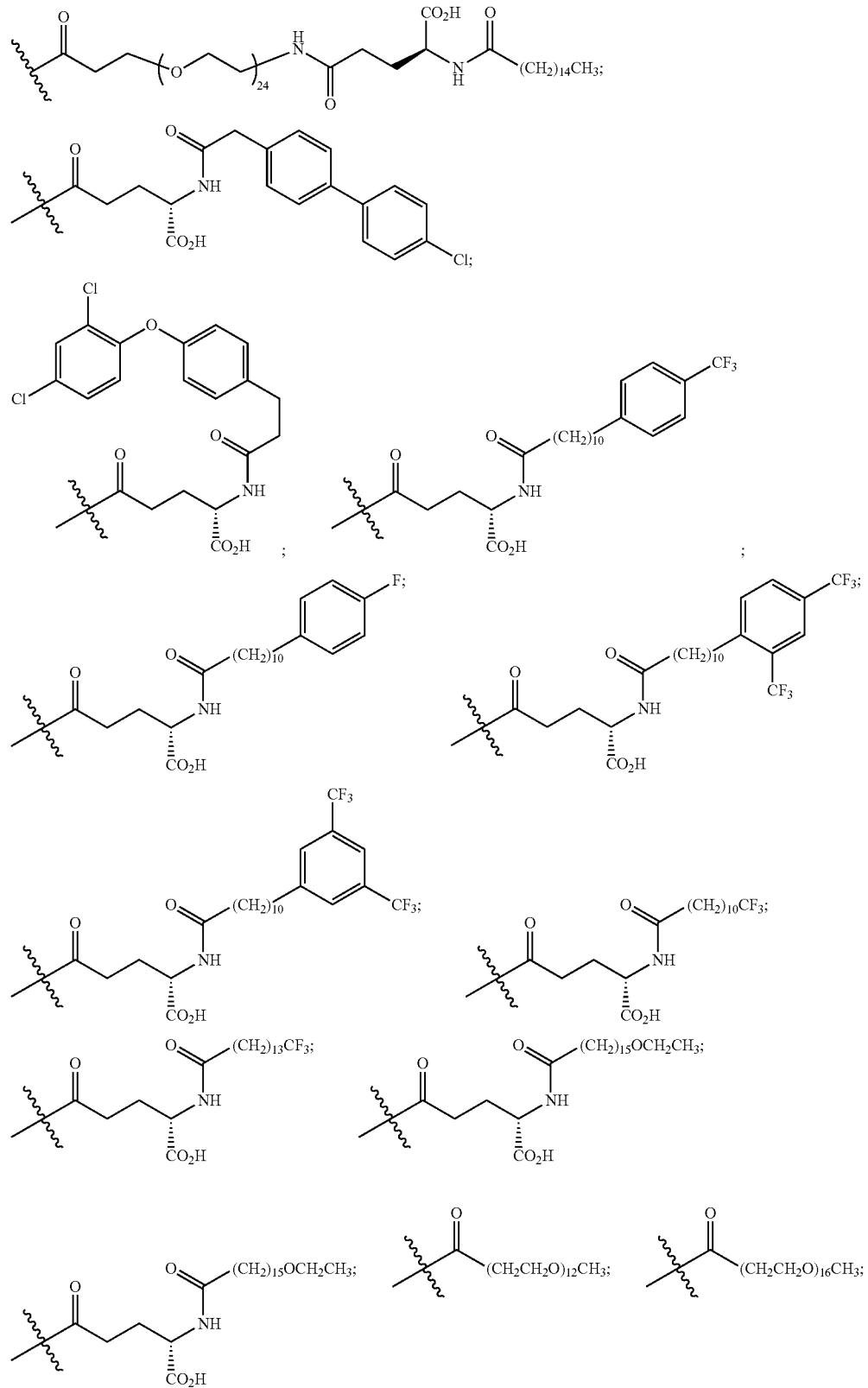

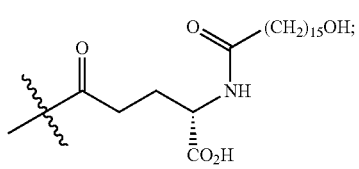

$Z_{34}$ is

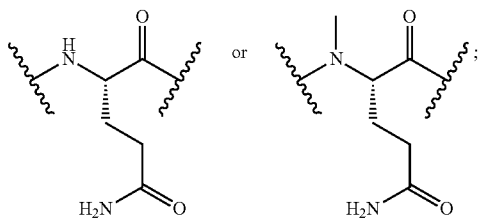 [SMILES: *N[C@@H](CCC(N)=O)C(*)=O ; "or" ; *C(=O)[C@H](CCC(N)=O)N(*)C ; ";"]

$Z_{35}$ is

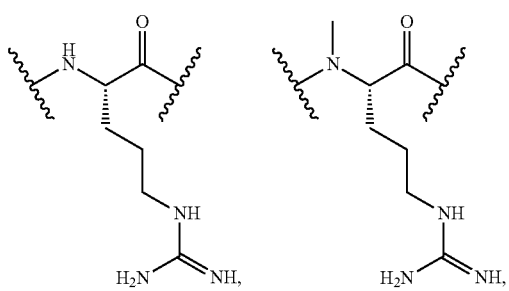

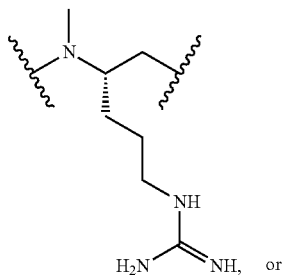

or

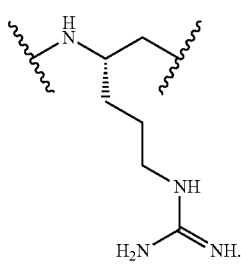

In certain embodiments, a conjugate comprises a monoclonal antibody or a fragment thereof conjugated to a cyclic PYY peptide, wherein the cyclic PYY peptide is selected from the group consisting of SEQ ID NOs:1-100 and SEQ ID NOs:147-156. In a preferred embodiment, the conjugate comprises a monoclonal antibody or a fragment thereof conjugated to a cyclic PYY peptide, wherein the cyclic PYY peptide is selected from the group consisting of SEQ ID NO: 1, SEQ ID NOs: 73-100, and SEQ ID NOs: 147-156.

In certain embodiments, a monoclonal antibody or the antigen binding fragment thereof is covalently linked to the cyclic PYY peptide at a lysine residue of the cyclic PYY peptide via a linker. The linker can, for example, comprise a linker selected from the group consisting of polyethylene glycol (PEG)8-triazolyl-$CH_2CH_2CO$-PEG4, a PEG chain of 2-24 PEG units, an alkyl chain containing 2-10 carbon atoms, (Gly4Ser)$_j$ wherein j=1-4, (AlaPro)$_u$ wherein u=1-10, or a bond.

A monoclonal antibody or the antigen binding fragment thereof according to an embodiment of the invention can be conjugated to a cyclic PYY petide at one or more amino acid positions of the cyclic PYY, such as amino acid residue 4, 7, 9, 10, 11, 13, 14, 15, 16, 17, 18, 19, 20, 21, 22, 23, 24, 26, 30, or 31 of the PYY using methods known in the art. The amino acid residue numbering follows that of hPYY$_{3-36}$. In certain embodiments, only one of $Z_7$, $Z_9$, $Z_{11}$, $Z_{22}$ and $Z_{23}$ in Formula I is lysine, and the lysine is covalently linked to an engineered cysteine residue of the monoclonal antibody or the antigen binding fragment thereof via the linker. In a preferred embodiment, a monoclonal antibody or the antigen binding fragment thereof according to an embodiment of the invention is conjugated to a cyclic PYY petide at residue 11 of the cyclic PYY. In another preferred embodiment, an electrophile, such as bromoacetamide or maleimide, is introduced onto a sidechain of a cyclic PYY, such as the amino side chain of a lysine at residue 11 of the cyclic PYY, and the electrophile reacts site specifically with the sulfhydryl group of the Cys residue engineered into a CDR, preferably HCDR3, of the monoclonal antibody or fragment thereof, thereby creating a covalent linkage between the cyclic PYY peptide and the monoclonal antibody or fragment thereof. More preferably, the cyclic PYY peptide is selected from the group consisting of SEQ ID NO: 1, SEQ ID NOs: 73-100, and SEQ ID NOs: 147-156. In one embodiment, the electrophile is introduced onto the sidechain of a cyclic PYY directly. In another embodiment, the electrophile is introduced onto the sidechain of a cyclic PYY indirectly via a linker.

Also provided are pharmaceutical compositions comprising the conjugates of the invention and further comprising a pharmaceutically acceptable carrier.

Also provided are conjugates comprising a monoclonal antibody or an antigen binding fragment thereof coupled to a cyclic PYY peptide, wherein the conjugates are represented by Formula IIIa-b, IVa-b, Va-b, and/or VIa-b, respectively.

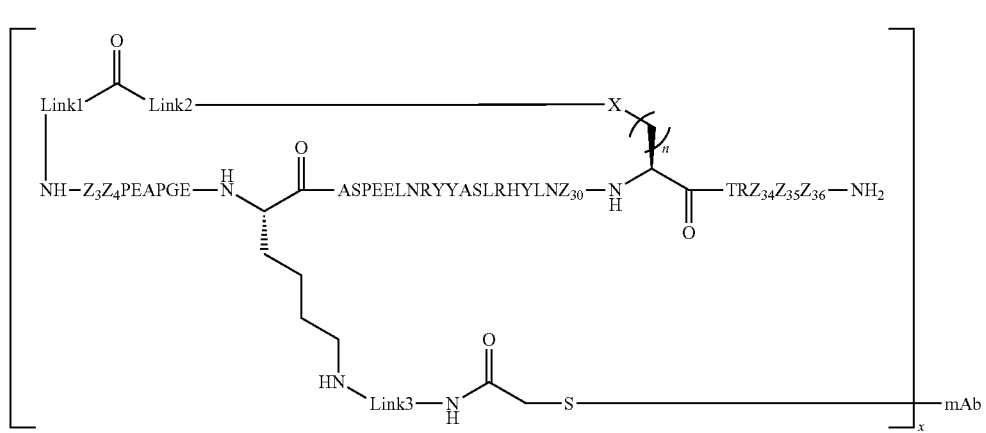
Formula IIIa
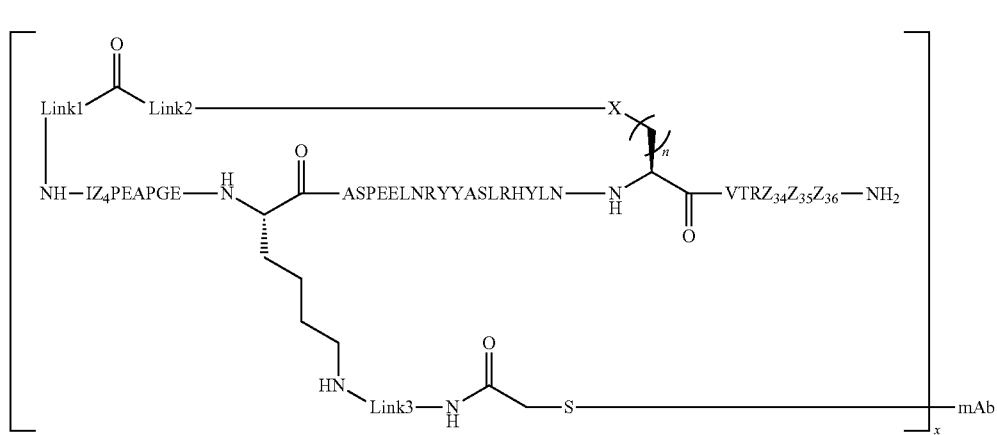
Formula IIIb
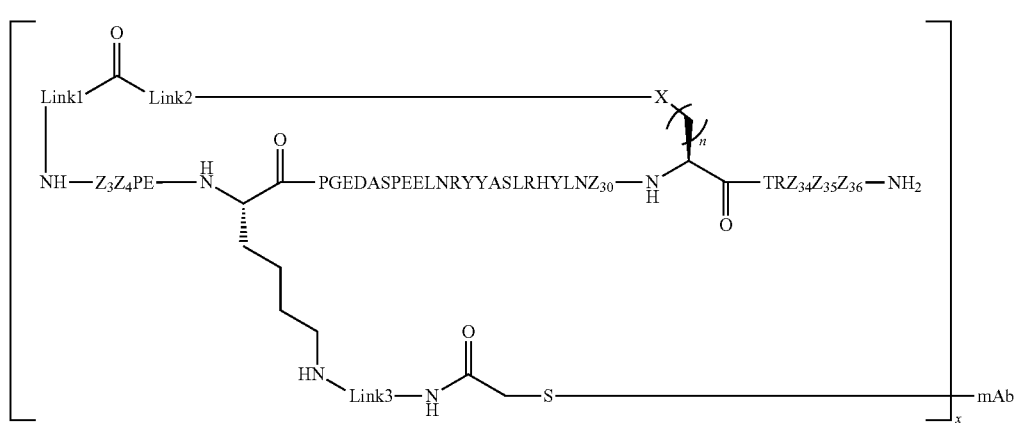
Formula IVa

Formula IVb
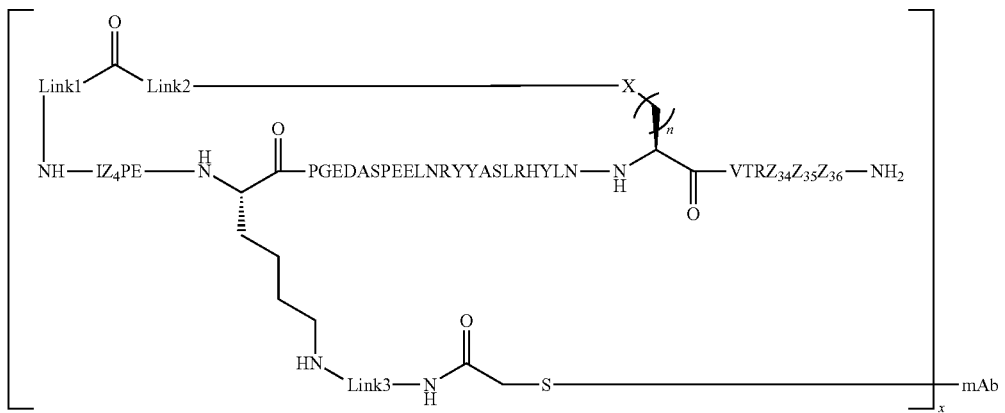
Formula Va
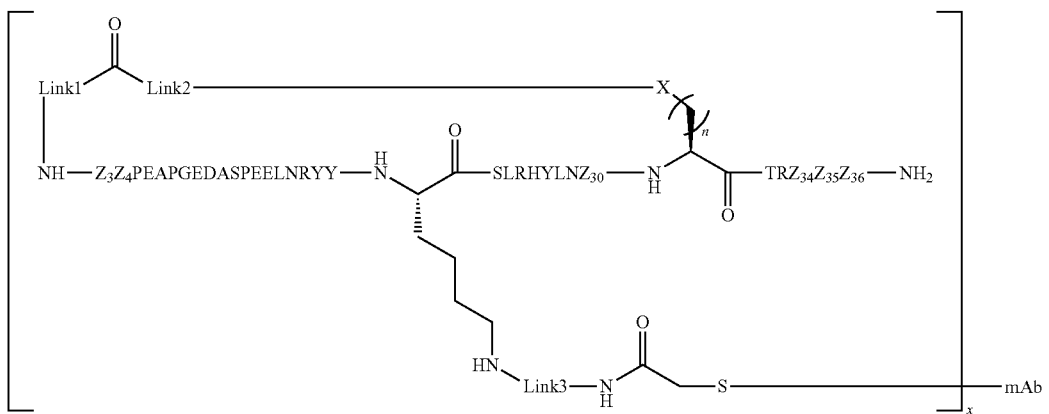
Formula Vb
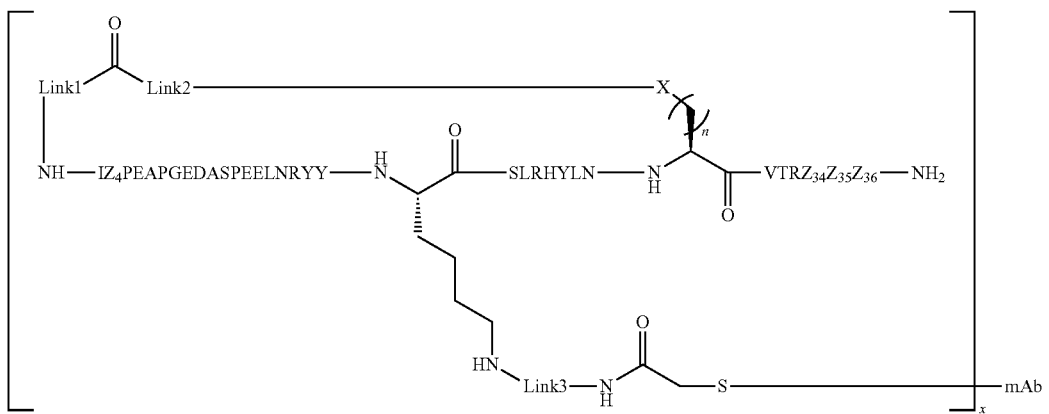

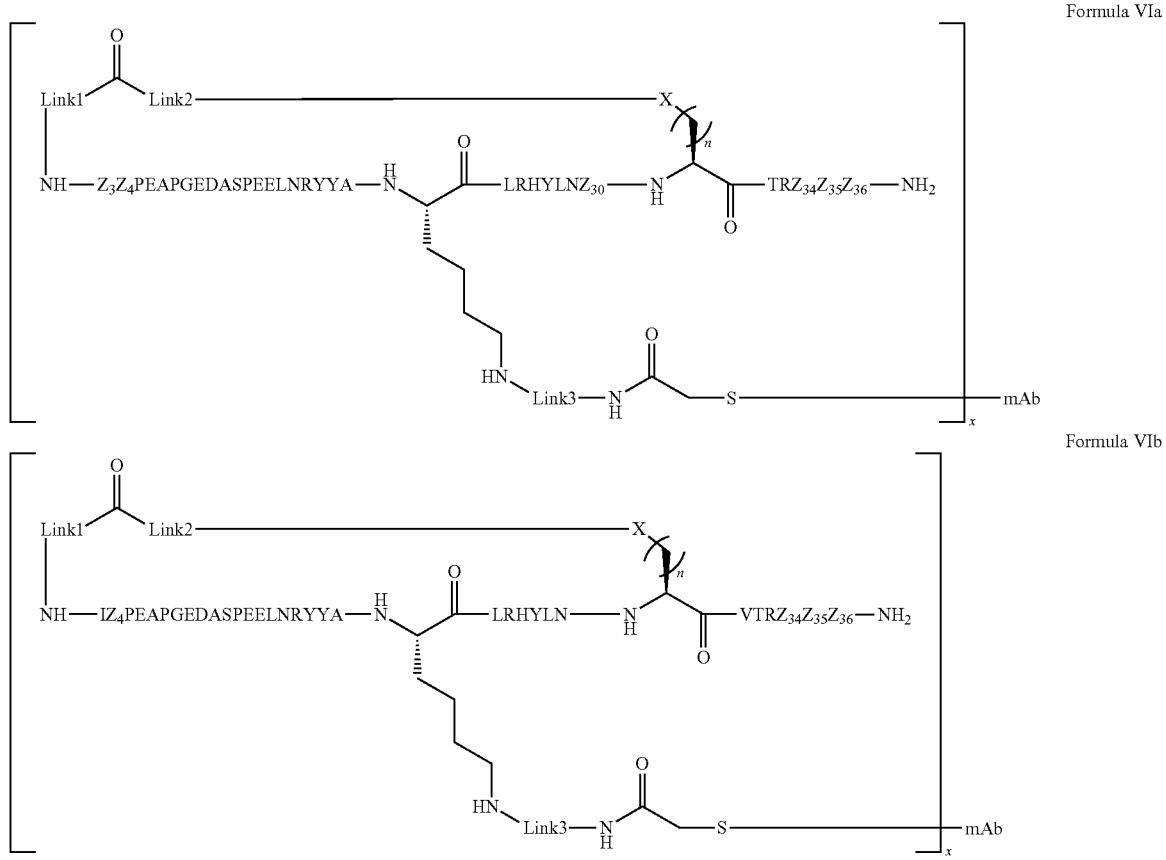

Formula VIa

Formula VIb

In Formulas IIIa-b, IVa-b, Va-b, and VIa-b, x can, for example, be 1, 2, 3, 4, 5, or 6, preferably 2.

link 1 can, for example, be G, βA, —COCH$_2$OCH$_2$CH$_2$OCH$_2$CH$_2$NH—, γ-aminobutanoyl, GG, —CO(CH$_2$)$_m$SCH$_2$— (provided that when Link 2=—NH—, m=1, 2) or a bond;

link 2 can, for example, be —CH$_2$—, benzyl, ethyltriazolyl, —NH—, or a bond;

n can, for example, be 1, 2, or 3;

X can, for example, be —S— or —CH$_2$—;

$Z_3$ can, for example, be I or a bond;

$Z_4$ can, for example, be K, S, or R;

$Z_{30}$ can, for example, be L, W, K (mPEG16), or K (mPEG12);

$Z_{34}$ can, for example, be Q, wherein said Q is optionally N-methylated on the alpha-amide nitrogen;

$Z_{35}$ can, for example, be R, wherein said R is optionally N-methylated on the alpha-amide nitrogen, or R is decarbonylated resulting in a psi-($Z_{35}Z_{36}$) amide bond, or R is both N-methylated on the alpha-amide nitrogen and decarbonylated resulting in a psi-($Z_{35}Z_{36}$) amide bond;

$Z_{36}$ can, for example, be Y (Tyr), Cha (β-cyclohexylalanine), Aic (2-aminoindane-2-carboxylic acid) or F (Phe), wherein said F is optionally para-substituted by Fluoro (4-F-Phe), Chloro (4-Cl-Phe), Bromo (4-Br-Phe), Iodo (4-I-Phe), Amino (4-NH$_2$-Phe); and Link 3 can, for example, comprise any of the following amidations to the lysine side chain: (PEG)8-triazolyl-CH$_2$CH$_2$CO-PEG4 (including

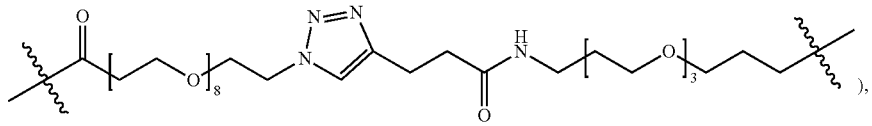), a PEG chain of 2-24 PEG units (including

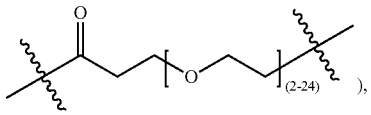), an alkyl chain containing 2-10 carbon atoms (including

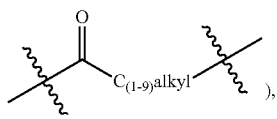

(Gly4Ser)$_j$ wherein j=1-4, (AlaPro)$_u$ wherein u=1-10, or —NH-Link 3- can be replaced by a bond.

Also provided is a conjugate comprising a monoclonal antibody or an antigen binding fragment thereof (mAb) coupled to a cyclic PYY peptide (cPYY) via a linker (L): cPYY-L]$_2$-mAb, wherein the conjugate comprises a cyclic PYY sequence selected from the group consisting of SEQ ID NOs: 102-127 or a pharmaceutically acceptable salt thereof, the mAb represents a monoclonal antibody or the antigen binding fragment thereof according to an embodiment of the invention, and ]$_2$ represents that 1 or 2 of the cyclic PYY peptide are covalently conjugated to the mAb.

Also provided herein are N-terminus to side chain cyclic analogues of PYY exhibiting at least 70%, 75% 80%, 85%, 90%, 95%, or 99% sequence identity to human PYY$_{3-36}$ (hPYY$_{3-36}$). As an example of a method for determination of the sequence identity between two analogues the two peptides Cyclic PYY Peptides PYY$_{3-36}$ is an endogenous hormone secreted by L cells in the distal gut that acts as an agonist of the Y2 receptor to inhibit food intake. Given its role in controlling appetite and food intake as well as its anti-secretory and pro-absorptive effects in the gastrointestinal tract in mammals, PYY$_{3-36}$ may be effective in treating obesity and associated conditions as well as in a number of gastrointestinal disorders. However, the therapeutic utility of PYY$_{3-36}$ itself as a treatment agent is limited by its rapid metabolism and short circulating half-life. Thus, the present invention is generally directed to modified PYY$_{3-36}$ conjugates, which extend the half-life of the PYY$_{3-36}$ peptide and reduces the metabolism of the peptide in vivo.

In certain embodiments of the invention, the modified PYY3-36 peptides are cyclic PYY peptides. The terms "cyclic PYY peptide," "cyclic PYY3-36 analog," and "cyclic PYY3-36 peptide analog" can be used interchangeably. Examples of cyclic PYY peptides that can be used in the conjugates are described in U.S. Patent Application No. 62/413,613, filed on Oct. 27, 2016, and U.S. patent application Ser. No. 15/794,231 entitled "Cyclic peptide tyrosine tyrosine compounds as modulators of neuropeptide receptors," filed on the same day as this application, the contents of both applications are hereby incorporated by reference in their entireties.

The peptide sequences described herein are written according to the usual convention whereby the N-terminal

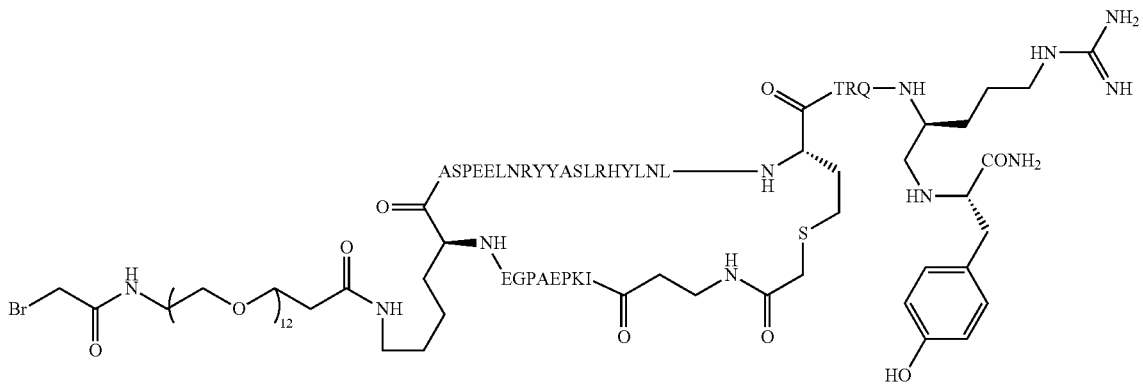

(SEQ ID 1) and hPYY$_{3-36}$

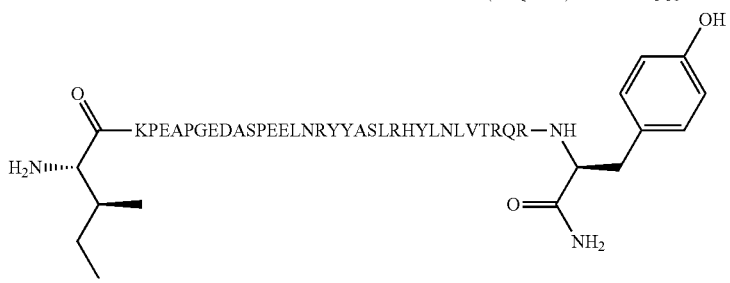

(SEQ ID NO:101)

are aligned. The sequence identity of the analogue relative to hPYY$_{(3-36)}$ is given by the total number of aligned residues minus the number of different residues (i.e. the number of aligned identical residues) divided by the total number of residues in hPYY$_{3-36}$. In this example the different residues are D11 which has been exchanged for a substituted K11, followed by V31 which has been exchanged for hC31, and finally R35 has been decarbonylated. Accordingly, in said example the sequence identity is (34-3)/34×100.

region of the peptide is on the left and the C-terminal region is on the right. Although isomeric forms of the amino acids are known, it is the L-form of the amino acid that is represented unless otherwise expressly indicated. For convenience in describing the molecules of this invention, conventional and non-conventional abbreviations for various amino acids (both single and three-letter codes) and functional moieties are used. These abbreviations are familiar to those skilled in the art, but for clarity are listed as follows: A=Ala=alanine; R=Arg=arginine; N=Asn=asparagine; D=Asp=aspartic acid; βA=βAla=beta-alanine; C=Cys=cysteine; hC=hCys=homocysteine; E=Glu=glutamic acid; Q=Gln=glutamine; G=Gly=glycine; H=His=histidine; I=Ile=isoleucine; L=Leu=leucine; K=Lys=lysine; Nle=norleucine; F=Phe=phenylalanine; P=Pro=proline; S=Ser=serine; T=Thr=threonine; W=Trp=tryptophan; Y=Tyr=tyrosine and V=Val=valine.

For convenience, the amino acid residue numbering convention used in naming the NTSC-PYY peptides of the present invention follows that of hPYY$_{3-36}$. Specific amino acid replacements that have been introduced into the NTSC-PYY peptides, relative to the native residues at the corresponding positions in hPYY$_{3-36}$, are indicated by the appropriate amino acid code, followed by the position of the substitution. Thus, "S4" in the NTSC-PYY peptide refers to a peptide in which serine has replaced the corresponding native lys4 residue of hPYY$_{3-36}$. Similarly, "hC31" in the NTSC-PYY peptide refers to a peptide in which homocysteine has replaced the corresponding native val31 residue of hPYY$_{3-36}$. Additional amino acid replacements occurring within NTSC-PYY peptides are described according to this convention and will be recognized as such by one skilled in the art.

Also for convenience, the naming convention used for the NTSC-PYY peptides of the present invention incorporates the amino residues involved in the cycle along with the linking group(s) between them in a left-to-right direction, starting from the N-terminal residue involved in the cycle. In all cases, the N-terminal amino acid residue of the cycle links by way of its α-amino functionality to the linking group, which in turn connects to the side chain residue of the amino acid at position 31 of the NTSC-PYY peptide. Thus, "cyclo-(I3-m-COPhCH$_2$-hC31)" is used to describe the cycle of an NTSC-PYY peptide in which the α-amino functionality of Ile3 is acylated with a meta-toluic acid residue, whose methyl group is further linked by way of a thioether bond to the side chain of a hCys31 residue. Similarly, "cyclo-(K4-CO(CH$_2$)$_2$NHCOCH$_2$-hC31)" is used to describe the cycle of an NTSC-PYY peptide, in which the native Ile3 residue has been deleted and whose (now N-terminal) α-amino functionality of lys4 is acylated by a 3-acetamidopropanoyl group, whose acetamido methylene carbon is connected to the side chain of a hCys31 residue by way of a thioether bond.

Lysine residues can be incorporated at various positions of the hPYY$_{3-36}$ sequence to provide a convenient functional handle for further derivatization. The lysine residues can be modified to be coupled to the monoclonal antibody either directly or indirectly. In an indirect coupling to the monoclonal antibody, the lysine residue can be modified to comprise a linker which will allow for the cyclic PYY peptide to be coupled to the monoclonal antibody. One skilled in the art will recognize that related orthologues could also be effectively employed as such and are contemplated herein.

The term, "K(γ-Glu)", appearing in the peptide sequence, represents a lysinyl residue whose side chain ε-amino group has been acylated by the γ-carboxyl group of glutamic acid.

The term, "K(γ-Glu-Pal (palmitoyl))" represents a lysinyl residue whose side chain ε-amino group has been acylated by the γ-carboxyl group of N-hexadecan-1-oylglutamic acid.

The term, "K(γ-Glu-Stear (stearoyl))" represents a lysinyl residue whose side chain ε-amino group has been acylated by the γ-carboxyl group of N-octadecan-1-oylglutamic acid.

The term, "K(γ-Glu-Arach (arachidoyl))" represents a lysinyl residue whose side chain ε-amino group has been acylated by the γ-carboxyl group of N-dodecan-1-oylglutamic acid.

The term, "K(OEG) (8-amino-3,6-dioxaoctanoyl)" represents a lysinyl residue whose side chain ε-amino group has been acylated by 8-amino-3,6-dioxaoctanoic acid.

The term, "(OEG)$_2$" represents two OEG units linked together in succession via an amide linkage (i.e., 17-amino-10-oxo-3,6,12,15-tetraoxa-9-azaheptadecanoic acid).

The term, "K(OEG)$_2$" represents a lysinyl residue whose side chain ε-amino group has been acylated by 17-amino-10-oxo-3,6,12,15-tetraoxa-9-azaheptadecanoic acid.

The term, "K((OEG)$_2$-γ-Glu" represents a lysinyl residue whose side chain ε-amino group has been acylated by (22S)-22-amino-10,19-dioxo-3,6,12,15-tetraoxa-9,18-diazatricosanedioic acid via its 1-carboxylic acid functionality.

The term, "K((OEG)$_2$-γ-Glu-Stear)" represents a lysinyl residue whose side chain ε-amino group has been acylated by (22S)-10,19-dioxo-22-stearamido-3,6,12,15-tetraoxa-9,18-diazatricosanedioic acid via its 1-carboxylic acid functionality.

The term, "K((OEG)$_2$-γ-Glu-COCl$_6$CO$_2$H)" represents a lysinyl residue whose side chain ε-amino group has been acylated by (21S)-9,18,23-trioxo-2,5,11,14-tetraoxa-8,17,22-triazanonatriacontane-1,21,39-tricarboxylic acid via its 1-carboxylic acid functionality.

Similarly, the term, "K((OEG)$_2$-γ-Glu-COCl$_8$CO$_2$H)" represents a lysinyl residue whose side chain ε-amino group has been acylated by (21S)-9,18,23-trioxo-2,5,11,14-tetraoxa-8,17,22-triazahentetracontane-1,21,41-tricarboxylic acid via its 1-carboxylic acid functionality.

The term, "K((OEG)$_2$-COCl$_6$CO$_2$H)" represents a lysinyl residue whose side chain ε-amino group has been acylated by 10,19-dioxo-3,6,12,15-tetraoxa-9,18-diazahexatriacontanedioic acid via its 1-carboxylic acid functionality.

The term "K(PEG24-AcBr)" represents a lysinyl residue whose side chain ε-amino group has been acylated by N-bromoacetyl-75-amino-4,7,10,13,16,19,22,25,28,31,34,37,40,43,46,49,52,55,58,61,64,67,70,73-tetracosaoxapentaheptacontanoic acid via its 1-carboxylic acid functionality.

The term "K(PEG12-AcBr)" represents a lysinyl residue whose side chain ε-amino group has been acylated by N-bromoacetyl-39-amino-4,7,10,13,16,19,22,25,28,31,34,37-dodecaoxanonatriacontanoic acid via its 1-carboxylic acid functionality.

The term "K(PEG6-AcBr)" represents a lysinyl residue whose side chain ε-amino group has been acylated by N-bromoacetyl-3-[(17-amino-3,6,9,12,15-pentaoxaheptadec-1-yl)oxy]-propanoic acid via its 1-carboxylic acid functionality.

The term "K(PEG8-triazolyl-CH$_2$CH$_2$CO-PEG4-AcBr)" represents a lysinyl residue whose side chain ε-amino group has been acylated by 27-[4-[2-[3-[2-[2-[3-(N-bromoacetylamino)propoxy]ethoxy]ethoxy]propylaminocarbonyl]ethyl]tetrazol-1-yl]-4,7,10,13,16,19,22,25-octaoxaheptacosanoic acid via its 1-carboxylic acid functionality.

The term "K(mPEG16) represents a lysinyl residue whose side chain ε-amino group has been acylated by 4,7,10,13,16,19,22,25,28,31,34,37,40,43,46,49-hexadecaoxapentacontanoic acid via its 1-carboxylic acid functionality.

The term "K(mPEG12)" represents a lysinyl residue whose side chain ε-amino group has been acylated by 4,7,10,13,16,19,22,25,28,31,34,37-dodecaoxaoctatriacontanoic acid via its 1-carboxylic acid functionality.

The term, "VitE" represents an α-tocopherolyl unit in the molecule.

The term, "AcVitE" represents an α-tocopheroxyl unit whose phenolic group bears an ether-linked methylenylcarboxy functionality.

The term, K-γ-Glu-AcVitE" represents a lysinyl residue whose side chain ε-amino group has been acylated by (2-(((2R)-2,5,7,8-tetramethyl-2-((4R,8R)-4,8,12-trimethyltridecyl)chroman-6-yl)oxy)acetyl)-L-glutamic acid via its γ-carboxylic acid functionality.

Many of the compounds/conjugates of the present invention incorporate a reduced amide bond between the C-terminal residue of the sequence, Y36, and its adjacent residue, R35. This reduced amide linkage is represented by the term, "psi-(R35,Y36)".

Various amino acid residues comprising certain sequences of the present invention contain α-amino groups that have been methylated. Thus, the terms, "N-Me-Q34" or "N-Me-R35" represent α-N-methylated glutamine at position 34 of a sequence, and α-N-methylated arginine at position 35 of a sequence, respectively.

The term, "N-Me-Q34, psi-(R35,Y36)" in a sequence description refers to a sequence containing both an α-methyl glutamine residue at position 34, as well as a reduced amide bond between residues R35 and Y36.

Similarly, the term, "N-Me-R35, psi-(R35,Y36)" in a sequence description refers to a sequence containing both an α-methyl arginine residue at position 35, as well as a reduced amide bond between this residue and Y36.

Half-Life Extending Moieties

In addition to the antibody of the present invention or an antigen binding fragment thereof, the conjugates of the invention can incorporate one or more other moieties for extending the half-life of the pharmaceutical active moiety (e.g., the cyclic PYY peptide), for example via covalent interaction. Exemplary other half-life extending moieties include, but not limited to, albumin, albumin variants, albumin-binding proteins and/or domains, transferrin and fragments and analogues thereof. Additional half-life extending moieties that can be incorporated into the conjugates of the invention include, for example, polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties can be direct fusions with the protein scaffold coding sequences and can be generated by standard cloning and expression techniques. Alternatively, well known chemical coupling methods can be used to attach the moieties to recombinantly and chemically produced conjugates of the invention.

A pegyl moiety can, for example, be added to the peptide molecules of the invention by incorporating a cysteine residue to the C-terminus of the molecule and attaching a pegyl group to the cysteine using well known methods.

Peptide molecules of the invention incorporating additional moieties can be compared for functionality by several well-known assays. For example, the biological or pharmacokinetic activities of a therapeutic peptide of interest, alone or in a conjugate according to the invention, can be assayed using known in vitro or in vivo assays and compared.

Pharmaceutical Compositions

In another general aspect, the invention relates to a pharmaceutical composition, comprising the conjugates and compounds of the invention and a pharmaceutically acceptable carrier. The term "pharmaceutical composition" as used herein means a product comprising a conjugate of the invention together with a pharmaceutically acceptable carrier. Conjugates and compounds of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, chloroprocaine, choline, cyclohexylamine, diethanolamine, ethylenediamine, lithium, L-lysine, magnesium, meglumine, N-methyl-D-glucamine, piperidine, potassium, procaine, quinine, sodium, triethanolamine, or zinc.

In some embodiments of the invention, pharmaceutical formulations are provided comprising the conjugates of the invention in an amount from about 0.001 mg/ml to about 100 mg/ml, from about 0.01 mg/ml to about 50 mg/ml, or from about 0.1 mg/ml to about 25 mg/ml. The pharmaceutical formulation may have a pH from about 3.0 to about 10, for example from about 3 to about 7, or from about 5 to about 9. The formulation may further comprise at least one ingredient selected from the group consisting of a buffer system, preservative(s), tonicity agent(s), chelating agent(s), stabilizer(s) and surfactant(s).

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier may be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation may comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition may be formulated as an injectable which can be injected, for example, via an injection device (e.g., a syringe or an infusion pump). The injection may be delivered subcutaneously, intramuscularly, intraperitoneally, or intravenously, for example.

In another embodiment, the pharmaceutical composition is a solid formulation, e.g., a freeze-dried or spray-dried composition, which may be used as is, or whereto the physician or the patient adds solvents, and/or diluents prior to use. Solid dosage forms may include tablets, such as compressed tablets, and/or coated tablets, and capsules (e.g., hard or soft gelatin capsules). The pharmaceutical composition may also be in the form of sachets, dragees, powders, granules, lozenges, or powders for reconstitution, for example.

The dosage forms may be immediate release, in which case they may comprise a water-soluble or dispersible carrier, or they may be delayed release, sustained release, or modified release, in which case they may comprise water-insoluble polymers that regulate the rate of dissolution of the dosage form in the gastrointestinal tract.

In other embodiments, the pharmaceutical composition may be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris (hydroxymethyl)-aminomethane, and mixtures thereof. The buffer may be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of buffers include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative may be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent may be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent may be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer may be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may, for example, be selected from the group consisting of anionic surfactants, cationic surfactants, nonionic surfactants, and/or zwitterionic surfactants. The surfactant may be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor may be present individually or in the aggregate, in a concentration from about 0.1 mg/ml to about 20 mg/ml. Pharmaceutical compositions comprising each one of these specific protease inhibitors constitute alternative embodiments of the invention.

The pharmaceutical composition of the invention may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present. The amino acid base may be present individually or in the combination with other amino acid bases, in a concentration from about 0.01 mg/ml to about 50 mg/ml, for example from about 0.1 mg/ml to about 20 mg/ml.

Pharmaceutical compositions comprising each one of these specific amino acid bases constitute alternative embodiments of the invention.

It is also apparent to one skilled in the art that the therapeutically effective dose for conjugates of the present invention or a pharmaceutical composition thereof will vary according to the desired effect. Therefore, optimal dosages to be administered may be readily determined by one skilled in the art and will vary with the particular conjugate used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

For all indications, the conjugates of the invention are preferably administered peripherally at a dose of about 1 μg to about 5 mg per day in single or divided doses (e.g., a single dose can be divided into 2, 3, 4, 5, 6, 7, 8, 9, or 10 subdoses), or at about 0.01 g/kg to about 500 μg/kg per dose, more preferably about 0.05 μg/kg to about 250 μg/kg, most preferably below about 50 μg/kg. Dosages in these ranges will vary with the potency of each agonist, of course, and are readily determined by one of skill in the art.

The above dosages are thus exemplary of the average case. There can, of course, be individual instances where higher or lower dosage ranges are merited, and such are within the scope of this invention.

In certain embodiments, the conjugates of the invention are administered at a dose of about 1 μg to about 5 mg, or at a dose of about 0.01 μg/kg to about 500 μg/kg, more preferably at a dose of about 0.05 μg/kg to about 250 μg/kg, most preferably at a dose below about 50 μg/kg with a dose of a second therapeutic agent (e.g., liraglutide) at a dose of about 1 jag to about 5 mg, or at a dose of about 0.01 μg/kg to about 500 μg/kg, more preferably at a dose of about 0.05 μg/kg to about 250 μg/kg, most preferably at a dose below about 50 μg/kg.

The pharmaceutically-acceptable salts of the conjugates of the invention include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Administration may be by the oral route. Suitable formulations for parenteral administration include aqueous solutions of the active conjugates in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the conjugates of the present invention. Additionally, the present invention includes pharmaceutical compositions made by mixing one or more pharmaceutically acceptable carriers with any of the conjugates of the present invention.

Furthermore, the conjugates of the present invention may have one or more polymorph or amorphous crystalline forms and as such are intended to be included in the scope of the invention. In addition, the conjugates may form solvates, for example with water (i.e., hydrates) or common organic solvents. As used herein, the term "solvate" means a physical association of the conjugates of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the conjugates of the present invention. Thus, in the methods of treatment of the present invention, the term "administering" shall encompass the means for treating, ameliorating or preventing a syndrome, disorder or disease described herein with the conjugates of the present invention or a polymorph or solvate thereof, which would obviously be included within the scope of the invention albeit not specifically disclosed.

In another embodiment, the invention relates to the conjugates of the invention for use as a medicament.

The present invention includes within its scope prodrugs of the conjugates of this invention. In general, such prodrugs will be functional derivatives of the conjugates which are readily convertible in vivo into the required conjugate. Thus, in the methods of treatment of the present invention, the term "administering" shall encompass the treatment of the various disorders described with the conjugate specifically disclosed or with a conjugate which may not be specifically disclosed, but which converts to the specified conjugate in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to the conjugates of the invention, shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively 12C, $^{13}$C and $^{14}$C and $^{16}$O and $^{18}$O. The isotopes may be radioactive or non-radioactive. Radiolabeled conjugates of the invention may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Some conjugates of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the conjugates according to this invention have at least one stereo center, they may accordingly exist as enantiomers or diastereomers. It is to be understood that all such isomers and mixtures thereof are encompassed within the scope of the present invention.

Where the processes for the preparation of the conjugates according to the invention give rise to mixture of stereoisomers, these isomers may be separated by conventional techniques such as preparative chromatography. The conjugates may be prepared in racemic form, or individual enantiomers may be prepared either by enantiospecific synthesis or by resolution. The conjugates may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The conjugates may also be resolved by formation of diastereomeric esters or amides, followed by chromatographic separation and removal of the chiral auxiliary. Alternatively, the conjugates may be resolved using a chiral column via high performance liquid chromatography (HPLC) or SFC. In some instances rotamers of conjugates may exist which are observable by 1H NMR leading to complex multiplets and peak integration in the 1H NMR spectrum.

During any of the processes for preparation of the conjugates of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, each of which is herein incorporated by reference in its entirety for all purposes. The protecting groups may be removed at a convenient subsequent stage using methods known from the art.

Methods of Use

The present invention is directed to a method for preventing, treating or ameliorating a Y2 receptor mediated syndrome, disorder or disease in a subject in need thereof comprising administering to the subject in need thereof an effective amount of a conjugate, compound, or pharmaceutical composition of the invention.

The present invention also provides a method for preventing, treating, delaying the onset of, or ameliorating a disorder, disease, or condition or any one or more symptoms of said disorder, disease, or condition in a subject in need thereof, comprising administering to the subject in need thereof an effective amount of a conjugate, compound, or pharmaceutical composition of the invention.

According to particular embodiments, the disease disorder, or condition is selected from the group consisting of obesity, type I or II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and/or eczema.

According to particular embodiments, a therapeutically effective amount refers to the amount of therapy which is sufficient to achieve one, two, three, four, or more of the following effects: (i) reduce or ameliorate the severity of the disease, disorder, or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

As used herein, the terms "treat," "treating," and "treatment" are all intended to refer to an amelioration or reversal of at least one measurable physical parameter related the disease, disorder, or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat,"

"treating," and "treatment" refer to an alleviation, prevention of the development or onset, or reduction in the duration of one or more symptoms associated with the disease, disorder, or condition. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

In one embodiment, the invention provides a method for preventing, treating, delaying the onset of, or ameliorating obesity, or any one or more symptoms of obesity in a subject in need thereof, the method comprising administering to the subject in need thereof an effective amount of a conjugate, compound, or pharmaceutical composition of the invention. In some embodiments, the body weight of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to the body weight of a subject prior to administration of any of the conjugates, compounds, pharmaceutical compositions, forms, or medicaments of the invention described herein, or compared to control subjects not receiving any of the conjugates, compositions, forms, medicaments, or combinations of the invention described herein.

In some embodiments, the reduction in body weight is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of preventing, treating, delaying the onset of, or ameliorating a syndrome, disorder or disease, or any one or more symptoms of said syndrome, disorder, or disease in a subject in need thereof, wherein said syndrome, disorder or disease is selected from the group consisting of obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, comprising administering to the subject in need thereof an effective amount of a conjugate, compound, or pharmaceutical composition of the invention.

As used herein, metabolic syndrome refers to a subject having any one or more of the following: high blood sugar (e.g., high fasting blood sugar), high blood pressure, abnormal cholesterol levels (e.g., low HDL levels), abnormal triglyceride levels (e.g., high triglycerides), a large waistline (i.e., waist circumference), increased fat in the abdominal area, insulin resistance, glucose intolerance, elevated C-reactive protein levels (i.e., a proinflammatory state), and increased plasma plasminogen activator inhibitor-1 and fibrinogen levels (i.e., a prothrombotic state).

The present invention provides a method of reducing food intake in a subject in need thereof, the method comprising administering to the subject in need thereof an effective amount of a conjugate, compound, or pharmaceutical composition of the invention. In some embodiments, food intake of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to food intake of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

In some embodiments, the reduction in food intake is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of reducing glycated hemoglobin (A1C) in a subject in need thereof, the method comprising administering to the subject in need thereof an effective amount of a conjugate, compound, or pharmaceutical composition of the invention. In some embodiments, A1C of a subject is reduced, for example, by between about 0.001% and about 0.01%, between about 0.01% and about 0.1%, between about 0.1% and about 0.2%, between about 0.2% and about 0.3%, between about 0.3% and about 0.4%, between about 0.4% and about 0.5%, between about 0.5% and about 1%, between about 1% and about 1.5%, between about 1.5% and about 2%, between about 2% and about 2.5%, between about 2.5% and about 3%, between about 3% and about 4%, between about 4% and about 5%, between about 5% and about 6%, between about 6% and about 7%, between about 7% and about 8%, between about 8% and about 9%, or between about 9% and about 10% relative to the A1C of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

In other embodiments, methods are provided for reducing fasting blood glucose levels in a subject in need thereof, the methods comprising administering to the subject in need thereof an effective amount of a conjugate, compound, or pharmaceutical composition of the invention. Fasting blood glucose levels may be reduced to less than about 140 to about 150 mg/dL, less than about 140 to about 130 mg/dL, less than about 130 to about 120 mg/dL, less than about 120 to about 110 mg/dL, less than about 110 to about 100 mg/dL, less than about 100 to about 90 mg/dL, or less than about 90 to about 80 mg/dL, relative to the fasting blood glucose levels of a subject prior to administration of any of the conjugates, compounds, compositions, forms, medicaments, or combinations of the invention described herein, or compared to control subjects not receiving any of the conjugates, compounds, compositions, forms, medicaments, or combinations of the invention described herein.

The present invention provides a method of modulating Y2 receptor activity in a subject in need thereof, the method comprising administering to the subject in need thereof an effective amount of a conjugate, compound, or pharmaceutical composition of the invention. As used herein, "modulating" refers to increasing or decreasing receptor activity.

In some embodiments, an effective amount of a conjugate or compound of the invention or a form, composition or medicament thereof is administered to a subject in need thereof once daily, twice daily, three times daily, four times daily, five times daily, six times daily, seven times daily, or eight times daily. In other embodiments, an effective amount of a conjugate or compound of the invention or a form, composition or medicament thereof is administered to a subject in need thereof once every other day, once per week, twice per week, three times per week, four times per week, five times per week, six times per week, two times per month, three times per month, or four times per month.

Another embodiment of the invention comprises a method of preventing, treating, delaying the onset of, or ameliorating a disease, disorder or syndrome, or one or more symptoms of any of said diseases, disorders, or syndromes in a subject in need thereof, the method comprising administering to the subject in need thereof an effective amount of a conjugate, compound, or pharmaceutical composition of the invention in a combination therapy. In certain embodiments, the combination therapy is a second therapeutic agent. In certain embodiments, the combination therapy is a surgical therapy.

As used herein, the term "in combination," in the context of the administration of two or more therapies to a subject, refers to the use of more than one therapy.

As used herein, combination therapy refers to administering to a subject in need thereof one or more additional therapeutic agents, or one or more surgical therapies, concurrently with an effective amount of a conjugate or compound of the invention or a form, composition or medicament thereof. In some embodiments, the one or more additional therapeutic agents or surgical therapies can be administered on the same day as an effective amount of a conjugate of the invention, and in other embodiments, the one or more additional therapeutic agents or surgical therapies may be administered in the same week or the same month as an effective amount of a conjugate or compound of the invention.

In certain embodiments, wherein the disease or disorder is selected from the group consisting of obesity, type II diabetes, metabolic syndrome, insulin resistance and dyslipidemia, the second therapeutic agent can be an antidiabetic agent. In certain embodiments, the antidiabetic agent can be a glucagon-like peptide-1 (GLP-1) receptor modulator.

The present invention also contemplates preventing, treating, delaying the onset of, or ameliorating any of the diseases, disorders, syndromes, or symptoms described herein in a subject in need thereof with a combination therapy that comprises administering to the subject in need thereof an effective amount of a conjugate, compound, or pharmaceutical composition of the invention, in combination with any one or more of the following therapeutic agents: a dipeptidyl peptidase-4 (DPP-4) inhibitor (e.g., sitagliptin, saxagliptin, linagliptin, alogliptin, etc.); a GLP-1 receptor agonist (e.g., short-acting GLP-1 receptor agonists such as exenatide and lixisenatide; intermediate-acting GLP-1 receptor agonists such as liraglutide; long-acting GLP-1 receptor agonists such as exenatide extended-release, albiglutide, dulaglutide); a sodium-glucose co-transporter-2 (SGLT-2) inhibitors (e.g., canaglifozin, dapaglifozin, empaglifozin, etc.); bile acid sequestrants (e.g., colesevelam, etc.); dopamine receptor agonists (e.g., bromocriptine quick-release); biguanides (e.g., metformin, etc.); insulin; oxyntomodulin; sulfonylureas (e.g., chlorpropamide, glimepiride, glipizide, glyburide, glibenclamide, glibornuride, glisoxepide, glyclopyramide, tolazamide, tolbutamide, acetohexamide, carbutamide, etc.); and thiazolidinediones (e.g; pioglitazone, rosiglitazone, lobeglitazone, ciglitazone, darglitazone, englitazone, netoglitazone, rivoglitazone, troglitazone, etc.). In some embodiments, the dose of the additional therapeutic agent(s) is reduced when given in combination with a conjugate or compound of the invention. In some embodiments, when used in combination with a conjugate or compound of the invention, the additional therapeutic agent(s) may be used in lower doses than when each is used singly.

In certain embodiments, wherein the disease or disorder is selected from the group consisting of obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, the second therapeutic agent can be liraglutide.

The present invention contemplates preventing, treating, delaying the onset of, or ameliorating any of the diseases, disorders, syndromes, or symptoms described herein in a subject in need thereof, with a combination therapy that comprises administering to the subject in need thereof an effective amount of a conjugate, compound, or pharmaceutical composition of the invention in combination with a surgical therapy. In certain embodiments, the surgical therapy can be bariatric surgery (e.g., gastric bypass surgery, such as Roux-en-Y gastric bypass surgery; sleeve gastrectomy; adjustable gastric band surgery; biliopancreatic diversion with duodenal switch; intragastric balloon; gastric plication; and combinations thereof).

In embodiments in which the one or more additional therapeutic agents or surgical therapies is administered on the same day as an effective amount of a conjugate or compound of the invention, the conjugate or compound of the invention may be administered prior to, after, or simultaneously with the additional therapeutic agent or surgical therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Embodiments

The invention provides also the following non-limiting embodiments.

Embodiment 1 is a conjugate comprising a monoclonal antibody or an antigen binding fragment thereof coupled to a cyclic PYY peptide, wherein the cyclic PYY peptide is represented by Formula I or a derivative or pharmaceutically acceptable salt thereof:

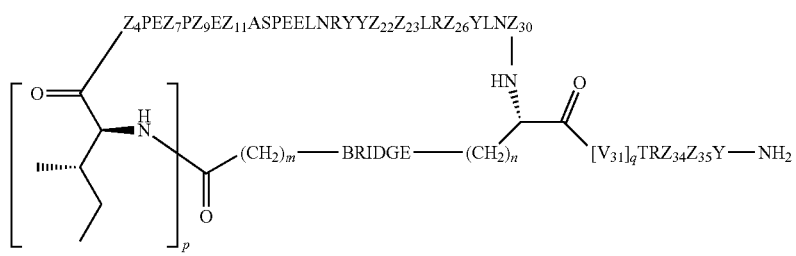

Formula I wherein
p is 0 or 1;
m is 0, 1, 2, 3, 4, or 5;
n is 1, 2, 3, or 4;
q is 0 or 1; provided that q is 1 only when $Z_{30}$ is absent;
BRIDGE is -Ph-$CH_2$—S—, -triazolyl-, —NHC(O)$CH_2$S—, —S$CH_2$C(O)NH—, —(O$CH_2CH_2$)$_2$NHC(O)$CH_2$S, —NHC(O)—, or —$CH_2$S—;
$Z_4$ is K, A, E, S, or R;
$Z_7$ is A or K;
$Z_9$ is G or K;
$Z_{11}$ is D or K;
$Z_{22}$ is A or K;
$Z_{23}$ is S or K;
$Z_{26}$ is A or H;
$Z_{30}$ is L, W, absent, or K;
provided that $Z_{30}$ is absent only when q is 1;
$Z_{34}$ is

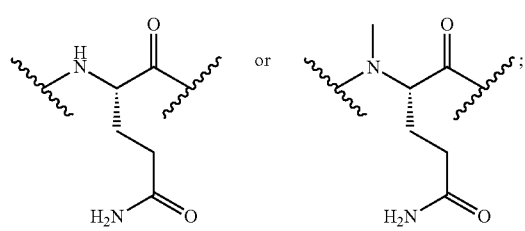 [SMILES: *N[C@@H](CCC(N)=O)C(*)=O ; "or" ; *C(=O)[C@H](CCC(N)=O)N(*)C ; ";"]

$Z_{35}$ is

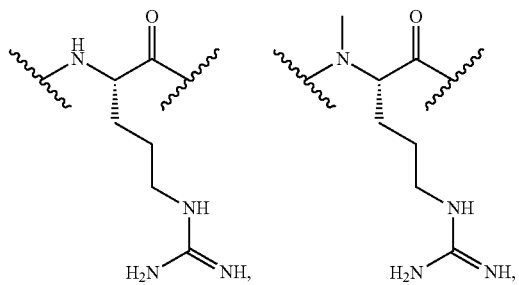

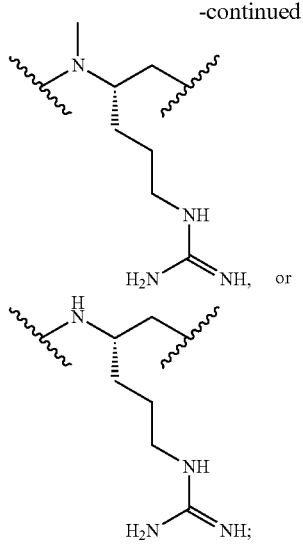

wherein the derivative is the compound of Formula I that is modified by one or more processes selected from the group consisting of amidation, glycosylation, carbamylation, sulfation, phosphorylation, cyclization, lipidation, and pegylation.

Embodiment 2 is the conjugate of embodiment 1, wherein the cyclic PYY peptide is a derivative of the cyclic PYY peptide of Formula I that is modified by one or more processes selected from the group consisting amidation, lipidation, and pegylation, or a pharmaceutically acceptable salt thereof.

Embodiment 3 is the conjugate of embodiment 1, wherein the cyclic PYY peptide is represented by Formula I or the derivative or pharmaceutically acceptable salt thereof, wherein:

p is 0 or 1;

m is 0, 1, 2, 3, 4, or 5;

n is 1, 2, 3, or 4;

q is 0 or 1; provided that q is 1 only when $Z_{30}$ is absent;

BRIDGE is -Ph-CH$_2$—S—, -triazolyl-, —NHC(O)CH$_2$S—, —SCH$_2$C(O)NH$_2$—, —(OCH$_2$CH$_2$)$_2$NHC(O)CH$_2$S, —NHC(O)—, or —CH$_2$S—;

$Z_4$ is K, A, E, S, or R;

$Z_7$ is A or K, $Z_9$ is G or K, $Z_{11}$ is D or K, $Z_{22}$ is A or K, $Z_{23}$ is S or K, $Z_{26}$ is A or H;

$Z_{30}$ is L or K, wherein the amino side chain of said K is substituted with

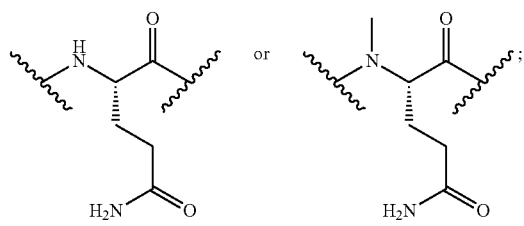 [SMILES: *N[C@@H](CCC(N)=O)C(*)=O ; "or" ; *C(=O)[C@H](CCC(N)=O)N(*)C ; ";"]

$Z_{34}$ is

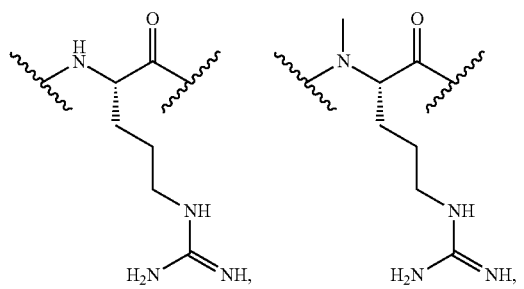

and $Z_{35}$ is

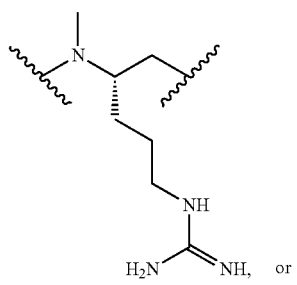

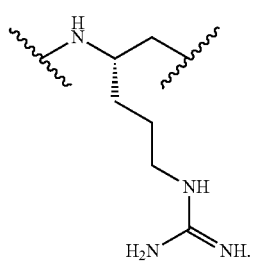

Embodiment 4 is the conjugate of embodiment 1, wherein the cyclic PYY peptide is represented by Formula I or the derivative or pharmaceutically acceptable salt thereof, wherein:

p is 0 or 1;

m is 0, 1, 2, 3, or 5;

n is 1, 2, or 4;

q is 0 or 1; provided that q may be 1 only when $Z_{30}$ is absent;

BRIDGE is -Ph-CH$_2$—S—, -triazolyl-, —NHC(O)CH$_2$S—, —SCH$_2$C(O)NH$_2$—, —(OCH$_2$CH$_2$)$_2$NHC(O)CH$_2$S, —NHC(O)—, or —CH$_2$S—;

$Z_4$ is K, A, E, S, or R;

$Z_7$ is A or K, $Z_9$ is G or K, $Z_{11}$ is D or K, $Z_{22}$ is A or K, $Z_{23}$ is S or K, $Z_{26}$ is A or H;

$Z_{30}$ is L or K, wherein the amino side chain of said K is substituted with

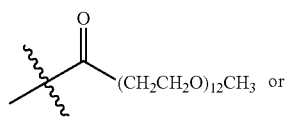

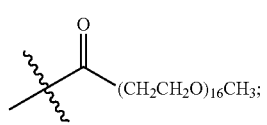

$Z_{34}$ is

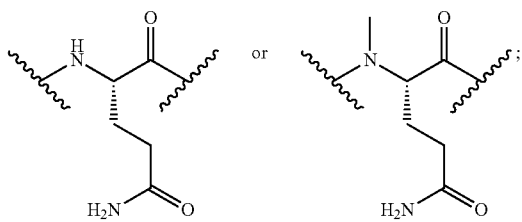 [SMILES: *N[C@@H](CCC(N)=O)C(*)=O ; "or" ; *C(=O)[C@H](CCC(N)=O)N(*)C ; ";"]

and
$Z_{35}$ is

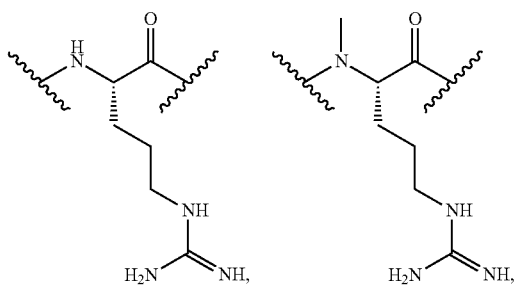

-continued

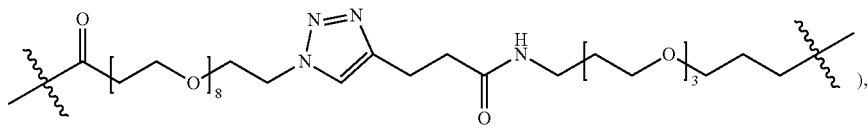

Embodiment 5 is a conjugate comprising a monoclonal antibody or an antigen binding fragment thereof coupled to a cyclic PYY peptide, wherein the conjugate is represented by Formula IIIa-b, IVa-b, Va-b, and/or VIa-b, wherein in Formula IIIa-b, IVa-b, Va-b, and VIa-b, x can, for example, be 1, 2, 3, 4, 5, or 6, preferably 2.

link 1 can, for example, be G, βA, —COCH$_2$OCH$_2$CH$_2$OCH$_2$CH$_2$NH—, γ-aminobutanoyl, GG, —CO(CH$_2$)$_m$SCH$_2$— (provided that when Link 2=—NH—, m=1, 2) or a bond;

link 2 can, for example, be —CH$_2$—, benzyl, ethyltriazolyl, —NH—, or a bond;

n can, for example, be 1, 2, or 3;

X can, for example, be —S— or —CH$_2$—;

$Z_3$ can, for example, be I or a bond;

$Z_4$ can, for example, be K, S, or R;

$Z_{30}$ can, for example, be L, W, K (mPEG16), or K (mPEG12);

$Z_{34}$ can, for example, be Q, wherein said Q is optionally N-methylated on the alpha-amide nitrogen;

$Z_{35}$ can, for example, be R, wherein said R is optionally N-methylated on the alpha-amide nitrogen, or R is decarbonylated resulting in a psi-($Z_{35}Z_{36}$) amide bond, or R is both N-methylated on the alpha-amide nitrogen and decarbonylated resulting in a psi-($Z_{35}Z_{36}$) amide bond;

$Z_{36}$ can, for example, be Y (Tyr), Cha (β-cyclohexylalanine), Aic (2-aminoindane-2-carboxylic acid) or F (Phe), wherein said F is optionally para-substituted by Fluoro (4-F-Phe), Chloro (4-Cl-Phe), Bromo (4-Br-Phe), Iodo (4-I-Phe), Amino (4-NH$_2$-Phe); and Link 3 can, for example, comprise any of the following amidations to the lysine side chain: (PEG)8-triazolyl-CH$_2$CH$_2$CO-PEG4 (including

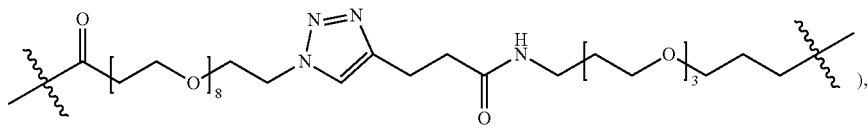

a PEG chain of 2-24 PEG units

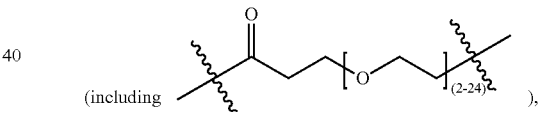

an alkyl chain containing 2-10 carbon atoms

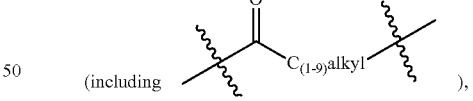

(Gly$_4$Ser)$_j$ wherein j=1-4, (AlaPro)$_u$ wherein u=1-10, or —NH-Link 3- can be replaced by a bond.

Embodiment 6 is the conjugate of embodiment 1, wherein the cyclic PYY peptide is selected from the group consisting of SEQ ID NOs: 1-100.

Embodiment 7 is the conjugate of any one of embodiments 1-6, wherein the monoclonal antibody or the antigen binding fragment thereof is covalently linked to the cyclic PYY peptide at a lysine residue of the cyclic PYY peptide via a linker.

Embodiment 8 is the conjugate of embodiment 7, wherein the linker comprises one selected from the group consisting of polyethylene glycol (PEG)8-triazolyl-CH$_2$CH$_2$CO-PEG4, a PEG chain of 2-24 PEG units, an alkyl chain containing 2-10 carbon atoms, (Gly$_4$Ser)$_j$ wherein j=1-4, (AlaPro)$_u$ wherein u=1-10, and a bond.

Embodiment 9 is the conjugate of embodiment 8, wherein only one of $Z_7$, $Z_9$, $Z_{11}$, $Z_{22}$ and $Z_{23}$ in Formula I is lysine, and the lysine is covalently linked to an engineered cysteine residue of the monoclonal antibody or the antigen binding fragment thereof via the linker.

Embodiment 10 is a conjugate comprising a monoclonal antibody or an antigen binding fragment thereof coupled to a cyclic PYY peptide, wherein the conjugate comprises a structure selected from the group consisting of SEQ ID NOs: 102-127 or a pharmaceutically acceptable salt thereof, wherein mAb represents the monoclonal antibody or the antigen binding fragment thereof, and ]$_2$ represents that 1 or 2 of the cyclic PYY peptide are covalently conjugated to the mAb.

Embodiment 11 is the conjugate of any one of embodiments 1-10, wherein the monoclonal antibody or the antigen binding fragment thereof comprises a heavy chain complementarity determining region 1 (HCDR1), HCDR2, HCDR3, and a light chain complementarity determining region 1 (LCDR1), LCDR2, and LCDR3, having the polypeptide sequences of SEQ ID NO: 141, 142, 143, 144, 145, and 146, respectively Embodiment 12 is the conjugate of embodiment 11, wherein the isolated monoclonal antibody comprises a heavy chain variable domain (VH) having the polypeptide sequence of SEQ ID NO: 137, and a light chain variable domain (VL) having the polypeptide sequence of SEQ ID NO: 139.

Embodiment 13 is the conjugate of embodiment 12, further comprising a Fc portion.

Embodiment 14 is the conjugate of embodiment 13, comprising a heavy chain (HC) having the polypeptide sequence of SEQ ID NO: 138 and a light chain (LC) having the polypeptide sequence of SEQ ID NO: 140.

Embodiment 15 is a method of producing the conjugate of any one of embodiments 1-14, comprising reacting an electrophile, preferably bromoacetamide or maleimide, introduced onto a sidechain of the cyclic PYY peptide, preferably the amino sidechain of a lysine residue of the cyclic PYY peptide, with the sulfhydryl group of the cysteine residue of SEQ ID NO: 143 of the monoclonal antibody or antigen-binding fragment thereof, thereby creating a covalent linkage between the cyclic PYY peptide and the monoclonal antibody or antigen-binding fragment thereof.

Embodiment 16 is a pharmaceutical composition comprising the conjugate of any one of embodiments 1-14 and a pharmaceutically acceptable carrier.

Embodiment 17 is a method for treating or preventing obesity in a subject in need thereof, comprising administering to the subject in need thereof an effective amount of the pharmaceutical composition of embodiment 16.

Embodiment 18 is the method of embodiment 17, wherein administration of the effective amount of the pharmaceutical composition to the subject in need thereof results in a reduction in body weight of about 5% to about 10%, about 10% to about 15%, about 15% to about 20%, or about 20% to about 25% as compared to the body weight of the subject prior to administration of the pharmaceutical composition.

Embodiment 19 is a method for treating or preventing a disease or disorder in a subject in need thereof, wherein said disease or disorder is selected from the group consisting of obesity, type I or type II diabetes, metabolic syndrome, insulin resistance, impaired glucose tolerance, hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, the method comprising administering to the subject in need thereof an effective amount of the pharmaceutical composition of embodiment 16.

Embodiment 20 is the method of embodiment 19, wherein said disease or disorder is obesity.

Embodiment 21 is the method of embodiment 19, wherein said disease or disorder is type I diabetes.

Embodiment 22 is the method of embodiment 19, wherein said disease or disorder is type II diabetes Embodiment 23 is the method of embodiment 19, wherein said disease or disorder is metabolic syndrome.

Embodiment 24 is the method of embodiment 19, wherein said disease or disorder is a renal disease.

Embodiment 25 is the method of embodiment 19, wherein said disease or disorder is non-alcoholic steatohepatitis (NASH).

Embodiment 26 is the method of embodiment 19, wherein said disease or disorder is non-alcoholic fatty liver disease (NAFLD).

Embodiment 27 is a method of reducing food intake in a subject in need thereof, the method comprising administering to the subject in need thereof an effective amount of the pharmaceutical composition of embodiment 16.

Embodiment 28 is the method of embodiment 27, wherein administration of the effective amount of the pharmaceutical composition to the subject in need thereof results in a reduction in food intake of about 5% to about 10%, about 10% to about 15%, about 15% to about 20%, about 20% to about 25%, about 25% to about 30%, about 30% to about 35%, about 35% to about 40%, about 40% to about 45%, or about 45% to about 50% as compared to the food intake of the subject prior to administration of the pharmaceutical composition.

Embodiment 29 is a method of modulating Y2 receptor activity in a subject in need thereof, the method comprising administering to the subject in need thereof an effective amount of the pharmaceutical composition of embodiment 16.

Embodiment 30 is the method of any one of embodiments 17-29, wherein the pharmaceutical composition is administered via an injection.

Embodiment 31 is the method of embodiment 30, wherein the injection is delivered subcutaneously, intramuscularly, intraperitoneally, or intravenously.

Embodiment 32 is the method of any one of embodiments 17-31, wherein the pharmaceutical composition is administered in a combination with a second therapeutic agent.

Embodiment 33 is the method of embodiment 32, wherein the disease or disorder is selected from the group consisting of obesity, type 2 diabetes, metabolic syndrome, insulin resistance and dyslipidemia and the second therapeutic agent is at least one antidiabetic agent.

Embodiment 34 is the method of embodiment 33, wherein said antidiabetic agent is a glucagon-like-peptide-1 receptor modulator.

Embodiment 35 is the method of embodiment 32, wherein the second therapeutic agent is liraglutide.

Embodiment 36 is the method of any one of embodiments 17-35, wherein the pharmaceutical composition is administered daily, weekly, or monthly to the subject in need thereof.

Embodiment 37 is the method of embodiment 36, wherein the pharmaceutical composition is administered once, twice, three, four, five, or six times per day.

Embodiment 38 is the method of embodiment 36, wherein the pharmaceutical composition is administered once, twice, three, four, five, or six times per week.

Embodiment 39 is the method of embodiment 36, wherein the pharmaceutical composition is administered once, twice, three, or four times per month.

Embodiment 40 is a kit comprising the conjugate of any one of embodiments 1-14 or a pharmaceutical composition of embodiment 16, preferably the kit further comprising an effective amount of a second therapeutic agent, more preferably, the kit further comprising an effective amount of liraglutide.

Embodiment 41 is the kit of embodiment 40, wherein the kit further comprises an injection device.

Embodiment 42 is a method of producing a pharmaceutical composition comprising the conjugate of any one of embodiments 1-14, comprising combining the conjugate with a pharmaceutically acceptable carrier to obtain the pharmaceutical composition.

EXAMPLES

Synthesis

Compounds or conjugates of the present invention can be synthesized in accordance with the general synthetic methods known to those who are skilled in the art. The following description of the synthesis is for exemplary purposes and is in no way meant to be a limit of the invention.

The NTSC cyclic PYY (NTSC-PYY) analogues or derivatives of this invention may be synthesized by a variety of known, conventional procedures for the formation of successive peptide linkages between amino acids, and are preferentially carried out by solid phase peptide synthesis (SPPS), as generally described by Merrifield (J. Am. Chem. Soc., 1963, 85, 2149-2154), using an automated peptide synthesizer, traditional bench synthesis, or a combination of both approaches. Conventional procedures for peptide synthesis involve the condensation between the free amino group of one amino acid residue, whose other reactive functionalities have been suitably protected, and the free carboxyl group of another amino acid, whose reactive functionalities have also been suitably protected. Examples of condensation agents typically utilized for peptide bond formation include diisopropylcarbodiimide (DIC) with or without 1-hydroxybenztriazole (HOBT) or ethyl cyano(hydroxyimino)acetate (Oxyma Pure), 2-(1H-benzotriazol-1-yl)-1,1,3,3-tetramethylaminium hexafluorophosphate (HBTU), 2-(1H-7-azabenztriazol-1-yl)-1,1,3,3-tetramethylaminium hexafluorophosphate (HATU), 2-(6-chloro-1H-benztriazol-1-yl)-1,1,3,3-tetramethylaminium hexafluorophosphate (HCTU), 1-cyano-2-ethoxy-2-oxoethylideneaminooxy-tris-pyrrolidino-phosphonium hexafluorophosphate (PyOxim), 2-(1H-benzotriazol-1-yl)-1,1,3,3-tetramethylaminium tetrafluoroborate (TB TU) bromo-tris-pyrrolidino-phosphonium hexafluorophosphate (PyBroP), and the like.

The automated peptide synthetic methodology may be carried out at room temperature (rt), or at elevated temperatures, preferably through the application of microwave heating, as described by Yu (J. Org. Chem., 1992, 57, 4781-4784) and as more recently refined by Palasek (J. Pept. Sci., 2007, 13, 143-148).

Compounds of the present invention (C-terminal amides) can be conveniently prepared using N-α-FMOC (9-fluroenylmethyloxycarbonyl) protected amino acid methodology, whereby the carboxy terminus of a suitably protected N-α-FMOC protected amino acid is coupled onto a conventional solid phase resin using a suitable coupling agent. Suitable conventional, commercially-available solid phase resins include Rink amide MBHA resin, Rink amide AM resin, Tentagel S RAM Resin, FMOC-PAL-PEG PS resin, SpheriTide Rink amide resin, ChemMatrix Rink resin, Sieber amide resin, TG Sieber resin and the like. The resin-bound FMOC-amino acid may then be deprotected by exposure to 20% piperidine in either N,N-dimethylformamide (DMF) or 1-methyl-2-pyrrolidone (NMP), treatment of which serves to selectively remove the FMOC protecting group. Additional FMOC-protected amino acids are then subsequently coupled and deprotected sequentially, thereby generating the desired resin-bound protected peptide. In certain instances, it may be necessary to utilize an orthogonally reactive protecting group for another amine in the peptide sequence that would withstand the FMOC deprotection conditions. Protecting groups such 4-methyltrityl (Mtt) or 4-methoxytrityl (Mmt), both removable by 1% trifluoroacetic acid (TFA)/dichloromethane (DCM) treatments, or preferably allyloxycarbonyl (alloc; removable by $Pd(PPh_3)_4$ (tetrakis(triphenylphosphine)palladium(0))/$PhSiH_3$ (phenylsilane) treatment), 1-(4,4-dimethyl-2,6-dioxocyclohex-1-yliden)ethyl (Dde; removable by treatment with 2-3% hydrazine/DMF) and 1-(4,4-dimethyl-2,6-dioxocyclohex-1-yliden)-3-methylbutyl (ivDde; removable by treatment with 2-3% hydrazine/DMF) can be used effectively in such instances.

In conventional peptide synthetic methodologies, reactive side chains of alpha amino acids are generally protected throughout the synthesis with suitable protecting groups to render them inert to the coupling and deprotection protocols. While multiple protecting groups for amino acid side chains are known in the art, herein the following protecting groups are most preferred: tert-butyl (t-Bu) for serine, threonine, glutamic acid, aspartic acid and tyrosine; trityl (Trt) for asparagine, glutamine, cysteine, homocysteine and histidine; tert-butyloxycarbonyl (Boc) for tryptophan and the ε-amino group of lysine; and 2,2,4,6,7-pentamethyldihydrobenzofuran-5-sulfonyl (Pbf) for arginine. These protecting groups are removed upon strong acid treatment, such as with high concentrations of trifluoroacetic acid (TFA).

Upon completion of the SPPS, the resin-bound, side chain-protected peptide is deprotected and concomitantly cleaved from the resin using a cleavage cocktail that consists predominantly of (TFA) along with various combinations of carbocation scavengers, such as triisopropylsilane (TIPS), water, phenol and anisole. The crude solid peptide is then isolated by precipitation of the peptide/cocktail filtrate with cold ether. In the special case of Sieber resin-bound protected peptides, cleavage of the protected peptide from the resin may be advantageously effected upon repeated treatment with 1-2% TFA in DCM without causing side chain deprotections. Once isolated, further manipulations of the protected peptide may be carried out in solution phase reactions. Finally, the protected peptide may be globally deprotected using a separate treatment with the cleavage cocktail and precipitated as described above. The crude peptide thus obtained is then dissolved at low concentration (ca., <4 mg/mL) in a largely aqueous (aq) solvent system containing an organic co-solvent such as acetonitrile or ethanol. Upon raising the pH of the solution to a >5, the peptide then undergoes an intramolecular cyclization reaction to form the corresponding crude NTSC PYY analogue of the present invention. NTSC PYY analogues thus formed may be purified using purification techniques generally known in the art. A preferable method of peptide purification used herein is reverse phase high performance liquid chromatography (HPLC). Purified peptides are then characterized by liquid chromatography/mass spectrometry (LC/MS).

It is understood that the following examples and embodiments described herein are for illustrative purposes only and that various modifications or changes in light thereof will be suggestive to persons skilled in the art and are to be included within the spirit and purview of this application and the scope of the appended claims. All publications, patents, and patent applications cited herein are hereby incorporate by reference in their entirety for all purposes.

General Schemes

A general synthetic procedure for the synthesis of C-terminal amide NTSC-PYY peptides are described in U.S. Provisional Patent Application No. 62/413,613, filed on Oct. 27, 2016 and U.S. patent application Ser. No. 15/794,231, entitled "Cyclic peptide tyrosine tyrosine compounds as modulators of neuropeptide receptors," filed on the same day as this application. The contents of both applications are hereby incorporated by reference in their entireties.

Example 1: Synthesis of Cyclic PYY Analog SEQ ID NO:1

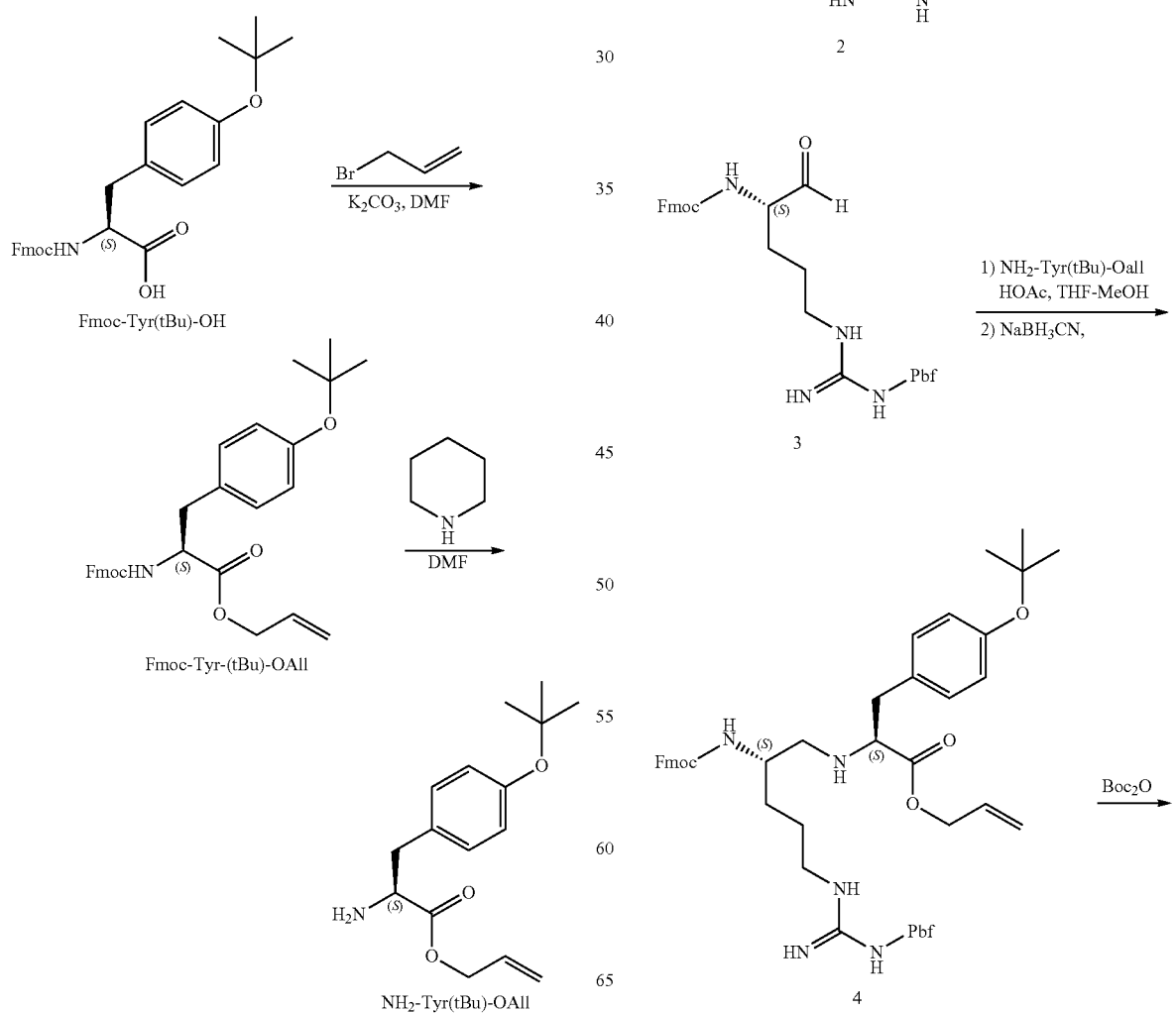
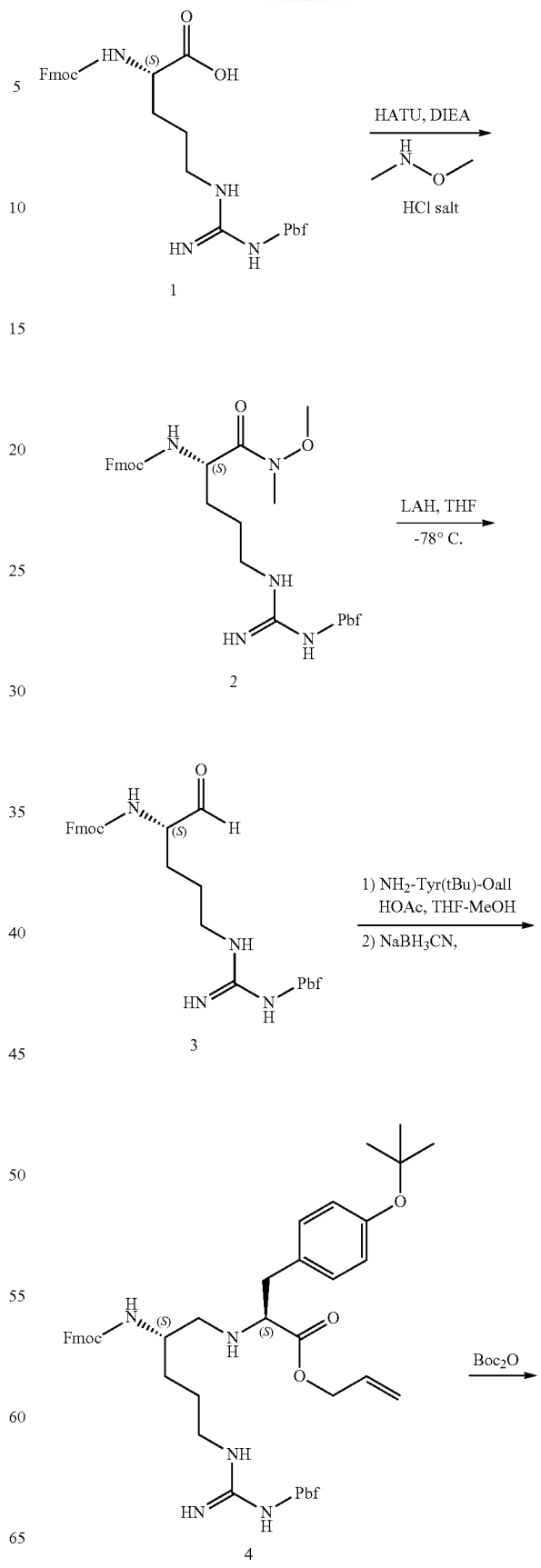

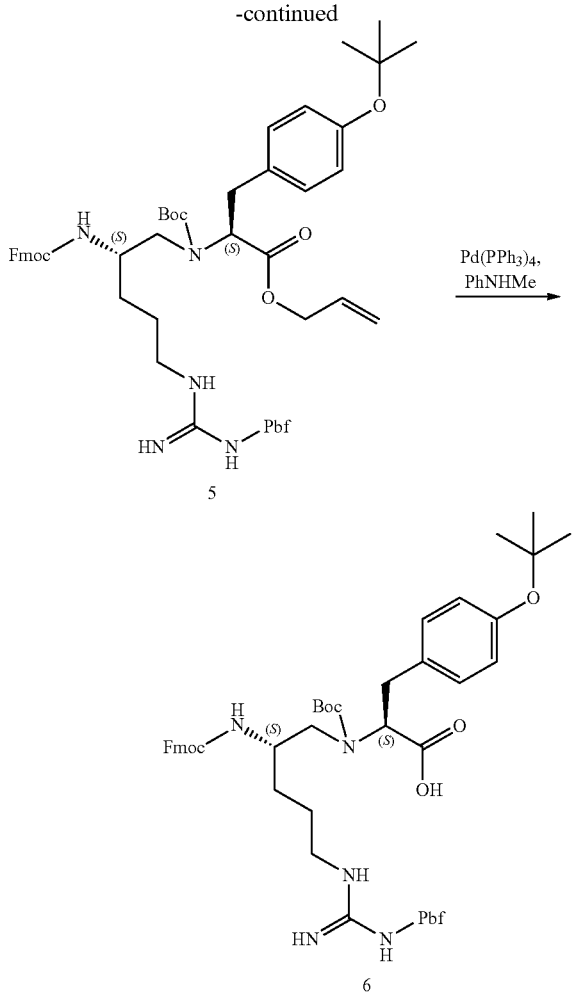

1. Synthesis of Fmoc-psi-[Arg(Pbf)-(N-Boc)Tyr(tBu)]—OH

A. Synthesis of H2N-Tyr(tBu)-OAll

To an ice-cooled solution of Fmoc-Tyr(tBu)-O (69 g, 150.15 mmol) and K2C03 (62 g, 445.36 mmol) in DMF (500 mL) was added allylbromide (72 g, 595.16 mmol), and the resultant mixture was stirred for 3 h. Ice/water (1 L) was then added and the mixture was extracted with EtOAc. The combined organic extracts were dried ($Na_2SO_4$) and concentrated under reduced pressure to afford Fmoc-Tyr(tBu)-OAll as a yellow oil. To an ice-cooled solution of Fmoc-Tyr(tBu)-OAll (70 g, 140.1 mmol) in DMF (600 mL) was added piperidine (150 mL) in drop-wise fashion over a period of 20 min. After 3 h the reaction solution was poured into water/ice (1 L), and extracted with EtOAc (2×2L). The combined organic extracts were dried ($Na_2SO_4$) and concentrated under reduced pressure. The residue thus obtained was purified by silica gel chromatography, eluting with EtOAc/petroleum ether (10:1) to afford 34 g of H2N-Tyr(tBu)-OAll as a yellow oil.

B. Synthesis of F Synthesis of Fmoc-Arg(Pbf)-N(Me)OMe (2)

To an ice-cooled mixture of Fmoc-Arg(Pbf)-OH (1) (64.8 g, 99.88 mmol), N,O-dimethylhydroxylamine hydrochloride (20 g, 206.2 mmol) and HATU (57 g, 149.91 mmol) in DCM (500 mL) was added DIEA (52 g, 402.2 mmol) in drop-wise fashion over a period of 10 min, and the resulting mixture was allowed to stir at room temperature overnight. The reaction was then poured into water/ice (1 L) and extracted with DCM (1 L). The organic extracts were dried ($Na_2SO_4$) and concentrated under reduced pressure to afford 70 g of crude Fmoc-Arg(Pbf)-N(Me)OMe (2) as a yellow solid, which was used without further purification.

C. Synthesis of Fmoc-Arg(Pbf)-CHO (3)

To a cooled (−78° C.) solution of LAH in THF (1M, 107 mL, 0.107 mmol) under an inert atmosphere of nitrogen was added through a cannula a cooled (−50° C.) solution of Fmoc-Arg(Pbf)-N(Me)OMe (2) (50 g, 72.3 mmol) in THF (100 mL) in a drop-wise fashion over a period of 1 h. After stirring at −78° C. for 5 h, the mixture was poured into 1N HCl solution (300 mL), and additional 1N HCl was added as necessary to adjust the pH to 4, and then extracted with EtOAc (2×2L). The combined organic extracts were dried ($Na_2SO_4$) and concentrated under reduced pressure to afford 45 g of crude Fmoc-Arg(Pbf)-CHO (3) as a yellow solid, which was used without further purification.

D. Synthesis of Fmoc-psi-[Arg(Pbf)-Tyr(tBu)]-OAll (4)

To an ice-cooled solution of Fmoc-Arg(Pbf)-CHO (3) from step C (45 g, 71.12 mmol) and H2N-Tyr(tBu)-OAll from step A (32 g, 115.37 mmol) in THF (200 mL), MeOH (200 mL) and HOAc (15 mL) was added sodium cyanoborohydride (18.0 g, 286.4 mmol) in portions over a period of 30 min, and the resulting solution was stirred at room temperature overnight. The reaction was quenched by addition of saturated aqueous $NaHCO_3$ (500 mL) solution and the mixture was extracted with EtOAc (2×2L). The combined organic extracts were dried ($Na_2SO_4$) and concentrated under reduced pressure. The residue was purified by silica gel chromatography eluting with EtOAc/petroleum ether (10:1) to afford 40 g of Fmoc-psi-[Arg(Pbf)-Tyr(tBu)]-OAll (4) as a yellow solid.

E. Synthesis of Fmoc-psi-[Arg(Pbf)-N(Boc)Tyr(tBu)]-OAll (5)

To a solution of Fmoc-psi-[Arg(Pbf)-Tyr(tBu)-OAll] (4) (53 g, 59.28 mmol) in MeCN (240 mL) was added di-tert-butyl dicarbonate (20 g, 91.3 mmol), and the resulting solution was stirred at 50° C. overnight. The mixture was then concentrated under reduced pressure and the residue was purified by silica gel chromatography eluting with EtOAc/petroleum ether (1:1) to afford 32 g of Fmoc-psi-[Arg(Pbf)-N(Boc)Tyr(tBu)]-OAll (5) as a yellow solid.

F. Synthesis of Fmoc-psi-[Arg(Pbf)-N(Boc)Tyr(tBu)]—OH (6)

To a cooled (−30° C.) solution of Fmoc-psi-[Arg(Pbf)-N(Boc)Tyr(tBu)]-OAll (5) (32 g, 32 mmol) in DCM (600 mL) under an inert atmosphere of nitrogen was added $Pd(PPh_3)_4$ (3.0 g, 4.33 mmol), followed by drop-wise addition of N-methylaniline (10 g, 93 mmol) over a period of 30 min. The resulting mixture was stirred at room temperature for 2 h, and then concentrated under reduced pressure. The residue was purified by silica gel chromatography eluting with EtOAc/petroleum ether (1:1) to afford 26.8 g of Fmoc-psi-

[Arg(Pbf)-N(Boc)Tyr(tBu)]—OH (6) as a yellowish solid. $^1$H NMR (300 MHz, CD$_3$OD) δ 7.75-7.77 (2H, m), 7.59-7.60 (2H, m), 7.32-7.33 (4H, m), 7.09-7.11 (2H, m), 6.87-7.00 (2H, m), 4.27-4.50 (3H, m), 3.30-3.50 (4H, m), 3.02-3.23 (3H, m), 2.75-2.98 (3H, m), 2.57 (3H, s), 2.48 (3H, s), 2.00 (3H, s), 1.31-1.41 (28H, m). LC/MS (ES, m/z): mass calcd. for C$_{52}$H$_{67}$N$_5$O$_{10}$S: 953.46, found: 954.55 [M+H]$^+$.

2. Loading of the Dipeptide Fmoc-psi-(R35-N(Boc)-Y36) onto Sieber Resin

In a fritted microwave reaction vessel (supplied by CEM Corporation), NovaSyn TG Sieber resin (supplied by Novabiochem) (0.2 mmol) was treated with 20% piperidine in DMF (10 mL) and heated at 50° C. for 2.5 min in a CEM microwave reactor. The reaction was drained and the resin was washed with DMF and treated again with 20% piperidine in DMF at 50° C. for 5 min in a CEM microwave reactor. After draining and washing the resin with DMF, the deprotection treatment was repeated one more time. The resin was then treated with a solution of Fmoc-psi-[Arg(Pbf)-(N-Boc)Tyr(tBu)]—OH obtained from above (3-5 eq.), HATU (2.75-4.8 eq.) and DIEA (6-10 eq.) in DMF (4 mL) and mixed at rt for 6 to 24 h. The mixture was drained and the resin was washed extensively with DMF, and then capped by treatment with 20% Ac$_2$O in DMF (5 mL) under microwave conditions at 50° C. for 5 min. The reaction was drained and the resin was washed extensively with DMF and DCM.

3. Synthesis of Fmoc-βA-IKPEAPGEK(Alloc)ASPEELNRYYASLRHYLNL(hC) TRQ(psi-R35Y36)-Sieber Resin Amino acid extensions onto the pre-loaded (psi-R35, Y36)-Sieber resin (0.2 mmol) were performed on a CEM Liberty Blue Microwave peptide synthesizer. Standard α-Fmoc-protected amino acids were double-coupled in 3.8-fold excess relative to the initial resin loading at 50° C. for 15 min using HBTU/DIEA as the coupling agents. Fmoc-Arg(Pbf)-OH was double-coupled using a two-stage protocol: 25 min at rt followed by 15 min at 50° C., and Fmoc-His(Trt)-OH was double-coupled using a two-stage protocol: 4 min at rt followed by 8 min at 50° C.

4. Synthesis of Fmoc-βA-IKPEAPGEK(NH$_2$)ASPEELNRYYASLRHYLNL(hC) TRQ(psi-R35Y36)-Sieber Resin: Alloc Deprotection The resulting resin from above was treated with a solution of phenylsilane (25 eq.) in deoxygenated DCM (10 mL). After stirring for ~2 min, a solution of the Pd(PPh$_3$)$_4$ (0.5 eq.) in DCM (10 mL) was added and the resin mixture was stirred for 30 min under argon. The reaction was drained and the resin was washed with deoxygenated DCM. The deprotection was repeated with fresh reagents, after which the reaction was drained and the resin was washed extensively with DCM and DMF.

5. Synthesis of Fmoc-βA-IKPEAPGEK(NH-dPEG$_{12}$-NHFmoc)ASPEELNRYY ASLRHYLNL(hC)TRQ(psi-R35Y36)-Sieber Resin: Coupling N-Fmoc dPEG$_{12}$ Carboxylic Acids onto 11K The Alloc-deprotected peptide-Sieber resin from above was treated with a solution of the N-Fmoc-dPEG12-carboxylic acid (5 eq), HBTU (4.8 eq.) and DIEA (10 eq.) in DMF (7 mL) in a CEM microwave reactor at 50° C. for 15 min, by which time the reaction showed a negative Kaiser test. The reaction was drained and the resin was washed extensively with DMF and DCM.

6. Synthesis of BrCH$_2$COHN-βA-IKPEAPGEK(NH-dPEG$_{12}$-NHCOCH$_2$Br)ASPEEL NRYYASL-RHYLNL(hC)TRQ(psi-R35Y36)-Sieber Resin: bis-bromoacetylation at βA and dPEG$_{12}$ The above resin was subjected to Fmoc-deprotection using fresh 20% piperidine in DMF at 50° C. for 5 min in a CEM microwave reactor. The deprotection was repeated twice. The Fmoc-deprotected peptide-resin thus obtained was treated with a solution of bromoacetic anhydride (20 eq.) in DMF (5 mL) in a CEM microwave reactor at 50° C. for 10 min, by which time the reaction showed a negative Kaiser test. The reaction was drained, and the resin was washed extensively with DMF and DCM, and then dried.

7. Synthesis of BrCH$_2$COHN-βA-IKPEAPGEK(NH-dPEG$_{12}$-NHCOCH$_2$Br)ASPEEL NRYYASL-RHYLNL(hC)TRQ(psi-R35Y36)-CONH$_2$: Cleavage from Resin and Global Deprotection The dried resin was treated with a solution of 1.5% TFA in DCM (10 mL) and mixed for 5 to 10 min, then filtered. This treatment was repeated for 9 additional times using fresh cocktail for each treatment. The combined filtrates were then combined and concentrated to afford the crude protected peptide as a yellow foam. This foam was treated with 20 mL of cleavage cocktail (TFA/phenol/H$_2$O/TIPS=88/5/5/2) at room temperature for 2.5 h and then concentrated under a stream of nitrogen to a volume of 2.5 mL, cold ether (40 mL) was then added to precipitate the peptide. The mixture was centrifuged (5 min; 5000 rpm) and decanted. This process was repeated for 2 more times to give the crude peptide as an off-white powder.

Alternatively, the resin was treated with cleavage cocktail without prior treating with 1-2% TFA in DCM to afford the fully deprotected peptide.

8. Cyclic PYY Analog SEQ ID NO: 1: Cyclization Procedure A and Purification

The crude peptide from above was dissolved in deoxygenated 50% MeCN/water (5-10 mg/mL), EDTA (1 mM) was added optionally. The pH of the reaction solution was then raised to about 8 through the addition of 7.5 w/v % NaHCO$_3$ solution. The resulting solution was stirred at rt for 0.5 to 2.5 h, and then acidified to pH<1 by addition of TFA. The solution was then concentrated under reduced pressure at rt to about half of the original volume (~24 mL). The resultant solution was purified by reverse phase preparative HPLC. Purifications were performed on a Gilson HPLC 2020 Personal Purification System using a Varian Pursuit XRs C18 column (30×250 mm, 100 Å, 5 μm). The mobile phase consisted of gradient elution of Buffer A (0.1% TFA in water) and Buffer B (0.1% TFA in MeCN) ranging from an initial concentration of 20% B to final concentration of 50% B over 36 min. UV detection was monitored at 220 and 254 nm. Product-containing fractions were analyzed by analytical HPLC on an Agilent 1100 HPLC system using the same column type as above (4.6×250 mm, 5 μm). Pure fractions were combined, and then lyophilized to give the product as a cotton-like solid. LCMS: 1225.5 (M+4H)/4, 1633.4 (M+3H)/3 and 2450.0 (M+2H)/2 for the product peak at 12.27 min (LC: Atlantis T3 C18 column, 5 um, 4.6×250 mm, 1.0 mL/min, 15-60% gradient)

Example 2: Synthesis of Cyclic PYY Analog SEQ ID NO:2

1. Synthesis of $H_2N$-IKPEAPGEDASPEELNRYYASLRHYLNL(hC) TRQRY-PAL-PEG Resin

The protected peptidyl resin was synthesized using Fmoc strategy as described above on a CEM Liberty Blue Microwave peptide synthesizer using low loading Rink amide resins, preferably, Fmoc-PAL-PEG PS resin (ca., 0.16-0.2 meq/g, supplied by Applied Biosystems) on a scale of 0.1 mmol, as depicted in Scheme 1 of U.S. Provisional Patent Application No. 62/413,613, filed on Oct. 27, 2016, and U.S. patent application Ser. No. 15/794,231, filed on Oct. 26, 2017. Standard Fmoc-protected amino acids were coupled in 5-fold excess relative to resin loading using DIC/Oxyma as the coupling agents and a reaction temperature of ca., 90° C. for 4 min. Fmoc-Arg(Pbf)-OH was double coupled at 90° C. for 4 min each and Fmoc-His(Trt)-OH was coupled using a two-stage protocol: 4 min at rt followed by 8 min at 50° C. Single Fmoc deprotections were carried out using 20% piperidine in DMF (deprotection solution) at 90° C. for 1.5 min.

2. Synthesis of m-BrCH$_2$PhCOHN-IKPEAPGE-DASPEELNRYYASLRHYLNL(hC) TRQRY-PAL-PEG Resin The Fmoc-deprotected peptide-resin (0.1 mmol) from above was treated with a solution of m-bromomethylbenzoic acid (20 eq.) and DIC (10 eq.) in DMF (4 mL) in a microwave reactor at 75° C. for 15 min, by which time the reaction was generally determined to be complete, as per a Kaiser ninhydrin test (Kaiser, et al., Anal. Biochem., 1970, 34, 595-598). In cases where the coupling was determined to be incomplete, the coupling was repeated with fresh reagents. The reaction was drained, and the resin was washed extensively with DMF and DCM.

3. Synthesis of m-BrCH$_2$PhCOHN-IKPEAPGE-DASPEELNRYYASLRHYLNL(hC) TRQRY-CONH$_2$: Deprotection and Cleavage from Resin The resin from above was then treated with a cleavage cocktail (10 mL/0.1 mmol scale) consisting of TFA/water/phenol/TIPS (88:5:5:2) and heated in a microwave reactor at 38° C. for 40 min, then filtered. The resin was washed with TFA and the combined filtrates were concentrated under a stream of nitrogen to a volume of ca. 2.5 mL and the peptide was precipitated by the addition of cold diethyl ether (40 mL). The peptide/ether suspension was centrifuged and the ether layer was decanted. The peptide pellet was re-suspended in ether, centrifuged and decanted, and this process was repeated a third time. The crude peptide thus obtained was dried under a mild nitrogen stream.

4. Cyclic PYY Analog SEQ ID NO:2: Cyclization Procedure A and Purification

The crude peptide from above was dissolved in deoxygenated MeCN/water (60% MeCN) at a concentration of ≤4 mg/mL. The pH of the peptide solution was then raised to ca. 7-9 through the addition of aq. NH$_4$OAc (200 mM, pH 8.4) and the resulting solution was stirred at rt until the cyclization was complete, as per LCMS (typically, 3-4 h). The cyclization reaction mixture was acidified to pH 1.5-3 by the addition of TFA, and the solution was concentrated to remove most of the organic co-solvent to a point where slight clouding occurred. A minimal amount of the MeCN was added back as necessary to render the mixture homogeneous and the resultant solution was then purified directly by preparative HPLC in multiple injections using a C18 Varian Pursuit XRs C18 (21×250 mm, 100 Å, 5 μm) column. The mobile phase consisted of gradient elutions of buffer A (0.1% TFA in water) and Buffer B (0.1% TFA in MeCN) ranging from an initial concentration of 20% B to a final concentration of 40% B over 45 min. UV detection was monitored at 220 and 254 nm. Product-containing fractions were analyzed by analytical HPLC on an Agilent 1100 HPLC system using an appropriate column. Pure fractions were combined, concentrated to remove most of the organic phase, and then lyophilized.

Example 3: Synthesis of Cyclic PYY Analog SEQ ID NO: 3

1. Synthesis of ($H_2N$)-IKPEAPGEDASPEELN-RYYASLRHYLNL-(azido-norLeu)-TRQRYPAL-PEG Resin The resin-bound peptide was prepared on a 0.1 mmol scale according to the method described in Example 2, step 1, substituting Fmoc-azidonorLeu-OH in place of Fmoc-hCys(trt)-OH at position 31.

2. Synthesis of (HCCH(CH$_2$)$_2$CONH)-IKPEAPGE-DASPEELNRYYASLRHYLNL-(azido-norLeu)-TRQRYPAL-PEG Resin 4-Pentynoic acid was coupled onto the above resin under microwave conditions using a DIC/HOBT protocol (75° C., 10 min). The reaction was drained and the resin was washed extensively with DMF and DCM.

3. Synthesis of (HCCH(CH$_2$)$_2$CONH)-IKPEAPGE-DASPEELNRYYASLRHYLNL-(azido-norLeu)-TRQRYPAL-CONH$_2$ The above resin was treated with 10 mL cleavage cocktail consisting of TFA/DODT/H$_2$O/TIS (92.5:2.5:2.5:2.5) under microwave conditions (38° C., 40 min). The reaction was drained and the resin was washed with TFA (10 mL). The combined filtrate was then concentrated under a stream of nitrogen to a volume of ~2.5 mL. Cold ether (40 mL) was then added to precipitate the peptide and the mixture was centrifuged (5 min; 5000 rpm) and decanted. This process was repeated for 2 more times to give the crude peptide as an off-white powder.

4. Cyclic PYY Analog SEQ ID NO: 3

Prepare 7 mg of CuSO$_4$ in 2 mL deoxygenated H$_2$O. Prepare 30 mg of TBTA in 5.4 mL of EtOH and 0.6 mL of MeCN. Premix 0.94 mL of CuSO$_4$ solution and 4.8 mL TBTA solution. Prepare 30 mg of Na Ascorbate in 3 mL of deoxygenated H$_2$O.

To a solution of the crude azido-containing peptide from Step 3 (100 mg) in 20 mL of deoxygenated water was added the premixed CuSO$_4$/TBTA solution followed by 2.4 mL of Na ascorbate solution (solution immediately became milky).

The mixture was warmed to 40° C. and stirred for 1.5 h, at which time LCMS analysis indicated a complete reaction. The mixture was diluted to ~40 mL with water (0.1% TFA); the mixture was centrifuged, and the supernatant was purified by reverse phase preparative HPLC. Purifications were performed using a Varian Pursuit XRs C18 column (21×250 mm, 100 Å, 5 µm) at 35° C. The mobile phase consisted of a gradient elution of Buffer A (0.1% TFA in water) and Buffer B (0.1% TFA in MeCN) ranging from an initial concentration of 10% B to an intermediate concentration of 18% B (21 mpm) and then to a final concentration of 33% B (10.5 mpm) over 35 min. UV detection was monitored at 220 and 254 nm. Product-containing fractions were analyzed by analytical HPLC on an Agilent 1100 HPLC system using the same column type as above (4.6×250 mm, 5 µm). Pure fractions were combined, and then lyophilized to give the product as a cotton-like solid.

Example 4: Synthesis of Cyclic PYY Analog SEQ ID NO: 4

1. Synthesis of (Dde)K(NH$_2$)ASPEELNRYYASLRHYLNL(hC) TRQRY-PAL-PEG Resin

The resin-bound peptide was prepared using the method described in Example 2, step 1.

2. Synthesis of (Dde)K(NH-Glu-(OtBu)NH$_2$)AS-PEELNRYYASLRHYLNL(hC) TRQRY-PAL-PEG Resin Fmoc-Glu-OtBu (5 eq.) was coupled onto the above resin under microwave conditions using DIC/Oxyma coupling methods (90° C., 6 min; dc). The resin was drained and washed with DMF. Fmoc deprotection was then carried out using 20% piperidine in DMF using a 3-stage protocol (75° C. for 0.5 min; 75° C. for 3 min; 75° C. for 3 min) with DMF washings at each stage.

3. Synthesis of (Dde)K(NH-Glu-(OtBu)NH-Pal) ASPEELNRYYASLRHYLNL(hC) TRQRY-PAL-PEG Resin Palmitic acid (5 eq.) was coupled onto the above resin under microwave conditions using DIC/Oxyma coupling methods (90° C., 5 min). The resin was drained and washed with extensively with DMF and DCM.

4. Synthesis of (H2N)K(NH-Glu-(OtBu)NH-Pal) ASPEELNRYYASLRHYLNL(hC) TRQRY-PAL-PEG Resin After washing the above resin with DMF, it was treated with a solution of 2% hydrazine in DMF (6 mL/0.1 mmol resin) at rt for 5 min, then drained and washed with DMF. The treatment was repeated 5 additional times.

5. Synthesis of (H$_2$N)IKPEAPGEK(NH-Glu-(OtBu) NH-Pal)ASPEELNRYYASLRHYLNL(hC) TRQRY-PAL-PEG Resin The remaining amino acid couplings were carried out using the method described in Example 2, step 1.

6. Cyclic PYY Analog SEQ ID NO: 4

The remainder of the synthesis was carried out using the methods described in Example 2, steps 2-4. Product purification was performed using a Varian Pursuit XRS C18 column (21×250 mm, 100 Å, 5 µm) at rt. The mobile phase consisted of a gradient elution of Buffer A (0.1% TFA in water) and Buffer B (0.1% TFA in MeCN) ranging from 23% B to an intermediate concentration of 33% B (21 mpm) over 5 min, and then to a final concentration of 48% B (10.5 mpm) over 55 min.

Example 5: Synthesis of Cyclic PYY Analog SEQ ID NO: 5

The title compound was prepared according to the procedure as described in Example 4 substituting ca-Tocopheryloxyacetic Acid (AcVitE) (8) in place of palmitic acid in step 3. Product purification was performed using an Agilent 300SB C8 column (21×250 mm, 100 Å, 5 µm) at rt. The mobile phase consisted of a gradient elution of Buffer A (0.1% TFA in water) and Buffer B (0.1% TFA in MeCN) ranging from an initial concentration of 35% B to an intermediate concentration of 45% B (21 mpm) over 5 min, and then to a final concentration of 60% B (10.5 mpm) over 60 min.

Example 6: Synthesis of Cyclic PYY Analog SEQ ID NO: 6

1. Synthesis of (HCCH(CH$_2$)$_2$CONH)-IKPEAPGE-DASPEELNRYYASLRHYLNK(Dde)-(azido-nor-Leu)-TRQRY-PAL-PEG Resin The resin-bound peptide was prepared as described in Example 3, step 1, substituting Fmoc-Lys(Dde)-OH in place of Fmoc-Leu-OH at position 30 and incorporating the 4-pentynoic acid (double coupled) in this step at position 2, following Fmoc-Ile-OH at position 3.

2. Synthesis of (HCCH(CH$_2$)$_2$CONH)-IKPEAPGE-DASPEELNRYYASLRHYLNK(NH$_2$)-(azido-nor-Leu)-TRQRY-PAL-PEG Resin The above resin was treated with 3% hydrazine in DMF (8 mL/0.1 mmol scale) for 5 min at rt and then the mixture was drained and washed with DMF. This procedure was repeated ca. 5×, after which the resin was washed extensively with DMF and then DCM.

3. Synthesis of (HCCH(CH$_2$)$_2$CONH)-IKPEAPGE-DASPEELNRYYASLRHYLNK(NH-γ-Glu-AcVitE)-(azido-norLeu)-TRQRY-PAL-PEG Resin Fmoc-Glu-OtBu was coupled onto the above resin using the coupling protocol described in Example 2, step 1 with a 5 min coupling time. The resin was deprotected by treatment with 20% piperidine in DMF using a 3-stage microwave protocol (75° C., 0.5 min; 75° C., 3 min; 75° C., 3 min), after which the resin was washed extensively with DMF and DCM. α-Tocopheryloxyacetic Acid (AcVitE) (8) was then coupled onto the resin using the same procedure used for coupling Fmoc-Glu-OtBu.

4. Synthesis of (HCCH(CH$_2$)$_2$CONH)-IKPEAPGE-DASPEELNRYYASLRHYLNK(NH-γ-Glu-AcVitE)-(azido-norLeu)-TRQRY-CONH$_2$ Cleavage and precipitation of the peptide from the above resin was carried out using the procedure described in Example 3, step 3.

5. Cyclic PYY Analog SEQ ID NO: 6

The title compound was prepared using the procedure described in Example 3, step 4. Product purification was performed on a Varian Pursuit XRs C8 column (21×250 mm, 100 Å, 5 μm) at 35° C. The mobile phase consisted of a gradient elution of Buffer A (0.1% TFA in water) and Buffer B (0.1% TFA in MeCN) ranging from an initial concentration of 35% B to an intermediate concentration of 48% B (21 mpm) over 5 min, and then to a final concentration of 63% B (10.5 mpm) over 40 min.

Example 7: Synthesis of Cyclic PYY Analog SEQ ID NO: 7

The title compound was prepared according to the procedure as described in Example 4 with the K(NH-γ-Glu-Pal) residue installed at position 9 instead of position 11. Product purification was performed using an Agilent 300SB C8 column (21×250 mm, 100 Å, 5 μm) at rt. The mobile phase consisted of a gradient elution of Buffer A (0.1% TFA in water) and Buffer B (0.1% TFA in MeCN) ranging from an initial concentration of 23% B to an intermediate concentration of 43% B (21 mpm) and then to a final concentration of 43% B (10.5 mpm) over 40 min. Impure product-containing fractions were re-purified on a Waters T3 C18 column (250×19 mm, 100 Å, 5 μm) at rt using a gradient from an initial concentration of 25% B to an intermediate concentration of 35% B (21 mpm) and then to a final concentration of 45% B (10.5 mpm) over 80 min.

Example 8: Synthesis of Cyclic PYY Analog SEQ ID NO: 8

The title compound was prepared according to the procedure as described in Example 4 with the K(NH-γ-Glu-Pal) residue installed at position 30 instead of position 11. Product purification was performed using an Agilent 300SB C8 column (21×250 mm, 100 Å, 5 μm) at 35° C. The mobile phase consisted of a gradient elution of Buffer A (0.1% TFA in water) and Buffer B (0.1% TFA in MeCN) ranging from an initial concentration of 21% B to an intermediate concentration of 31% B (21 mpm) and then to a final concentration of 41% B (10.5 mpm) over 40 min. Impure product-containing fractions were re-purified on a Waters T3 C18 column (250×19 mm, 100 Å, 5 μm) at rt using a gradient from an initial concentration of 21% B to an intermediate concentration of 31% B (21 mpm) and then to a final concentration of 40% B (10.5 mpm) over 80 min.

Example 9: Synthesis of Cyclic PYY Analog SEQ ID NO 9

1. Synthesis of H$_2$N-IKPEAPGEDASPEELNRYYASLRHYLNL(hC)TRQ(psi-R35Y36)-Sieber Resin Amino acid extensions onto the pre-loaded (psi-R35,Y36)-Sieber resin from Example 1, step 2 (0.1 mmol) were performed as described in Example 1, step 3 with the modification of using a 5-fold excess of protected amino acids.

2. Synthesis of m-BrCH$_2$PhCOHN-IKPEAPGE-DASPEELNRYYASLRHYLNL(hC) TRQ(psi-R35Y36)-Sieber Resin m-Bromomethylbenzoic acid was coupled onto the above resin according to the procedure described in Example 1, step, with the modification that the coupling was carried out at 50° C. instead of 75° C.

3. Cyclic PYY Analog SEQ ID NO: 9

The title compound was prepared from the above resin following the procedures described in Example 1, steps 7 and 8. Product purification was performed using a Varian Pursuit XRs C18 column (21×250 mm, 100 Å, 5 μm) at 35° C. The mobile phase consisted of a gradient elution of Buffer A (0.1% TFA in water) and Buffer B (0.1% TFA in MeCN) ranging from an initial concentration of 10% B to an intermediate concentration of 18% B (21 mpm) over 10 min, and then to a final concentration of 33% B (10.5 mpm) over 35 min.

Example 10: Synthesis of Cyclic PYY Analog SEQ ID NO 10

The title compound was prepared according to the procedure as described in Example 4 substituting Dde-Lys(Fmoc)-OH in place of Fmoc-Leu-OH at position 30 and α-Tocopheryloxyacetic Acid (AcVitE) (8) in place of palmitic acid in step 3. Product purification was performed using an Agilent 300SB C8 column (21×250 mm, 100 Å, 5 μm) at rt. The mobile phase consisted of a gradient elution of Buffer A (0.1% TFA in water) and Buffer B (0.1% TFA in MeCN) ranging from an initial concentration of 30% B to an intermediate concentration of 40% B (21 mpm) over 10 min, and then to a final concentration of 55% B (21 mpm) over 35 min. Impure product-containing fractions were re-purified using a modified gradient from an initial concentration of 35% B to an intermediate concentration of 43% B (21 mpm) over 5 min, and then to a final concentration of 58% B (10.5 mpm) over 40 min.

Example 11: Synthesis of Cyclic PYY Analog SEQ ID NO: 11

1. Synthesis of (Alloc)K(NH$_2$)-(hC)-TRQ(psi-R35Y36)-Sieber Resin

The above resin was prepared following the procedure described in Example 9, step 1 using Alloc-Lys(Fmoc)-OH in place of Fmoc-Leu-OH at position 30.

2. Synthesis of (Alloc)K(NH-γ-Glu-AcVitE)-(hC)-TRQ(psi-R35Y36)-Sieber Resin Fmoc-Glu-OtBu and α-Tocopheryloxyacetic Acid (AcVitE) (8) (5 eq. each) were sequentially coupled onto the above resin using HBTU/DIEA-mediated couplings under microwave conditions at 50° C. for 15-20 min.

3. Synthesis of H$_2$N—K(NH-γ-Glu-AcVitE)-(hC)-TRQ(psi-R35Y36)-Sieber Resin The alloc protecting group was removed following the procedure described in Example 1, step 4.

4. Cyclic PYY Analog SEQ ID NO: 11

The title compound was prepared from the above resin following the procedures described in Example 9, steps 1-3, with the modification that a 1M TRIS/HCl buffer, pH 7.5 was used in place of the NH$_4$OAc buffer to effect cyclization. Product purification was performed using a Varian Pursuit XRs C18 column (21×250 mm, 100 Å, 5 μm) at 35° C. The mobile phase consisted of a gradient elution of Buffer A (0.1% TFA in water) and Buffer B (0.1% TFA in MeCN) ranging from an initial concentration of 10% B to an intermediate concentration of 18% B (21 mpm) over 10 min, and then to a final concentration of 33% B (10.5 mpm) over 35 min.

Example 12: Synthesis of Cyclic PYY Analog SEQ ID NO: 12

The title compound was prepared according to the procedure as described in Example 2 substituting Fmoc-N-Me-Arg(pbf)-OH in place of Fmoc-Arg(pbf)-OH at position 35 in step 1 and with the modification that a 1M NaHCO$_3$ buffer was used in place of the NH$_4$OAc buffer to effect cyclization. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 10-60% B (30 mpm) over 36 min.

Example 13: Synthesis of Cyclic PYY Analog SEQ ID NO: 13

The title compound was prepared according to the procedures described in Example 11, using palmitic acid in place of α-Tocopheryloxyacetic Acid (AcVitE) (8) in step 2, and with the modifications that 60% EtOH/H$_2$O was used as solvent in place of MeCN/H$_2$O and sat'd aq. NaHCO$_3$ was used in place of the NH$_4$OAc buffer to effect cyclization. Product purification was performed using a Waters XBridge C18 OBD column (50×250 mm, 5 μm) at rt. The mobile phase consisted of a gradient elution of Buffer A (10 mM NH$_4$OH in water, pH~9) and Buffer B (MeCN) ranging from an initial concentration of 15% B to an intermediate concentration of 20% B (100 mpm) over 5 min, and then to a final concentration of 35% B (100 mpm) over 40 min.

Example 14: Synthesis of Cyclic PYY Analog SEQ ID NO: 14

The title compound was prepared according to the procedure as described in Example 4 with the Lys(NH-γ-Glu-Pal) residue installed at position 30 instead of position 11 and with Fmoc-N-Me-Arg(pbf)-OH in place of Fmoc-Arg(pbf)-OH at position 35 in step 1 and with the modification that a 1M NaHCO$_3$ buffer was used in place of the NH$_4$OAc buffer in step 6, to effect cyclization. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-70% B (30 mpm) over 36 min. Impure fractions were re-purified on a Varian Pursuit XRs diphenyl column (30×100 mm, 100 Å, 5 μm) at rt using a gradient of 30-50% B (30 mpm) over 25 min.

Example 15: Synthesis of Cyclic PYY Analog SEQ ID NO: 15

The title compound was prepared according to the procedure as described in Example 4 with the Lys(NH-γ-Glu-Pal) residue installed at position 30 instead of position 11, substituting Fmoc-βAla-OH in place of Fmoc-Ile-OH coupling at position 3, and with the modifications that a 1M NaHCO$_3$ buffer was used in place of the NH$_4$OAc buffer to effect cyclization, and coupling with bromoacetic anhydride was used in place of m-bromomethylbenzoic acid in step 6 (step 2 from Example 2) using the following procedure: The Fmoc-deprotected peptide-resin (0.1 mmol) was treated with a solution of bromoacetic anhydride (10 eq.) in DMF (5 mL) in a microwave reactor at 50° C. for 5-10 min, by which time the reaction was generally determined to be complete as per a Kaiser ninhydrin test. In cases where the coupling was determined to be incomplete, the coupling was repeated with fresh reagents. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-60% B (30 mpm) over 36 min. Impure fractions were re-purified on a Varian Pursuit XRs diphenyl column (30×100 mm, 100 Å, 5 μm) at rt using a gradient of 30-50% B (30 mpm) over 25 min.

Example 16: Synthesis of Cyclic PYY Analog SEQ ID NO: 16

The title compound was prepared according to the procedure as described in Example 4 with the Lys(NH-γ-Glu-Pal) residue installed at position 30 instead of position 11, omitting the Fmoc-Ile-OH coupling at position 3, and using p-bromomethylbenzoic acid in place of m-bromomethylbenzoic acid in step 6 (step 2 from Example 2). Additionally, a 1M NaHCO$_3$ buffer was used in place of the NH$_4$OAc buffer, to effect cyclization. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-70% B (30 mpm) over 36 min. Impure fractions were re-purified on a Varian Pursuit XRs diphenyl column (30×100 mm, 100 Å, 5 μm) at rt using a gradient of 30-50% B (30 mpm) over 25 min.

Example 17: Synthesis of Cyclic PYY Analog SEQ ID NO: 17

The title compound was prepared according to the procedure as described in Example 4 with the Lys(NH-γ-Glu-Pal) residue installed at position 30 instead of position 11 and Fmoc-Ala-OH used in place of Fmoc-Lys(Boc)-OH at position 4 in step 1. TRIS/HCl buffer (1M, pH 7.5) was used in place of the NH$_4$OAc buffer in step 6 to effect cyclization. Product purification was performed using an Agilent Polaris C18-A column (30×250 mm, 100 Å, 5 μm) at rt. The mobile phase consisted of a gradient elution of Buffer A (0.1% TFA in water) and Buffer B (0.1% TFA in MeCN) ranging from an initial concentration of 20% B to an intermediate concentration of 35% B (40 mpm) over 5 min, and then to a final concentration of 45% B (40 mpm) over 40 min.

Example 18: Synthesis of Cyclic PYY Analog SEQ ID NO: 18

The title compound was prepared according to the procedure as described in Example 4 with the Lys(NH-γ-Glu-Pal) residue installed at position 30 instead of position 11 and Fmoc-Glu(OtBu)-OH used in place of Fmoc-Lys(Boc)-OH at position 4 in step 1. TRIS/HCl buffer (1M, pH 7.5) was used in place of the NH$_4$OAc buffer in step 6 to effect cyclization. Product purification was performed using an Agilent Polaris C18-A column (30×250 mm, 100 Å, 5 µm) at rt. The mobile phase consisted of a gradient elution of Buffer A (0.1% TFA in water) and Buffer B (0.1% TFA in MeCN) ranging from an initial concentration of 20% B to an intermediate concentration of 35% B (40 mpm) over 5 min, and then to a final concentration of 45% B (40 mpm) over 40 min.

Example 19: Synthesis of Cyclic PYY Analog SEQ ID NO: 19

The title compound was prepared according to the procedure as described in Example 4 with the Lys(NH-γ-Glu-Pal) residue installed at position 30 instead of position 11, Fmoc-N-Me-Arg(pbf)-OH in place of Fmoc-Arg(pbf)-OH at position 35 in step 1, Fmoc-Cys(trt)-OH in place of Fmoc-hCys(trt)-OH, and using p-bromomethylbenzoic acid in place of m-bromomethylbenzoic acid in step 6 (step 2 from Example 2).

The following modification was made to step 6 (steps 3 and 4 from Example 2): The crude peptide obtained prior to cyclization was purified using a Varian Pursuit XRs C18 column (30×250 mm, 100 Å, 5 µm) at rt. The mobile phase consisted of a gradient elution of Buffer A (0.1% TFA in water) and Buffer B (0.1% TFA in MeCN) ranging from 20-70% B (30 mpm) over 36 min. Product-containing fractions were combined and treated with solid NaHCO$_3$ to raise the pH to ~7-8; the resulting solution was stirred at rt for 4 h, then acidified to pH 4 with TFA. The solution was concentrated to a volume of 5-10 mL and MeCN was added to solubilize any precipitate. Product purification was performed as above, with a gradient of 20-60% B (30 mpm) over 36 min.

Example 20: Synthesis of Cyclic PYY Analog SEQ ID NO: 20

The title compound was prepared according to the procedure as described in Example 4 with the Lys(NH-γ-Glu-Pal) residue installed at position 30 instead of position 11, Fmoc-N-Me-Arg(pbf)-OH in place of Fmoc-Arg(pbf)-OH at position 35 in step 1 and Fmoc-Cys(trt)-OH in place of Fmoc-hCys(trt)-OH. The crude linear peptide was purified and cyclized according to the modification described in Example 19. Final product purification was performed using a gradient of 20-60% B (30 mpm) over 36 min.

Example 21: Synthesis of Cyclic PYY Analog SEQ ID NO: 21

The title compound was prepared according to the procedure as described in Example 4 with the Lys(NH-γ-Glu-Pal) residue installed at position 30 instead of position 11, Fmoc-Ala-OH used in place of Fmoc-His(trt)-OH at position 26 and Fmoc-Ala-OH used in place of Fmoc-Lys(Boc)-OH at position 4 in step 1. TRIS/HCl buffer, (1M, pH 7.5) was used in place of the NH$_4$OAc buffer in step 6 to effect cyclization. Product purification was performed using an Agilent Polaris C18-A column (30×250 mm, 100 Å, 5 µm) at rt. The mobile phase consisted of a gradient elution of Buffer A (0.1% TFA in water) and Buffer B (0.1% TFA in MeCN) ranging from an initial concentration of 20% B to an intermediate concentration of 35% B (40 mpm) over 5 min, and then to a final concentration of 45% B (40 mpm) over 40 min.

Example 22: Synthesis of Cyclic PYY Analog SEQ ID NO: 22

The title compound was prepared according to the procedure as described in Example 4 with the Lys(NH-γ-Glu-Pal) residue installed at position 30 instead of position 11, Fmoc-Ala-OH used in place of Fmoc-His(trt)-OH at position 26 and Fmoc-Glu(OtBu)-OH used in place of Fmoc-Lys(Boc)-OH at position 4 in step 1. TRIS/HCl buffer, (1M, pH 7.5) was used in place of the NH$_4$OAc buffer in step 6 to effect cyclization. Product purification was performed using an Agilent Polaris C18-A column (30×250 mm, 100 Å, 5 µm) at rt. The mobile phase consisted of a gradient elution of Buffer A (0.1% TFA in water) and Buffer B (0.1% TFA in MeCN) ranging from an initial concentration of 20% B to an intermediate concentration of 33% B (40 mpm) over 5 min, and then to a final concentration of 43% B (40 mpm) over 40 min.

Example 23: Synthesis of Cyclic PYY Analog SEQ ID NO: 23

The title compound was prepared according to the procedures described in Example 11, using octadecanedioic acid, mono-tert-butyl ester (available from AstaTech, Inc.) in place of α-Tocopheryloxyacetic Acid (AcVitE) (8), a coupling protocol employing HATU/DIEA at 50° C. for 30 min and NMP as solvent in place of DMF in step 2, and coupling two units of Fmoc-OEG-OH in tandem prior to coupling Fmoc-Glu-OtBu, in step 2. The crude linear peptide was purified and cyclized according to the modification described in Example 19, using a gradient of 20-60% B. Final product purification was performed using a gradient of 20-70% B (30 mpm) over 36 min.

Example 24: Synthesis of Cyclic PYY Analog SEQ ID NO: 24

The title compound was prepared according to the procedures described in Example 23, using 20-(tert-butoxy)-20-oxoicosanoic acid (available from Key Organics, Inc.) in place of octadecanedioic acid, mono-tert-butyl ester. The crude linear peptide was purified and cyclized according to the modification described in Example 19, using a gradient of 20-60% B. Final product purification was performed using a gradient of 20-60% B (30 mpm) over 36 min.

Example 25: Synthesis of Cyclic PYY Analog SEQ ID NO: 25

The title compound was prepared according to the procedures described in Example 11, using stearic acid in place of α-Tocopheryloxyacetic Acid (AcVitE) (8), a coupling protocol employing HATU/DIEA at 50° C. for 30 min and NMP as solvent in place of DMF in step 2. The crude linear peptide was purified and cyclized according to the modification described in Example 19, using a gradient of 20-80% B. Final product purification was performed using a gradient of 20-80% B (30 mpm) over 36 min.

Example 26: Synthesis of Cyclic PYY Analog SEQ ID NO: 26

The title compound was prepared according to the procedures described in Example 11, using arachidic acid in place of α-Tocopheryloxyacetic Acid (AcVitE) (8), a coupling protocol employing HATU/DIEA at 50° C. for 30 min and NMP as solvent in place of DMF in step 2. The crude linear peptide was purified and cyclized according to the modification described in Example 19, using a gradient of 20-90% B. Final product purification was performed using a gradient of 20-90% B (30 mpm) over 36 min.

Example 27: Synthesis of Cyclic PYY Analog SEQ ID NO: 27

The title compound was prepared according to the procedures described in Example 23, but omitting the coupling of Fmoc-Glu-OtBu after the tandem Fmoc-OEG-OH couplings. The crude linear peptide was purified and cyclized according to the modification described in Example 19, using a gradient of 20-60% B. Final product purification was performed using a gradient of 20-60% B (30 mpm) over 36 min.

Example 28: Synthesis of Cyclic PYY Analog SEQ ID NO: 28

The title compound was prepared according to the procedures described in Example 11, using palmitic acid in place of α-Tocopheryloxyacetic Acid (AcVitE) (8), omitting the coupling of Fmoc-Ile-OH at position 3, and using p-bromomethylbenzoic acid in place of m-bromomethylbenzoic acid in step 4 (Example 9, step 2). The crude linear peptide was purified and cyclized according to the modification described in Example 19, using a gradient of 20-60% B. Final product purification was performed using a gradient of 20-60% B (30 mpm) over 36 min.

Example 29: Synthesis of Cyclic PYY Analog SEQ ID NO: 29

The title compound was prepared according to the procedures described in Example 11, using palmitic acid in place of α-Tocopheryloxyacetic Acid (AcVitE) (8), substituting Fmoc-βAla-OH in place of Fmoc-Ile-OH at position 3, and coupling bromoacetic anhydride in place of m-bromomethylbenzoic acid in step 4 (Example 9, step 2), using the modification described in Example 15. The crude linear peptide was purified and cyclized according to the modification described in Example 19, using a gradient of 20-60% B. Final product purification was performed using a gradient of 20-60% B (30 mpm) over 36 min.

Example 30: Synthesis of Cyclic PYY Analog SEQ ID NO: 30

The title compound was prepared according to the procedures described in Example 11, using palmitic acid in place of α-Tocopheryloxyacetic Acid (AcVitE) (8), substituting Fmoc-Aβυ-OH in place of Fmoc-Ile-OH at position 3, and coupling bromoacetic anhydride in place of m-bromomethylbenzoic acid in step 4 (Example 9, step 2), using the modification described in Example 15. The crude linear peptide was purified and cyclized according to the modification described in Example 19, using a gradient of 20-60% B. Final product purification was performed using a gradient of 20-60% B (30 mpm) over 36 min.

Example 31: Synthesis of Cyclic PYY Analog SEQ ID NO: 31

The title compound was prepared according to the procedures described in Example 23, using stearic acid in place of octadecanedioic acid, mono-tert-butyl ester. The crude linear peptide was purified and cyclized according to the modification described in Example 19, using a gradient of 20-60% B. Final product purification was performed using a gradient of 20-60% B (30 mpm) over 36 min.

Example 32: Synthesis of Cyclic PYY Analog SEQ ID NO: 32

The title compound was prepared according to the procedures described in Example 11, using palmitic acid in place of α-Tocopheryloxyacetic Acid (AcVitE) (8) in step 2, Fmoc-Ala-OH used in place of Fmoc-His(trt)-OH at position 26 and Fmoc-Ala-OH used in place of Fmoc-Lys(Boc)-OH at position 4 in step 4 (Example 9, step 1). TRIS/HCl buffer, (1M, pH 7.5) was used in place of the NH$_4$OAc buffer in step 6 to effect cyclization. Product purification was performed using an Agilent Polaris C18-A column (30×250 mm, 100 Å, 5 µm) at rt. The mobile phase consisted of a gradient elution of Buffer A (0.1% TFA in water) and Buffer B (0.1% TFA in MeCN) ranging from an initial concentration of 20% B to an intermediate concentration of 35% B (40 mpm) over 5 min, and then to a final concentration of 45% B (40 mpm) over 40 min.

Example 33: Synthesis of Cyclic PYY Analog SEQ ID NO: 33

The title compound was prepared according to the procedures described in Example 11, using palmitic acid in place of α-Tocopheryloxyacetic Acid (AcVitE) (8) in step 2 and Fmoc-N(Me)-Gln(trt)-OH in place of Fmoc-Gln(trt)-OH at position 34 in step 4 (Example 9, step 1). In this case, couplings were carried out at rt using NMP as solvent and an HATU/DIEA protocol (1 h, single coupling); Fmoc-N(Me)-Gln(trt)-OH and Fmoc-Arg(pbf)-OH were double coupled. A two-stage Fmoc deprotection protocol was used throughout (20% piperidine in DMF; rt; 10 min, 15 min). The crude linear peptide was purified and cyclized according to the modification described in Example 19, using a gradient of 20-70% B. Final product purification was performed using a gradient of 20-70% B (30 mpm) over 36 min.

Example 34: Synthesis of Cyclic PYY Analog SEQ ID NO: 34

The title compound was prepared according to the procedures described in Example 11, using palmitic acid in place of α-Tocopheryloxyacetic Acid (AcVitE) (8), substituting Fmoc-Cys(trt)-OH in place of Fmoc-hCys(trt)-OH at position 31, 6-Fmoc-aminohexanoic acid in place of Fmoc-Ile-OH at position 3, and coupling bromoacetic anhydride in place of m-bromomethylbenzoic acid in step 4 (Example 9, step 2), using the modification described in Example 15. Aq. NaHCO$_3$ (2N) was used in place of the NH$_4$OAc buffer to effect cyclization. Product purification was performed using a Varian Pursuit XRs C18 column (30×250 mm, 100 Å, 5 µm) at rt. The mobile phase consisted of a gradient elution of Buffer A (0.1% TFA in water) and Buffer B (0.1% TFA in MeCN) ranging from 20-70% B (30 mpm) over 36 min.

Example 35: Synthesis of Cyclic PYY Analog SEQ ID NO: 35

The title compound was prepared according to the procedures described in Example 9, with the following modifications: Fmoc-psi-[N-Me-Arg(Pbf)-N(Boc)Tyr(tBu)]—

OH, prepared from Fmoc-N-Me-Arg(pbf)-OH in place of Fmoc-Arg(Pbf)-OH, according to the procedure described in Example 1, step 1, was used in place of Fmoc-psi-[Arg(Pbf)-N(Boc)Tyr(tBu)]—OH (6) to prepare the loaded Sieber resin used herein; Fmoc-Lys(Pal-Glu-OtBu)-OH (from Active Peptide) was used in place of Leu at position 30; m-chloromethylbenzoic acid was used in place of m-bromomethylbenzoic acid in step 2; couplings were carried out at rt using NMP as solvent and an HATU/DIEA protocol (1 h, single coupling) was used; Fmoc-Arg(pbf)-OH was double coupled. A two-stage Fmoc deprotection protocol was used throughout (20% piperidine in DMF; rt; 10 min, 15 min). The crude linear peptide was purified and cyclized according to the modification described in Example 19, using a gradient of 20-70% B. Final product purification was performed using a gradient of 20-70% B (30 mpm) over 36 min.

Example 36: Synthesis of Cyclic PYY Analog SEQ ID NO: 36

The title compound was prepared according to the procedures described in Example 35, substituting Fmoc-βAla-OH in place of Fmoc-Ile-OH at position 3, and coupling bromoacetic anhydride in place of m-bromomethylbenzoic acid in step 4 (Example 9, step 2), using the modification described in Example 15. The modified workup of Example 19 was omitted. Fmoc-βAla-OH was coupled under microwave conditions at 50° C. for 20 min. Sat'd aq. NaHCO$_3$ was used in place of the NH$_4$OAc buffer to effect cyclization. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-70% B (30 mpm) over 36 min.

Example 37: Synthesis of Cyclic PYY Analog SEQ ID NO: 37

The title compound was prepared according to the procedures described in Example 9, substituting Fmoc-Cys(trt)-OH in place of Fmoc-hCys(trt)-OH at position 31 and Fmoc-Lys(Pal-Glu-OtBu)-OH (from Active Peptide) in place of Fmoc-Leu-OH at position 30. In addition, Fmoc-Abu-OH was appended onto the sequence at position 2, in step 1, and coupling with bromoacetic anhydride was used in place of m-bromomethylbenzoic acid in step 2, using the modification described in Example 15. Sat'd aq. NaHCO$_3$ was used in place of the NH$_4$OAc buffer in step 3 to effect cyclization. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-70% B (30 mpm) over 36 min.

Example 38: Synthesis of Cyclic PYY Analog SEQ ID NO: 38

The title compound was prepared according to the procedures described in Example 35, with the following modifications: Fmoc-βAla-OH was appended onto the sequence at position 2, following step 1 using microwave conditions at 50° C. for 20 min, and coupling with bromoacetic anhydride was used in place of m-bromomethylbenzoic acid in step 2, using the modification described in Example 15. Sat'd aq. NaHCO$_3$ was used in place of the NH$_4$OAc buffer to effect cyclization. Product purification was performed using a Varian Pursuit XRs C18 column (30×250 mm, 100 Å, 5 μm) at rt. The mobile phase consisted of a gradient elution of Buffer A (0.1% TFA in water) and Buffer B (0.1% TFA in MeCN) ranging from 20-80% B (30 mpm) over 36 min.

Example 39: Synthesis of Cyclic PYY Analog SEQ ID NO: 39

The title compound was prepared according to the procedures described in Example 11, using arachidic acid in place of ca-Tocopheryloxyacetic Acid (AcVitE) (8) in step 2. Fmoc-Ser(tBu)-OH was used in place of Fmoc-Lys(Boc)-OH at position 4 in step 4 (Example 9, step 1) and m-chloromethylbenzoic acid was used in place of m-bromomethylbenzoic acid in step 4 (Example 9, step 2). 60% EtOH/H$_2$O was used as solvent in place of MeCN/H$_2$O and sat'd aq. NaHCO$_3$ was used in place of the NH$_4$OAc buffer in step 4 to effect cyclization. Product purification was performed using a Waters XBridge C18 OBD column (50×250 mm, 5 μm) at rt. The mobile phase consisted of a gradient elution of Buffer A (10 mM NH$_4$OH in water, pH~9) and Buffer B (MeCN) ranging from an initial concentration of 20% B to an intermediate concentration of 25% B (100 mpm) over 5 min, and then to a final concentration of 40% B (100 mpm) over 40 min.

Example 40: Synthesis of Cyclic PYY Analog SEQ ID NO: 40

1. Synthesis of (HCCH(CH$_2$)$_2$CONH)-IKPEAPGE-DASPEELNRYYASLRHYLNK(Dde)-(azido-nor-Leu)-TRQ(psi-R35Y36)-Sieber Resin Amino acid extensions onto the pre-loaded (psi-R35, Y36)-Sieber resin from Example 1, step 2 (0.1 mmol) were carried out at rt using NMP as solvent, a 5-fold excess of protected amino acids and an HATU/DIEA protocol (1 h, single coupling); Fmoc-Arg(pbf)-OH and Fmoc-His(trt)-OH were double coupled. A two-stage Fmoc deprotection protocol was used throughout (20% piperidine in DMF; rt; 10 min, 15 min).

2. Synthesis of (HCCH(CH$_2$)$_2$CONH)-IKPEAPGE-DASPEELNRYYASLRHYLNK(NH$_2$)-(azido-nor-Leu)-TRQ(psi-R35Y36)-Sieber Resin The above resin was treated with 2% hydrazine in DMF (12 mL/0.2 mmol scale) for 2 min at rt and then the mixture was drained. This procedure was repeated ca. 4×, after which the resin was washed extensively with DMF and then DCM.

3. Synthesis of (HCCH(CH$_2$)$_2$CONH)-IKPEAPGE-DASPEELNRYYASLRHYLNK((OEG)$_2$-γ-Glu-Pal)-(azido-norLeu)-TRQ(psi-R35Y36)-Sieber Resin The above resin was coupled with (S)-10,19-dioxo-22-palmitamido-3,6,12,15-tetraoxa-9,18-diazatricosanedioic acid (5 eq,) [prepared according to the procedure described for synthesis of intermediate 3, by substituting palmitic acid in place of 18-tert-butoxy-18-oxooctadecanoic acid in step G], using an HBTU/DIEA protocol at rt for 1.5 h. The resin was drained and washed extensively with DMF and DCM.

4. Synthesis of (HCCH(CH$_2$)$_2$CONH)-IKPEAPGE-DASPEELNRYYASLRHYLNK((OEG)$_2$-γ-Glu-Pal)-(azido-norLeu)-TRQ(psi-R35Y36)-CONH$_2$ The dried resin was treated with a solution of 2% TFA in DCM (20 mL) and mixed for 20 min, then filtered. This treatment was repeated for 2 additional times using fresh cocktail for each treatment. The combined filtrates were then combined and concentrated to afford the crude protected peptide as a yellow foam. This foam was treated with 20 mL of cleavage cocktail (TFA/H$_2$O/TIPS=95/2.5/2.5) at rt for 2.5 h and then concentrated under a stream of nitrogen to a volume of about 2.5 mL. Cold ether (40 mL) was then added to precipitate the peptide and the mixture was centrifuged (5 min; 5000 rpm) and decanted. This process was repeated for 2 more times to give the crude peptide as an off-white powder.

Alternatively, the resin was treated with cleavage cocktail without prior treatment with 1-2% TFA in DCM, to afford the fully deprotected peptide directly. The crude peptide was purified by reverse phase preparative HPLC using a Varian Pursuit XRs C18 column (30×250 mm, 100 Å, 5 μm). The mobile phase consisted of gradient elution of Buffer A (0.1% TFA in water) and Buffer B (0.1% TFA in MeCN) ranging from 20-70% B over 36 min. UV detection was monitored at 220 and 254 nm. Product-containing fractions were analyzed by analytical HPLC on an Agilent 1100 HPLC system using the same column type as above (4.6×250 mm, 5 μm). Pure fractions were combined, and then lyophilized to give the product as a cotton-like solid. LCMS: 1211.8 (M+4H)/4, 1615.4 (M+3H)/3 and 2422.9 (M+2H)/2 for the product peak at 16.87 min (LC: Atlantis T3 C18 column, 5 m, 4.6×250 mm, 1.0 mL/min, 30-60% gradient).

5. Cyclic PYY Analog SEQ ID NO: 40

Prepare 5.1 mg of CuSO$_4$ in 1 mL H$_2$O. Prepare 10.4 mg of TBTA in 3 mL of EtOH. Premix 400 μL of CuSO$_4$ solution and 3 mL TBTA solution. Prepare 13 mg of Na Ascorbate in 2 mL of H$_2$O.

To a solution of the purified azido-containing peptide from Step 4 (37 mg) in 4 mL of HEPES (0.1M, pH 7.4) was added 1.7 mL of the premixed CuSO$_4$/TBTA solution followed by 1 mL of Na Ascorbate solution. Adjust EtOH/H$_2$O ratio until the reaction solution turned clear. The mixture was stirred at rt and monitored by HPLC. After 30 min, the reaction was completed. The mixture was adjusted to pH 4 and purified by reverse phase preparative HPLC. Purifications were performed using a Varian Pursuit XRs C18 column (30×250 mm, 100 Å, 5 μm). The mobile phase consisted of gradient elution of Buffer A (0.1% TFA in water) and Buffer B (0.1% TFA in MeCN) ranging from 20-60% B over 36 min. UV detection was monitored at 220 and 254 nm. Product-containing fractions were analyzed by analytical HPLC on an Agilent 1100 HPLC system using the same column type as above (4.6×250 mm, 5 μm). Pure fractions were combined, and then lyophilized to give the product as a cotton-like solid.

Example 41: Synthesis of Cyclic PYY Analog SEQ ID NO: 41

The title compound was prepared according to the procedure described in Example 40, substituting L-Glutamic acid, N-(1-oxohexadecyl)-, 1-(1,1-dimethylethyl) ester in place of (S)-10,19-dioxo-22-palmitamido-3,6,12,15-tetraoxa-9,18-diazatricosanedioic acid, in step 3.

Example 42: Synthesis of Cyclic PYY Analog SEQ ID NO: 42

The title compound was prepared according to the procedure described in Example 40, substituting (S)-22-(tert-butoxycarbonyl)-43,43-dimethyl-10,19,24,41-tetraoxo-3,6,12,15,42-pentaoxa-9,18,23-triazatetratetracontan-1-oic acid (16) (intermediate 2) in place of (S)-10,19-dioxo-22-palmitamido-3,6,12,15-tetraoxa-9,18-diazatricosanedioic acid, in step 3.

Example 43 Synthesis of Cyclic PYY Analog SEQ ID NO: 43

1. Synthesis of (Alloc)Lys((OEG)$_2$-γ-Glu-NH$_2$)-(hC)-TRQ(psi-R35Y36)-Sieber Resin Amino acid extensions onto the pre-loaded (psi-R35, Y36)-Sieber resin from Example 1, step 2 (0.1 mmol) were carried out at rt using NMP as solvent, a 5-fold excess of protected amino acids and an HATU/DIEA protocol (1 h, single coupling); Fmoc-Arg(pbf)-OH was double coupled. A two-stage Fmoc deprotection protocol was used throughout (20% piperidine in DMF; rt; 10 min, 15 min).

2. Synthesis of (Alloc)Lys((OEG)$_2$-γ-Glu-Pal)-(hC)-TRQ(psi-R35Y36)-Sieber Resin Palmitic acid was coupled onto the resin from step 1, using microwave conditions employing HATU/DIEA at 50° C. for 20-30 min and NMP as solvent.

3. Synthesis of (H$_2$N)Lys((OEG)$_2$-γ-Glu-Pal)-(hC)-TRQ(psi-R35Y36)-Sieber Resin The alloc protecting group of the above resin was removed following the procedure described in Example 1, step 4.

4. Cyclic PYY Analog SEQ ID NO: 43

The title compound was prepared from the above resin following the procedures described in Example 9, steps 1-3, using m-chloromethylbenzoic acid in place of m-bromomethylbenzoic acid in step 2. The crude linear peptide was purified and cyclized according to the modification described in Example 19, using a gradient of 20-60% B. Final product purification was performed using a gradient of 20-60% B (30 mpm) over 36 min.

Example 44 Synthesis of Cyclic PYY Analog SEQ ID NO: 44

The title compound was prepared according to the procedures described in Example 43, modified such that the tandem Fmoc-OEG-OH units and the Fmoc-Glu-OtBu unit were incorporated in step 2 instead of step 1. Octadecanedioic acid, mono-tert-butyl ester (AstaTech, Inc.) was used in place of palmitic acid in step 2 and the linker-lipid sequence was installed at position 11 instead of position 30. The crude linear peptide was purified and cyclized according to the modification described in Example 19, using a gradient of 20-70% B. Final product purification was performed using a gradient of 20-70% B (30 mpm) over 36 min.

Example 45 Synthesis of Cyclic PYY Analog SEQ ID NO: 45

The title compound was prepared according to the procedures described in Example 43, modified such that Fmoc-dPEG24-carboxylic acid was used in place of the tandem Fmoc-OEG-OH units and were, along with palmitic acid, incorporated into step 2. The linker-lipid sequence was installed at position 11 instead of position 30. The crude linear peptide was purified and cyclized according to the modification described in Example 19, using a gradient of 20-90% B. Final product purification was performed using a gradient of 20-90% B (30 mpm) over 36 min.

Example 46 Synthesis of Cyclic PYY Analog SEQ ID NO: 46

The title compound was prepared according to the procedures described in Example 9, using Fmoc-Lys(Pal-Glu-OtBu)-OH (from Active Peptide) in place of Leu at position 30. In addition, Fmoc-βAla-OH was appended onto the sequence at position 2, following step 1 using microwave conditions at 50° C. for 20 min, and coupling with bromoacetic anhydride was used in place of m-bromomethylbenzoic acid in step 2, using the modification described in Example 15. Solid The crude linear peptide was purified and cyclized according to the modification described in Example 19, using a gradient of 20-70% B. Final product purification was performed using a gradient of 20-70% B (30 mpm) over 36 min.

Example 47 Synthesis of Cyclic PYY Analog SEQ ID NO: 47

The title compound was prepared according to the procedures described in Example 44, installing the linker-lipid sequence at position 7 instead of position 11. Product purification was performed using a Varian Pursuit XRs C18 column (30×250 mm, 100 Å, 5 μm) at rt. The crude linear peptide was purified and cyclized according to the modification described in Example 19, using a gradient of 20-60% B. Final product purification was performed using a gradient of 20-60% B (30 mpm) over 36 min.

Example 48 Synthesis of Cyclic PYY Analog SEQ ID NO: 48

The title compound was prepared according to the procedures described in Example 43, using octadecanedioic acid, mono-tert-butyl ester (AstaTech, Inc.) in place of palmitic acid in step 2 with a coupling time of 30 min, and installing the linker-lipid sequence at position 22 instead of position 30. The crude linear peptide was purified and cyclized according to the modification described in Example 19, using a gradient of 20-70% B. Final product purification was performed using a gradient of 20-70% B (30 mpm) over 36 min.

Example 49 Synthesis of Cyclic PYY Analog SEQ ID NO: 49

The title compound was prepared following the procedures described in Example 11, substituting 16-tetrahydropyran-2-yloxypalmitic acid in place of ca-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 μm) at rt. The mobile phase consisted of a gradient elution of Buffer A (10 mM $NH_4OH$ in water, pH~9) and Buffer B (MeCN) ranging from an initial concentration of 20% B to an intermediate concentration of 10% B (100 mpm) over 5 min, and then to a final concentration of 30% B (100 mpm) over 40 min.

Example 50 Synthesis of Cyclic PYY Analog SEQ ID NO: 50

The title compound was prepared according to the procedures described in Example 48, and installing the linker-lipid sequence at position 23 instead of position 30.

Example 51 Synthesis of Cyclic PYY Analog SEQ ID NO: 51

The title compound was prepared according to the procedures described in Example 9, using Fmoc-Lys(Pal-Glu-OtBu)-OH (from Active Peptide) in place of Fmoc-Leu-OH at position 30 and Fmoc-Ser(tBu)-OH in place of Fmoc-Lys (Boc)-OH at position 4, in step 1. 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 μm) at rt. The mobile phase consisted of a gradient elution of Buffer A (10 mM $NH_4OH$ in water, pH~9) and Buffer B (MeCN) ranging from an initial concentration of 10% B to an intermediate concentration of 20% B (100 mpm) over 5 min, and then to a final concentration of 30% B (100 mpm) over 40 min. Impure fractions were re-chromatographed using a gradient comprised of an initial concentration of 10% B to an intermediate concentration of 20% B (100 mpm) over 5 min, and then to a final concentration of 30% B (100 mpm) over 60 min.

Example 52 Synthesis of Cyclic PYY Analog SEQ ID NO: 52

The title compound was prepared according to the procedures described in Example 43, using Fmoc-dPEG12-carboxylic acid in place of the tandem Fmoc-OEG-OH units and incorporating it along with Fmoc-Glu-OtBu and palmitic acid in step 2. The linker-lipid sequence was installed at position 11 instead of position 30. The crude linear peptide was purified and cyclized according to the modification described in Example 19, using a gradient of 20-70% B. Final product purification was performed using a gradient of 20-70% B (30 mpm) over 36 min.

Example 53 Synthesis of Cyclic PYY Analog SEQ ID NO: 53

The title compound was prepared according to the procedures described in Example 52, using four units of Fmoc-OEG-OH in tandem in place of Fmoc-dPEG12-carboxylic acid.

Example 54 Synthesis of Cyclic PYY Analog SEQ ID NO: 54

The title compound was prepared according to the procedures described in Example 53, installing two units of Fmoc-OEG-OH in tandem instead of two.

Example 55 Synthesis of Cyclic PYY Analog SEQ ID NO: 55

The title compound was prepared according to the procedures described in Example 43, installing the linker-lipid sequence at position 23 instead of position 30. The crude linear peptide was purified and cyclized according to the modification described in Example 19, using a gradient of 20-70% B. Final product purification was performed using a gradient of 20-70% B (30 mpm) over 36 min

Example 56: Synthesis of Cyclic PYY Analog SEQ ID NO: 56

The title compound was prepared using the methods described in Example 11, substituting (4'-chlorobiphenyl-4-yl)-acetic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 µm) at rt. The mobile phase consisted of a gradient elution of Buffer A (10 mM $NH_4OH$ in water, pH~9) and Buffer B (MeCN) ranging from 10-28% B (100 mpm) over 40 min.

Example 57: Synthesis of Cyclic PYY Analog SEQ ID NO: 57

The title compound was prepared following the procedures described in Example 11, substituting 3-[(2,4-dichlorophenoxy)phen-4-yl]propionic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 µm) at rt. The mobile phase consisted of a gradient elution of Buffer A (10 mM $NH_4OH$ in water, pH 9) and Buffer B (MeCN) ranging from 10-30% B (80 mpm) over 40 min. Product-containing fractions were combined, acidified with TFA, concentrated and re-chromatographed on an Agilent Polaris C18-A column (30×250 mm, 100 Å, 5 µm) at rt. The mobile phase consisted of a gradient elution of Buffer A (0.1% TFA in water) and Buffer B (0.1% TFA in MeCN) ranging from an initial concentration of 20% B to an intermediate concentration of 15% B (40 mpm) to a final concentration of 45% B (40 mpm) over 45 min.

Example 58: Synthesis of Cyclic PYY Analog SEQ ID NO: 58

The title compound was prepared following the procedures described in Example 11, substituting 11-(4-fluorophenyl}undecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 µm) at rt. The mobile phase consisted of a gradient elution of Buffer A (10 mM $NH_4OH$ in water, pH~9) and Buffer B (MeCN) ranging from 15-35% B (100 mpm) over 40 min.

Example 59: Synthesis of Cyclic PYY Analog SEQ ID NO: 59

The title compound was prepared according to the procedures described in Example 43, omitting step 2 and incorporating the palmitic acid coupling into step 1. The linker-lipid sequence was installed at position 22 instead of position 11. The crude linear peptide was purified and cyclized according to the modification described in Example 19, using a gradient of 20-70% B. Final product purification was performed using a gradient of 20-70% B (30 mpm) over 36 min

Example 60: Synthesis of Cyclic PYY Analog SEQ ID NO: 60

The title compound was prepared according to the procedures described in Example 53, incorporating two FMOC-OEG-OH units in tandem instead of four and installing linker-lipid sequence was at position 7 instead of position 11. The crude linear peptide was purified and cyclized according to the modification described in Example 19, using a gradient of 20-80% B. Final product purification was performed using a gradient of 20-80% B (30 mpm) over 36 min.

Example 61: Synthesis of Cyclic PYY Analog SEQ ID NO: 61

The title compound was prepared following the procedures described in Example 11, substituting 11-[(4-trifluoromethyl)phenyl]undecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 µm) at rt. The mobile phase consisted of a gradient elution of Buffer A (10 mM $NH_4OH$ in water, pH~9) and Buffer B (MeCN) ranging from 15-35% B (100 mpm) over 40 min.

Example 62: Synthesis of Cyclic PYY Analog SEQ ID NO: 62

The title compound was prepared following the procedures described in Example 11, substituting 11,11,11-trifluoroundecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/$H_2O$ was used as solvent in place of MeCN/$H_2O$ and sat'd aq. $NaHCO_3$ was used in place of the $NH_4OAc$ buffer in step 4 to effect cyclization. Product purification was performed using a Waters XBridge C18 OBD column (50×250 mm, 5 µm) at rt. The mobile phase consisted of a gradient elution of Buffer A (10 mM NH₄OH in water, pH~9) and Buffer B (MeCN) ranging from 10-28% B (100 mpm) over 40 min.

Example 63: Synthesis of Cyclic PYY Analog SEQ ID NO: 63

The title compound was prepared following the procedures described in Example 11, substituting 15,15,15-trifluoropentadecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H₂O was used as solvent in place of MeCN/H₂O and sat'd aq. NaHCO₃ was used in place of the NH₄OAc buffer in step 4 to effect cyclization. Product purification was performed using a Waters XBridge C18 OBD column (50×250 mm, 5 μm) at rt. The mobile phase consisted of a gradient elution of Buffer A (10 mM NH₄OH in water, pH~9) and Buffer B (MeCN) ranging from 15-30% B (100 mpm) over 40 min.

Example 64: Synthesis of Cyclic PYY Analog SEQ ID NO: 64

The title compound was prepared following the procedures described in Example 11, substituting 16-ethoxypalmitic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H₂O was used as solvent in place of MeCN/H₂O and sat'd aq. NaHCO₃ was used in place of the NH₄OAc buffer in step 4 to effect cyclization. Product purification was performed using a Waters XBridge C18 OBD column (50×250 mm, 5 μm) at rt. The mobile phase consisted of a gradient elution of Buffer A (10 mM NH₄OH in water, pH~9) and Buffer B (MeCN) ranging from 15-30% B (100 mpm) over 40 min.

Example 65: Synthesis of Cyclic PYY Analog SEQ ID NO: 65

The title compound was prepared following the procedures described in Example 11, substituting 13,13,14,14,15,15,16,16,16-D9-palmitic acid (Cambridge Isotopes) in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H₂O was used as solvent in place of MeCN/H₂O and sat'd aq. NaHCO₃ was used in place of the NH₄OAc buffer in step 4 to effect cyclization. Product purification was performed using a Waters XBridge C18 OBD column (50×250 mm, 5 μm) at rt. The mobile phase consisted of a gradient elution of Buffer A (10 mM NH₄OH in water, pH~9) and Buffer B (MeCN) ranging from 15-20% B (100 mpm) over 5 min, and then to 35% B (100 mpm) over 40 min.

Example 66: Synthesis of Cyclic PYY Analog SEQ ID NO: 66

The title compound was prepared following the procedures described in Example 11, substituting 11-[(2,4-bis(trifluoromethyl)phenyl]undecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H₂O was used as solvent in place of MeCN/H₂O and sat'd aq. NaHCO₃ was used in place of the NH₄OAc buffer in step 4 to effect cyclization. Product purification was performed using a Waters XBridge C18 OBD column (50×250 mm, 5 μm) at rt. The mobile phase consisted of a gradient elution of Buffer A (10 mM NH₄OH in water, pH 9) and Buffer B (MeCN) ranging from 15-35% B (100 mpm) over 40 min.

Example 67: Synthesis of Cyclic PYY Analog SEQ ID NO: 67

The title compound was prepared following the procedures described in Example 11, substituting 11-[(3,5-bis(trifluoromethyl)phenyl]undecanoic acid in place of α-Tocopheryloxyacetic Acid (AcVitE) (8) in step 2, and using m-chloromethylbenzoic acid in place of m-bromomethylbenzoic acid in step 4 (Example 9, step 2). 60% EtOH/H₂O was used as solvent in place of MeCN/H₂O and sat'd aq. NaHCO₃ was used in place of the NH₄OAc buffer in step 4 to effect cyclization. Product purification was performed using a Waters XBridge C18 OBD column (50×250 mm, 5 μm) at rt. The mobile phase consisted of a gradient elution of Buffer A (10 mM NH₄OH in water, pH 9) and Buffer B (MeCN) ranging 15-35% B (100 mpm) over 40 min.

Example 68: Synthesis of Cyclic PYY Analog SEQ ID NO: 68

1. Synthesis of (Fmoc)-βA-IKPEAPGEK(Alloc)ASPEELNRYYASLRHYLNCVTRQ(psi-R35Y36)-Sieber Resin Amino acid extensions onto the pre-loaded (psi-R35, Y36)-Sieber resin from Example 1, step 2 (0.1 mmol) were carried out at rt using DMF as solvent, a 6-fold excess of protected amino acids and an HATU/DIEA protocol (10 min, double coupling). A two-stage Fmoc deprotection protocol was used throughout (20% piperidine in DMF; rt; 10 min, 15 min).

2. Synthesis of (Fmoc)-βA-IKPEAPGEK((OEG)₂-γ-Glu-NHCO(CH₂)₁₆CO₂tBu)-ASPEELNRYYASL-RHYLNCVTRQ(psi-R35Y36)-Sieber Resin Deprotection of the above resin was carried out following the method described in Example 1, step 4, using modified reaction times of 10 min for each treatment. The resin was then coupled with intermediate 2 (15) (5 eq.), using an HATU/DIEA protocol in DMF (1 h, rt).

3. Synthesis of (BrAc)-βA-IKPEAPGEK((OEG)₂-γ-Glu-NHCO(CH₂)₁₆CO₂tBu)-ASPEELNRYYASL-RHYLNCVTRQ(psi-R35Y36)-Sieber Resin Following Fmoc deprotection (20% piperidine/DMF), the above resin was treated with bromoacetic anhydride (10 eq.; rt, 30 min) to provide the bromoacetylated resin.

4. Synthesis of (BrAc)-βA-IKPEAPGEK((OEG)₂-γ-Glu-NHCO(CH₂)₁₆CO₂tBu)-ASPEELNRYYASL-RHYLNCVTRQ(psi-R35Y36)-CONH₂

The above resin was treated with a cleavage cocktail consisting of TFA/H₂O/TIPS (95:2.5:2.5) for 1.5 h at rt. The crude peptide was precipitated with ether following the procedure described in Example 1, step 7.

5. Cyclic PYY Analog SEQ ID NO: 68

The crude peptide obtained above was dissolved at a concentration of 10 mg/mL in 10% MeCN/H₂O, and TEA was added to raise the solution pH to 8-9. After stirring at rt for ~20 min, TFA was added to lower the pH to 2, and the solution was purified directly by preparative HPLC on a Kinetics C18 Evo column (30×100 mm, 100 Å, 5 µm). The mobile phase consisted of gradient elution of Buffer A (0.1% TFA in water) and Buffer B (0.1% TFA in MeCN) ranging from 20-60% B over 22 min. UV detection was monitored at 220 and 254 nm. Pure fractions were combined, and then lyophilized to give the product as a cotton-like solid.

Example 69: Synthesis of Cyclic PYY Analog SEQ ID NO: 69

1. Synthesis of (Boc)-G-ISPEAPGEK(dde)AS-PEELNRYYASLRHYLNLE(OAllyl)TRQ(psi-R35Y36)-Sieber Resin Amino acid extensions onto the pre-loaded (psi-R35, Y36)-Sieber resin from Example 1, step 2 (0.1 mmol) were carried out at rt using DMF as solvent, a 6-fold excess of protected amino acids and an HATU/NMM protocol (10 min, double coupling). A two-stage Fmoc deprotection protocol was used throughout (20% piperidine in DMF; rt; 10 min, 15 min).

2. Synthesis of (Boc)-G-ISPEAPGEK(dde)AS-PEELNRYYASLRHYLNLE(NHS)TRQ(psi-R35Y36)-Sieber Resin Alloc-deprotection of the above resin was carried out following the method described in Example 1, step 4, using modified reaction times of 10 min for each treatment. The resin was then coupled with NHS (10 eq.), using an HATU/DIEA protocol in DMF (1 h, rt, double coupling).

3. Synthesis of (NH$_2$)-G-ISPEAPGEK(dde)AS-PEELNRYYASLRHYLNLE(NHS)TRQ(psi-R35Y36)

The above resin was treated with a cleavage cocktail consisting of TFA/H$_2$O/TIPS (95:2.5:2.5) for 1.5 h at rt. The crude peptide was precipitated with ether following the procedure described in Example 1, step 7.

4. Cyclic PYY Analog SEQ ID NO: 69

The crude peptide obtained above was dissolved at a concentration of 80 mg/mL in DMSO, and TEA (25 eq.) was added to effect lactamization. After stirring at rt for ~30 min, the reaction was diluted 10-fold with 10% MeCN/water, the pH adjusted to 2 and the crude peptide purified directly by preparative HPLC on a Kinetics C18 Evo column (30×100 mm, 100 Å, 5 µm). The mobile phase consisted of gradient of Buffer A (0.1% TFA in water) and Buffer B (0.1% TFA in MeCN) ranging from 10-60% B over 22 min. UV detection was monitored at 220 and 254 nm. Pure fractions were combined, and then lyophilized to give the K(Dde)-protected peptide. The Dde protecting group was removed using 2% hydrazine/DMF (10 mg peptide/ml), 30 mins at rt. The reaction was diluted 10-fold with 10% MeCN/water, and the pH was adjusted to 2 with TFA and the crude peptide solution was purified as above to give the product as a cotton-like solid.

Example 70: Synthesis of Cyclic PYY Analog SEQ ID NO: 70

The title compound was prepared according to the procedure in Example 69, substituting Fmoc-E(OAll)-OH for Fmoc-Leu-OH at position 30 and substituting Fmoc-Val-OH for Fmoc-E(OAll)-OH in position 31.

Example 71: Synthesis of Cyclic PYY Analog SEQ ID NO: 71

1. Synthesis of (Boc)-G-ISPEAPGEK(dde)AS-PEELNRYYASLRHYLN E(OAllyl)VTRQ(N-Me-R)Y-NovaSyn TGR Resin Amino acid extensions onto a NovaSyn TGR resin (0.1 mmol) were carried out using the procedure described in Example 69, step 1.

2. Cyclic PYY Analog SEQ ID NO: 71

The title compound was prepared from the above resin according to the procedures described in Example 69, steps 2-4.

Example 72: Synthesis of Cyclic PYY Analog SEQ ID NO: 72

1. Synthesis of (S)-22-(tert-butoxycarbonyl)-43,43-dimethyl-10,19,24,41-tetraoxo-3,6,12,15,42-pentaoxa-9,18,23-triazatetratetracontan-1-oic N-hydroxysuccinimide ester To a solution of (S)-22-(tert-butoxycarbonyl)-43,43-dimethyl-10,19,24,41-tetraoxo-3,6,12, 15,42-pentaoxa-9,18,23-triazatetratetracontan-1-oic acid (Intermediate 2 (16)) (54.0 mg, 0.063 mmol), N-hydroxysuccinimide (14.6 mg, 0.127 mmol), and HATU (24.1 mg, 0.063 mmol) in 1.0 ml of DMF was added DIEA (0.022 ml, 0.127 mmol) and the mixture stirred for 30 mins at RT and used directly in the next step without further purification.

2. Synthesis of Cyclic PYY Analog SEQ ID NO: 72

To a solution of [cyclo-(G2-E30), S4, K11, psi-(R35, Y36)]-PYY$_{2-36}$ (prepared in Example 70) (4 mg, 0.96 µmol) in DMF (0.2 mL) was added 24 µL of the N-hydroxy ester solution (prepared in Step 1), and TEA (0.66 µL; 5 eq) and the mixture stirred overnight at rt. The reaction was diluted 10-fold with 10% MeCN/water, the pH adjusted to 2 with TFA and the crude peptide purified directly by preparative HPLC on a Kinetics C18 Evo column (30×100 mm, 100 Å, 5 µm). The mobile phase consisted of gradient elution of Buffer A (0.1% TFA in water) and Buffer B (0.1% TFA in MeCN) ranging from 10-60% B over 22 min. UV detection was monitored at 220 and 254 nm. Pure fractions were combined, and then lyophilized to give the t-butyl ester-protected peptide. The t-butyl ester protecting groups were removed using a mixture of TFA/H$_2$O/TIPS (95:2.5:2.5) for 1.5 h at rt. The mixture was concentrated and the peptide purified as above to give the product as a cotton-like solid.

Example 73: Synthesis of Cyclic PYY Analog SEQ ID NO: 73

The title compound was prepared according to the procedure as described in Example 1 substituting N-Fmoc-dPEG6-carboxylic acid for N-Fmoc-dPEG12-carboxylic acid in step 5.

Example 74: Synthesis of Cyclic PYY Analog SEQ ID NO: 74

The title compound was prepared according to the procedure as described in Example 1 but skipping the PEG linker coupling step 5.

Example 75: Synthesis of Cyclic PYY Analog SEQ ID NO: 75

The title compound was prepared according to the procedure as described in Example 1 substituting Fmoc-C(trt)-OH for Fmoc-hC(trt)-OH at position 31, and skipping the Fmoc-βA-OH coupling step in step 3.

Example 76: Synthesis of Cyclic PYY Analog SEQ ID NO: 76

The title compound was prepared according to the procedure as described in Example 1 with modified step 3 and step 4. In step A, Fmoc-K(Alloc)-OH and Fmoc-K(dde)-OH were used for position 30 and position 11, respectively. After Alloc at position at 30 was deprotected with $Pd(PPh_3)_4$-phenylsilane, mPEG16-carboxylic acid was coupled with HATU-DIPEA. In step 4, dde at position 11 was removed with 2% hydrazine in DMF.

Example 77: Synthesis of Cyclic PYY Analog SEQ ID NO: 77

The title compound was prepared according to the procedure as described in Example 76 substituting mPEG12-carboxylic acid for mPEG16-carboxylic acid in step A, and skipping the Fmoc-dPEG12-carboxylic acid coupling step in step 5.

Example 78: Synthesis of Cyclic PYY Analog SEQ ID NO: 78

The title compound was prepared according to the procedure as described in Example 1 substituting Fmoc-N-Me-Q(trt)-OH for Fmoc-Q(trt)-OH in step 3.

Example 79: Synthesis of Cyclic PYY Analog SEQ ID NO: 79

The title compound was prepared according to the procedure as described in Example 1 substituting Fmoc-N-Me-R(pbf)-OH for Fmoc-R(pbf)-OH in step 1B.

Example 80: Synthesis of Cyclic PYY Analog SEQ ID NO: 80

The title compound was prepared according to the procedure as described in Example 79 substituting Fmoc-R(pbf)-OH for Fmoc-K(Boc)-OH at position 4, and substituting Fmoc-W(Boc)-OH for Fmoc-L-OH at position 30 in step 3.

Example 81: Synthesis of Cyclic PYY Analog SEQ ID NO: 81

The title compound was prepared according to the procedure as described in Example 80 substituting Fmoc-C(trt)-OH for Fmoc-hC(trt)-OH at position 31, and substituting Fmoc-γ-aminobutanoic acid for Fmoc-βA-OH in step 3.

Example 82: Synthesis of Cyclic PYY Analog SEQ ID NO: 82

The title compound was prepared according to the procedure as described in Example 1 substituting Fmoc-PEG2-carboxylic acid for Fmoc-βA-OH and Fmoc-C(trt)-OH for Fmoc-hC(trt)-OH at position 31 as well as skipping the coupling of Fmoc-Ile-OH in step 3.

Example 83: Synthesis of Cyclic PYY Analog SEQ ID NO: 83

The title compound was prepared according to the procedure as described in Example 1 substituting Fmoc-K(N3)-OH for Fmoc-hC(trt)-OH at position 31, substituting pent-4-ynoic acid for Fmoc-βA-OH in step 3, and following the cyclization procedure B as below.

Cyclization procedure B: To a solution of fully deprotected peptide with PEG12-AcBr installed at position 11 (38 mg, 0.0067 mmol) in 2 mL of HEPES (pH 7.4) was added 1.7 mL of the premixed $CuSO_4$/TBTA solution (the solution was prepared by mixing a solution of 2.2 mg of $CuSO_4$ in water (0.4 mL) with a solution of 11 mg of TBTA in EtOH), followed by addition of 7 mg of sodium ascorbate in water (1 mL). The clear reaction solution was left mixing at room temperature and monitored by HPLC. After 30 min, the reaction was completed, and the reaction mixture was adjusted to pH 4 using TFA and subjected to HPLC purification (Pursuit XRS 5 250×30 mm C18 column, running @ 30 mpm flow, monitoring 214 nM wavelength, with a gradient ranging from 20-60% ACN-water/water both with 0.1% TFA over 36 minutes). The desired fraction was collected and lyophilized.

Example 84: Synthesis of Cyclic PYY Analog SEQ ID NO: 84

The title compound was prepared according to the procedure as described in Example 1 skipping the Fmoc-βA-OH coupling step, substituting N3-PEG8-carboxylic acid for Fmoc-dPEG12-carboxylic acid in step 5, and substituting 3-(bromomethyl)benzoic acid coupling with DIC for bromoacetic anhydride acylation in step 3, and following the cyclization procedure C as below.

Cyclization procedure C: To a solution of fully deprotected peptide (20 mg, 0.0035 mmol) in 5 mL of degassed water, aq. $NaHCO_3$ solution was added to adjust the reaction mixture to pH 6.4 or higher. After 20 min, the LCMS indicated the reaction was complete, and the reaction mixture was adjusted to pH 4 using TFA and subjected to HPLC purification (Pursuit XRS 5 250×30 mm C18 column, running @ 30 mpm flow, monitoring 214 nM wavelength, with a gradient ranging from 10-60% ACN-water/water both with 0.1% TFA over 36 minutes). The desired fraction was collected and lyophilized.

After the cyclization, the cyclized intermediate was subjected to linker extension by click chemistry following the cyclization procedure B with N-(1-bromo-2-oxo-7,10,13-trioxa-3-azahexadecan-16-yl)pent-4-ynamide, which was prepared by coupling of N-Boc-PEG4-NH2 with pent-4-ynoic acid using HATU-DIPEA, followed by deprotection of Boc with TFA and acylation with bromoacetic anhydride in the presence of TEA.

Example 85: Synthesis of Cyclic PYY Analog SEQ ID NO: 85

The title compound was prepared according to the procedure as described in Example 1 with PEG12-AcBr linker installed at position 23 instead of position 11.

Example 86: Synthesis of Cyclic PYY Analog SEQ ID NO: 86

The title compound was prepared according to the procedure as described in Example 1 with PEG12-AcBr linker installed at position 22 instead of position 11.

Example 87: Synthesis of Cyclic PYY Analog SEQ ID NO: 87

The title compound was prepared according to the procedure as described in Example 1 with PEG12-AcBr linker installed at position 7 instead of position 11.

Example 88: Synthesis of Cyclic PYY Analog SEQ ID NO: 88

The title compound was prepared according to the procedure as described in Example 1 substituting Fmoc-V—OH for Fmoc-hC(trt)-OH at position 31, substituting Fmoc-C(trt)-OH for Fmoc-L-OH at position 30, and substituting Fmoc-G-OH for Fmoc-βA-OH in step 3.

Example 89: Synthesis of Cyclic PYY Analog SEQ ID NO: 89

The title compound was prepared according to the procedure as described in Example 88 skipping step 1 to make the reduced dipeptide, and substituting Fmoc-Y(tBu)-OH loading followed by coupling with Fmoc-(N-Me)R—OH for Fmoc-psi-(R35-N(Boc)-Y36)-OH loading in step 2.

Example 90: Synthesis of Cyclic PYY Analog SEQ ID NO: 90

The title compound was prepared according to the procedure as described in Example 89 substituting Fmoc-βA-OH for Fmoc-G-OH in step 3.

Example 91: Synthesis of Cyclic PYY Analog SEQ ID NO: 91

The title compound was prepared according to the procedure as described in Example 89 substituting Fmoc-hC(trt)-OH for Fmoc-C(trt)-OH at position 30 in step 3.

Example 92: Synthesis of Cyclic PYY Analog SEQ ID NO: 92

The title compound was prepared according to the procedure as described in Example 90 substituting Fmoc-hC(trt)-OH for Fmoc-V—OH at position 31, and substituting Fmoc-L-OH for Fmoc-C(trt)-OH at position 30 in step 3.

Example 93: Synthesis of Cyclic PYY Analog SEQ ID NO: 93

The title compound was prepared according to the procedure as described in Example 1 substituting Fmoc-V—OH for Fmoc-hC(trt)-OH at position 31, substituting Fmoc-C(trt)-OH for Fmoc-L-OH at position 30, and substituting Fmoc-G-OH for Fmoc-βA-OH at the N-terminus in step 3.

Example 94: Synthesis of Cyclic PYY Analog SEQ ID NO: 94

The title compound was prepared according to the procedure as described in Example 1 substituting Fmoc-V—OH for Fmoc-hC(trt)-OH at position 31 and substituting Fmoc-C(trt)-OH for Fmoc-L-OH at position 30 in step 3.

Example 95: Synthesis of Cyclic PYY Analog SEQ ID NO: 95

The title compound was prepared (0.05 mmol scale) according to the procedures as described in Example 1 substituting Fmoc-V—OH for Fmoc-hC(trt)-OH at position 31, substituting Fmoc-Glu(OAlloc)-OH for Fmoc-L-OH at position 30, substituting Fmoc-Lys(dde)-OH for Fmoc-Lys(Alloc)-OH at position 11, substituting Fmoc-Ser(tBu)-OH for Fmoc-K(Boc)-OH in position 4 and substituting Boc-G-OH for Fmoc-βA-OH at the N-terminus in step 3.

To the resulting resin from above was added deoxygenated DCM (10 mL), phenylsilane (10 eq.) and a solution of the Pd(PPh3)4 (0.2 eq.) in DCM (1 mL) and the mixture was stirred for 10 mins. The reaction was drained and the resin was washed with deoxygenated DCM and the deprotection was repeated one time.

To the resulting resin from above was added DMF (10 ml), HATU (5 eq), and DIEA (10 eq) and the mixture stirred for 5 mins then a solution of N-hydroxysuccinimide (10 eq) in DMF was added and stirred for an additional 20 mins. The resin was filtered and the procedure repeated one time.

The resin from above was deprotected for 2 hrs at RT in TFA/TIPS/water (95/2.5/2.5)(10 ml). The cleavage cocktail was concentrated to approx. 1 ml and then added to 40 ml of ether. The resulting precipitate was collected by centrifugation and dried under N2.

The resulting material from above was dissolved in 9 mL of DMSO to which 10 eq of TEA was added and the reaction allowed to proceed for 3 hrs at RT. The resulting solution was diluted to 30 ml with water, the pH adjusted to 2 and purified by RP-HPLC on a 30 mm×250 mm C18 column eluting with a linear gradient of 20-40% ACN in water (0.1% TFA) in 30 mins. The fractions containing product were lyophilized.

The resulting material from above was then treated with 1-2% hydrazine/DMF (1 mL) to remove the Dde from lysine. The resulting mixture was diluted to 10 ml with water, the pH adjusted to 2 and then purified by RP-HPLC as above.

The resulting product was then dissolved in 10% ACN/water, the pH adjusted to 10, and a solution of bromoacetic N-hydroxysuccinimide ester (3 eq of 0.1M/DMF soln) was added and the reaction allowed to proceed for 10 mins at RT. The resulting mixture was diluted to 10 ml with water, the pH adjusted to 2 and then purified by RP-HPLC as above to give the title product.

Example 96: Synthesis of Cyclic PYY Analog SEQ ID NO: 96

The title compound was prepared according to the procedure as described in Example 1 substituting N-Fmoc-dPEG24-carboxylic acid for N-Fmoc-dPEG12-carboxylic acid in step 5.

Example 97: Synthesis of Cyclic PYY Analog SEQ ID NO: 97

The title compound was prepared according to the procedure as described in Example 1 substituting Fmoc-G-OH for Fmoc-βA-OH in step 3.

Example 98: Synthesis of Cyclic PYY Analog SEQ ID NO: 98

The title compound was prepared according to the procedure as described in Example 89 but skipping the Fmoc-dPEG12-carboxylic acid coupling step in step 5.

Example 99: Synthesis of Cyclic PYY Analog SEQ ID NO: 99

The title compound was prepared according to the procedure as described in Example 90 but skipping the Fmoc-dPEG12-carboxylic acid coupling step in step 5.

Example 100: Synthesis of Cyclic PYY Analog SEQ ID NO: 100

The title compound was prepared according to the procedure as described in Example 94 but skipping the Fmoc-dPEG12-carboxylic acid coupling step in step 5.

Example 101: Identification and Production of mAb MSCB97

Selection of PH9L3 VL and PH9H5 VH as Starting V Regions for Engineering

The antibody light chain variable region (VL) designated PH9L3 (SEQ ID NO: 128) (Teplyakov et al., "Structural diversity in a human antibody germline library," mAbs August-September 8(6): 1045-63 (2016)) and the antibody heavy chain variable region (VH) designated PH9H5 (SEQ ID NO: 129) (Teplyakov et al., "Structural diversity in a human antibody germline library," mAbs August-September 8(6):1045-63 (2016)) were selected as the starting variable regions from which to engineer a mAb enabled for peptide conjugation. PH9L3 is comprised completely of human Ig germline V gene sequences and as such does not contain any sequence mutations from the in vivo affinity maturation process that would result in high affinity, antigen-specific binding. The CDR3 of PH9H5 is the only segment not comprised of human germline V gene sequences in that VH. CDR3 of PH9H5 is from an anti-human CCL2 antibody, CNTO 888 and is provided by SEQ ID NO: 130. A Fab containing the PH9H5/PH9L3 VH/VL pair was generated.

The PH9L3, PH9H5 and the human Ig germline V-region and J-region sequences to which these are most similar were aligned to determine sequence identity or similarity to the germline sequences. PH9H5 was aligned to a concatenation (SEQ ID NO:131) of human Ig germline genes IGHV3-23*01 (PubMed ID: M99660) (SEQ ID NO:132) and human IGHJ1*01 (PubMed ID: J00256) (SEQ ID NO:133), with the only difference between the PH9H5 amino acid sequence and the concatenated human IGHV3-23*01-IGHJ1*01 sequence being at VH CDR3, which was SEQ ID NO:130 for PH9H5.

PH9L3 was aligned to a concatenation (SEQ ID NO:134) of human Ig germline genes IGKV3-11*01 (PubMed ID: X01668) (SEQ ID NO:135) and IGKJ1*01 (PubMed ID: J00242) (SEQ ID NO: 136), with the only difference being one deviation in the V gene/J gene junction.

Design and Generation of Cys Substituted Variants of PH9H5 and PH9L3

Variants of the PH9H5 VH that contain a single Cys substitution at select CDR residues across all three CDRs of the V region were designed, generated and cloned as complete heavy chains with a human IgG1 constant region into a mammalian host expression vector. The PH9H5/PH9L3 Fab structure was utilized to aid in selection of CDR residues for substitution that appear more accessible for conjugation and in some of the variants, additional glycine (Gly) residues were inserted on either side of the introduced Cys residue to potentially increase accessibility of the Cys for conjugation.

Similar variants of the PH9L3 VL were designed and generated except these were cloned as complete light chains with a human kappa constant region into the expression vector.

A total of 24 expression constructs of PH9H5 single Cys variants and 22 expression constructs of PH9L3 single Cys variants were generated. The residues selected for substitution within PH9H5_VH (SEQ ID NO: 129) and within PH9L3_VL (SEQ ID NO: 128) are summarized in FIG. 2.

The expression constructs generated were used to express the Cys variants by transiently co-transfecting each PH9H5 based HC Cys variant construct with the wild type PH9L3 LC construct or co-transfecting each PH9L3 based LC Cys variant construct with the wild type PH9H5 HC construct. Initial test transfections used HEK-derived Expi293 as expression host and were at 20 ml scale. The majority of both HC and LC Cys variants expressed well based on variant protein quantitation from culture supernatant.

Five initial HC Cys variants, MSCB33-MSCB37, were expressed in Expi293 at 750 ml scale and variant proteins purified. The purification yield and quality properties of the purified variants were fairly similar and sufficient for using the purified proteins in initial peptide conjugation reactions.

Evaluation of Peptide Conjugation to PH9H5-Based HC Cys Variants

Analytical mass determination of MSCB33 protein and other variant proteins indicated the presence of cysteine adducts at the Cys engineered for conjugation, with two per mAb, as well as removal of the HC C-terminal Lys residue, which is commonly seen in recombinantly produced mAbs. To prepare the variant mAbs for conjugation, adducts were removed by a reduction process developed to maintain the native disulfide bonds within the mAb (see Example 103). Initial test conjugations with a human oxyntomodulin (OXM) peptide analogue (GCG Aib2, Glu16,24, Arg20, Leu27, Lys30-ε-(PEG12)-NH$_2$) were done using maleimide chemistry on all five HC Cys variant mAbs. Conjugation efficiency differed between mAb variants, which was qualitatively estimated by the conjugation reaction products and the relative percentage of each. Greatest efficiency, as measured by greatest percentage of homodimer product, was observed with MSCB33, as compared to the other I102C variants containing flanking Gly residues, and little or no conjugation was observed with the Y103C variants MSCB35 or MSCB37.

Several other HC and LC Cys variants, with engineered cysteine substitutions in various CDRs (a T28C, S30C, and S54C substitution in PH9H5_VH (SEQ ID NO: 129), and an S30C and S92C substitution in PHpL3_VL (SEQ ID NO: 128)) were expressed at large scale in Expi293. Removal of the Cys adducts from these purified proteins by reduction was challenging and these variants were not pursued further. Due to the challenges observed with most of the Cys variants and the initial good conjugation efficiency observed with the I102C PH9H5 variant mAb, MSCB33, process development and further engineering efforts focused on this particular variant.

Fc Engineering of MSCB33

MSCB33 was re-engineered to contain the silent, human IgG4_PAA Fc to reduce Fc function in vivo. Human IgG4_PAA has mutations S228P/F234A/L235A on the human IgG4 allotype nG4m(a) (based on IGHG4*01 allele as defined in IMGT). An expression construct with the VH of MSCB33 fused to the IgG4_PAA Fc was generated and used together with the same LC expression construct used for MSCB33 expression to produce the IgG4_PAA variant of MSCB33, which is designated MSCB97. The amino acid sequences of MSCB97 VH, HC, VL, and LC are provided by SEQ ID NO: 137, 138, 139, and 140, respectively.

Test expression of MSCB97 was done transiently at 20 ml scale in Expi293 cells and this mAb variant expressed well. MSCB97 was purified from a large scale, Expi293 expression run. The purification yield of MSCB97 was 264.53 mg/L, and the quality was determined at 85% monomer species. Subsequent large scale expression runs and purifications were similar or better in yield and quality and indicated the consistency with which this mAb could be produced.

Evaluation of Peptide Conjugation to MSCB97 and Conjugation Reaction Scalability The LC-HC disulfide connectivity differs between the IgG1 and IgG4 isotypes, so the reduction and maleimide conjugation was tested and confirmed to be translatable from the IgG1 mAb MSCB33 to the IgG4_PAA mAb MSCB97 using TCEP reduction and conjugation of the OXM-maleimide test peptide described above. The linkage resulting from maleimide conjugation is known to be potentially reversible, so bromoacetamide conjugation chemistry, which produces a more stable linkage, was adopted and implemented successfully on a 10 mg scale based on starting MSCB97.

The MSCB97 conjugate of the OXM analogue GCG Aib2, Glu16,24, Arg20, Leu27, Lys30-ε-(PEG12)-NH$_2$ (MSCB97-OXM1) generated through bromoacetamide chemistry was assayed to determine in vitro GLP-1R and GCGR potencies. Potencies relative to reference peptides and reference unstructured polypeptide conjugates were reasonable and similar to that of the conjugate generated with the same peptide to MSCB33 (IgG1). This demonstrated that the single difference between MSCB97 (IgG4_PAA) and MSCB33 (IgG1), which is isotype, had no impact on the potency of conjugates containing the same peptide. Additionally, these data showed that desirable in vitro potencies could be retained in a peptide-mAb conjugate generated with bromoacetamide chemistry that produces a linkage that is stable in vivo. Other OXM analogues were also conjugated to MSCB97 and in vitro potencies of these conjugates assayed. These conjugates had similar GLP-1R and GCGR potencies to MSCB97-OXM1, highlighting the ability to conjugate a variety of peptides to MSCB97, while retaining peptide potency.

Evaluation of Peptide-MSCB97 Conjugate Binding to Human CCL2

While MSCB97 was selected and engineered for lack of specific antigen binding, the most likely antigen that this mAb might bind, if any, is human CCL2 based on the origin of the VH CDR3. Whether MSCB97 does demonstrate any specific CCL2 binding was evaluated using two peptide-MSCB97 conjugates, with an OXM peptide analogue or a PYY peptide analogue.

Potential CCL2 binding was directly measured by surface plasmon resonance (SPR) in which the conjugates were surface-immobilized using an anti-Fc capture method. A commercially available anti-CCL2 mouse mAb served as a positive control and two non-specific human antibodies, CNTO 9412 and HH3B33, served as negative controls. All controls were similarly surface-immobilized and recombinant human CCL2 was flowed over immobilized conjugates and controls at concentrations up to 400 nM. Based on the pre-established assay criteria, CCL2 accumulation, indicating specific antigen binding, was seen with the positive control but not with the negative controls nor with either peptide-MSCB97 conjugate. This confirmed that MSCB97, in the relevant therapeutic form of a peptide-mAb conjugate, lacks human CCL2 binding.

Example 102: Expression and Purification of the mAb

The fully human monoclonal antibody (mAb) can be recombinantly expressed in a mammalian expression host and purified from the cell culture supernatant using standard methods that are known in the field. For example, a cDNA sequence encoding the light (LC) and heavy chains (HC) of the mAb, each including an appropriate signal peptide to enable secretion, can be cloned into separate mammalian expression vectors or into a single expression vector using standard molecular biology methods. Expression vectors used can be any of those commercially available such as pEE12.4, pcDNA™3.1(+) or pIRESpuro3 or any custom expression vector with similar functionalities. In such vectors transcription of the heavy and light chains of the mAb are each driven by any of the known effective promoters such as the hCMV-MIE promoter. Transfection grade plasmid DNA is prepared for separate LC and HC expression constructs or a single construct expressing both LC and HC using standard methods such as a QIAGEN Plasmid Midi Kit.

Purified plasmid DNA is prepared for transfection with a lipid-based transfection reagent such as Freestyle™ Max transfection reagent, following manufacturer's instructions, and is then transfected into a standard mammalian expression host cell line, such as CHO-S or HEK 293-F. If the mAb LC and HC are encoded by separate expression constructs, the two constructs are simultaneously transfected. Prior to and after transfection, mammalian cells are cultured for maintenance or for mAb expression following standard cell culture methods whereby the cell density ranges to maintain, the culture media to use, and the other cell culture conditions followed are determined by the specific mammalian host cell line utilized. These parameters are typically documented by the vendor from which the cell line was obtained or in the scientific literature. For example, CHO-S cells are maintained in CHO Freestyle™ media in suspension, shaking at 125 RPM in a humidified incubator set at 37° C. and 8% $CO_2$, and split when the cell concentration is between 1.5 and $2.0 \times 10^6$ cells per ml.

Cell culture supernatants from the transiently transfected mammalian cells expressing the mAb are harvested several days after transfection, clarified by centrifugation and filtered. Duration of expression for CHO-S cells is typically four days but can be adjusted and can differ for different mammalian host cell lines. Large scale transfections (>10 liters) are concentrated 10-fold using a concentrator such as a Centramate. The mAb is purified from the clarified supernatant using a Protein A affinity column such as the HiTrap MabSelect Sure utilizing standard methods for binding mAb to Protein A resin, washing the resin and eluting the protein using low pH buffer. The protein fractions are neutralized immediately by elution into tubes containing pH 7 buffer and peak fractions are pooled, filtered and dialyzed against phosphate buffered saline (PBS), pH 7.2 overnight at 4° C. After dialysis the mAb is filtered again (0.2μ filter) and the protein concentration is determined by absorbance at 280 nm. Quality of the purified mAb protein is assessed by SDS-polyacrylamide gel electrophoresis (PAGE) and analytical size exclusion HPLC and endotoxin levels are measured using a limulus amebocyte lysate (LAL) assay. Purified mAb is stored at 4° C.

Expression and Purification of MSCB97 from Transiently Transfected CHO Cells

MSCB97 was expressed in ExpiCHO-S™ cells (ThermoFisher Scientific, Waltham, Mass.; Cat # A29127) by transient transfection of the cells with purified plasmid DNA of a MSCB97 expression construct following manufacturer's recommendations. Briefly, ExpiCHO-S™ cells were maintained in suspension in ExpiCHO™ expression medium (ThermoFisher Scientific, Cat # A29100) in a shaking incubator set at 37° C., 8% $CO_2$ and 125 RPM. The cells were passaged so that on the day of transfection, dilution down to $6.0 \times 10^6$ cells per ml could be achieved, maintaining cell viability at 98% or better. Transient transfections were done using the ExpiFectamine™ CHO transfection kit (ThermoFisher Scientific Cat # A29131). For each ml of diluted cells to be transfected, one microgram of plasmid DNA is used and diluted into OptiPRO™ SFM complexation medium. ExpiFectamine™ CHO reagent is used at a 1:3 ratio (v/v, DNA:reagent) and also diluted into OptiPRO™. The diluted DNA and transfection reagent were combined for one minute, allowing DNA/lipid complex formation, and then added to the cells. After overnight incubation, ExpiCHO™ feed and ExpiFectamine™ CHO enhancer were added to the cells. Cells were cultured with shaking at 32° C. for five days prior to harvesting the culture supernatants.

Culture supernatants from the transiently transfected ExpiCHO-S™ cells were harvested by clarifying through centrifugation (30 min, 6000 rpm) followed by filtration (0.24 PES membrane, Corning). Large scale transfections (5 to 20 liters) were first concentrated 10-fold using a Pall Centramate Tangential Flow Filtration system. 10×DPBS (Dulbecco's phosphate buffered saline), pH7.2 was added to the supernatant to 1× final concentration prior to loading onto an equilibrated (DPBS, pH 7.2) HiTrap MabSelect Sure Protein A column (GE Healthcare; Little Chalfont, United Kingdom) at a relative concentration of ~20 mg protein per ml of resin, using an AKTA FPLC chromatography system. After loading, the column was washed with 10 column volumes of DPBS, pH7.2. The protein was eluted with 10 column volumes of 0.1 M Na-Acetate, pH 3.5. Protein fractions were neutralized immediately by elution into tubes containing 2.0 M Tris, pH 7 at 20% the elution fraction volume. Peak fractions were pooled and the pH adjusted to ~5.5 with additional Tris, if necessary. The purified protein was filtered (0.2μ) and the concentration was determined by absorbance at 280 nm on a BioTek SynergyHT™ spectrophotometer. The quality of the purified protein was assessed by SDS-PAGE and analytical size exclusion HPLC (Dionex HPLC system). The endotoxin level was measured using a turbidometric LAL assay (Pyrotell®-T, Associates of Cape Cod).

Example 103: Conjugation of mAb and Cyclic PYY Analog

Method A: Partial Reduction of mAb with TCEP

A 10 mg/mL solution of mAb in tris-acetate buffer (20 mL, 1 mM in EDTA) was treated with 3 equivalents of TCEP. The solution was adjusted to pH 6 and after 1 hr at rt high pressure liquid chromatography with mass spectrometer (LCMS) showed that the disulfide adducts at position C102 had been completely reduced. The reduced mAb was purified by protein A adsorption and elution (4 CV 100 mM acetic acid) to provide 180 mg of reduced mAb.

Conjugation of Reduced mAb and Cyclic PYY Analog

Lyophilized peptide (5 eq vs mAb) was added to the reduced mAb described above. EDTA was added to a final concentration of 1 mM and the pH was adjusted to 7.

The concentration was adjusted to 8 mg/mL and the reaction was allowed to proceed with gentle agitation for 16 h at rt. TCEP (0.5 eq vs mAb) was added and the reaction was allowed to proceed further for 4 hr at rt with gentle agitation, after which time the high molecular weight (MW) species were reduced to less than 3%.

The reaction mixture was adjusted to pH 5.5 and purified by ion exchange chromatography on CaptoSP resin using a gradient 100% A (100 mM TRIS-acetate, pH 5.5) to 100% B (100 mM TRIS-acetate, pH 5.5; 0.5 M NaCl) over 20 CV. Fractions containing the desired conjugate were pooled and 140 mg of conjugate were recovered, coeluting with a small amount of unreacted peptide. Final purification was by protein A adsorption and elution (4 CV 100 mM acetic acid). The pH of the product was adjusted to 6 to give 120 mg of conjugate (60% yield) at >90% purity with <3% high MW species.

Method B

Hydrophobic Interaction Chromatography (HIC) Purification of mAb

A 20 mg/mL solution of mAb in tris-acetate buffer was loaded on a hydrophobic interaction column (TOSOH TSKgel phenyl 7.5×21 cm) and eluted with a linear gradient (0-70% B/A, solvent A: 5% iPrOH, 1M $(NH_4)_2SO_4$, 100 mM phosphate buffer, pH 6.0; solvent B: 20% iPrOH, 100 mM phosphate buffer). The mAb monomer peaks were pooled, concentrated (5-10 mg/mL) and dialyzed against 3-(N-morpholino) propanesulfonic acid (MOPS) buffer (100 mM, pH 5.5).

Partial Reduction with TCEP and Conjugation of Reduced mAb with Cyclic PYY Analog To the purified mAb (27 mL, 9.28 mg/mL) was added 4 eq. TCEP followed by EDTA (1 mM). After 2 hr at room temperature LCMS showed that the disulfide adducts at position C102 had been completely reduced. The reduced mAb was treated with Zebra desalting spin column (7×10 mL, 7K MWCO, pre-equilibrium with MOPS 100 mM pH 5.5) to remove the liberated cysteines/GSH. To the combined fractions of the reduced mAb (28 mL) was added a solution of PYY peptide in Milli Q grade water (6.5 eq vs mAb, 15-20 mg/mL) followed by EDTA (1 mM). The pH of the reaction was adjusted to 7.2 to 7.4 by dropwise addition of 1N NaOH. The reaction was allowed to proceed 18 h at room temperature with gentle agitation. The reaction was continued for another 12 h after addition of a further 0.5 equiv TCEP to reduce mAb-mAb dimer formed during the course of the reaction and allow conversion to the desired mAb homodimer. The pH of the reaction was lowered to pH 5.5 by addition of 2 M acetic acid and the crude conjugate was purified by hydrophobic interaction chromatography and eluted with a linear gradient (0-100% B/A, solvent A: 5% iPrOH, 1M (NH4)2SO4, 100 mM phosphate buffer, pH 6.0; solvent B: 20% iPrOH, 100 mM phosphate buffer). Final purification was by protein A adsorption (PBS) and elution (NaOAc, pH 3.5). The pH of the product was adjusted to 6 and dialyzed against PBS to give the final sample (56%).

Alternatively, the mAb was reduced with GSH and/or Cys. After removal of the reducing agent by Tangential Flow Filtration (TFF), an excess of the peptide was added to the reduced mAb optionally in the presence of 0.2-0.5 equivalents of TCEP.

Example 104: mAb Conjugate Characterization

Analytical characterization of PYY-mAb conjugates was performed using (i) hydrophobic interaction chromatography (HIC), (ii) intact mass measurement by LC-ESIMS, (iii) size-exclusion chromatography (SEC). Results of the analytical characterization of the PYY-mAb conjugates and conjugation method are shown in Table 1.

TABLE 1

Analytical data for PYY-mAb conjugates.

| Cpd. No. | Conjugation | MS (Calc'd) Da | MS (Found) Da | SEC purity % | HIC purity % |
|---|---|---|---|---|---|
| 1 | Method B | 156144 | 156142 | 97.89 | 100 |
| 2 | Method B | 155616 | 155617 | NA | 100 |
| 3 | Method B | 154945 | 154947 | NA | 100 |
| 4 | Method B | 155972 | 155966 | NA | 100 |
| 5 | Method B | 157668 | 157670 | NA | 100 |
| 6 | Method B | 156116 | 156118 | NA | 100 |
| 7 | Method B | 156172 | 156155 | NA | 100 |
| 8 | Method B | 156173 | 156154 | NA | 100 |
| 9 | Method B | 156347 | 156350 | NA | 98 |
| 10 | Method B | 156347 | 156349 | NA | 100 |
| 11 | Method B | 156039 | 156040 | NA | 100 |
| 12 | Method B | 156450 | 156448 | NA | 100 |
| 13 | Method B | 156138 | 156162 | NA | 100 |
| 14 | Method B | 156201 | 156202 | NA | 100 |
| 15 | Method B | 156233 | 156145 | 93.79 | 97 |
| 16 | Method B | 156233 | 156236 | NA | 100 |
| 17 | Method B | 156060 | 156062 | 98.64 | 100 |
| 18 | Method A | 156116 | 156104 | 98.64 | ND |
| 19 | Method A | 156144 | 156129 | 98.15 | ND |
| 20 | Method A | 156144 | 156130 | 98.21 | ND |
| 21 | Method A | 156200 | 156187 | 98.22 | ND |
| 22 | Method B | 156082 | 156082 | 100 | 96 |
| 23 | Method B | 156082 | 156083 | 93 | 100 |
| 24 | Method B | 154714 | 154722 | 86 | 81 |
| 25 | Method B | 157202 | 157196 | 97.55 | 100 |
| 26 | Method B | 156117 | 156111 | 99.00 | 100 |

Example 105: In Vitro Assays

Compound 1 was evaluated for its ability to activate NPY receptors in vitro in clonal cells (HEK or CHO) expressing human, rat, mouse and rhesus monkey Y2 receptors, and human Y1, Y4 and Y5 receptors. $PYY_{3-36}$, NPY and PP were included in these assays as study controls.

Cell Lines

Stable transfected clonal cell lines expressing NPY receptors were developed for use in cAMP assays. In brief, HEK293 cell lines were transfected using the Lipofectamine 2000 kit (Invitrogen) according to its protocol with expression plasmids carrying the coding sequences for the human Y2 receptor (Accession No.: NM_000910.2), the human Y5 receptor (Accession No.: NM_006174.2), the mouse Y2 receptor (Accession No.: NM_008731) and the rhesus monkey Y2 receptor (Accession No.: NM_001032832). Forty eight hours after transfection, cells were re-plated with selection media (DMEM high glucose with 10% fetal bovine serum (FBS), 50 I.U. penicillin, 50 µg/ml streptomycin, 2 mM L-glutamine, 1 mM sodium pyruvate and 600 g/ml G418). Cells were kept in selection media for 2 weeks before single clones were picked using limited dilution method. The transfected cells were subsequently maintained by culturing in DMEM-high glucose media (Cellgro) supplemented with 10% fetal bovine serum, 1% L-glutamine, 1% sodium pyruvate, 1% penicillin/streptomycin and 600 µg/ml G418.

In addition, CHO-K1 cell lines were obtained from DiscoverX Corporation, expressing the human Y1 receptor (Catalog No.: 93-0397C2) and the human Y4 receptor (Catalog No.: 95-0087C2). The DiscoverX cells cultured in F12 media (Gibco) supplemented with 10% FBS and under the G418 selection (800 µg/mL). The rat Y2 receptor was expressed in a Glo-Sensor CHO-K1 line obtained from Promega Corporation. These cells were transfected with the pGloSensor™-23F cAMP plasmid for a luminescent based cAMP assay but had been tested and validated for use with the Perkin-Elmer LANCE cAMP assay. The rat Y2 cells were grown in F12 media (Gibco) supplemented with 10% FBS and 800 µg/ml G418.

All the cell lines were banked in vials ($4 \times 10^6$ cells/vial) and stored in liquid nitrogen until use. The day before the assay, the vials were thawed and added to 15 mls of appropriate media. Cells were centrifuged at 450×g for 5 min, supernatants were aspirated and cells were re-suspended in media without G418 at a density of $0.2 \times 10^6$ cells/ml. Cells were dispensed (25 µl/well) into Biocoat collagen-coated white 384 well plates to a final density of 5000 cells/well. The cell plates were incubated overnight in a 37° C. humidified tissue culture incubator under 5% $CO_2$/90% $O_2$ atmosphere.

Experimental Protocol

The cAMP assay was the same for the various receptor assays. The LANCE cAMP kit (Perkin Elmer Corporation; Waltham, Mass.) was used in all experiments to quantitate intracellular cAMP levels. On the day of the assay, the cell media was decanted from the cells and 6 µl of peptides (2× concentration) was added to the wells. Peptides were made up as an 11 point dose response (starting at 100 nM or 10 µM with serial 1:3 dilutions) in stimulation buffer. Stimulation buffer consists of 5 mM HEPES (4-(2-hydroxyethyl)-1-piperazineethanesulfonic acid), 500 µM IBMX and 0.1% bovine serum albumin (BSA) in HBSS (Hank's balanced salt solution). Next 6 µl of stimulation buffer containing forskolin (2×, 5 µM final concentration) and LANCE cAMP antibody (1:100) was added to the cells. After incubation for 25 minutes at rt, 12 µl of assay detection mix was added to each well. The detection mix was prepared by diluting biotin-cAMP (1:750) and Europium-W8044 (1:2250) in detection buffer as provided with the LANCE cAMP kit. The plate was incubated for 2 hours at rt and then read as a TR-FRET assay on the Envision plate reader (excitation 320 nm, emission 615 nm and 665 nm). Channel 1 fluorescence (relative fluorescent units at 615 nm) and channel 2 fluorescence (relative fluorescent units at 665 nm) along with their ratio were exported into an Excel file.

Data Analysis

Data from the Envision plate reader were expressed as relative fluorescence units (RFU) calculated as (615 nm/665 nm)×10,000. All samples were measured in triplicate. Data were analyzed using the Crucible in-house data analysis software, designed by Eudean Shaw. The unknown cAMP concentrations within each well were interpolated from the reference standards of known cAMP concentrations included within each plate. Parameters such as $EC_{50}$, Log ($EC_{50}$), HillSlope (nH), top, and bottom, were derived by plotting cAMP concentration values over log compound concentrations fitted with 4-P model using a non-linear weighted least squares application within R environment (Open Source http://cran.us.r-project.org/) implemented by the Non-Clinical Statistics & Computing department at Janssen R&D.

TABLE 2 in vitro Data

| Compound | Human isoform potency ($EC_{50}$ nM) | | | | Cross-species potency ($EC_{50}$ nM) | | |
|---|---|---|---|---|---|---|---|
| | hY2 | hY1 | hY4 | hY5 | Mouse Y2 | Rat Y2 | Rhesus Monkey Y2 |
| Compound 1 | 0.006 | >2910 | >2910 | 345.7 | 0.004 | 0.04 | 0.004 |
| PYY3-36 | 0.08 | 66.4 | 136.7 | 12.3 | 0.03 | 0.50 | 0.06 |

TABLE 3 in vitro human isoform and cross species $EC_{50}$

| | Human EC50 (nM) | | | | Cross species EC50 (nM) | | |
|---|---|---|---|---|---|---|---|
| Cpd No | hY2 | hY1 | hY4 | hY5 | mY2 | rY2 | rhY2 |
| 1 | 0.0065 | >2910 | >2910 | 345.7 | 0.004 | 0.04 | 0.004 |
| 2 | 0.012 | | | | | | |
| 3 | 0.012 | | | | | | |
| 4 | 7.75 | | | | | | |
| 5 | 0.42 | | | | | | |
| 6 | 0.065 | | | | | | |
| 7 | 0.02 | 678.7 | >1186 | 10.8 | | | |
| 8 | 0.295 | | | | | | |
| 9 | 0.01 | | | | | | |
| 10 | 0.06 | | | | | | |
| 11 | 0.015 | | | | | | |
| 12 | 0.015 | 1990 | 520.8 | 154.5 | | | |
| 13 | 0.008 | >3000 | >3000 | 294.2 | | | |
| 14 | 0.04 | | | | | | |
| 15 | 0.25 | | | | | | |
| 16 | 0.04 | | | | | | |
| 17 | 0.007 | | | | | | |
| 18 | 0.0085 | | | | | | |
| 19 | 0.015 | | | | | | |
| 20 | 0.0075 | | | | | | |
| 21 | 0.08 | | | | | | |
| 22 | 0.0085 | | | | | | |
| 23 | 0.0075 | | | | | | |
| 24 | | | | | | | |
| 25 | 0.0055 | | | | | | |
| 26 | 0.0085 | | | | | | |

Example 106: In Vivo Mouse Stability Assay

Male C57BL/6N mice (9-12 weeks of age) were obtained from Taconic Laboratory. Mice were housed one mouse per cage with AlphaDri bedding in a temperature-controlled room with 12-h light/dark cycle. Mice were allowed ad libitum access to water and maintained on chow diet (5001, Lab Diet).

Mice were dosed subcutaneously with 1 mg/kg compound. Approximately 100 L of blood from 3 animals was collected at t=4, 24, and 48 hours via tail snip. Blood (approximately 600 μL) from 2-3 animals per time point was also collected at t=4, 24 and 48 hours via cardiac puncture. Blood samples were collected in K3E (EDTA) tubes containing 4% ratio of complete protease inhibitor solution and 1% ratio of DPPIV inhibitor. Blood samples were placed on wet ice prior to being centrifuged at 10,000 rpm for 10 minutes under refrigerated conditions (~5° C.) for cell removal within 30 minutes following collection at each time point and all available plasma was transferred to a 96-well plate. The well plate was stored in a −80° C. freezer. The levels of compound were measured using the LCMS method described below. Data are shown in Table 4.

Mass Spec Assays for Determination of % Remaining of Intact Conjugate

Plasma samples were processed by immuno-affinity capture using an anti-human Fc antibody, followed by reversed phase LC-high resolution full scan MS analysis on a triple TOF (Time-of-Flight) mass spectrometer. The raw MS spectra were deconvoluted to elucidate the molecular weights of the components in the injected samples. The peak of the molecule ion of the intact conjugate was used for quantitation of unchanged intact conjugate. In a separate assay, plasma samples were processed by immuno-affinity capture using an anti-human Fc antibody, followed by trypsin digestion and reversed phase LC-MSMS analysis on a triple quadrupole mass spectrometer. A peptide located on Fc of the mAb were monitored for quantitation of total mAb. For both assays, standard curve and quality control samples were prepared by spiking the reference standard in plasma and processed using the same procedure at the same time as the incurred samples. The ratio of the concentration of intact conjugate to that of total mAb was calculated to be % Remaining.

TABLE 4

In vivo mouse stability data

| Cpd. No. | % Rem @ 48 hr in Mouse |
|---|---|
| 1 | 90.8 |
| 2 | 65.6 |
| 3 | 51.8 |
| 4 | NA |
| 5 | 80.4 |
| 6 | 49.7 |
| 7 | 75.4 |
| 8 | 51.6 |
| 9 | 51.5 |
| 10 | 42.4 |
| 11 | 60 |
| 12 | 63.5 |
| 13 | 74.4 |
| 14 | 102 |
| 15 | NA |
| 16 | 96 |
| 17 | |
| 18 | 77 |
| 19 | 87.4 |
| 20 | 74.4 |
| 21 | 85.8 |
| 22 | |
| 23 | |
| 24 | |
| 25 | 81.5 |
| 26 | 71.9 |

Example 107: Pharmacokinetics (PK)

DIO Mouse PK

Male DIO C57BL/6N mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet).

Mice were dosed subcutaneously (s.c.) with 1 mg/kg compound 1, 3 animals were sacrificed at each time point and blood was collected at t=4, 8, 24, 48, 72, 120, and 168 hours. Blood from 3 naïve animals was also collected. Approximately 300 µL of blood from each animal was collected via jugular vein after decapitation while under gas anesthesia induced with 70% $CO_2$ and 30% $O_2$ mixture. Blood samples (approximately 300 µL) was collected in K3E (EDTA) coated Sarstedt Microvette® tubes containing 12 µl (4% ratio) of complete protease inhibitor solution and 3 µL (1% ratio) of DPP-IV inhibitor. Blood samples were placed on wet ice prior to being centrifuged at 10,000 rpm for ~4 minutes under refrigerated conditions (~5° C.) for cell removal within 30 minutes following collection at each time point and all available plasma was transferred to a 96-well plate. The well plate was stored on dry ice until it was placed in a −80° C. freezer. Data are shown in Table 5 and FIG. 3.

Rat PK

Compound 1 was administered subcutaneously and intravenously to male Sprague-Dawley rats (Charles River Laboratories, Wilmington, Mass.) at a dose level of 1.0 mg/kg in PBS, (pH 7.0-7.6). Approximately 500 µL of blood was collected from three animals per time point via a saphenous vein (t=1, 4, 24, 48, 72, 96, 168, and 240 hours post-dose). A 336 hour post-dose blood sample was collected via jugular vein after decapitation while under gas anesthesia induced with 70% $CO_2$ and 30% $O_2$ mixture. Blood samples were collected in K3E (EDTA) coated Sarstedt Microvette® tubes containing 20 µl (4% ratio) of complete protease inhibitor solution and 5 µL (1% ratio) of DPPIV inhibitor. Blood samples were placed on wet ice prior to being centrifuged at 10,000 rpm for ~4 minutes under refrigerated conditions (~5° C.) for cell removal within 60 minutes following collection at each time point and all available plasma was transferred to a 96-well plate. The levels of Compound 1 were measured using the LCMS method described below. Data are shown in Table 6.

Cynomolgus Monkey (Cyno) PK

All animals were fasted for at least eight hours prior to dosing and through the first four hours of blood sample collection. Three animals received a single IV dose of 1 mg/kg Compound 1 and three animals received a single SC dose of 1 mg/kg Compound 1. Blood was collected pre-dose and at 1, 6, 10, 24, 36, 48, 72, 120, 168, 240, 336, 432, and 504 hours post-dose. An additional sample was collected at 0.5 hours post-dose for the IV group. Approximately 1 ml of blood from each animal was collected in K3E (EDTA) coated Sarstedt Microvette® tubes containing 4% ratio of complete protease inhibitor solution and 1% ratio of DPPIV inhibitor. Blood samples were placed on wet ice prior to being centrifuged within 30 minutes following collection at each time point and the resulting plasma was split in thirds and transferred into triplicate 96-well plate. The well plate was stored on dry ice until it was placed in a −80° C. freezer. Data are shown in Table 7 and FIG. 4.

Intact Mass Spec Assay for Determination of Plasma Levels

Plasma samples were processed by immuno-affinity capture using an anti-human Fc antibody, followed by reversed phase LC-high resolution full scan MS analysis on a triple TOF (time-of-flight) mass spectrometer. The raw MS spectra were deconvoluted to elucidate the molecular weights of the components in the injected samples. The peak of the molecule ion of the intact conjugate was used for quantitation. Standard curve and quality control samples were prepared by spiking the reference standard in plasma and processed using the same procedure at the same time as the incurred samples. PK data for DIO mouse, rat, and cyno are shown in Table 5, Table 6, and Table 7, respectively. PK data for DIO mouse and Cyno are also shown in FIGS. 3 and 4, respectively.

TABLE 5

PK in DIO Mouse

| Assay | Dose (mg/kg) | $T_{1/2}$ hr | $T_{max}$ hr | $C_{max}$ ng/mL | $AUC_{last}$ hr * ng/mL |
|---|---|---|---|---|---|
| Intact | 1.0 | 81.05 | 48 | 8750 | 995460 |

TABLE 6

PK in rat

| Route | Dose (mg/kg) | $T_{1/2}$ hr | $T_{max}$ hr | $C_{max}$ ng/mL | $AUC_{last}$ hr * ng/mL |
|---|---|---|---|---|---|
| IV | 1.0 | 93.0 | 1 | 19.5 | 809.2 |
| SC | 1.0 | 88.7 | 48 | 4.2 | 602.0 |

TABLE 7

PK in Cyno

| Route | Dose (mg/kg) | $T_{1/2}$ hr | $T_{max}$ hr | $C_{max}$ ng/mL | $AUC_{last}$ hr * ng/mL |
|---|---|---|---|---|---|
| IV | 1.0 | 178.39 | 0.67 | 30290 | 1207.39 |
| Sc | 1.0 | 104.32 | 10 | 5590 | 712.19 |

Example 108: Efficacy Studies In Vivo

Weight Loss in Diet-Induced Obese (DIO) Mice: Acute Dosing

Compound 1 was evaluated for its ability to reduce foot intake and body weight in male DIO C57Bl/6 mice after a single dose. Male DIO C57BL/6N mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet). Animals were acclimated to the facility for at least one week prior to the start of the experiment.

Figure 5:
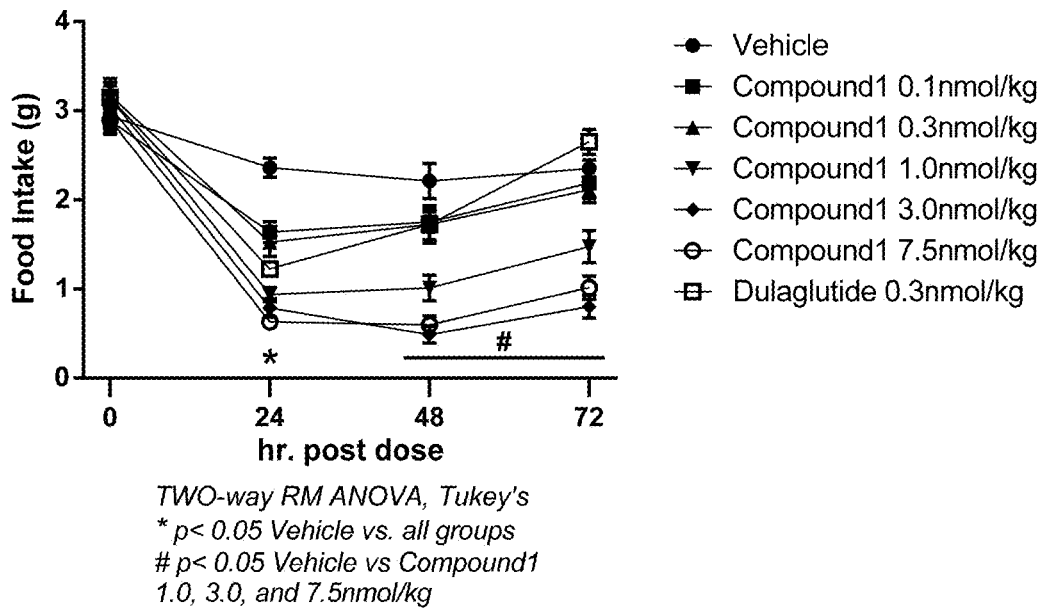
FIG. 5: Food intake in DIO mice treated with the compound 1: acute dosing.
Figure 6:
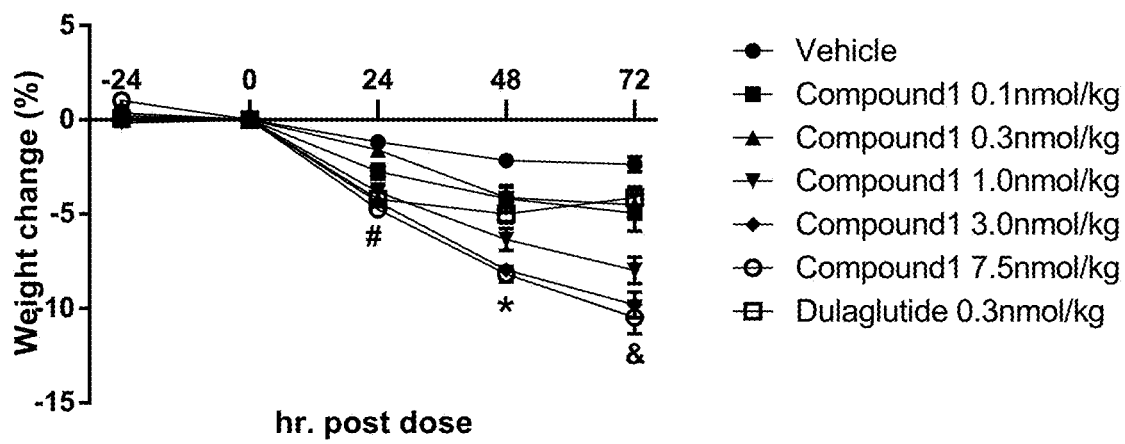
FIG. 6: Weight loss in DIO mice treated with the compound 1: acute dosing.

The day prior to dosing, mice were grouped into cohorts of eight animals based on individual body weights. At 3:00-4:00 µm the following day, animals were weighed and treated with vehicle (dPBS, pH 7.2), Compound 1 at a dose of 0.1, 0.3, 1.0, 3.0, or 7.5 nmol/kg, or Dulaglutide at 0.3 nmol/kg via subcutaneous (s.c.) administration. Body weights and food intake were measured 24 h, 48 h and 72 h after dosing and the percentages of weight loss and reduction in food intake were calculated. Statistical analyses were performed using two-way repeated measures ANOVA with Tukey's post-test in Prism. All data are presented as the mean±SEM (FIG. 5 and FIG. 6).

Weight Loss in Diet-Induced Obese Mice: Chronic Dosing

Compound 1 was evaluated for its ability to reduce foot intake and body weight and improve glucose homeostasis on repeat dosing in male DIO C57Bl/6 mice over a period of 8 days. Male DIO C57BL/6N mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet). Animals were acclimated to the facility for at least one week prior to the start of the experiment.

Figure 7:
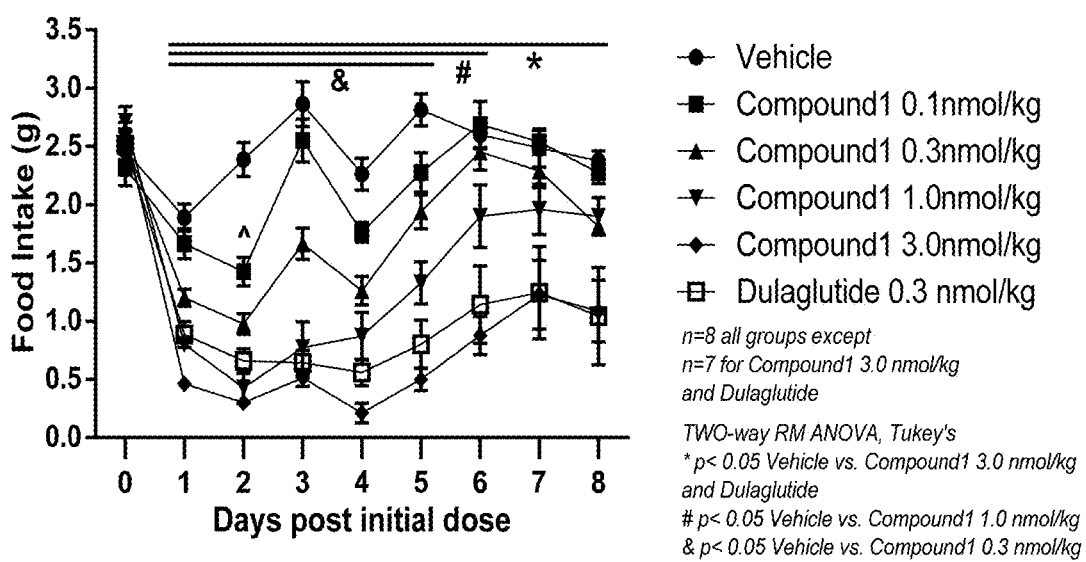
FIG. 7: Food intake in DIO mice treated with the compound 1: chronic dosing.
Figure 8:
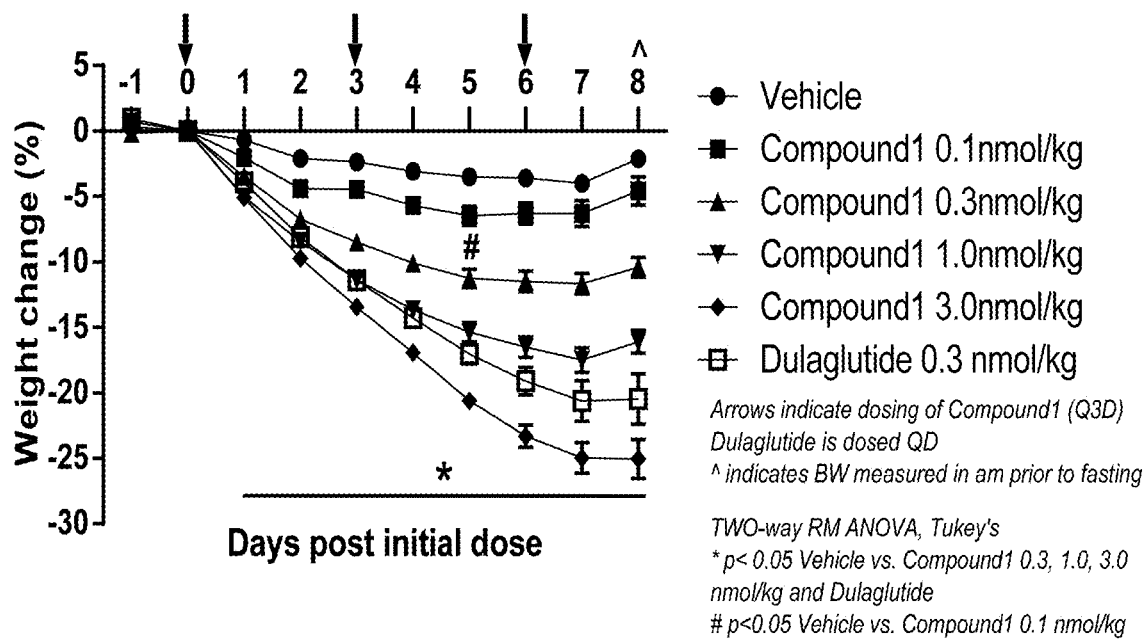
FIG. 8: Weight loss in DIO mice treated with the compound 1: chronic dosing.

The day prior to dosing, mice were grouped based on individual body weights. At 3:00-4:00 μm for each of the next 8 days, animals and food intake were weighed. Animals were treated with vehicle (dPBS, pH 7.2) or dulaglutide at 0.3 nmol/kg via subcutaneous administration every day or Compound 1 at doses of 0.1, 0.3, 1.0, 3.0 nmol/kg via subcutaneous administration every three days. After 8 days, mice are fasted for 5 hours and then given a 2 g/kg bolus of glucose orally at t=0. At t=0, 30, 60, 90, and 120 minutes post glucose challenge blood glucose is measured and at t=0, 30, and 90 minutes blood in drawn to measure plasma insulin. Statistical analyses were performed using one-way ANOVA or two-way repeated measures ANOVA with Tukey's post-test in Prism. All data are presented as the mean±SEM (FIG. 7, FIG. 8, and Tables 8-11).

TABLE 8

Effect of compound 1 on body weight (g) over 8 days treatment

| | | Treatment | | | | |
| --- | --- | --- | --- | --- | --- | --- |
| | Vehicle | Compound 1 (nmol/kg) | | | | Dulaglutide (nmol/kg) |
| Day | n/a | 0.1 | 0.3 | 1.0 | 3.0 | 0.3 |
| −1 | 46.3 ± 0.6 | 46.3 ± 0.6 | 46.7 ± 0.8 | 46.3 ± 0.6 | 46.3 ± 0.6 | 46.3 ± 0.6 |
| 0 | 46.1 ± 0.7 | 46.0 ± 0.6 | 46.8 ± 0.7 | 46.3 ± 0.6 | 46.3 ± 0.6 | 45.9 ± 0.6 |
| 1 | 45.8 ± 0.7 | 45.0 ± 0.6 | 45.2 ± 0.7 | 43.9 ± 0.5 | 43.9 ± 0.6 | 44.1 ± 0.6 |
| 2 | 45.2 ± 0.7 | 43.9 ± 0.6 | 43.6 ± 0.7 | 42.4 ± 0.7* | 41.8 ± 0.7* | 42.2 ± 0.6* |
| 3 | 45.1 ± 0.7 | 43.9 ± 0.6 | 42.8 ± 0.6 | 41.0 ± 0.6* | 40.1 ± 0.6* | 40.6 ± 0.6* |
| 4 | 44.7 ± 0.7 | 43.4 ± 0.6 | 42.0 ± 0.6 | 39.9 ± 0.6* | 38.5 ± 0.6* | 39.3 ± 0.6* |
| 5 | 44.5 ± 0.7 | 43.0 ± 0.6 | 41.5 ± 0.5* | 39.1 ± 0.6* | 36.8 ± 0.7* | 38.1 ± 0.7* |
| 6 | 44.5 ± 0.7 | 43.1 ± 0.6 | 41.4 ± 0.5* | 38.6 ± 0.6* | 35.5 ± 0.8* | 37.1 ± 0.8* |
| 7 | 44.3 ± 0.7 | 43.1 ± 0.7 | 41.3 ± 0.5* | 38.2 ± 0.6* | 34.8 ± 0.9* | 36.4 ± 1.0* |
| 8 | 45.2 ± 0.6 | 46.3 ± 0.7 | 41.9 ± 0.5* | 38.8 ± 0.6 | 34.7 ± 1.0* | 36.5 ± 1.1* |

Values represent mean ± SEM for data from 8 animals per time per group
*$p < 0.05$, versus vehicle; two-way ANOVA RM, Tukey's multiple comparison test

TABLE 9

Effect of compound 1 on blood glucose (mg/dL) levels during an OGTT after 8 days of treatment

| Treatment | Dose (nmol/kg) | Time after glucose challenge (min) | | | | | Total AUC (mg/dl/120 min) | Delta AUC (mg/dl/120 min) |
| --- | --- | --- | --- | --- | --- | --- | --- | --- |
| | | 0 | 30 | 60 | 90 | 120 | | |
| Vehicle | NA | 148 ± 6 | 227 ± 15 | 272 ± 12 | 206 ± 9 | 209 ± 13 | 26492 ± 1232 | 8702 ± 1082 |
| Comp. 1 | 0.1 | 151 ± 4 | 213 ± 9 | 249 ± 10 | 186 ± 11 | 194 ± 15 | 24598 ± 849 | 6433 ± 677 |
| | 0.3 | 137 ± 6 | 191 ± 11 | 208 ± 10* | 146 ± 8* | 160 ± 8* | 20786 ± 728* | 4379 ± 364* |
| | 1.0 | 117 ± 5 | 146 ± 9* | 203 ± 10* | 135 ± 8* | 136 ± 5* | 18285 ± 769* | 4319 ± 522* |
| | 3.0 | 73 ± 11* | 129 ± 5* | 149 ± 10* | 93 ± 9* | 101 ± 9* | 13703 ± 913* | 5004 ± 585 |
| Dulaglutide | 0.3 | 76 ± 9* | 151 ± 14* | 174 ± 17* | 104 ± 10* | 119 ± 9* | 15758 ± 1054* | 6668 ± 1846 |

Values represent mean ± SEM for data from 8 animals per time per group
*$p < 0.05$, versus vehicle; two-way ANOVA RM, Tukey's multiple comparison test for glucose values; one-way ANOVA, Tukey's multiple comparison test for AUC

TABLE 10

Effect of compound 1 on insulin (ng/mL) levels during an OGTT after 8 days of treatment

| Treatment | Dose (nmol/kg) | Time after glucose challenge (min) | | | Total AUC (mg/dl/120 min) |
| --- | --- | --- | --- | --- | --- |
| | | 0 | 30 | 90 | |
| Vehicle | NA | 5.6 ± 1.4 | 11.3 ± 3.0 | 4.0 ± 0.6 | 711.4 ± 164.1 |
| Comp. 1 | 0.1 | 3.0 ± 0.4 | 6.6 ± 0.8* | 2.4 ± 0.2 | 415.6 ± 44.2 |
| | 0.3 | 2.3 ± 0.2 | 4.0 ± 0.6* | 1.7 ± 0.2 | 264.3 ± 33.0* |

TABLE 10-continued

Effect of compound 1 on insulin (ng/mL) levels during an OGTT after 8 days of treatment

| Treatment | Dose (nmol/kg) | Time after glucose challenge (min) | | | Total AUC (mg/dl/120 min) |
|---|---|---|---|---|---|
| | | 0 | 30 | 90 | |
| | 1.0 | 1.3 ± 0.2* | 2.2 ± 0.1* | 1.1 ± 0.2 | 151.6 ± 12.5* |
| | 3.0 | 0.4 ± 0.1* | 1.2 ± 0.1* | 0.4 ± 0.1* | 73.9 ± 9.0* |
| Dulaglutide | 0.3 | 0.6 ± 0.1* | 1.7 ± 0.2* | 0.7 ± 0.2 | 108.8 ± 12.3* |

Values represent mean ± SEM for data from 8 animals per time per group
*p <0.05, versus vehicle;
two-way ANOVA RM, Tukey's multiple comparison test for glucose values;
one-way ANOVA, Tukey's multiple comparison test for AUC

TABLE 11

Effect of compound 1 on fed blood glucose (mg/dL) levels after 8 days of treatment

| Treatment | Dose (nmol/kg) | Blood Glucose (mg/dL) |
|---|---|---|
| Vehicle | NA | 180 ± 5 |
| Compound 1 | 0.1 | 164 ± 6 |
| | 0.3 | 160 ± 5 |
| | 1.0 | 149 ± 6 |
| | 3.0 | 105 ± 12* |
| Dulaglutide | 0.3 | 114 ± 13* |

Values represent mean ± SEM for data from 8 animals per time per group
*p <0.05, versus vehicle;
one-way ANOVA, Tukey's multiple comparison test Weight Loss in Diet-Induced Obese Mice in Combination with Liraglutide: Chronic Dosing Compound 1 was evaluated for its ability to reduce foot intake and body weight and improve glucose homeostasis in combination with a long-acting GLP-1 agonist, liraglutide, on repeat dosing in male DIO C57Bl/6 mice over a period of 9 days.

Male DIO C57BL/6N mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet). Animals were acclimated to the facility for at least one week prior to the start of the experiment.

Figure 9:
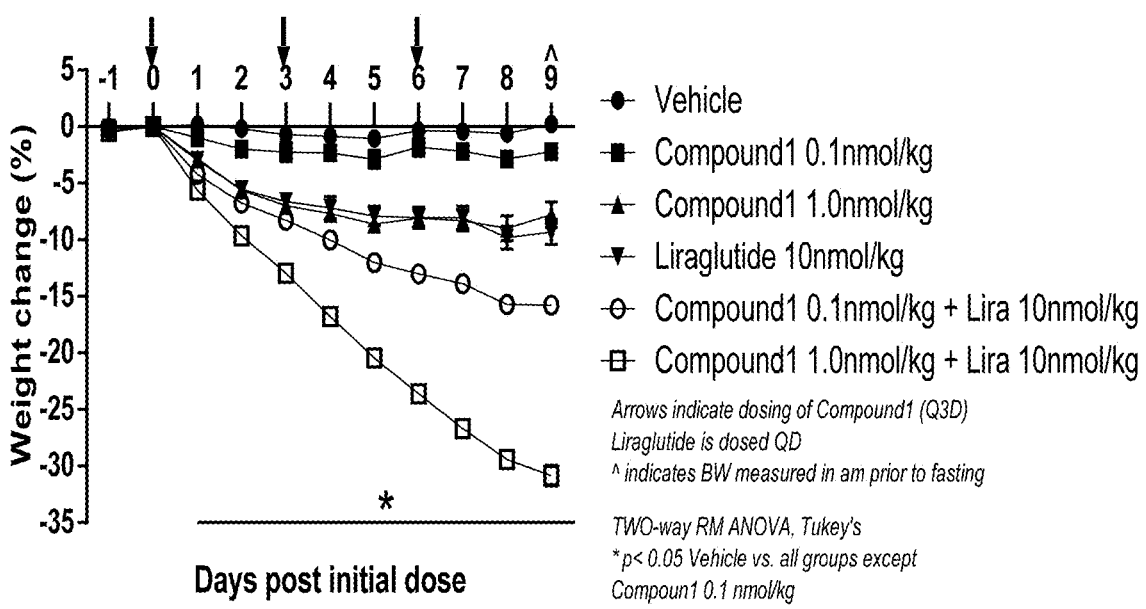
FIG. 9: Weight loss in DIO mice treated with the compound 1 in combination with liraglutide: chronic dosing.

The day prior to dosing, body composition was measured by MRI and mice were grouped based on individual body weights. On day 0 at 3:00-4:00 μm, animals and food intake were weighed. Animals in the single treatment groups were treated with vehicle (dPBS, pH 7.2) or liraglutide at 10 nmol/kg via subcutaneous administration every day or Compound 1 at doses of 0.1, or 1.0 nmol/kg via subcutaneous administration every three days. Animals in the combination groups received liraglutide (10 nmol/kg) daily and compound 1 at doses of 0.1 or 1.0 nmol/kg every three days. On day 8, body composition was measured by MRI. On day 9, mice are fasted for 5 hours and fasting blood glucose and insulin were measured. Statistical analyses were performed using one-way ANOVA or two-way repeated measures ANOVA with Tukey's post-test in Prism. All data are presented as the mean±SEM (FIG. 9 and Tables 12-17).

TABLE 12

Effect of compound 1, liraglutide, and combinations of compound 1 and liraglutide on daily food intake (g) over 9 days of treatment.

| | Treatment | | | | | |
|---|---|---|---|---|---|---|
| | | Compound 1 (nmol/kg) | | | | |
| | | 0.1 | 1.0 | n/a | 0.1 | 1.0 |
| | Vehicle | | | Liraglutide (nmol/kg) | | |
| Day | n/a | n/a | n/a | 10.0 | 10.0 | 10.0 |
| 0 | 2.6 ± 0.1 | 2.4 ± 0.1 | 2.3 ± 0.1 | 2.4 ± 0.1 | 2.5 ± 0.1 | 2.8 ± 0.1 |
| 1 | 2.5 ± 0.1 | 2.0 ± 0.2* | 1.2 ± 0.1* | 1.1 ± 0.1* | 0.8 ± 0.1* | 0.5 ± 0.1* |
| 2 | 2.5 ± 0.1 | 2.0 ± 0.2 | 0.8 ± 0.1* | 1.1 ± 0.1* | 0.7 ± 0.1* | 0.2 ± 0.1* |
| 3 | 2.5 ± 0.1 | 2.3 ± 0.2 | 1.5 ± 0.2* | 1.5 ± 0.2* | 1.2 ± 0.1*^ | 0.5 ± 0.1* |
| 4 | 2.6 ± 0.1 | 2.4 ± 0.1 | 1.8 ± 0.1* | 1.9 ± 0.2* | 1.2 ± 0.2* | 0.3 ± 0.1* |
| 5 | 2.4 ± 0.1 | 2.4 ± 0.1 | 2.0 ± 0.2 | 1.9 ± 0.1* | 1.3 ± 0.2*^ | 0.5 ± 0.1* |
| 6 | 2.8 ± 0.2 | 2.8 ± 0.1 | 2.4 ± 0.1 | 2.2 ± 0.1* | 1.5 ± 0.2*^ | 0.3 ± 0.1*^ |
| 7 | 2.6 ± 0.1 | 2.6 ± 0.1 | 2.3 ± 0.1 | 2.3 ± 0.1 | 1.6 ± 0.1* | 0.3 ± 0.2*^ |
| 8 | 2.9 ± 0.2 | 2.2 ± 0.1*^ | 2.3 ± 0.1* | 1.8 ± 0.1* | 1.4 ± 0.1* | 0.5 ± 0.2*^ |
| 9 | 1.8 ± 0.3 | 2.0 ± 0.1 | 2.2 ± 0.1 | 1.7 ± 0.1 | 1.6 ± 0.2 | 0.7 ± 0.2*^ |

Values represented mean ± SEM for data from 8 animals per time per group, except n == 7 when noted by^
*p < 0.05, versus vehicle; two-way ANOVA RM, Tukey's multiple comparison test

TABLE 13

Effect of compound 1, liraglutide, and combinations of compound 1 and liraglutide on body weight (g) over 9 days of treatment.

| | | | Treatment | | | |
|---|---|---|---|---|---|---|
| | | Compound 1 (nmol/kg) | | | | |
| | Vehicle | 0.1 | 1.0 | n/a | 0.1 | 1.0 |
| | | | | Liraglutide (nmol/kg) | | |
| Day | n/a | n/a | n/a | 10.0 | 10.0 | 10.0 |
| −1 | 46.8 ± 0.5 | 46.8 ± 0.5 | 46.8 ± 0.5 | 46.8 ± 0.5 | 46.8 ± 0.5 | 46.8 ± 0.4 |
| 0 | 46.9 ± 0.4 | 46.8 ± 0.5 | 46.8 ± 0.5 | 47.0 ± 0.5 | 46.8 ± 0.5 | 47.0 ± 0.4 |
| 1 | 47.0 ± 0.5 | 46.4 ± 0.5 | 45.5 ± 0.5 | 45.6 ± 0.4 | 44.9 ± 0.5* | 44.3 ± 0.4* |
| 2 | 46.8 ± 0.5 | 45.9 ± 0.5 | 44.1 ± 0.4* | 44.4 ± 0.5* | 43.7 ± 0.5* | 42.4 ± 0.5* |
| 3 | 46.6 ± 0.5 | 45.8 ± 0.5 | 43.5 ± 0.5* | 43.9 ± 0.6* | 43.0 ± 0.5* | 40.9 ± 0.4* |
| 4 | 46.5 ± 0.4 | 45.7 ± 0.5 | 43.2 ± 0.4* | 43.6 ± 0.6* | 42.1 ± 0.4* | 39.1 ± 0.5* |
| 5 | 46.4 ± 0.5 | 45.5 ± 0.6 | 42.7 ± 0.4* | 43.3 ± 0.6* | 41.2 ± 0.5* | 37.4 ± 0.4* |
| 6 | 46.8 ± 0.5 | 46.0 ± 0.6 | 43.0 ± 0.5* | 43.2 ± 0.6* | 40.7 ± 0.5* | 35.9 ± 0.5* |
| 7 | 46.7 ± 0.5 | 45.8 ± 0.6 | 42.9 ± 0.5* | 43.2 ± 0.7* | 40.3 ± 0.5* | 34.4 ± 0.4* |
| 8 | 46.6 ± 0.5 | 45.5 ± 0.6 | 42.6 ± 0.5* | 42.4 ± 0.6* | 39.5 ± 0.4* | 33.2 ± 0.5* |
| 9 | 47.0 ± 0.6 | 45.8 ± 0.6 | 43.1 ± 0.5* | 42.6 ± 0.6* | 39.4 ± 0.4* | 32.5 ± 0.5* |

Values represent mean ± SEM for data from 8 animals per time per group
*$p < 0.05$, versus vehicle; two-way ANOVA RM, Tukey's multiple comparison test

TABLE 14

Comparison of co-dosed compound 1 and liraglutide on percent body weight change versus the sum of percent body weight change of compound 1 or liraglutide dosed alone on day 9.

| | | Treatment | | | | | | |
|---|---|---|---|---|---|---|---|---|
| | Compound 1 (nmol/kg) | | | Sum of | Compound 1 (nmol/kg) | | | Sum of |
| | 0.1 | n/a | 0.1 | Comp 1 | 1.0 | n/a | 1.0 | Comp 1 |
| | Liraglutide (nmol/kg) | | | (0.1) and | Liraglutide (nmol/kg) | | | (1.0) and |
| Day | n/a | 10.0 | 10.0 | Lira (10.0) | n/a | 10.0 | 10.0 | Lira (10.0) |
| 9 | −2.2 ± 0.7 | −9.3 ± 1.1 | −15.8 ± 0.8* | −11.5 ± 1.1* | −7.8 ± 1.1 | −9.3 ± 1.1 | −30.8 ± 0.9* | −17.1 ± 1.9* |

Values represent mean ± SEM for data from 8 animals per time per group
*$p < 0.05$, sum of compound 1 and liraglutide versus co-dosing; one-way ANOVA, Tukey's multiple comparison test

TABLE 15

Effect of compound 1, liraglutide, and combinations of compound 1 and liraglutide on blood glucose (mg/dL), insulin, and HOMA-IR after 9 days treatment.

| | | Compound 1 (nmol/kg) | | | | |
|---|---|---|---|---|---|---|
| | Vehicle | 0.1 | 1.0 | n/a | 0.1 | 1.0 |
| | | | | Liraglutide (nmol/kg) | | |
| | n/a | n/a | n/a | 10.0 | 10.0 | 10.0 |
| Fed blood glucose (mg/dL) | 140.8 ± 11.7 | 132.6 ± 2.9 | 126.4 ± 5.1 | 112.5 ± 4.3 | 112.9 ± 6.7 | 79.4 ± 10.1* |
| Fasting blood glucose (mg/dL) | 173.8 ± 7.8 | 149.8 ± 4.9 | 133.1 ± 6.6* | 124.1 ± 4.9* | 109.8 ± 4.3* | 68.6 ± 7.7* |
| Fasting insulin (ng/mL) | 7.2 ± 1.1 | 8.1 ± 1.1 | 5.8 ± 0.9 | 3.9 ± 0.6* | 1.9 ± 0.3* | 0.5 ± 0.1* |
| HOMA-IR | 92.1 ± 18.6 | 86.4 ± 10.7 | 54.7 ± 9.2 | 34.8 ± 6.0* | 14.5 ± 2.6* | 2.9 ± 0.6* |

Values represent mean ± SEM for data from 8 animals per time per group
*$p < 0.05$, versus vehicle; one-way ANOVA, Tukey's multiple comparison test

TABLE 16

Effect of compound 1, liraglutide, and combinations of compound 1 and liraglutide on body composition (g) measured by MRI after 8 days treatment.

| | Treatment | | | | | |
|---|---|---|---|---|---|---|
| | | Compound 1 (nmol/kg) | | | | |
| | Vehicle | 0.1 | 1.0 | n/a | 0.1 | 1.0 |
| | | | | Liraglutide (nmol/kg) | | |
| | n/a | n/a | n/a | 10.0 | 10.0 | 10.0 |
| Fat(g) Day 1 | 18.6 ± 0.4 | 18.6 ± 0.4 | 18.8 ± 0.6 | 18.2 ± 0.5 | 18.1 ± 0.6 | 18.1 ± 0.7 |
| Fat(g) Day 8 | 18.9 ± 0.4 | 18.3 ± 0.5 | 16.1 ± 0.8* | 15.6 ± 0.5* | 13.3 ± 0.4* | 9.3 ± 0.7* |
| Lean(g) Day 1 | 26.3 ± 0.4 | 26.3 ± 0.4 | 26.1 ± 0.7 | 26.6 ± 0.5 | 26.7 ± 0.5 | 27.0 ± 0.6 |
| Lean(g) Day 8 | 25.9 ± 0.5 | 25.4 ± 0.3 | 24.7 ± 0.6 | 25.0 ± 0.5 | 24.4 ± 0.4 | 22.1 ± 0.4* |

Values represent mean ± SEM for data from 8 animals per time per group
*$p < 0.05$, versus vehicle; one-way ANOVA, Tukey's multiple comparison test

TABLE 17

Effect of compound 1, liraglutide, and combinations of compound 1 and liraglutide on body composition (%) measured by MRI after 8 days treatment.

| | Treatment | | | | | |
|---|---|---|---|---|---|---|
| | | Compound 1 (nmol/kg) | | | | |
| | Vehicle | 0.1 | 1.0 | n/a | 0.1 | 1.0 |
| | | | | Liraglutide (nmol/kg) | | |
| | n/a | n/a | n/a | 10.0 | 10.0 | 10.0 |
| Fat(%) Day 1 | 39.0 ± 0.8 | 39.1 ± 0.6 | 39.4 ± 1.3 | 38.3 ± 0.9 | 38.1 ± 1.1 | 38.1 ± 1.3 |
| Fat(%) Day 8 | 39.9 ± 0.8 | 39.6 ± 0.6 | 37.3 ± 1.6 | 36.2 ± 0.9 | 33.4 ± 0.9* | 27.7 ± 1.7* |
| Lean(%) Day 1 | 55.3 ± 0.8 | 55.2 ± 0.6 | 54.9 ± 1.3 | 56.0 ± 1.0 | 56.0 ± 1.2 | 56.8 ± 1.3 |
| Lean(%) Day 8 | 54.7 ± 0.7 | 55.1 ± 0.6 | 57.4 ± 1.5 | 58.1 ± 0.9 | 61.2 ± 1.0*. | 66.3 ± 1.7* |

Values represent mean ± SEM for data from 8 animals per time per group
*$p < 0.05$, versus vehicle; one-way ANOVA, Tukey's multiple comparison test

Example 109: Effect of a Single Dose of Compound 1 on Food Intake and Body Weight in Sprague-Dawley Rats Compound 1 was evaluated for its ability to reduce foot intake and body weight in Sprague-Dawley after a single dose. The animals were obtained from Charles River Labs (Wilmington, Mass.) at 200-225 g body weight and used within one week of delivery. They were housed one per cage on alpha dry bedding and a plastic tube for enrichment in a temperature-controlled room with 12-hour light/dark cycle. They were allowed ad libitum access to water and were fed laboratory rodent diet; Irradiated Certified PicoLab® Rodent Diet 20, 5K75* (supplied from Purina Mills, St. Louis, Mo. via ASAP Quakertown, Pa.). Animal weights were taken and recorded for each rat prior to dosing.

The day prior to dosing, rats were grouped into cohorts of eight animals based on individual body weights. The following day, animals were weighed and treated with vehicle (dPBS, pH 7.2), Compound 1 at a dose of 0.1, 0.3, 1.0, or 3.0 nmol/kg, or dulaglutide at 0.3 nmol/kg via subcutaneous administration. Body weights and food intake were measured 1, 2 and 3 days after dosing and the percentages of weight loss and reduction in food intake were calculated. Statistical analyses were performed using two-way repeated measures ANOVA with Tukey's post-test in Prism. All data are presented as the mean±SEM (Tables 18-20).

TABLE 18

Effect of a single dose of compound 1 on daily food intake and total food consumption over three days in Sprague-Dawley rats.

| Treatment | Dose (nmol/kg) | Day 0 | Day 1 | Day 2 | Day 3 | Total Food Consumption |
|---|---|---|---|---|---|---|
| Vehicle | | 26.7 ± 0.7 | 28.6 ± 1.0 | 29.4 ± 0.7 | 29.7 ± 0.8 | 87.7 ± 1.6 |
| Compound 1 | 0.1 | 25.9 ± 1.0 | 27.6 ± 1.0 | 29.1 ± 1.0 | 29.1 ± 1.0 | 85.7 ± 2.7 |
| | 0.3 | 24.3 ± 0.7 | 25.8 ± 1.1 | 27.2 ± 1.3 | 27.9 ± 0.9 | 80.9 ± 2.7 |
| | 1 | 27.0 ± 1.1 | 23.7 ± 0.6* | 25.0 ± 2.0* | 27.1 ± 0.9 | 75.8 ± 3.2* |
| | 3 | 27.0 ± 0.8 | 19.6 ± 1.4* | 19.1 ± 1.0* | 23.6 ± 1.0* | 62.3 ± 2.5* |
| Dulaglutide | 0.3 | 26.6 ± 0.8 | 27.3 ± 1.2 | 30.0 ± 0.7 | 30.1 ± 0.7 | 87.4 ± 2.0 |

Values represent mean ± SEM for data from 8 animals per time per group
*$p < 0.05$, versus vehicle; one-way ANOVA, Dunnett's multiple comparison test for total food consumption; two-way ANOVA, Tukey's multiple comparison test for daily food consumption

TABLE 19

Effect of a single dose of compound 1 on absolute body weight over three days in Sprague-Dawley rats.

| Treatment | Dose (nmol/kg) | Day −1 | Day 0 | Day 1 | Day 2 | Day 3 |
|---|---|---|---|---|---|---|
| Vehicle | | 263.9 ± 4.9 | 271.6 ± 4.7 | 281.2 ± 5.0 | 289.5 ± 5.3 | 299.0 ± 5.9 |
| Compound 1 | 0.1 | 266.0 ± 2.3 | 274.1 ± 2.9 | 284.3 ± 2.7 | 293.3 ± 2.8 | 301.4 ± 2.8 |
| | 0.3 | 264.9 ± 3.6 | 270.8 ± 3.8 | 278.2 ± 4.5 | 285.9 ± 4.8 | 294.3 ± 4.9 |
| | 1 | 266.5 ± 3.6 | 276.1 ± 3.7 | 280.9 ± 3.7 | 287.1 ± 4.5 | 294.3 ± 4.1 |
| | 3 | 265.1 ± 3.6 | 272.7 ± 3.4 | 274.8 ± 3.8 | 275.7 ± 3.4* | 282.1 ± 3.7* |
| Dulaglutide | 0.3 | 264.0 ± 3.1 | 270.3 ± 3.0 | 280.8 ± 4.2 | 292.47 ± 3.6 | 299.0 ± 3.3 |

Values represent mean ± SEM for data from 8 animals per time per group
*p < 0.05, versus vehicle; two-way ANOVA, Tukey's multiple comparison test

TABLE 20

Effect of a single dose of compound 1 on body weight change over three days in Sprague-Dawley rats.

| Treatment | Dose (nmol/kg) | Day −1 | Day 0 | Day 1 | Day 2 | Day 3 |
|---|---|---|---|---|---|---|
| Vehicle | | −7.7 ± 1.5 | 0.0 ± 0.0 | 9.6 ± 1.5 | 18.0 ± 1.4 | 27.4 ± 1.8 |
| Compound 1 | 0.1 | −8.2 ± 0.9 | 0.0 ± 0.0 | 10.2 ± 1.6 | 19.1 ± 1.0 | 27.3 ± 1.4 |
| | 0.3 | −5.9 ± 0.9 | 0.0 ± 0.0 | 7.3 ± 1.1 | 15.1 ± 1.1 | 23.4 ± 1.7 |
| | 1 | −9.7 ± 0.8 | 0.0 ± 0.0 | 4.7 ± 0.8* | 11.0 ± 1.4* | 18.2 ± 1.0* |
| | 3 | −7.6 ± 1.4 | 0.0 ± 0.0 | 2.2 ± 1.6* | 3.0 ± 1.5* | 9.4 ± 1.9* |
| Dulaglutide | 0.3 | −6.3 ± 0.8 | 0.0 ± 0.0 | 10.6 ± 1.6 | 22.5 ± 0.8 | 28.7 ± 0.6 |

Values represent mean ± SEM for data from 8 animals per time per group
*p < 0.05, versus vehicle; one-way ANOVA, Dunnett's multiple comparison test for net change in body weight on day 3; two-way ANOVA, Tukey's multiple comparison test for daily change in body weight

Figure 10:
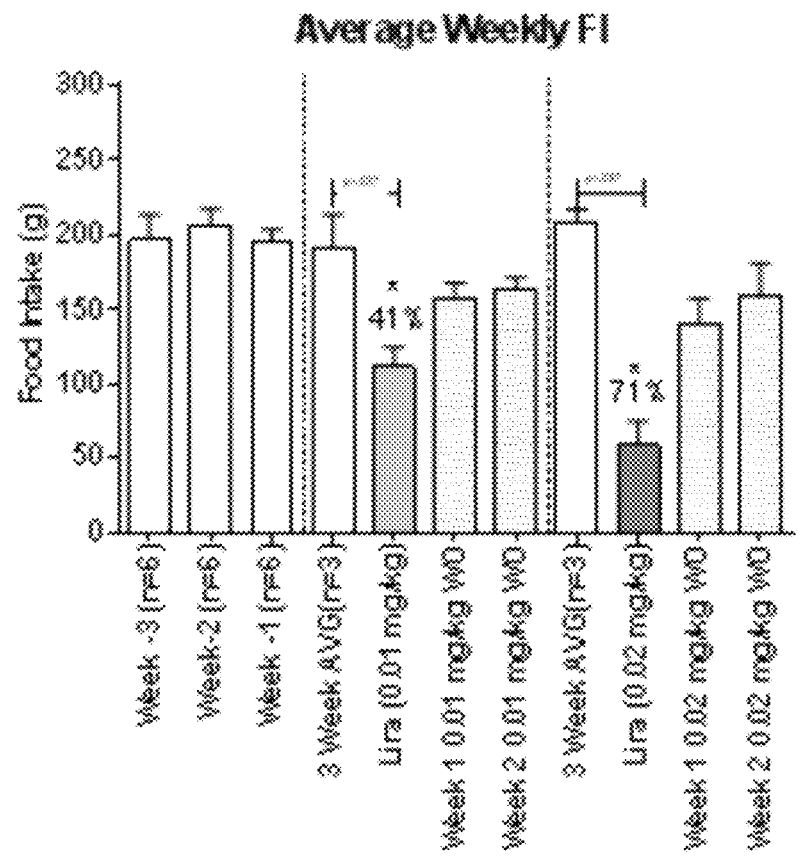
FIG. 10: Shows a graph demonstrating the average weekly food intake for 3 weeks prior to starting liraglutide, 1 week of treatment with liraglutide, and 2 weeks following liraglutide administration. Percent reduction of average weekly food intake of treatment versus the 3 week baseline average is indicated.
Figure 11A:
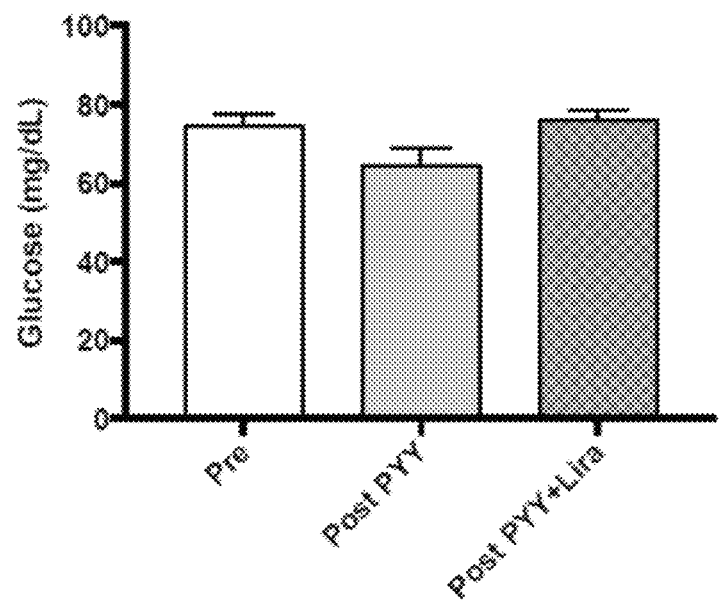
FIGS. 11A-11D: Show graphs demonstrating the effect of compound 1 with liraglutide add-on on glucose, insulin, and triglycerides in obese rhesus macaques.
Figure 11B:
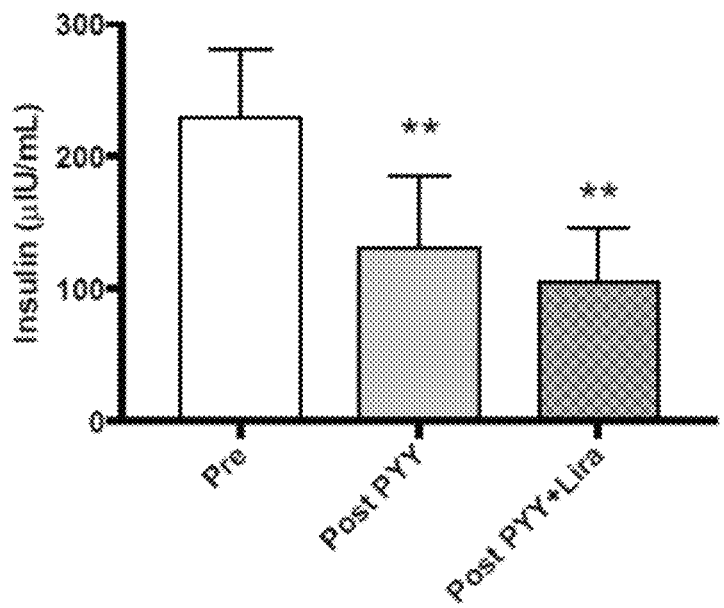
Figure 11C:
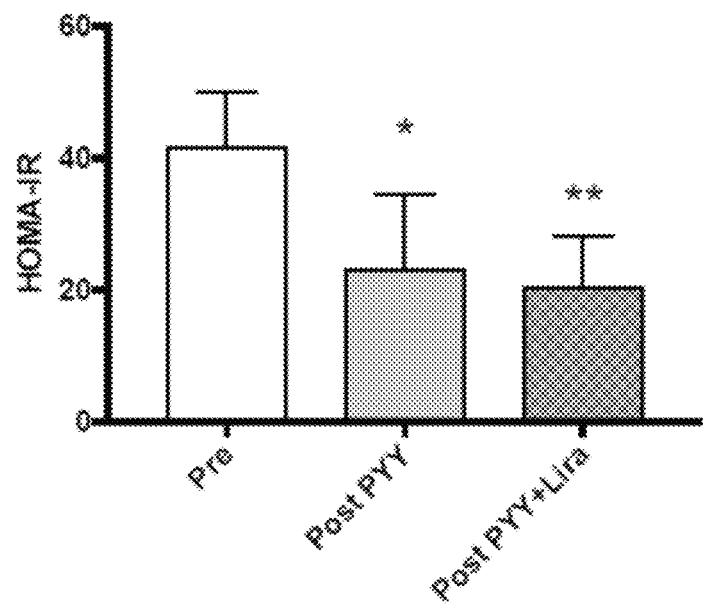
Figure 11D:
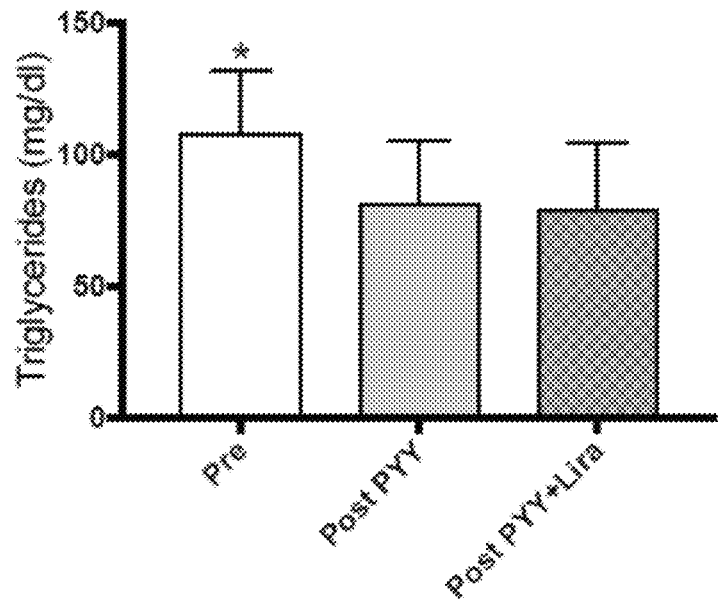
Figure 12A:
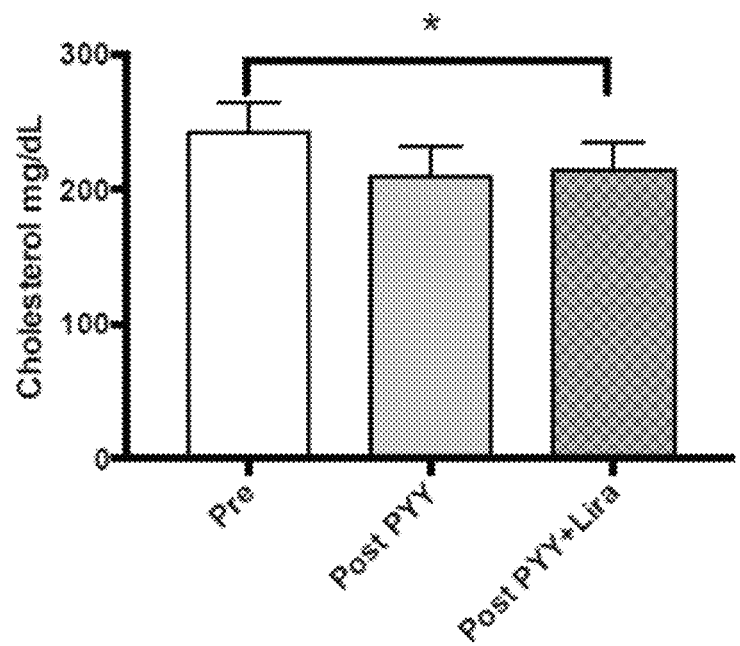
FIGS. 12A-12D: Show graphs of the effect of compound 1 with liraglutide add-on on cholesterol and liver enzymes in obese rhesus macaques.
Figure 12B:
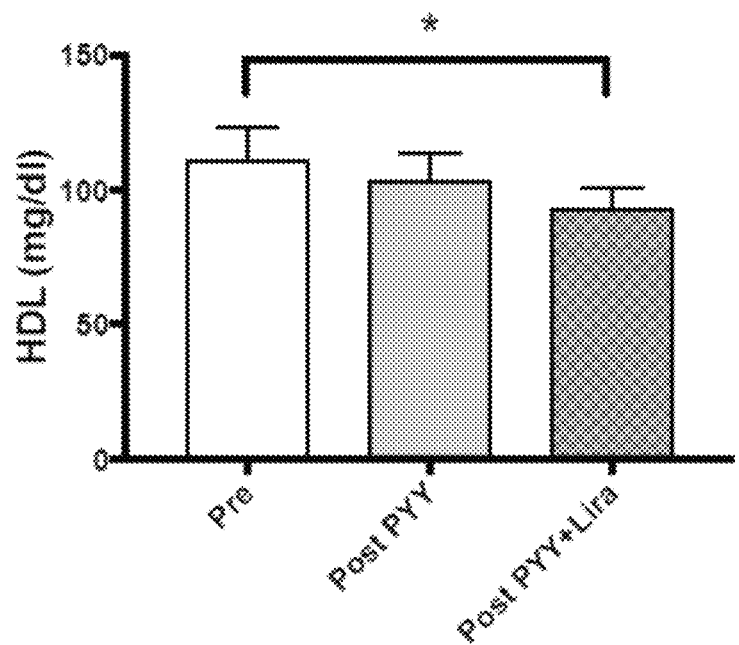
Figure 12C:
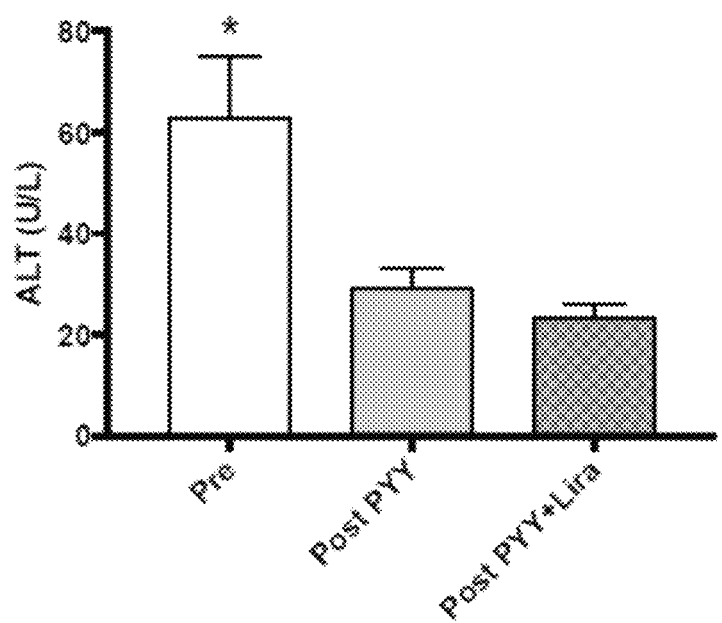
Figure 12D:
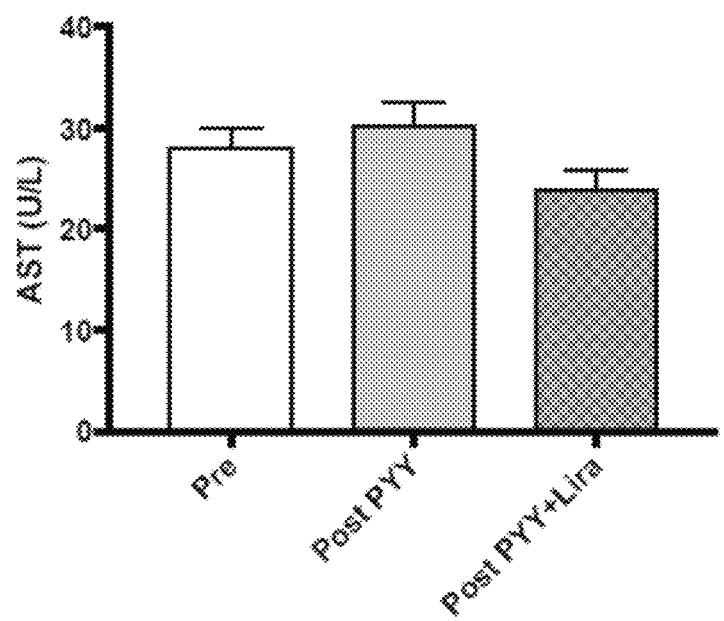

Example 110: Effects of Compound 1, Alone or in Combination with Liraglutide, in Obese Rhesus Macaques Compound 1 was evaluated for its ability to reduce foot intake in obese rhesus macaques. The additional efficacy observed when liraglutide is co-administered with an efficacious dose of compound 1 was also evaluated. First, an abbreviated dose-ranging study was conducted to determine the dose of liraglutide to be used during co-administration. Six animals received a single daily sc administration of saline for three weeks. Food intake was measured daily and the baseline food intake was set as the average daily intake over the three weeks of vehicle treatment. The six animals were then divided into two groups; 0.01 mg/kg (n=3) and 0.02 mg/kg (n=3). Each received a daily subcutaneous dose of liraglutide for one week to determine the effects on food intake relative to baseline and to identify a maximal tolerable dose. Food intake was also measured for two weeks after discontinuing liraglutide treatment. All data are presented as the mean weekly food intake±SEM (FIG. 10).

Ten (10) obese rhesus macaques were used to assess the efficacy of compound 1. After a 2-week baseline period, compound 1 was administered s.c. daily for 4 weeks. Animals were dosed for 7 days at 0.01 mg/kg, then 7 days at 0.03 mg/kg, then 9 days at 0.015 mg/kg, and finally 5 days of co-dosing compound 1 at 0.015 mg/kg in combination with liraglutide at 0.01 mg/kg. Food intake was monitored daily and body weight was measured weekly. Glucose, insulin, total cholesterol, HDL, LDL, ALT and AST levels were assessed at baseline, after compound 1 treatment and after combination treatment. All data are presented as the mean±SEM (Tables 21-22 and FIGS. 11 and 12).

TABLE 21

Effect of compound 1 with liraglutide add-on on food intake in obese *rhesus macaques*

| Days of Treatment | Compound 1 (mg/kg) | | | |
|---|---|---|---|---|
| | 0.01 | 0.03 | 0.015 | 0.015 ± liraglutide |
| 2 wk baseline | 190 ± 15 | | | |
| 1 | 160 ± 9 | 149 ± 12 | 117 ± 18 | 50 ± 11 |
| 2 | 167 ± 19 | 149 ± 14 | 72 ± 14 | 13 ± 5 |
| 3 | 175 ± 13 | 94 ± 16 | 72 ± 12 | 15 ± 10 |
| 4 | 196 ± 14 | 181 ± 13 | 86 ± 14 | 34 ± 17 |
| 5 | 166 ± 15 | 101 ± 12 | 77 ± 8 | 34 ± 12 |
| 6 | 180 ± 14 | 99 ± 27 | 91 ± 12 | |
| 7 | 146 ± 12 | 73 ± 11 | 75 ± 4 | |
| 8 | | | 97 ± 12 | |
| 9 | | | 118 ± 21 | |

TABLE 22

Effect of compound 1 with liraglutide add-on on body weight in obese *rhesus macaques*

| Treatment | Dose (mg/kg) | BW (kg) |
|---|---|---|
| Pre-Dose | NA | 15.8 ± 0.9 |
| Compound 1 | 0.01 | 15.9 ± 0.9 |
| | 0.03 | 15.7 ± 0.9 |
| | 0.015 | 15.4 ± 0.8* |
| Compound 1 ± liraglutide | 0.015 | 15.0 ± 0.8* |

Values represent mean ± SEM for data from 8 animals per group
*p < 0.05, versus vehicle
One-way ANOVA RM, Dunnett multiple comparison test It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

All documents cited herein are incorporated by reference.

Exemplary cyclic PYY sequences or conjugates thereof of the invention include:

SEQ ID NO: 1

Structure:

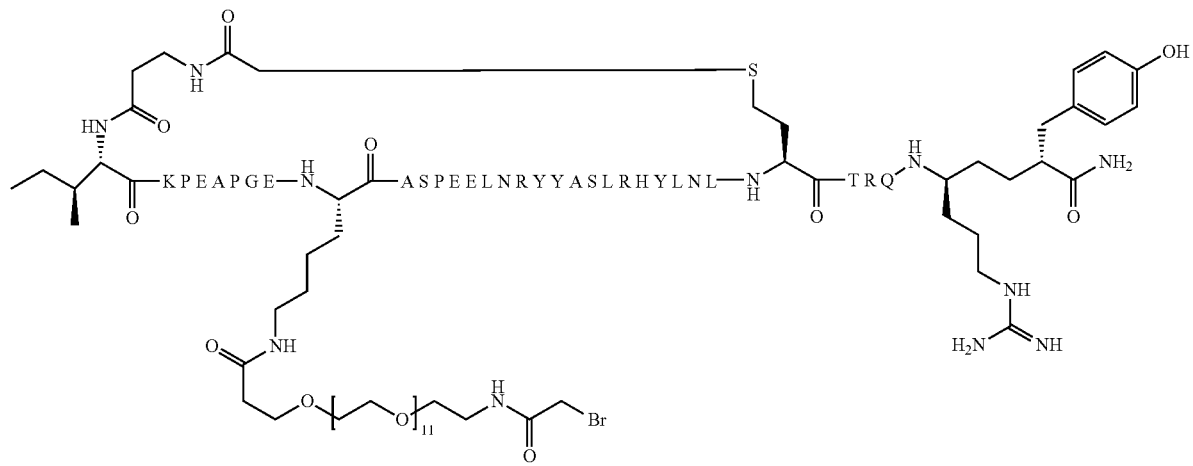

Name: [Cyclo-(βA2-COCH₂-hC31), K(PEG12-AcBr)11, psi-(35R, 36Y)]-PYY2-36

SEQ ID NO: 2

Structure:

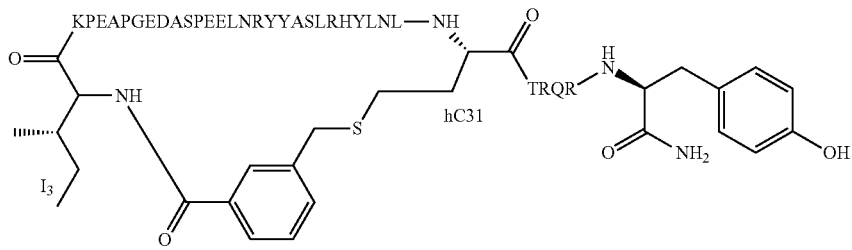

Name: [cyclo-(I3-m-COPhCH₂-hC31)]-PYY3-36

SEQ ID NO: 3

Structure:

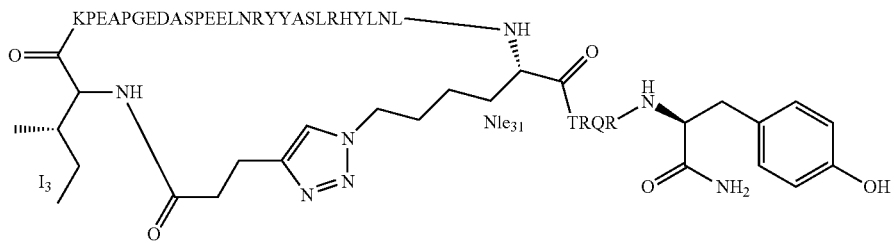

Name: [cyclo-(I3-CO(CH₂)₂triazolyl-Nle31]-PYY3-36

SEQ ID NO: 4
Structure:
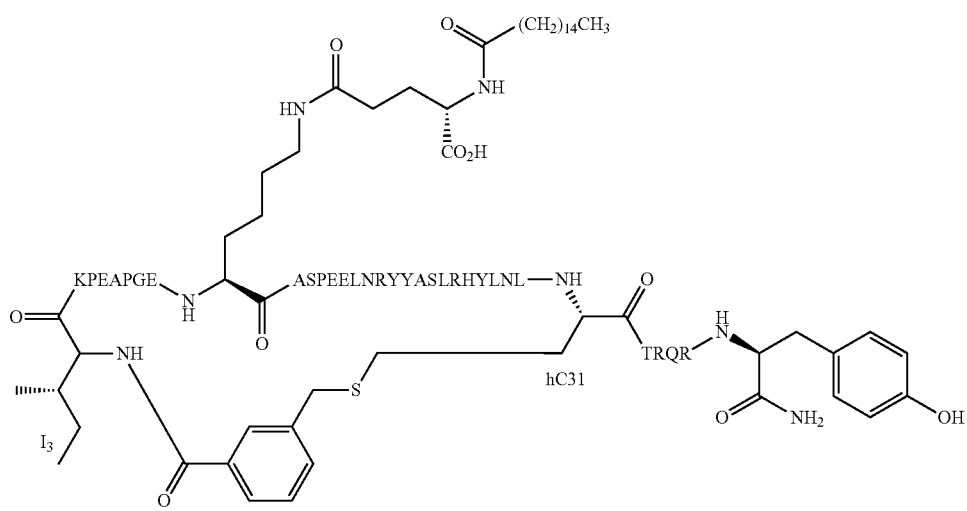
Name: [cyclo-(I3-m-COPhCH₂-hC31), K(γ-Glu-Pal)11]-PYY3-36
SEQ ID NO: 5
Structure:
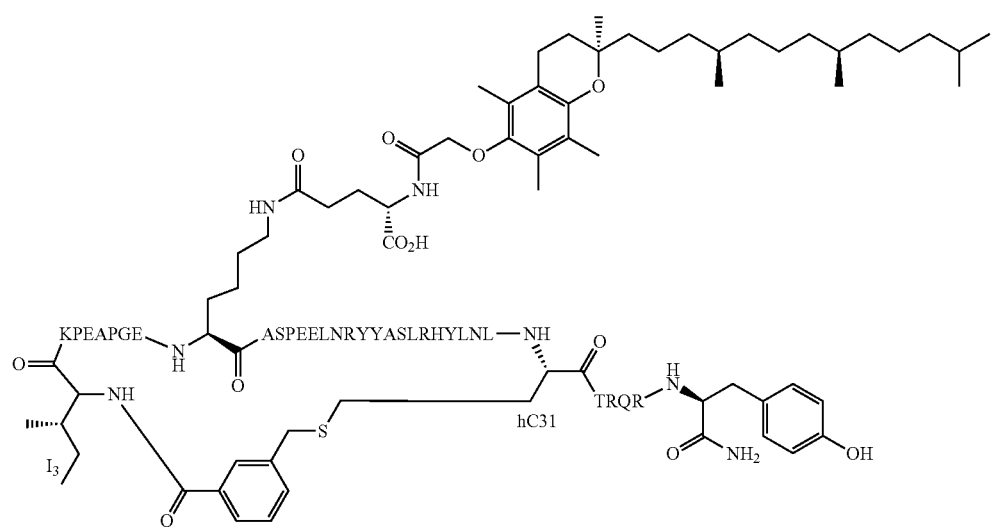
Name: [cyclo-(I3-m-COPhCH2-hC31), K(γ-Glu-AcVitE)11]-PYY3-36

SEQ ID NO: 6
Structure:
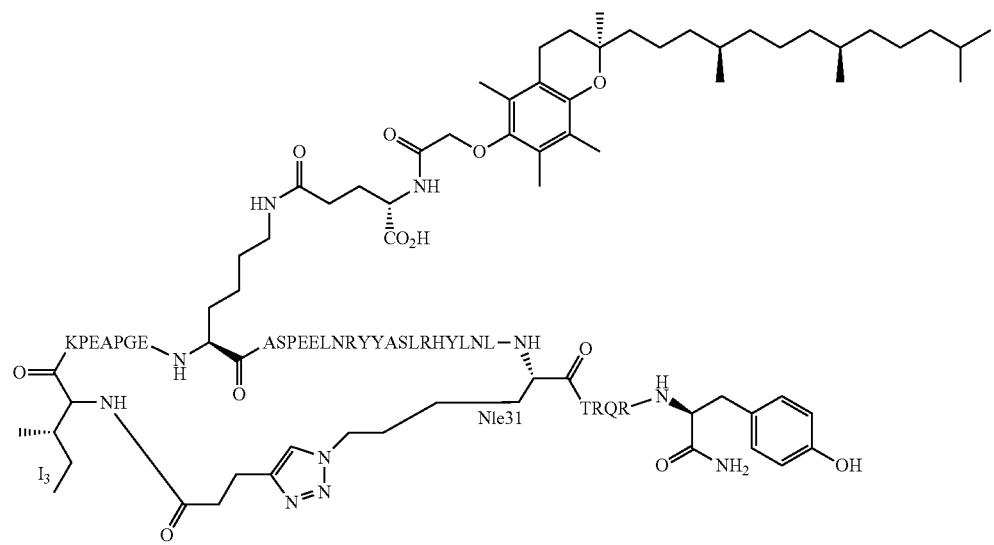
Name: [cyclo-(I3-CO(CH$_2$)$_2$triazolyl-Nle31), K(γ-Glu-AcVitE)11]-PYY3-36
SEQ ID NO: 7
Structure:
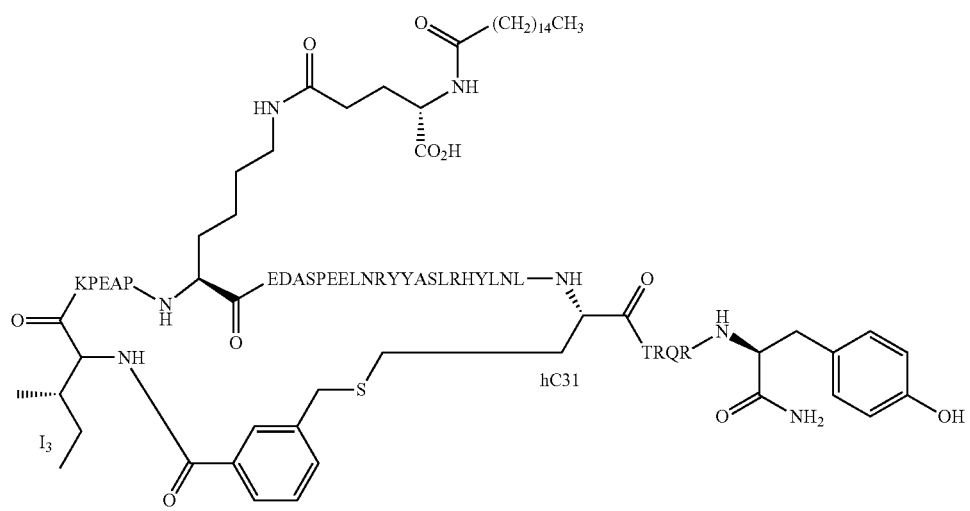
Name: [cyclo-(I3-m-COPhCH$_2$-hC31), K(γ-Glu-Pal)9]-PYY3-36

SEQ ID NO: 8
Structure:
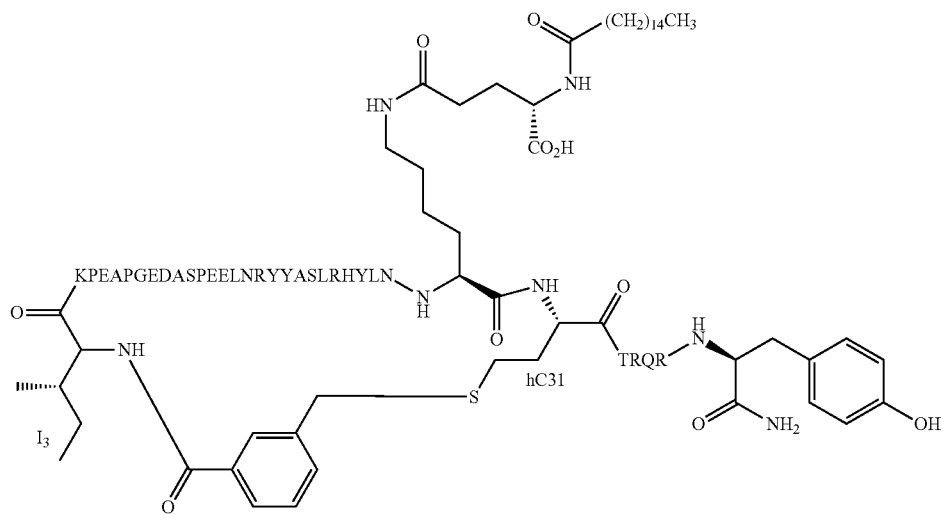
Name: [cyclo-(I3-m-COPhCH₂-hC31), K(γ-Glu-Pal)30]-PYY3-36
SEQ ID NO: 9
Structure:
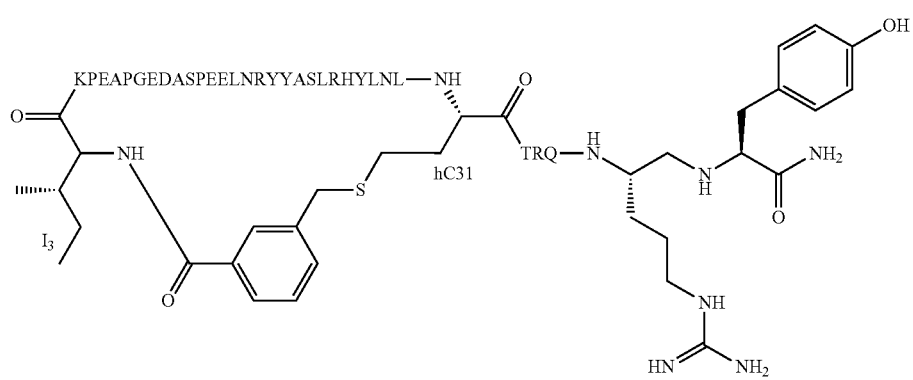
Name: [cyclo-(I3-m-COPhCH₂-hC31), psi-(R35Y36)]-PYY3-36

SEQ ID NO: 10
Structure:
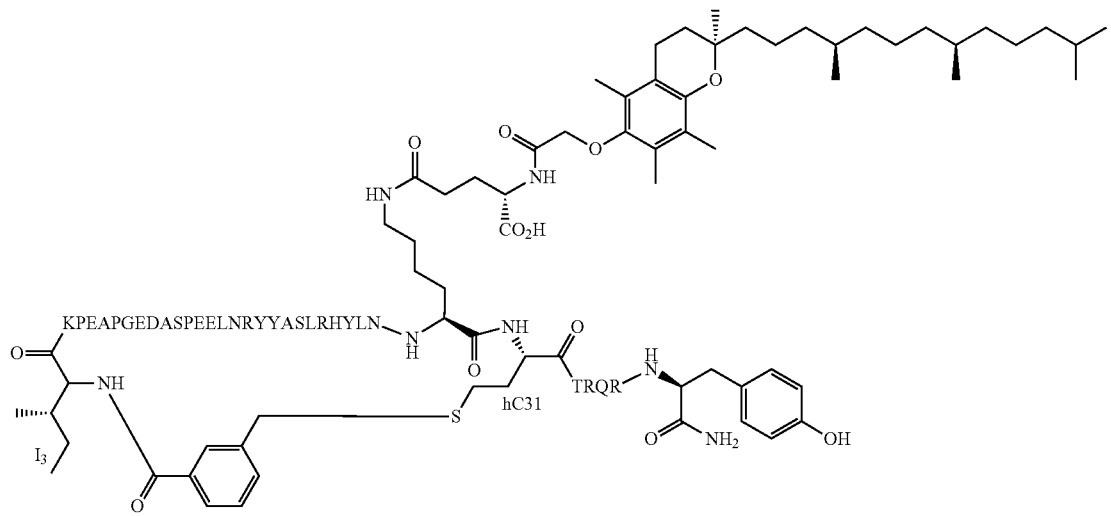
Name: [cyclo-(I3-m-COPhCH2-hC31), K(γ-Glu-AcVitE)30]-PYY3-36
SEQ ID NO: 11
Structure:
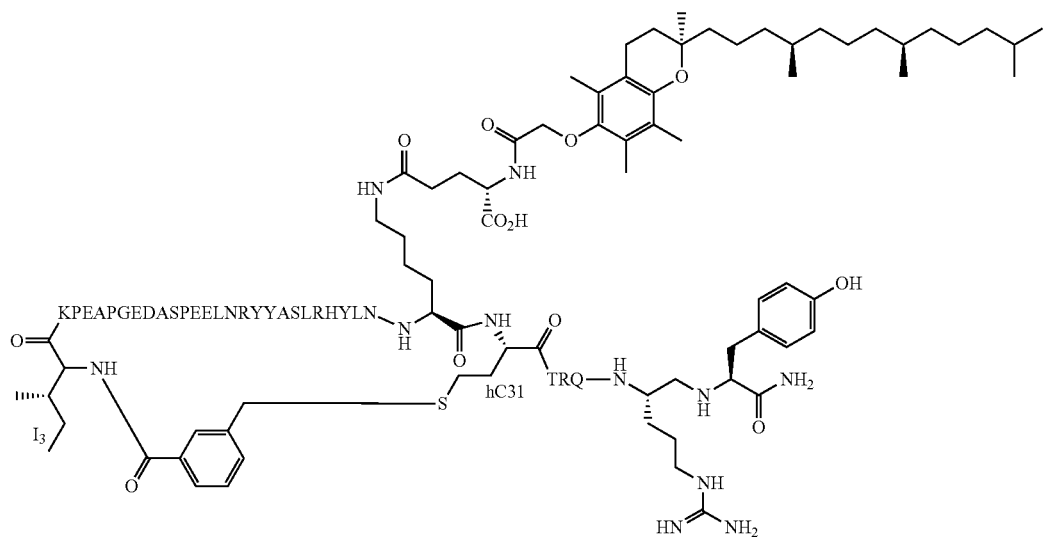
Name: [cyclo-(I3-m-COPhCH2-hC31), K(γ-Glu-AcVitE)30,psi-(R35, Y36)]-PYY3-36

SEQ ID NO: 12
Structure:
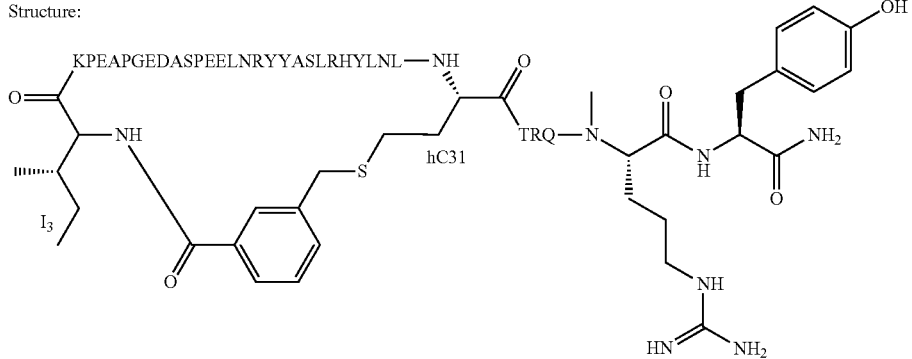
Name: [cyclo-(I3-m-COPhCH₂-hC31), (N-Me-R35)]-PYY3-36
SEQ ID NO: 13
Structure:
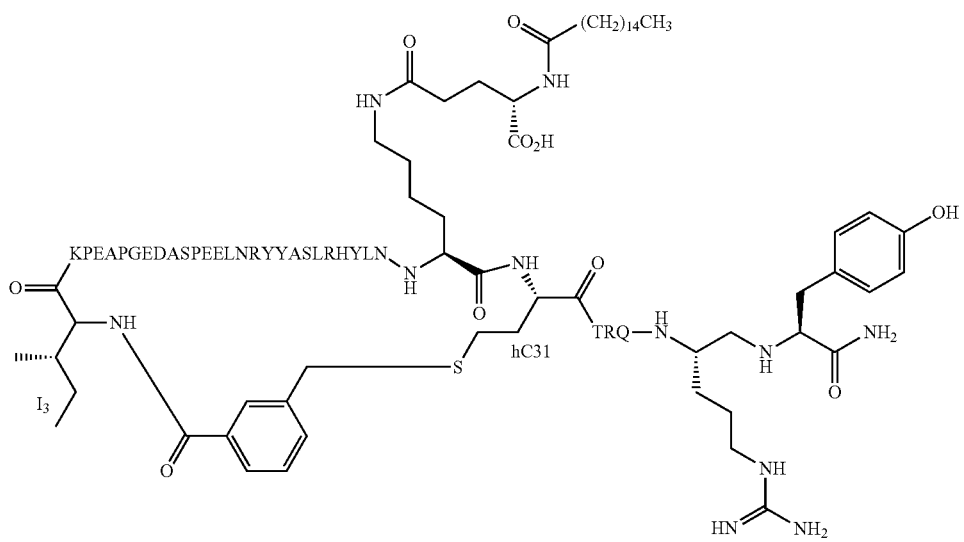
Name: [cyclo-(I3-m-COPhCH₂-hC31), K(γ-Glu-Pal)30, psi-(R35, Y36)]-PYY3-36
SEQ ID NO: 14
Structure:
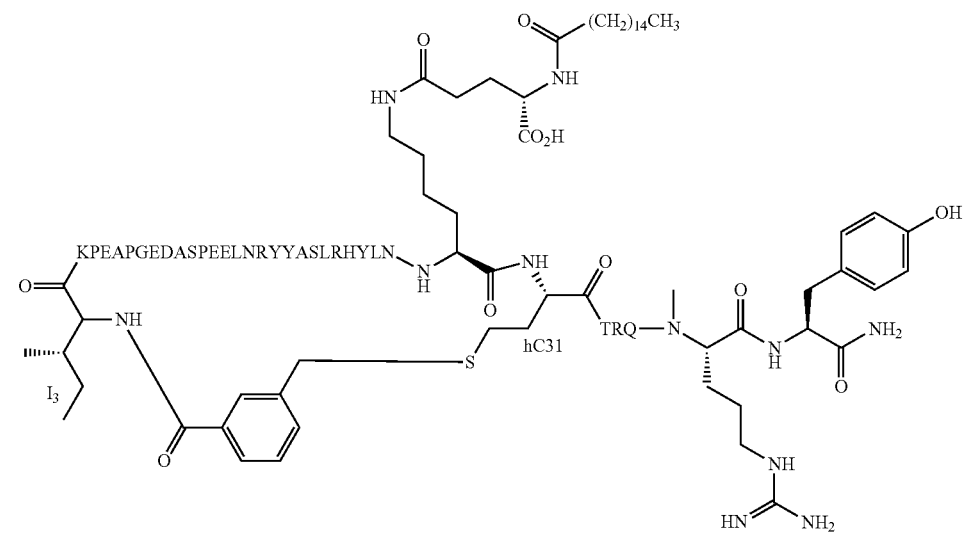
Name: [cyclo-(I3-m-COPhCH₂-hC31), K(γ-Glu-Pal)30, (N-Me-R35)]-PYY3-36

SEQ ID NO: 15
Structure:
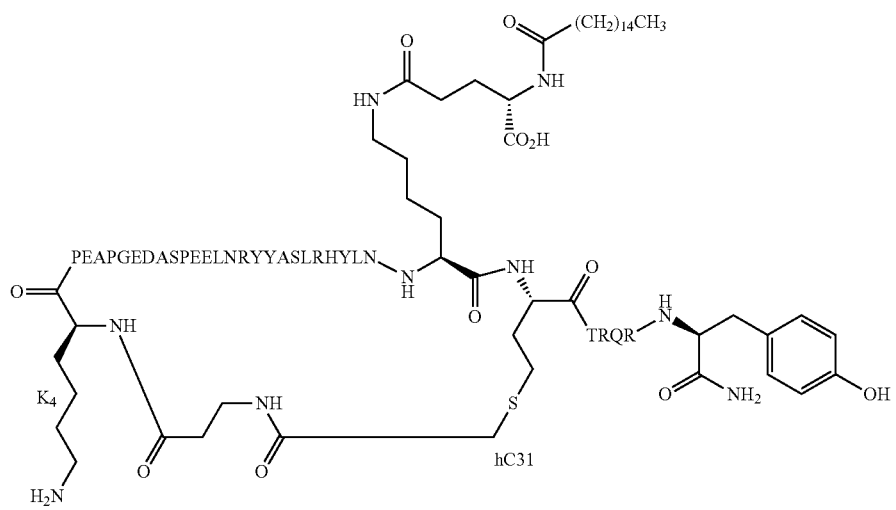
Name: [cyclo-(K4-CO(CH₂)₂NHCOCH₂-hC31), K(γ-Glu-Pal)30]-PYY4-36
SEQ ID NO: 16
Structure:
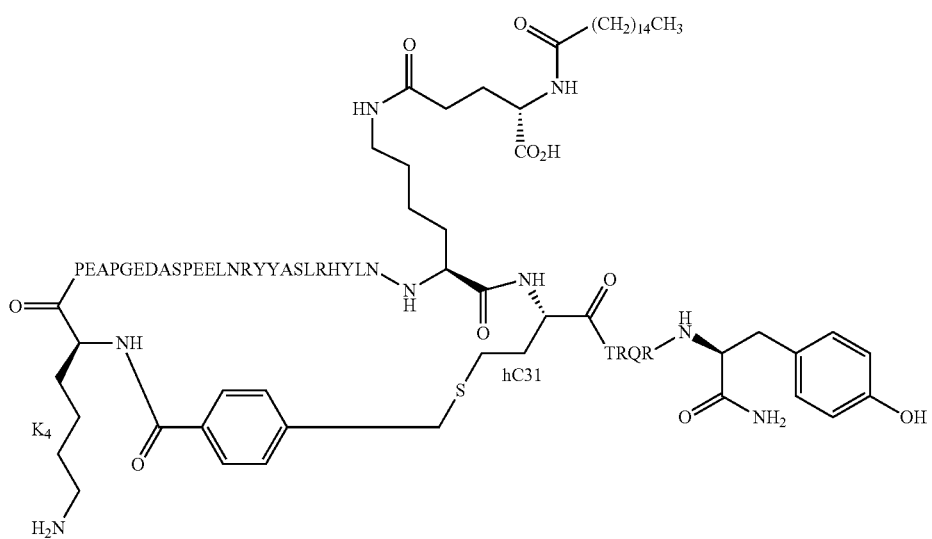
Name: [cyclo-(K4-p-COPhCH₂-hC31), K(γ-Glu-Pal)30]-PYY4-36

SEQ ID NO: 17
Structure:
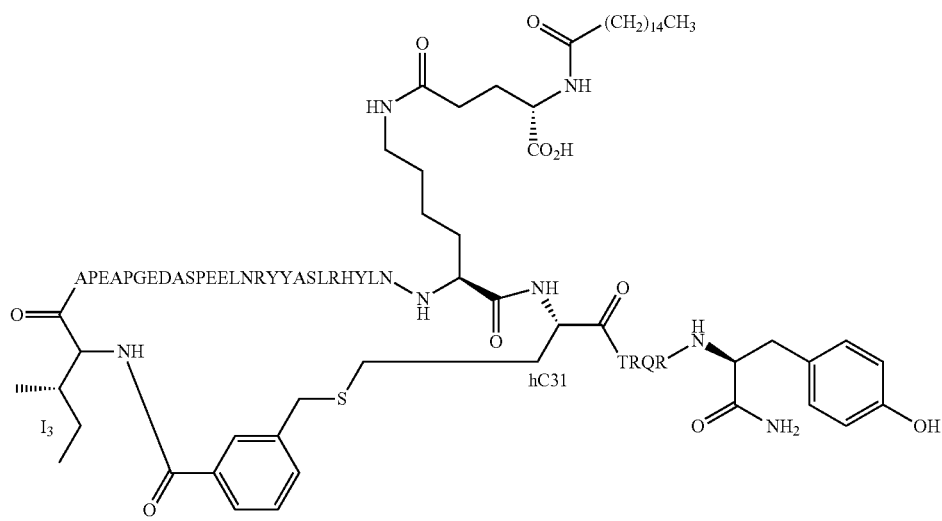
Name: [cyclo-(I3-m-COPhCH2-hC31), A4, K(γ-Glu-Pal)30]-PYY3-36
SEQ ID NO: 18
Structure:
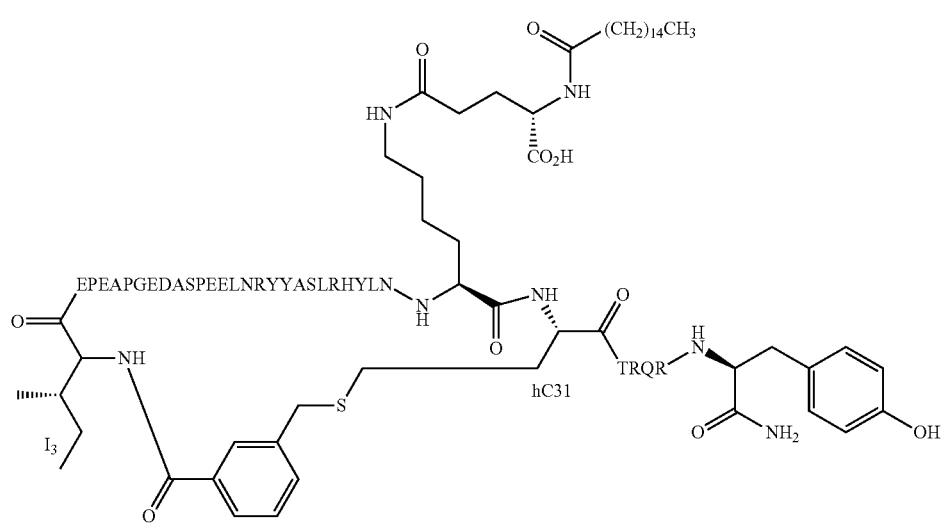
Name: [cyclo-(I3-m-COPhCH2-hC31), E4, K(γ-Glu-Pal)30]-PYY3-36

SEQ ID NO: 19
Structure:
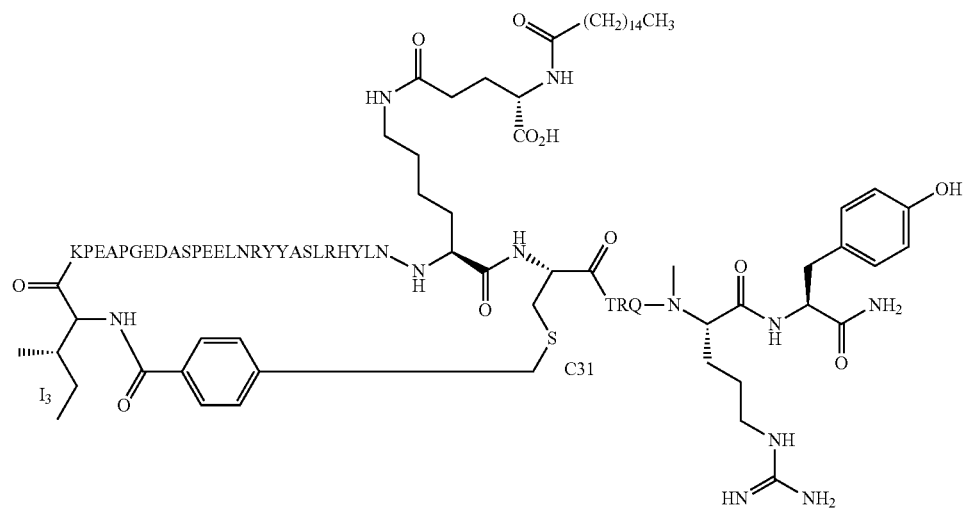
Name: [cyclo-(I3-p-COPhCH2-C31), K(γ-Glu-Pal)30, (N-Me-R35)]-PYY3-36
SEQ ID NO: 20
Structure:
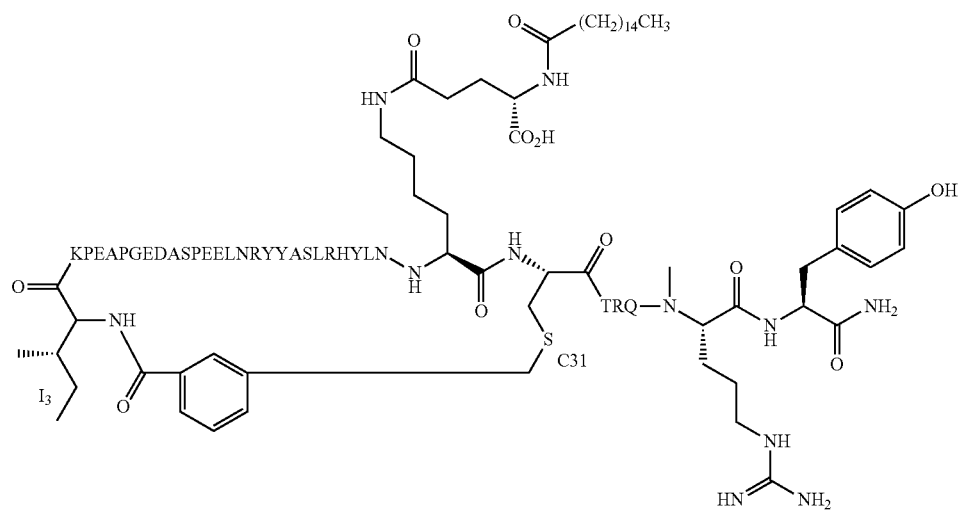
Name: [cyclo-(I3-p-COPhCH2-C31), K(γ-Glu-Pal)30, (N-Me-R35)]-PYY3-36

SEQ ID NO: 21
Structure:
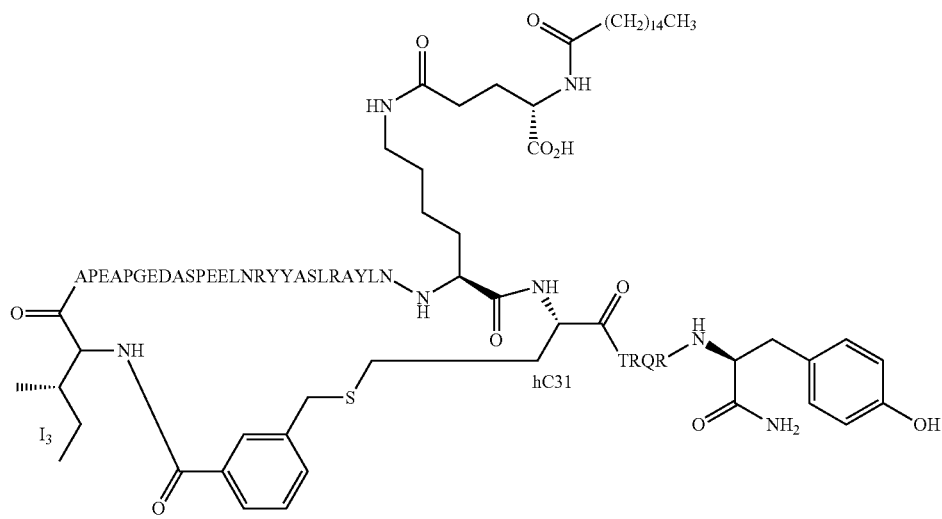
Name: [cyclo-(I3-m-COPhCH₂-hC31), A4, A26, K(γ-Glu-Pal)30]-PYY3-36
SEQ ID NO: 22
Structure:
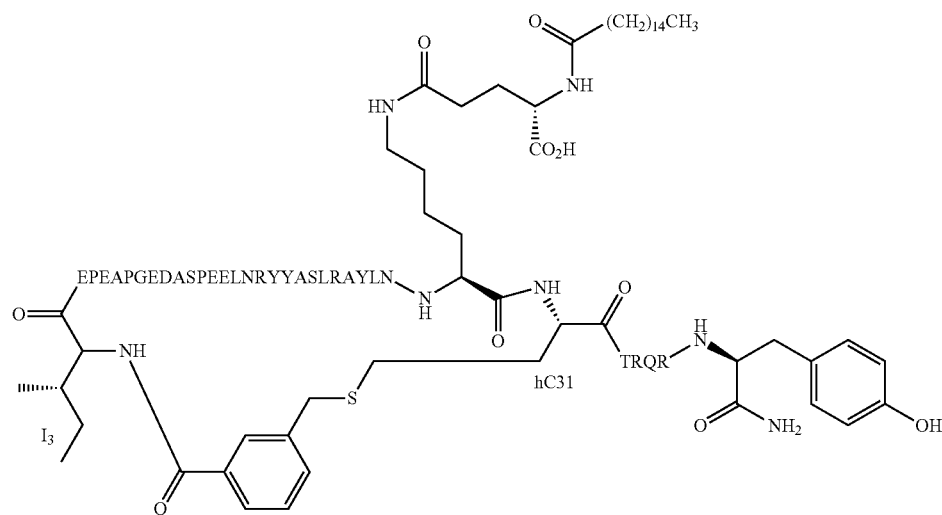
Name: [cyclo-(I3-m-COPhCH₂-hC31), E4, A26, K(γ-Glu-Pal)30]-PYY3-36

SEQ ID NO: 23
Structure:
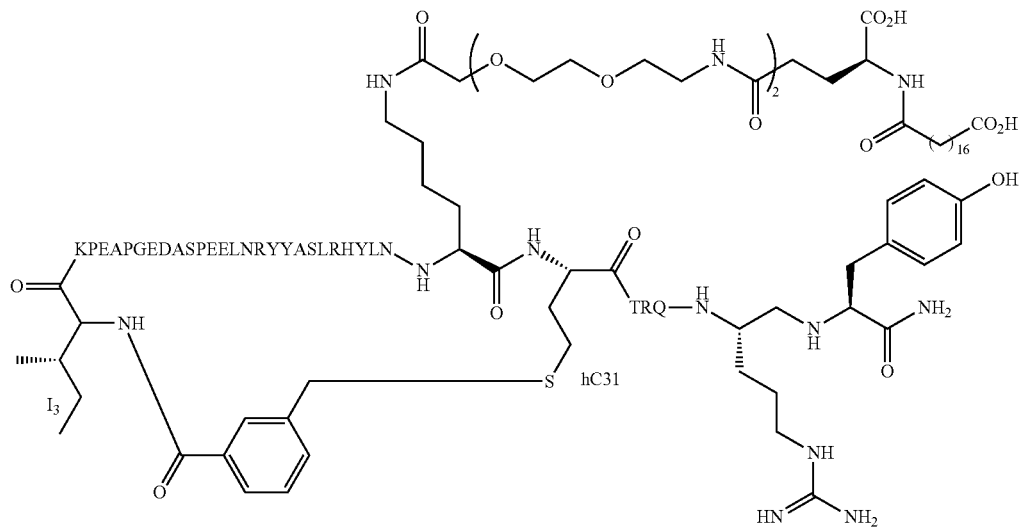
Name: [cyclo-(I3-m-COPhCH₂-hC31), K((OEG)₂-γ-Glu-COC₁₆CO₂H)30, psi-(R35, Y36)]-PYY3-36
SEQ ID NO: 24
Structure:
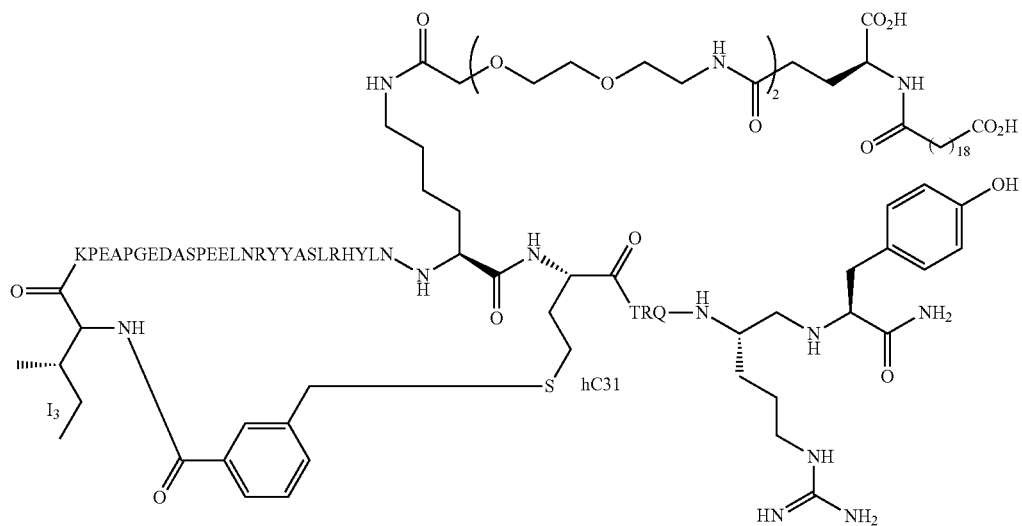
Name: [cyclo-(I3-m-COPhCH₂-hC31), K((OEG)₂-γ-Glu-COC₁₈CO₂H)30, psi-(R35, Y36)]-PYY3-36

SEQ ID NO: 25
Structure:
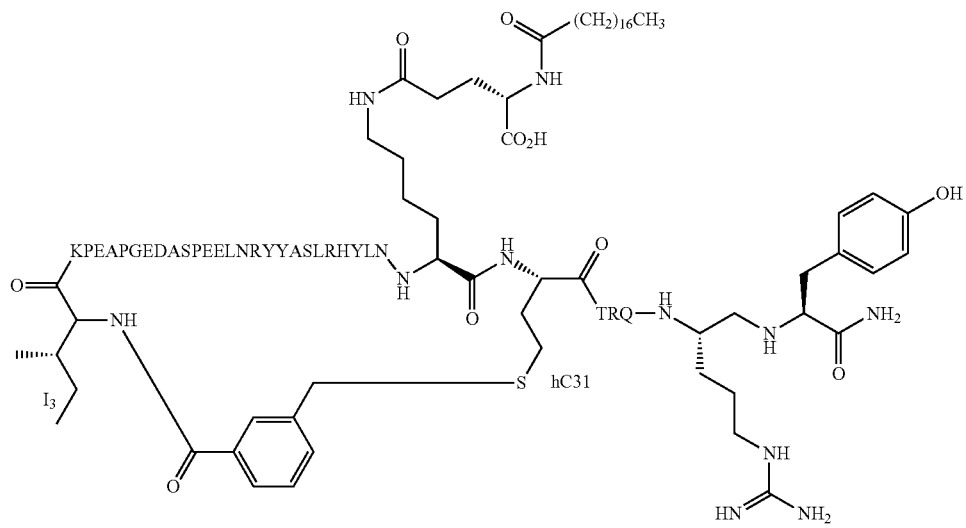
Name: [cyclo-(I3-m-COPhCH₂-hC31), K(γ-Glu-Stear)30, psi-(R35, Y36)]-PYY3-36
SEQ ID NO: 26
Structure:
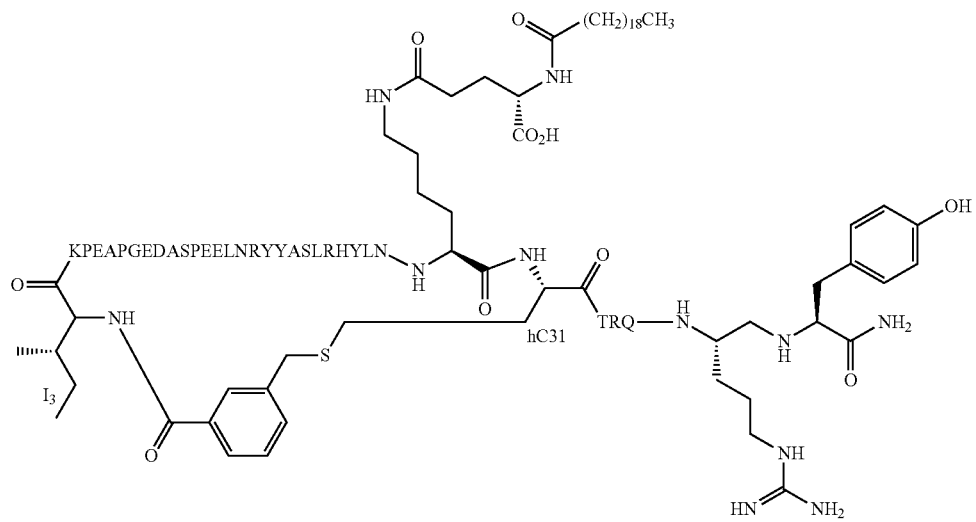
Name: [cyclo-(I3-m-COPhCH₂-hC31), K(γ-Glu-Arach)30, psi-(R35, Y36)]-PYY3-36

SEQ ID NO: 27
Structure:
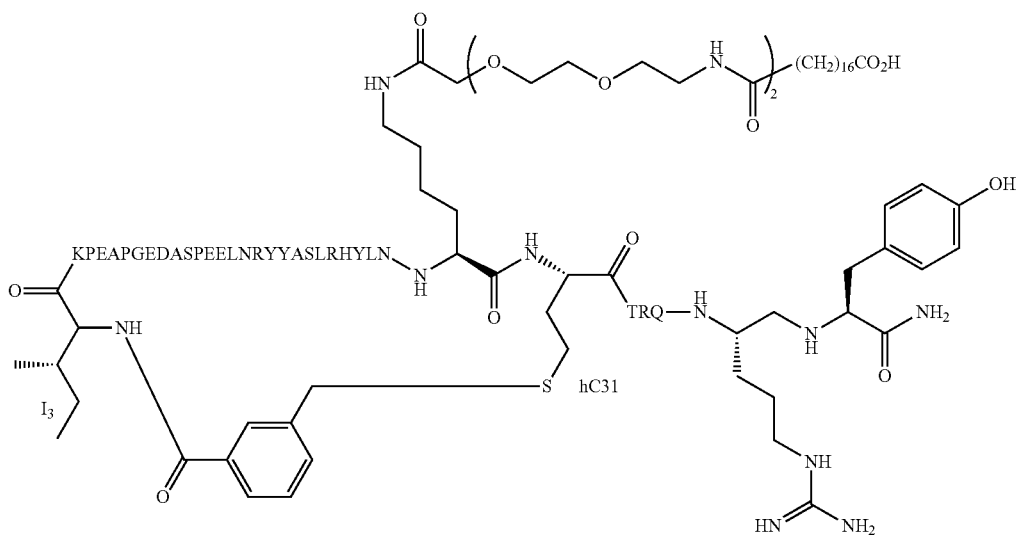
Name: [cyclo-(I3-m-COPhCH2-hC31), K((OEG)2-COC16CO2H)30, psi-(R35, Y36)]-PYY3-36
SEQ ID NO: 28
Structure:
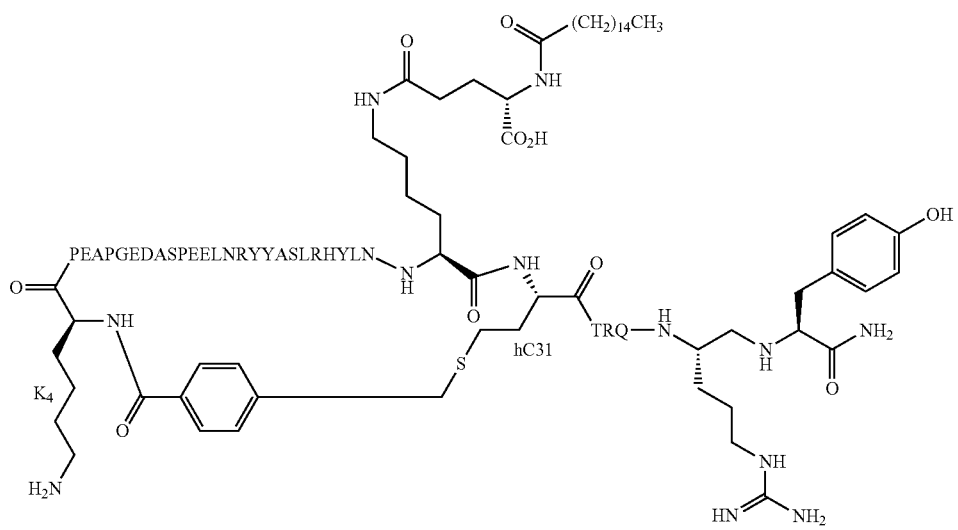
Name: [cyclo-(K4-p-COPhCH2-hC31), K(γ-Glu-Pal)30, psi-(R35, Y36)]-PYY4-36

SEQ ID NO: 29
Structure:
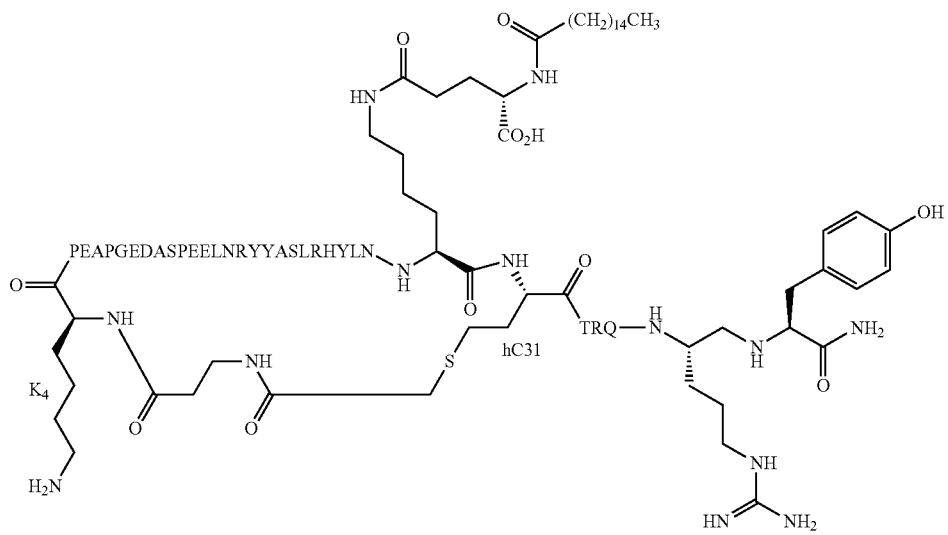
Name: [cyclo-(K4-CO(CH₂)₂NHCOCH₂-hC31), K(γ-Glu-Pal)30, psi-(R35, Y36)]-PYY4-36
SEQ ID NO: 30
Structure:
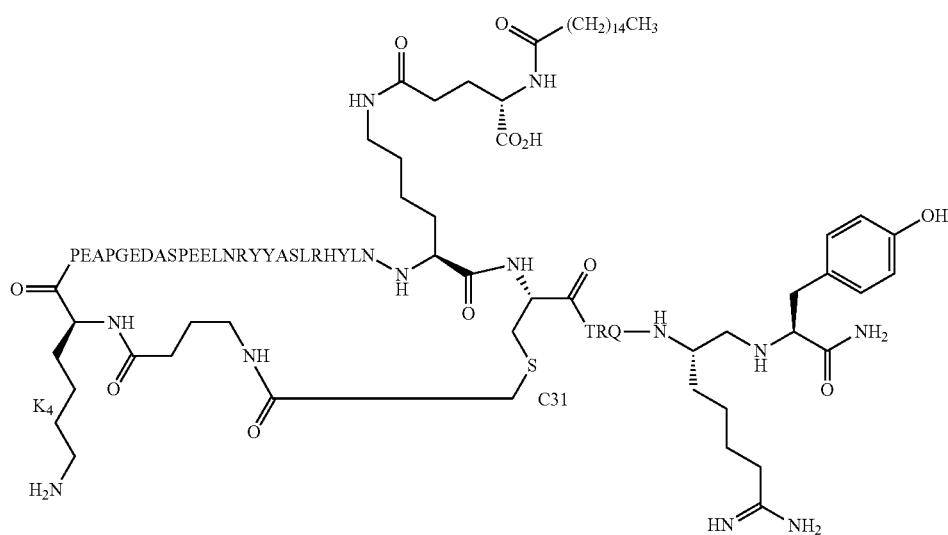
Name: [cyclo-K4-CO(CH₂)₃NHCOCH₂-C31), K(γ-Glu-Pal)30, psi-R35, Y36)]-PYY4-36

SEQ ID NO: 31
Structure:
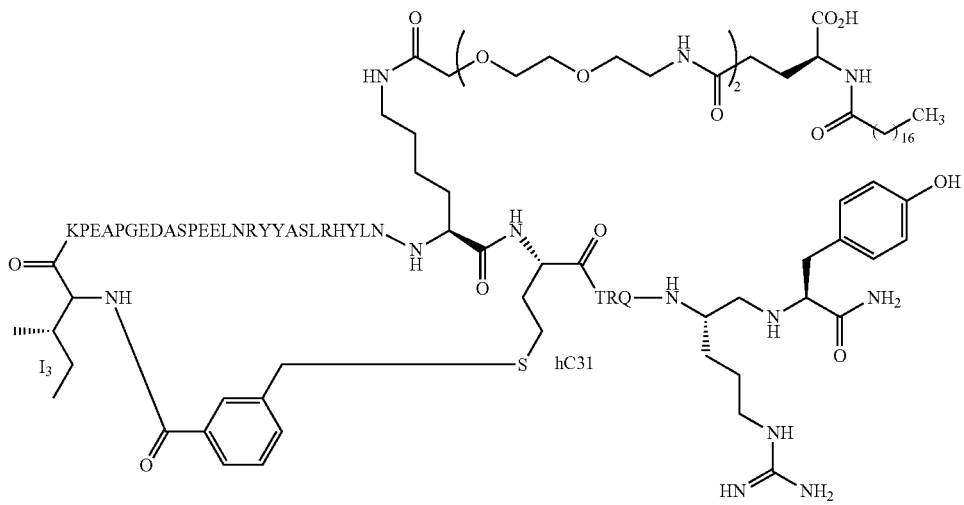
Name: [cyclo-(I3-m-COPhCH2-hC31), K((OEG)2-γ-Glu-Stear)30, psi-(R35, Y36)]-PYY3-36
SEQ ID NO: 32
Structure:
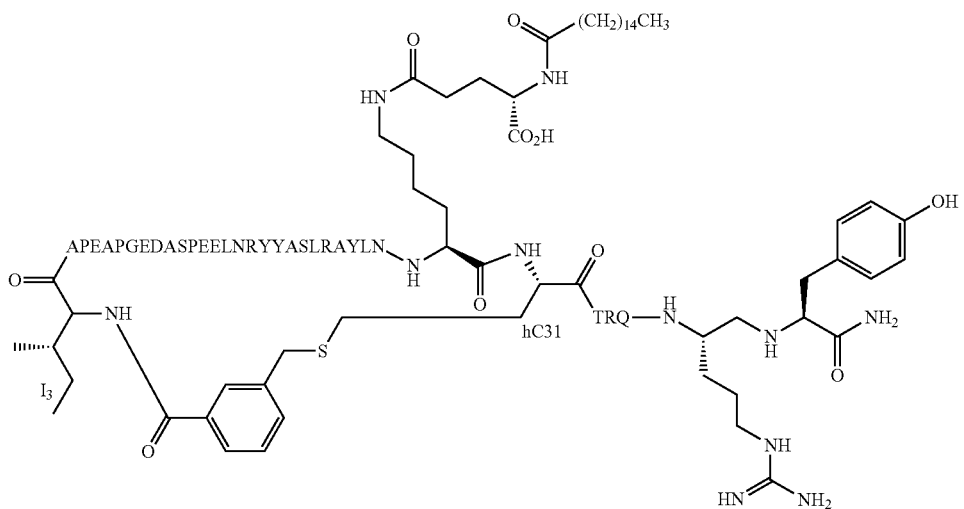
Name: [cyclo-(I3-m-COPhCH2-hC31), A4, A26, K(γ-Glu-Pal)30, psi-(R35, Y36)]-PYY3-36

SEQ ID NO: 33
Structure:
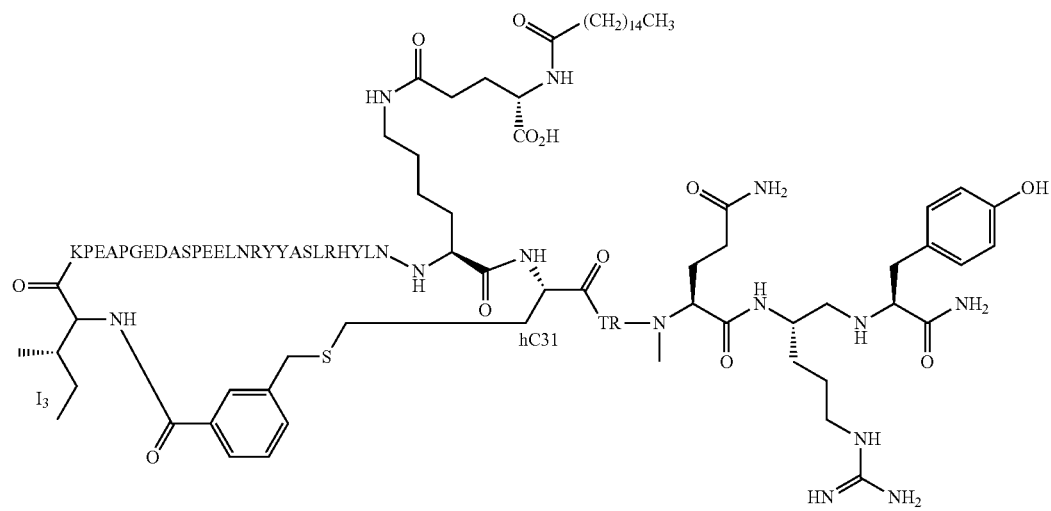
Name: [cyclo-(I3-m-COPhCH₂-hC31), K(γ-Glu-Pal)30, (N-Me-Q34), psi-(R35, Y36)]-PYY3-36
SEQ ID NO: 34
Structure:
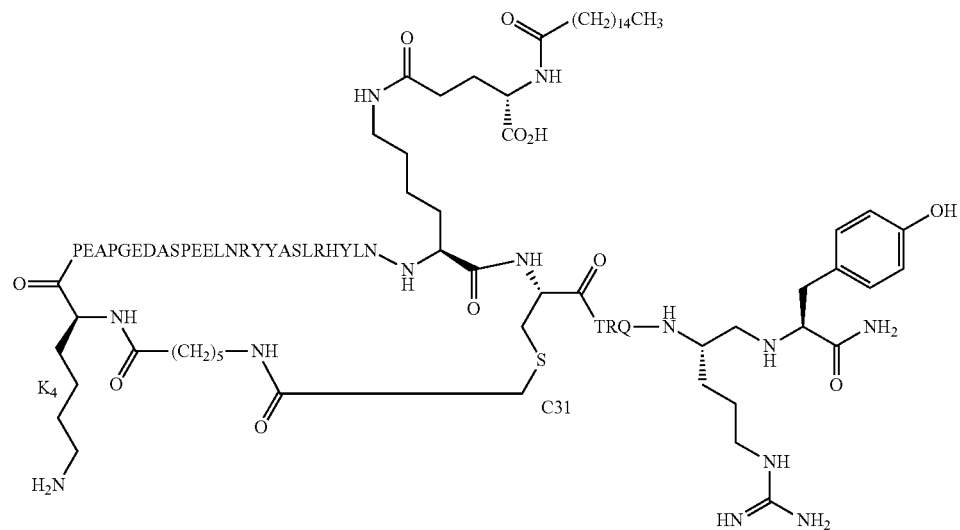
Name: [cyclo-K4-CO(CH₂)₅NHCOCH₂-C31), K(γ-Glu-Pal)30, psi-(R35, Y36)]-PYY4-36

SEQ ID NO: 35
Structure:
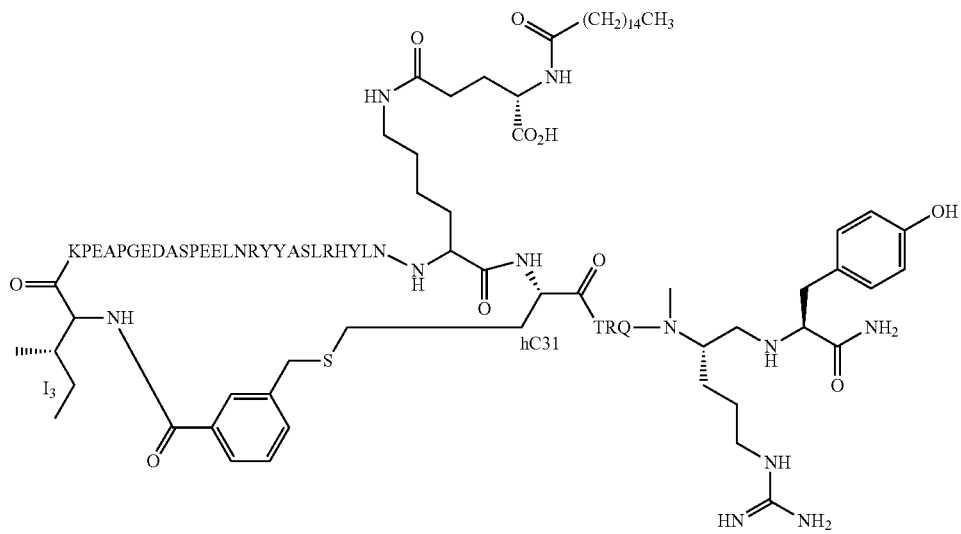
Name: [cyclo-(I3-m-COPhCH₂-hC31), K(γ-Glu-Pal)30, (N-Me-R35), psi-(R35, Y36)]-PYY3-36
SEQ ID NO: 36
Structure:
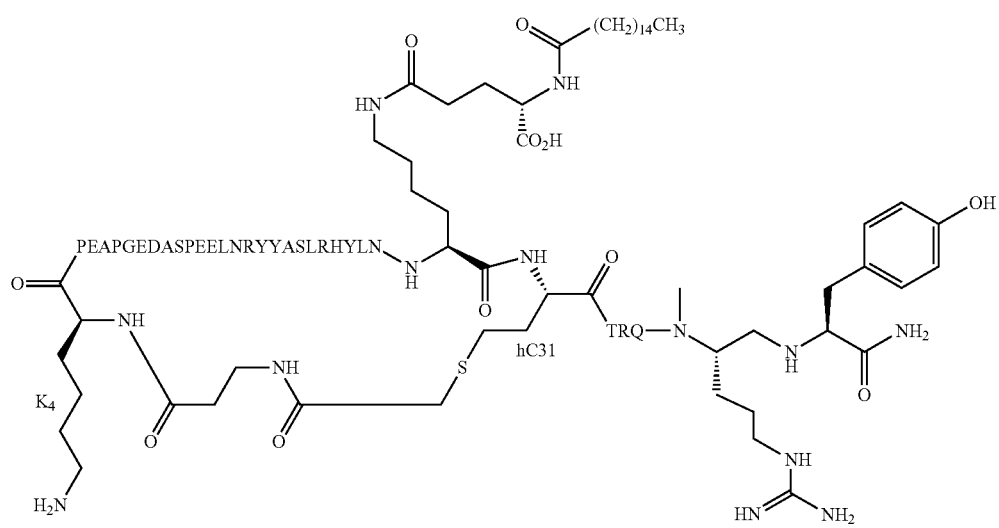
Name: [cyclo-K4-CO(CH₂)₂NHCOCH₂-hC31), K(γ-Glu-Pal)30, (N-Me-R35), psi-(R35, Y36)]-PYY4-36

SEQ ID NO: 37
Structure:
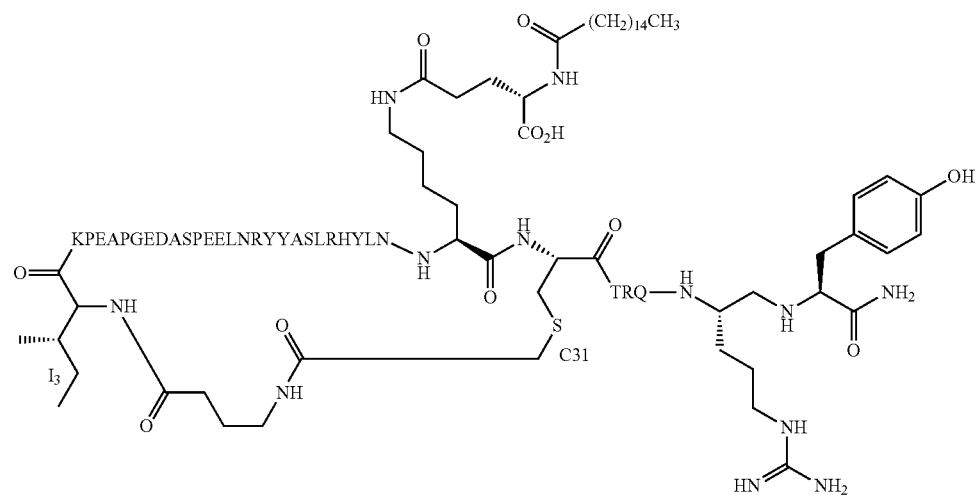
Name: [cyclo-(I3-CO(CH₂)₃NHCOCH₂-C31), K(γ-Glu-Pal)30, psi-(R35, Y36)]-PYY3-36
SEQ ID NO: 38
Structure:
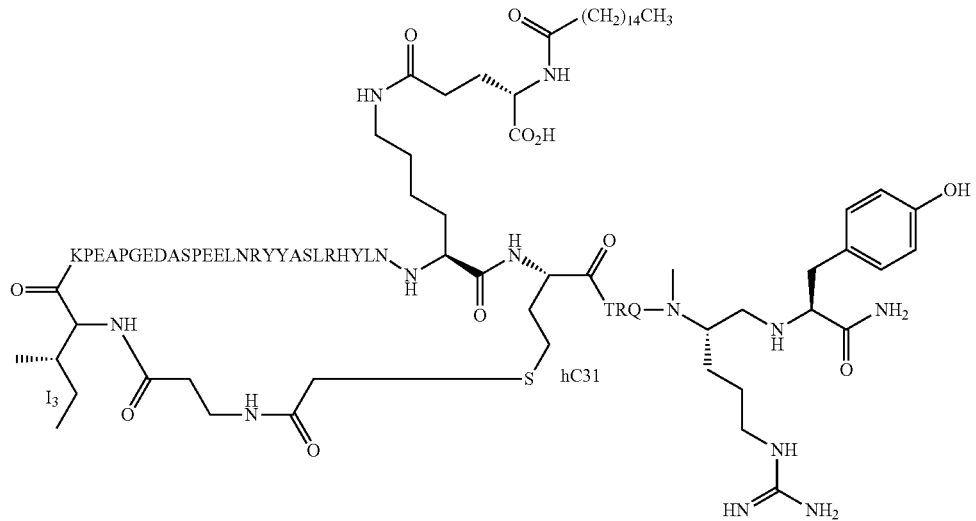
Name: [cyclo-(I3-CO(CH₂)₂NHCOCH₂-hC31), K(γ-Glu-Pal)30, (N-Me-R35), psi(R35, Y36)]-PYY3-36

SEQ ID NO: 39
Structure:
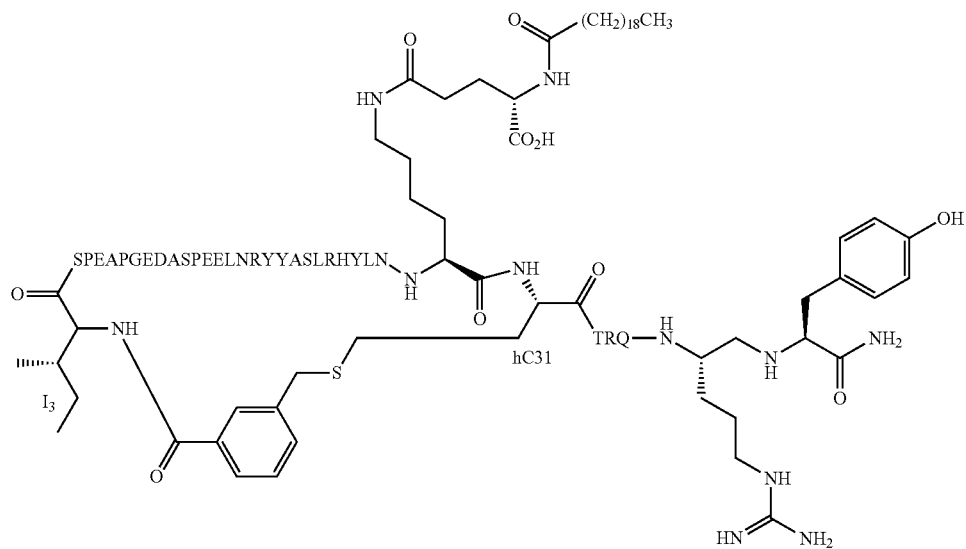
Name: [cyclo-(I3-m-COPhCH₂-hC31), S4, K(γ-Glu-Arach)30, psi-(R35, Y36)]-PYY3-36
SEQ ID NO: 40
Structure:
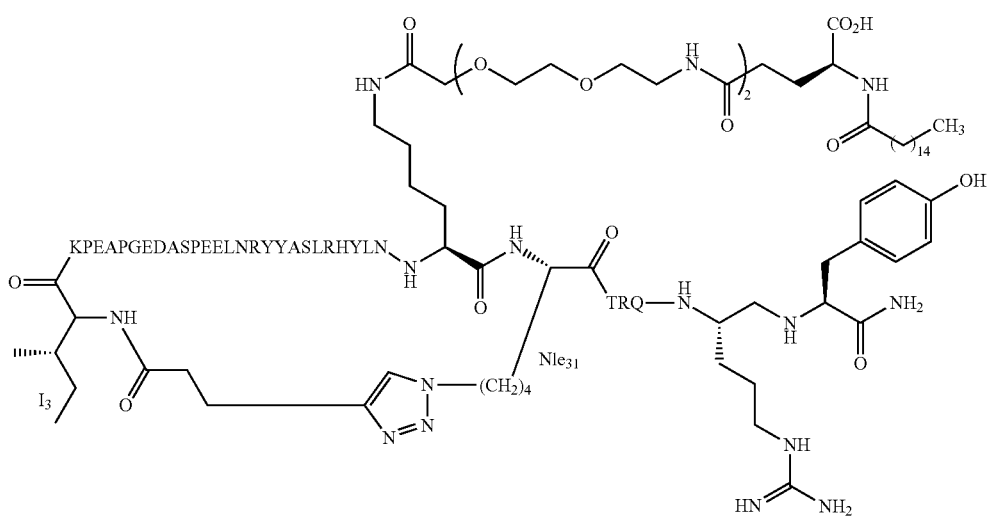
Name: [cyclo-(I3-CO(CH₂)₂triazolyl-Nle31), K((OEG)₂-γ-Glu-Pal)30, psi-(R35, Y36)]-PYY3-36

-continued
SEQ ID NO: 41
Structure:
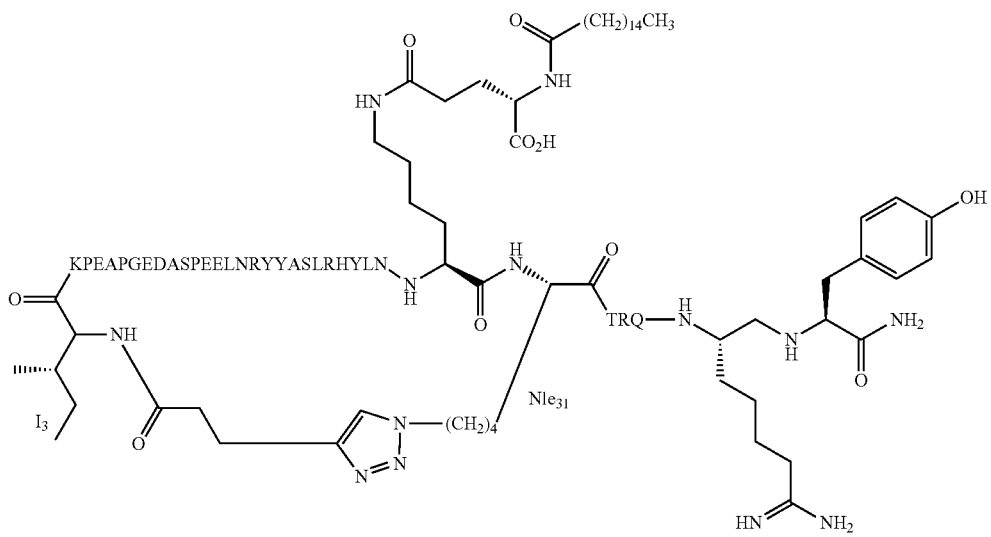
Name: [cyclo-(I3-CO(CH$_2$)$_2$triazolyl-Nle31), K(γ-Glu-Pal)30, psi-(R35, Y36)]-PYY3-36
SEQ ID NO: 42
Structure:
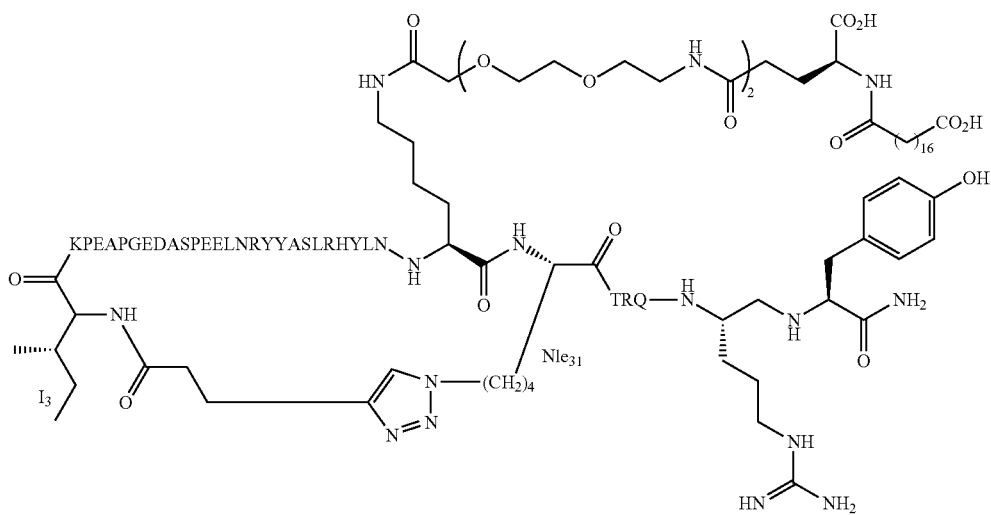
Name: [cyclo-(I3-CO(CH$_2$)$_2$triazolyl-Nle31), K((OEG)$_2$-γ-Glu-COC$_{16}$CO$_2$H)30, psi-(R35, Y36)]-PYY3-36

SEQ ID NO: 43
Structure:
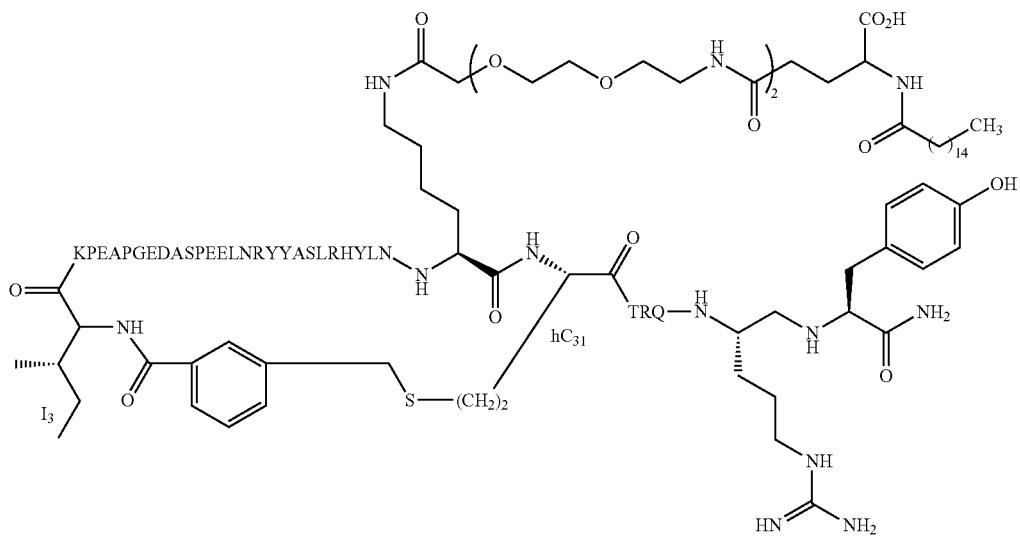
Name: [cyclo-(I3-m-COPhCH$_2$-hC31), K((OEG)$_2$-γ-Glu-Pal)30, psi-(R35, Y36)]-PYY3-36
SEQ ID NO: 44
Structure:
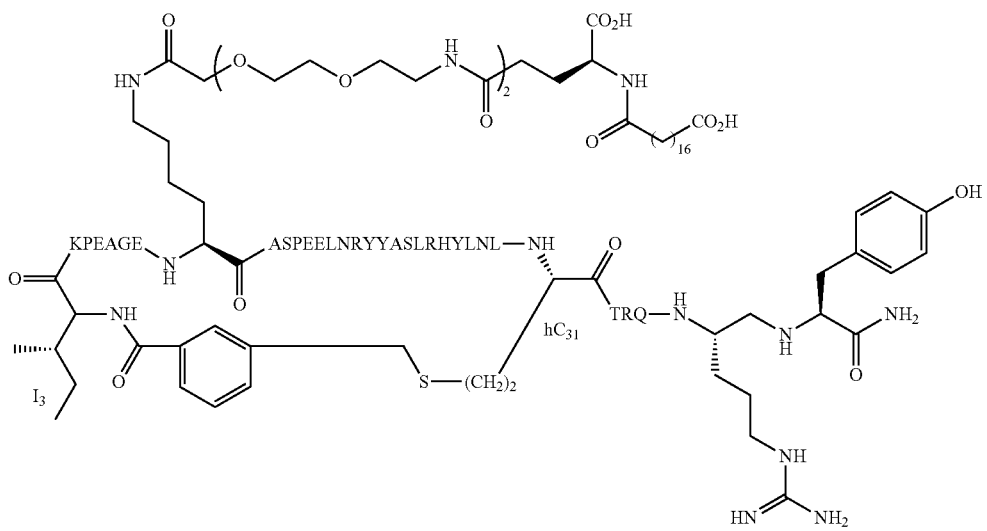
Name: [cyclo-(I3-m-COPhCH$_2$-hC31), K((OEG)$_2$-γ-Glu-COC$_{16}$CO$_2$H)11, psi-(R35, Y36)]-PYY3-36

SEQ ID NO: 45
Structure:
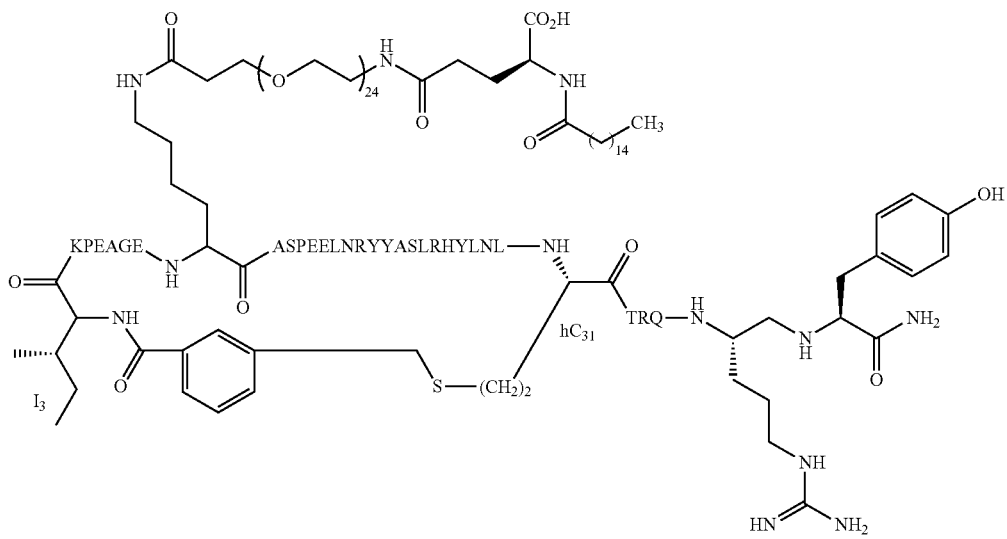
Name: [cyclo-(I3-m-COPhCH2-hC31), K(COCH2CH2(OCH2CH2)24NH-γ-Glu-Pal)11, psi-(R35, Y36)]-PYY3-36
SEQ ID NO: 46
Structure:
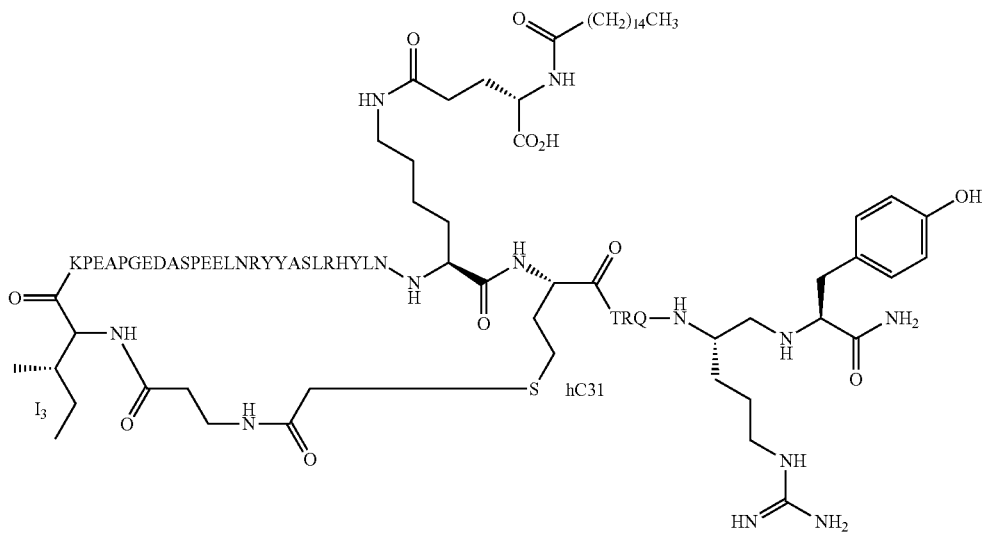
Name: [cyclo-(I3-CO(CH2)2NHCOCH2-hC31), K(γ-Glu-Pal)30, psi-(R35, Y36)]-PYY3-36

SEQ ID NO: 47
Structure:
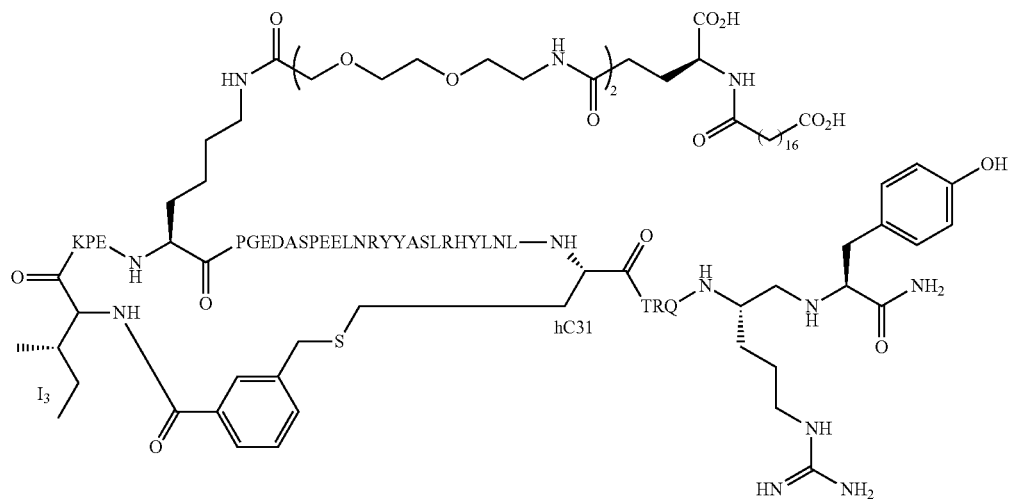
Name: [cyclo-(I3-m-COPhCH₂-hC31), K((OEG)₂-γ-Glu-COC₁₆H)7, psi-(R35, Y36)]-PYY3-36
SEQ ID NO: 48
Structure:
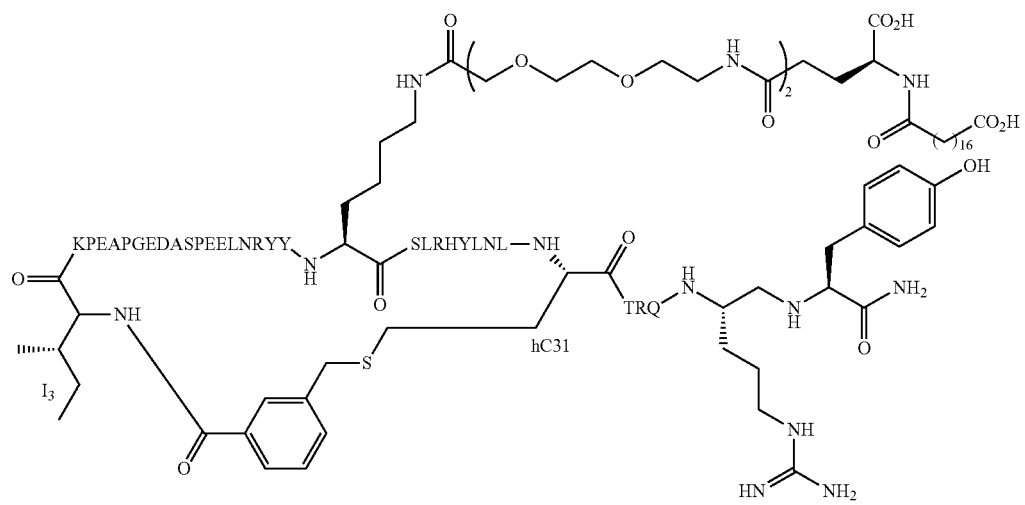
Name: [cyclo-(I3-m-COPhCH₂-hC31), K((OEG)₂-γ-Glu-COC₁₆CO₂H)22, psi-(R35, Y36)]-PYY3-36

-continued
SEQ ID NO: 49
Structure:
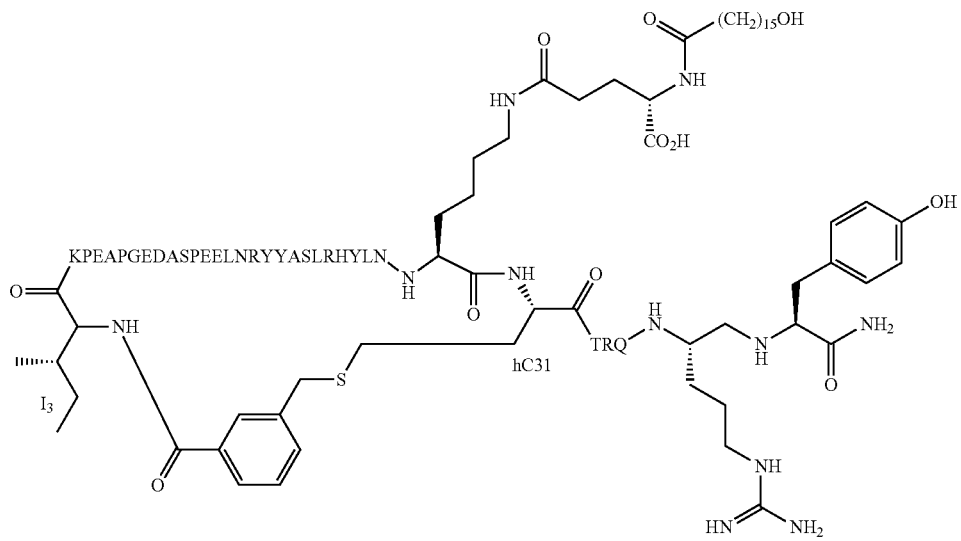
Name: [cyclo-(I3-m-COPhCH2-hC31), K(γ-Glu-(Pal-16-OH))30, psi-(R35, Y36)]PYY3-36
SEQ ID NO: 50
Structure:
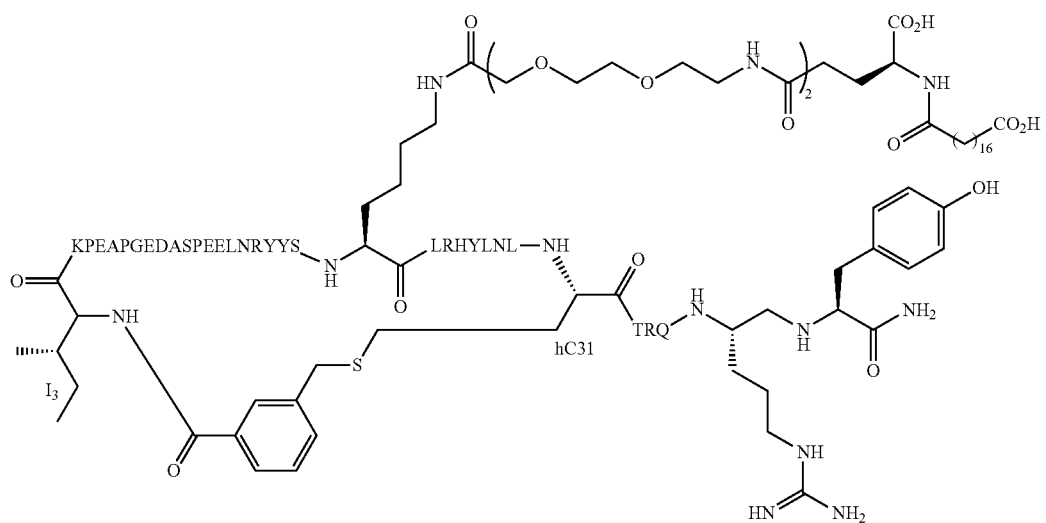
Name: [cyclo-(I3-m-COPhCH2-hC31), K((OEG)2-γ-Glu-COC16CO2H)23, psi-(R35, Y36)]-PYY3-36

SEQ ID NO: 51
Structure:
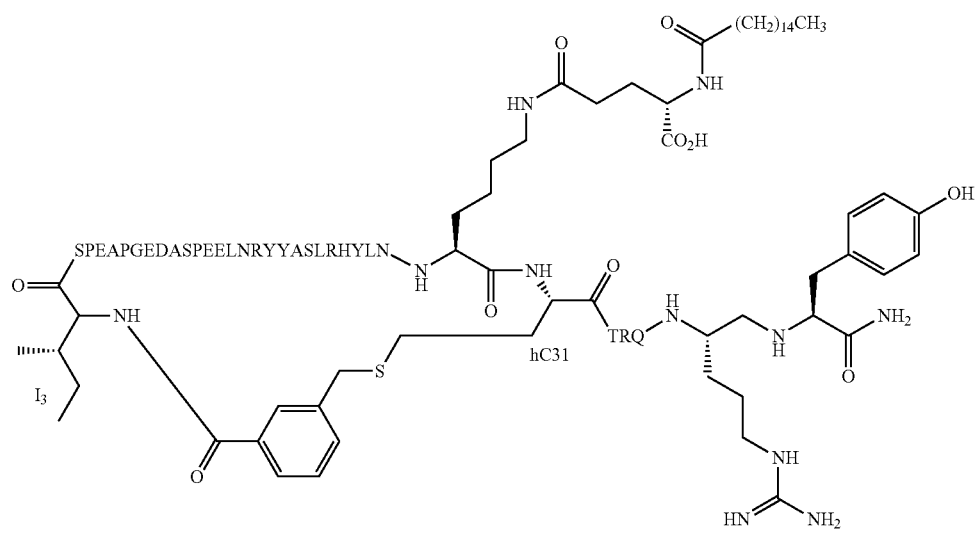
Name: [cyclo-(I3-m-COPhCH2-hC31), S4, K(γ-Glu-Pal)30, psi-(R35, Y36)]-PYY3-36
SEQ ID NO: 52
Structure:
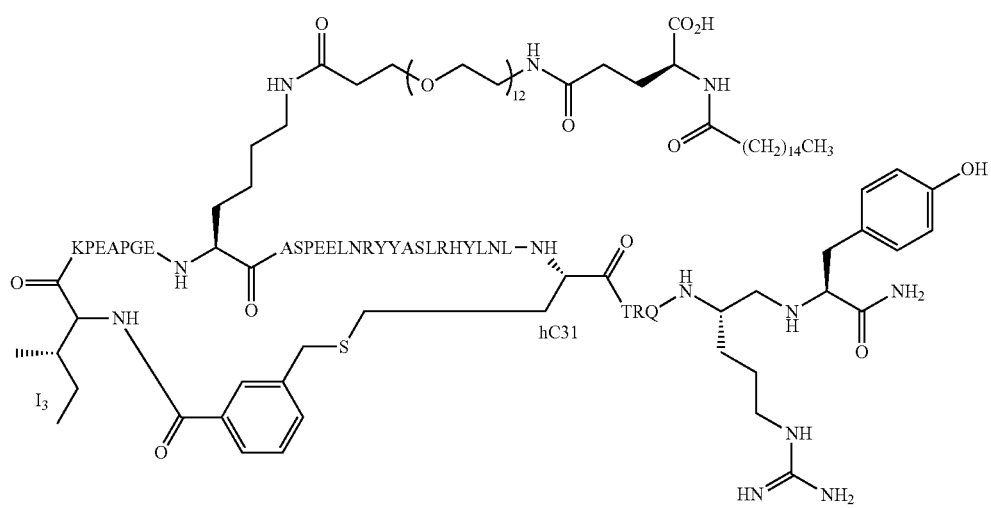
Name: [cyclo-(I3-m-COPhCH2-hC31), K(COCH2CH2(OCH2CH2)12NH-γ-Glu-Pal)11, psi-((R35, Y36)]-PYY3-36

SEQ ID NO: 53
Structure:
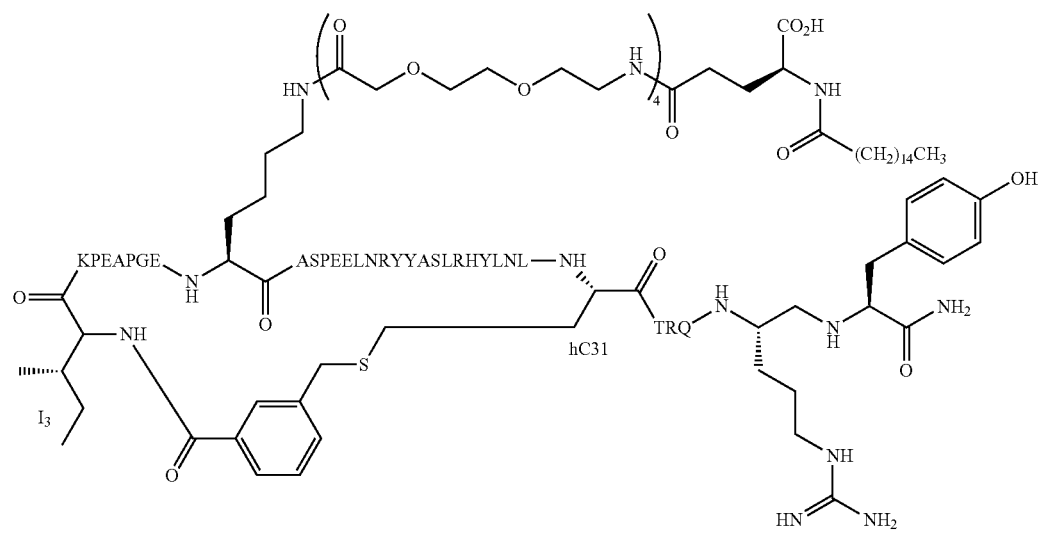
Name: [cyclo-(I3-m-COPhCH2-hC31), K((OEG)4-γ-Glu-Pal)11, psi(R35, Y36)]-PYY3-36
SEQ ID NO: 54
Structure:
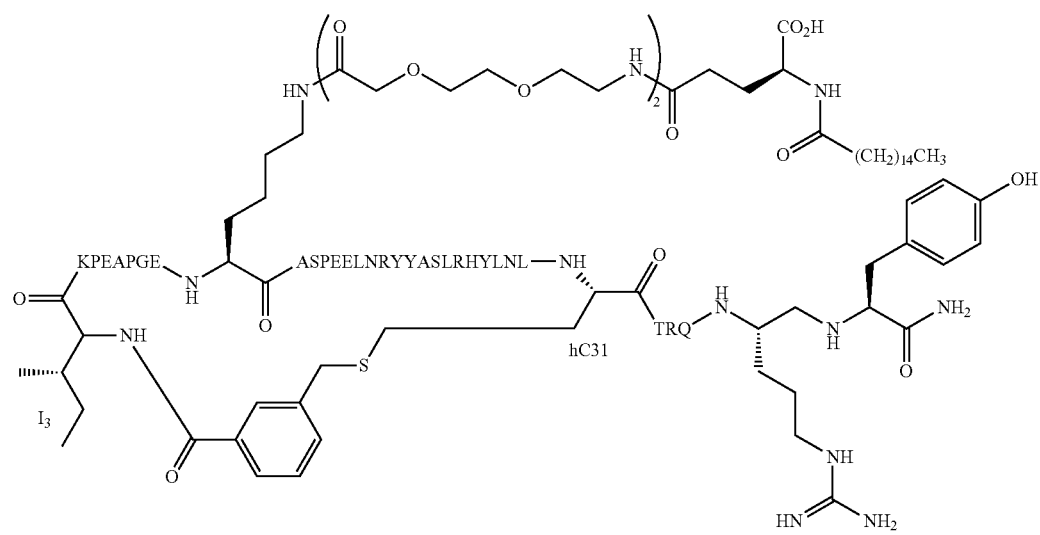
Name: [cyclo-(I3-m-COPhCH2-hC31), K((OEG)2-γ-Glu-Pal)11, psi(R35, Y36)]-PYY3-36

SEQ ID NO: 55
Structure:
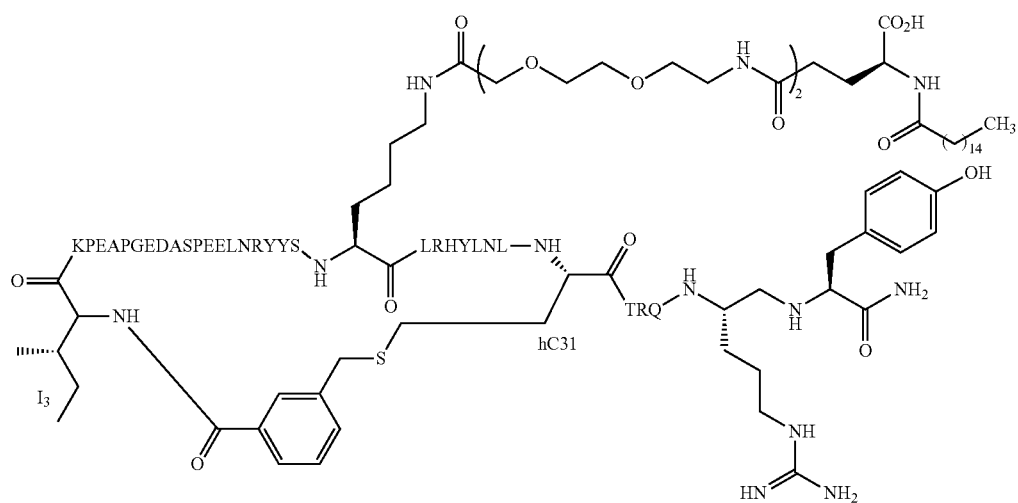
Name: [cyclo-(I3-m-COPhCH2-hC31), K((OEG)2-γ-Glu-Pal)23, psi-(R35, Y36)]-PYY3-36
SEQ ID NO: 56
Structure:
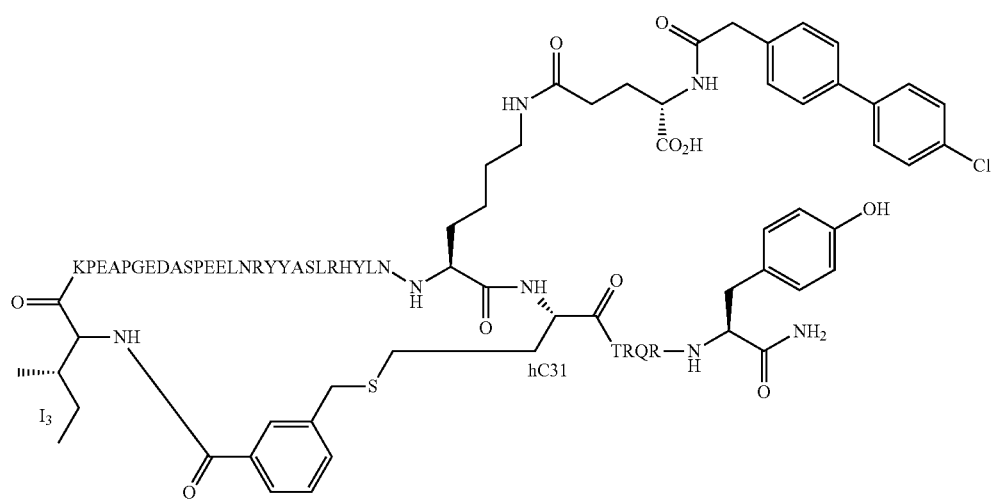
Name: [cyclo-(I3-m-COPhCH2-hC31), K(γ-Glu-COCH2Ph-(4-ClPh)30, psi-(R35, Y36)]-PYY3-36

SEQ ID NO: 57
Structure:
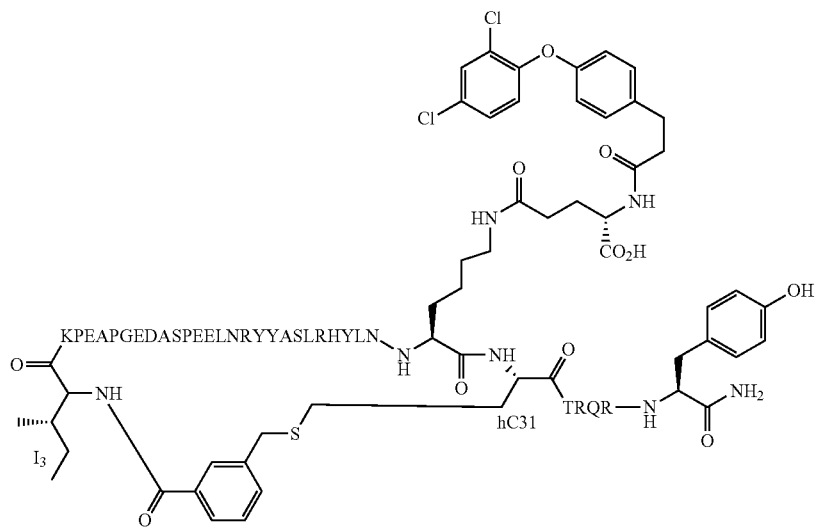
Name: [cyclo-I3-m-COPhCH2-hC31), K(γ-Glu-CO(CH2)2PhO-(2,4-Cl2Ph)30, psi-(R35, Y36)]-PYY3-36
SEQ ID NO: 58
Structure:
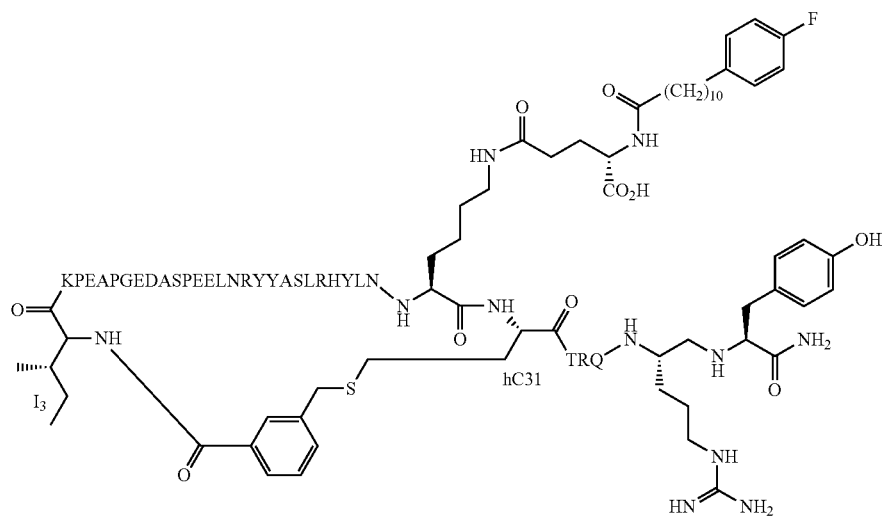
Name: [cyclo-(I3-m-COPhCH2-hC31), K(γ-Glu-CO(CH2)10-(4-F-Ph))30, psi-(R35, Y36)]-PYY3-36

Structure:
SEQ ID NO: 59
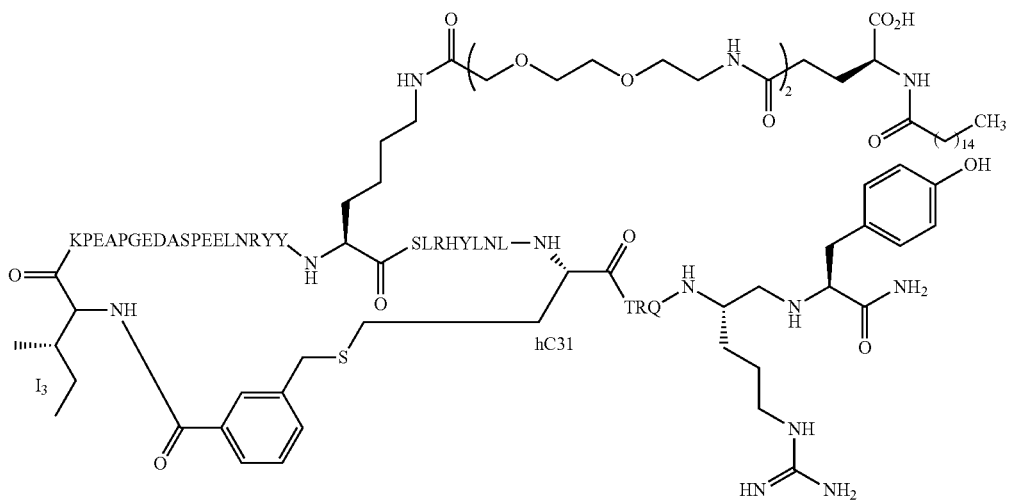
Name: [cyclo-(I3-m-COPhCH$_2$-hC31), K((OEG)$_2$-γ-Glu-Pal)22, psi-(R35, Y36)]-PYY3-36
SEQ ID NO: 60
Structure:
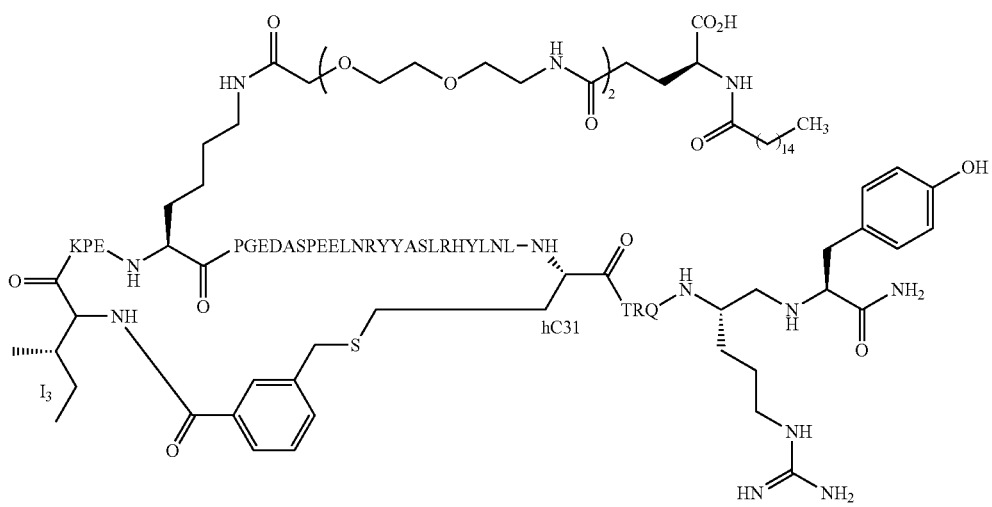
Name: [cyclo-(I3-m-COPhCH$_2$-hC31), K((OEG)$_2$-γ-Glu-Pal)7, psi-(R35, Y36)]-PYY3-36

SEQ ID NO: 61
Structure:
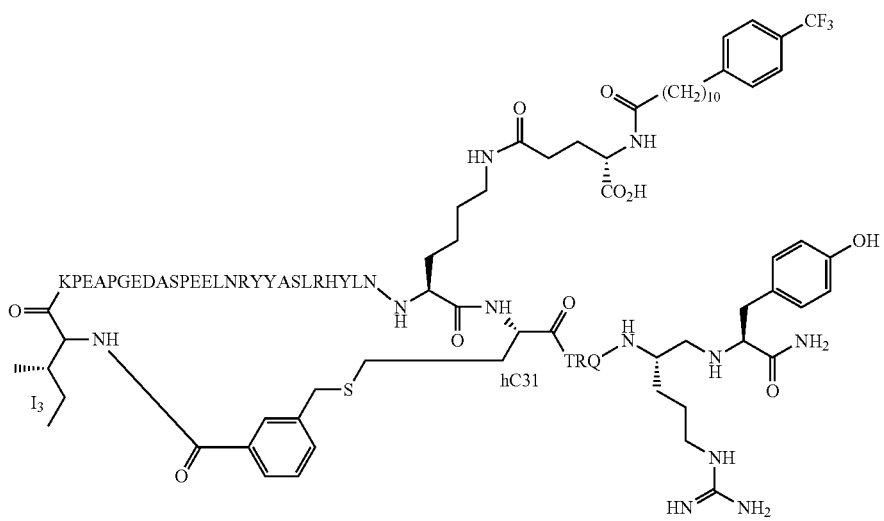
Name: [cyclo-(I3-m-COPhCH₂-hC31), K(γ-Glu-CO(CH₂)₁₀-(4-F₃C-Ph))30, psi-(R35, Y36)]-PYY3-36
SEQ ID NO: 62
Structure:
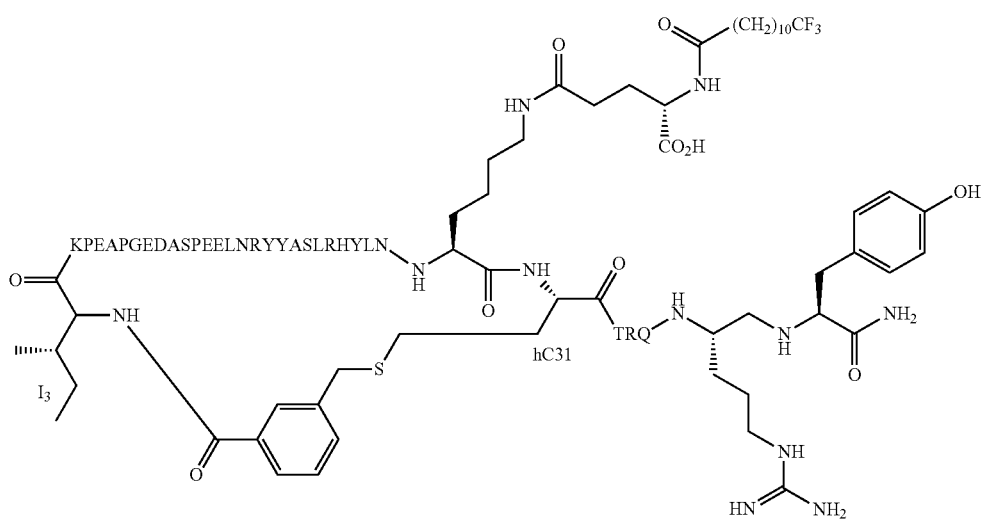
Name: [cyclo-(I3-m-COPhCH₂-hC31), K(γ-Glu-CO(CH₂)₁₀-CF₃)30, psi-(R35, Y36)]-PYY3-36

SEQ ID NO: 63
Structure:
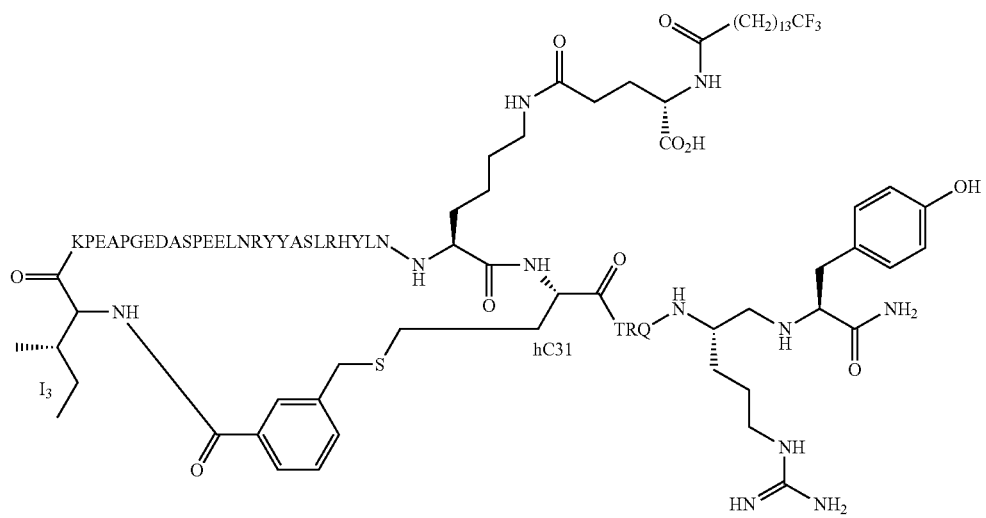
Name: [cyclo-(I3-m-COPhCH₂-hC31), K(γ-Glu-CO(CH₂)₁₃-CF₃)30, psi-(R35, Y36)]-PYY3-36
SEQ ID NO: 64
Structure:
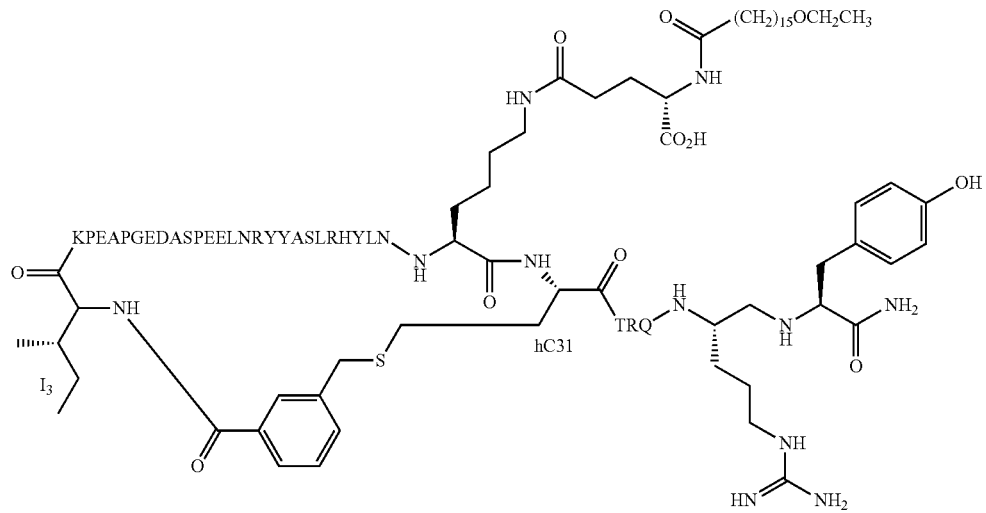
Name: [cyclo-(I3-m-COPhCH₂-hC31), K(γ-Glu-(Pal-16-OEt))30, psi-(R35, Y36)]-PYY3-36

SEQ ID NO: 65
Structure:
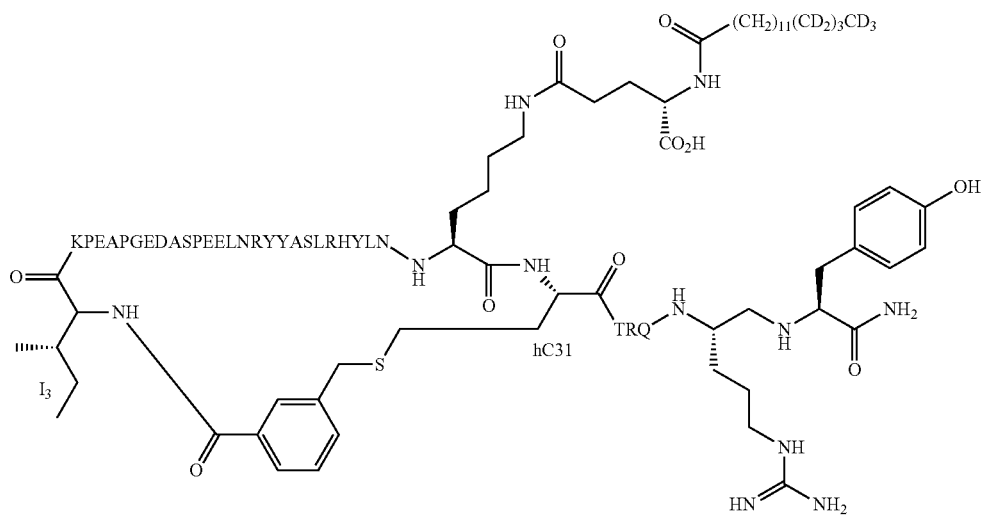
Name: [cyclo-(I3-m-COPhCH$_2$-hC31), K(γ-Glu-CO(CH$_2$)$_{11}$(CD$_2$)$_3$CD$_3$)30, psi-(R35, Y36)]-PYY3-36
SEQ ID NO: 66
Structure:
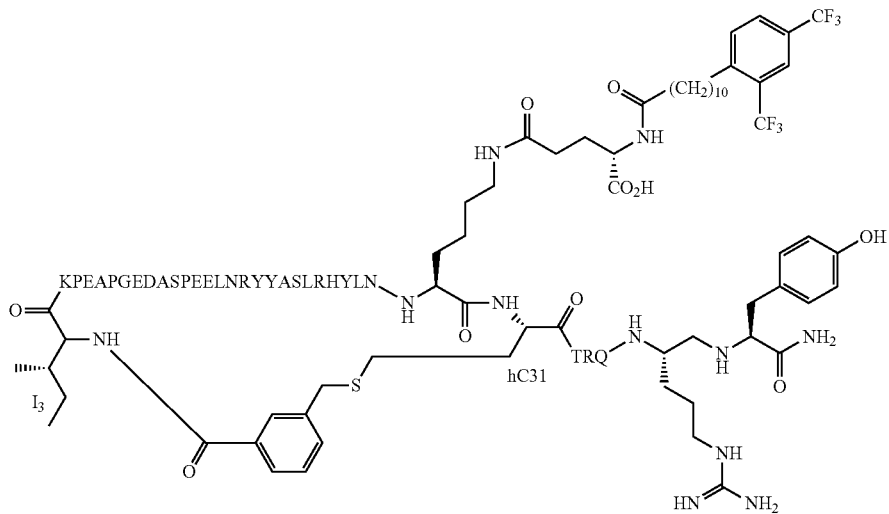
Name: [cyclo-(I3-m-COPhCH$_2$-hC31), K(γ-Glu-CO(CH$_2$)$_{10}$-(2,4-(CF$_3$)$_2$-Ph))30, psi-(R35, Y36)]-PYY3-36

SEQ ID NO: 67
Structure:
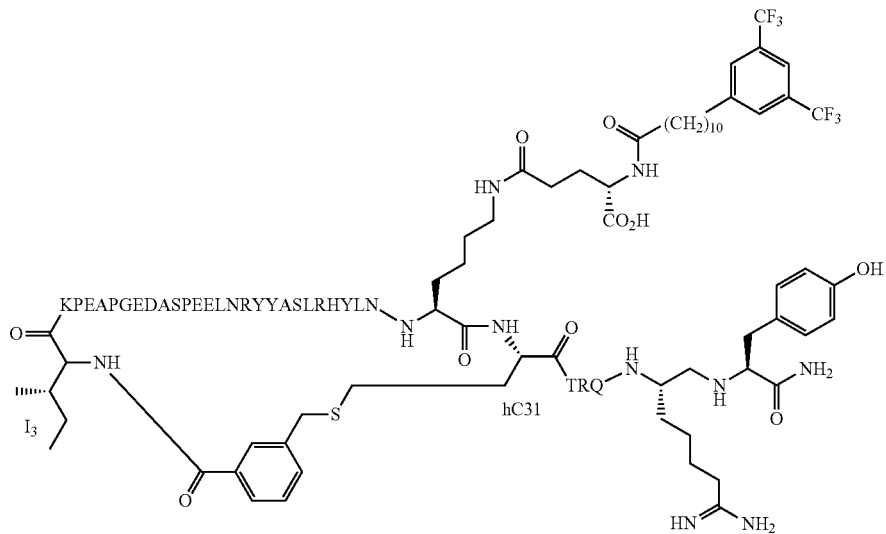
Name: [cyclo-(I3-m-COPhCH$_2$-hC31), K(γ-Glu-CO(CH$_2$)$_{10}$-(3,5-(CF$_3$)$_2$-Ph))30, psi-(R35, Y36)]-PYY3-36
SEQ ID NO: 68
Structure:
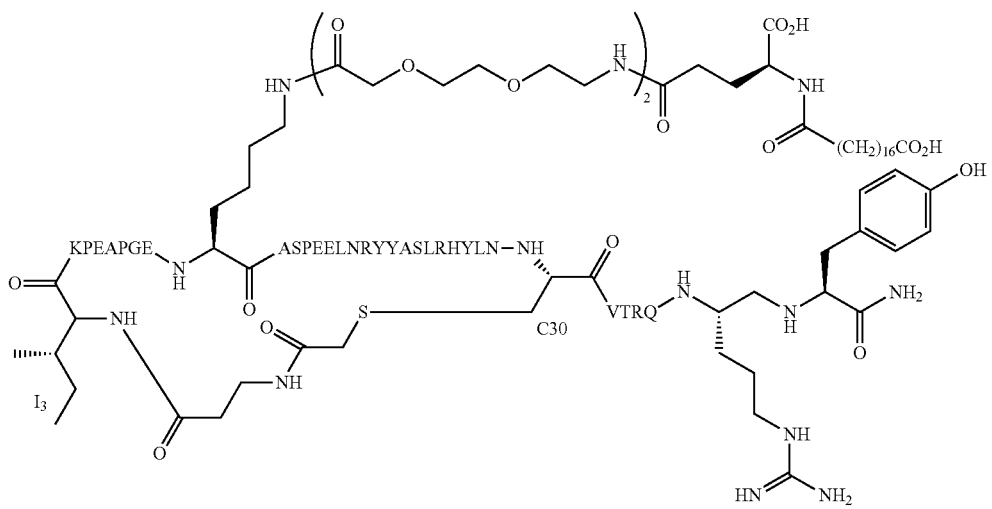
Name: [cyclo-(I3-CO(CH$_2$)$_2$NHCOCH$_2$-C30), K((OEG)$_2$-γ-Glu-COC$_{16}$CO$_2$H)11, psi-R35, Y36)]-PYY3-36
SEQ ID NO: 69
Structure:
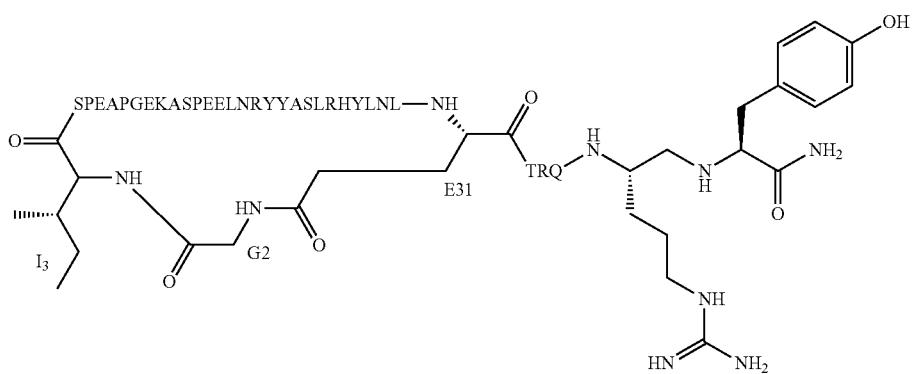
Name: [cyclo-(G2-E31), S4, K11, psi-(R35, Y36)]-PYY2-36

SEQ ID NO: 70
Structure:
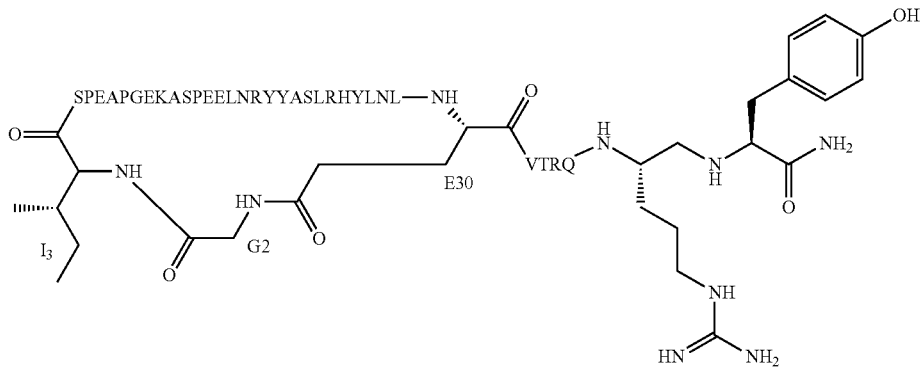
Name: [cyclo-(G2-E30), S4, K11, psi-(R35, Y36)]-PYY2-36
SEQ ID NO: 71
Structure:
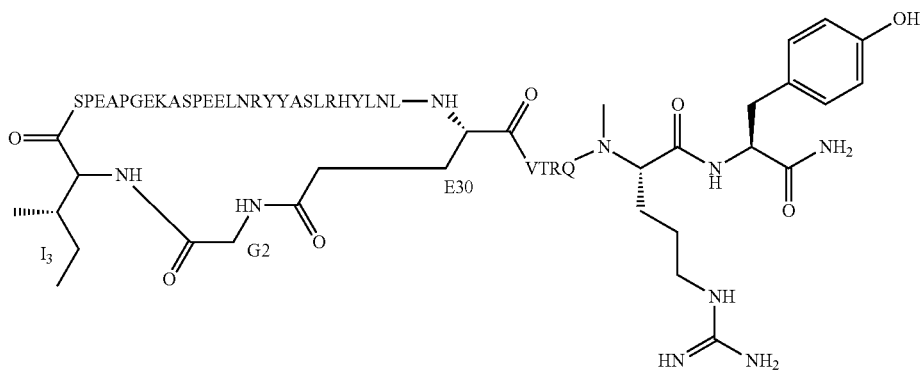
Name: [cyclo-(G2-E30), S4, K11, (N-Me-R35)]-PYY3-36
SEQ ID NO: 72
Structure:
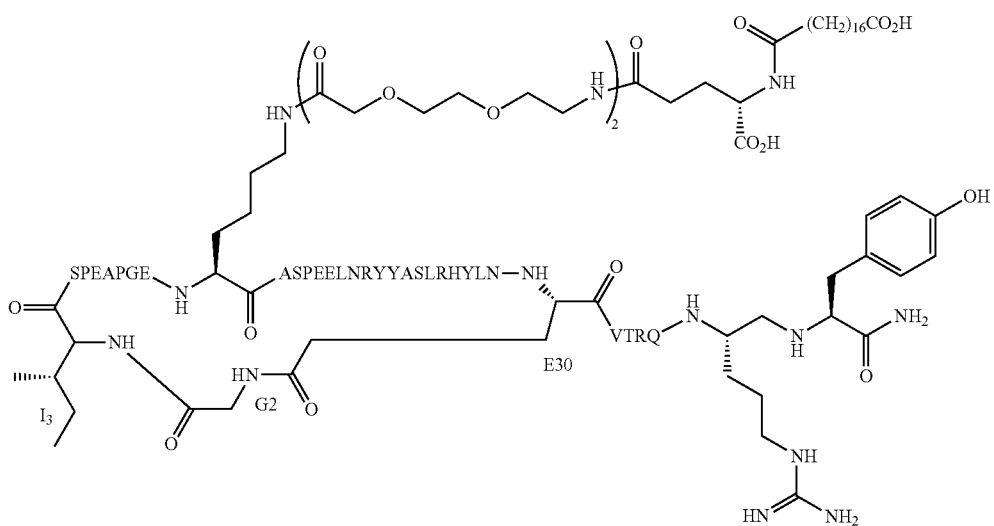
Name: [cyclo-(G2-E30), S4, K((OEG)$_2$-γ-Glu-COC$_{16}$CO$_2$H)11, psi-(R35, Y36)]-PYY2-36

-continued
SEQ ID NO: 73
Structure:
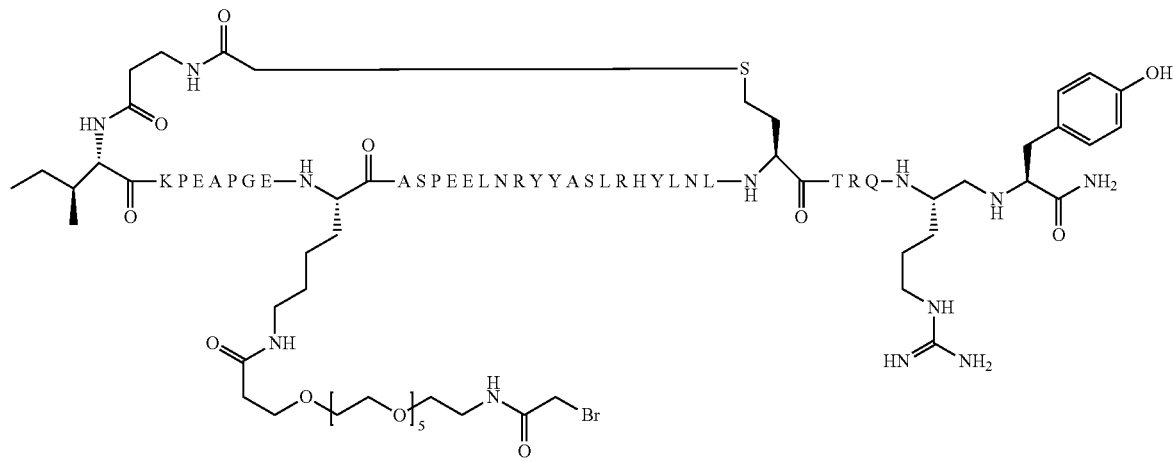
Name: [Cyclo-(βA2-COCH₂-hC31), K(PEAG6-AcBr)11, psi-(R35, Y36)]-PYY2-36
SEQ ID NO: 74
Structure:
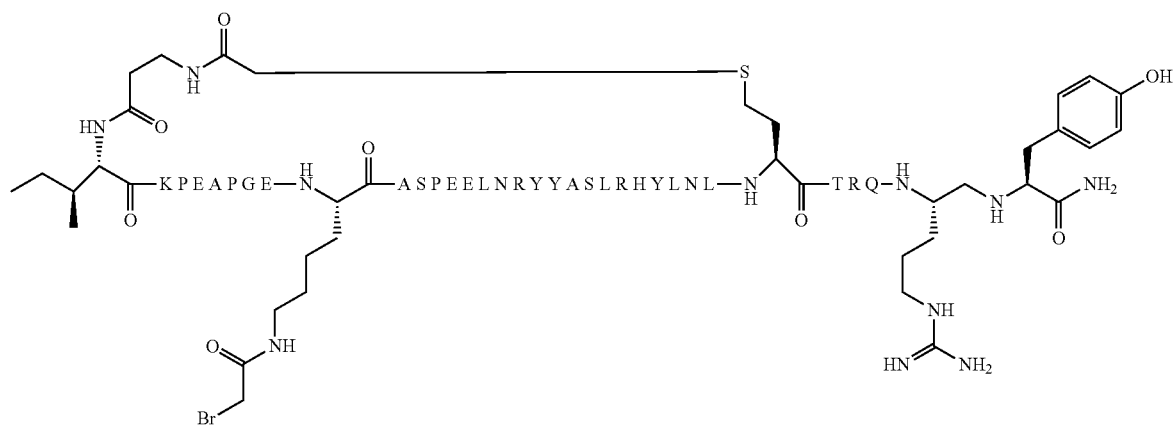
Name: [Cyclo-(βA2-COCH₂-hC31), K(AcBr)11, psi-(R35, Y36)]-PYY2-36
SEQ ID NO: 75
Structure:
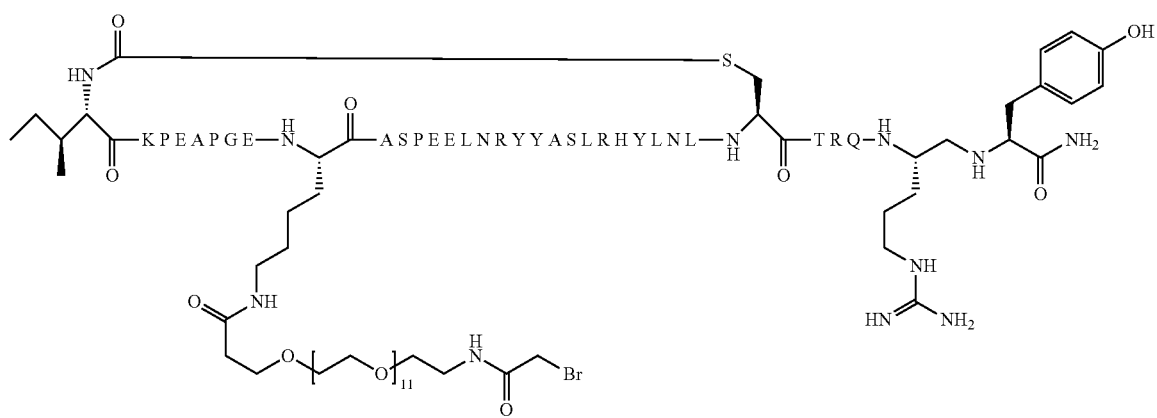
Name: [Cyclo-(I3-COCH₂-C31), K(PEG12-AcBr)11, psi-(R35, Y36)]-PYY3-36

SEQ ID NO: 76
Structure:
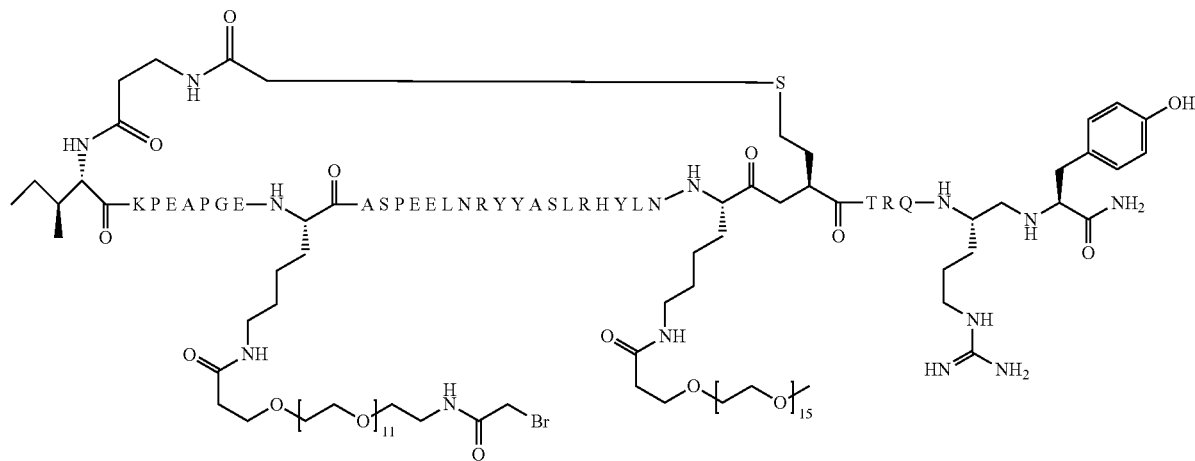
Name: [Cyclo-(βA2-COCH₂-hC31), K(PEG12-AcBr)11, K(mPEG16)30, psi-(R35, Y36)]-PYY2-36
SEQ ID NO: 77
Structure:
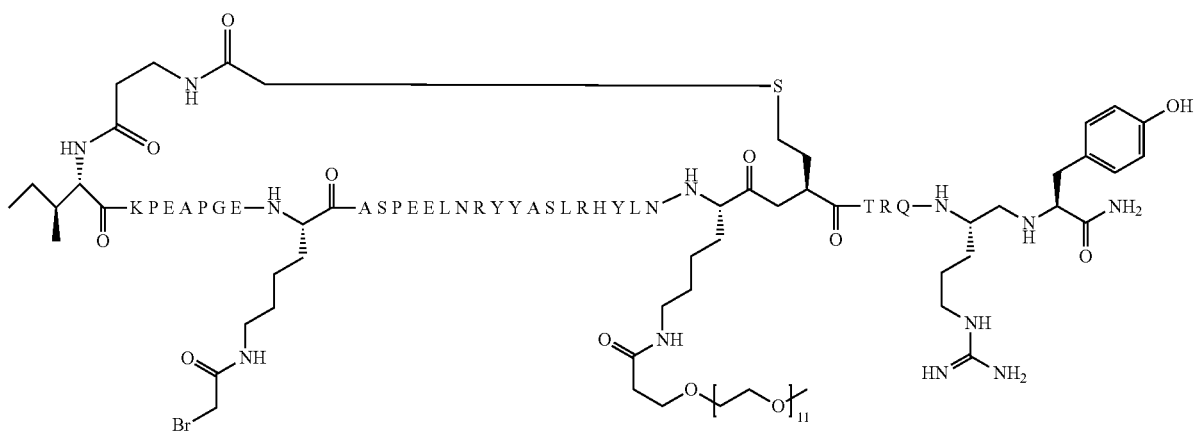
Name: [Cyclo-(βA2-COCH₂-hC31), K(AcBr)11, K(mPEG12)20, psi-(R35, Y36)]-PYY2-36
SEQ ID NO: 78
Structure:
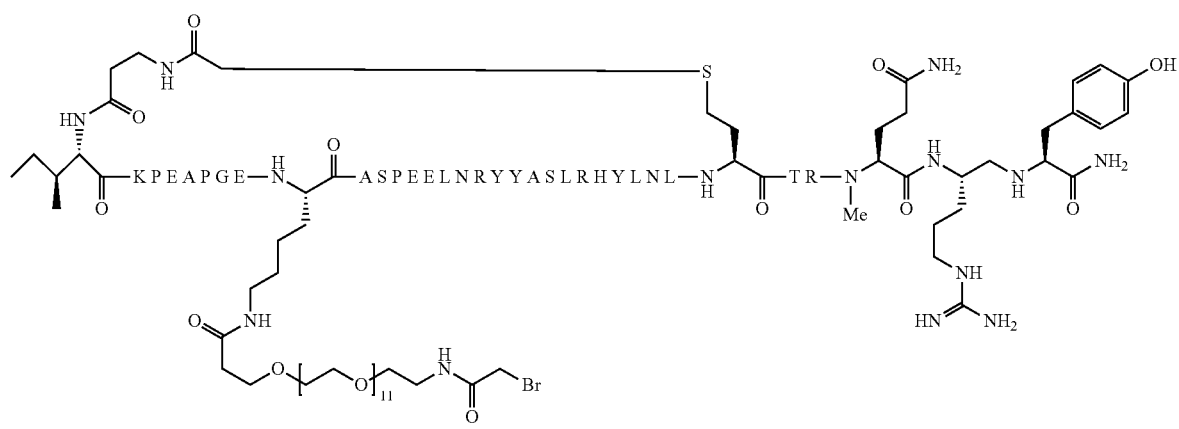
Name: [Cyclo-(βA2-COCH₂-hC31), K(PEG12-AcBr)11, (N-Me)Q34, psi-(R35, Y36)]-PYY2-36

SEQ ID NO: 79
Structure:
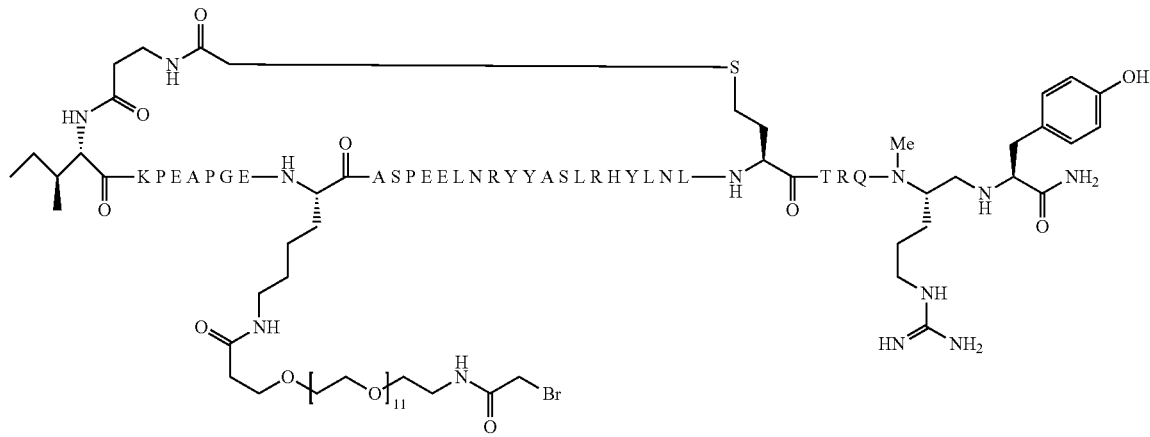
Name: [Cyclo-(βA2-COCH₂-hC31), K(PEG12-AcBr)11, (N-Me)R35, psi-(R35, Y36)]-PYY2-36
SEQ ID NO: 80
Structure:
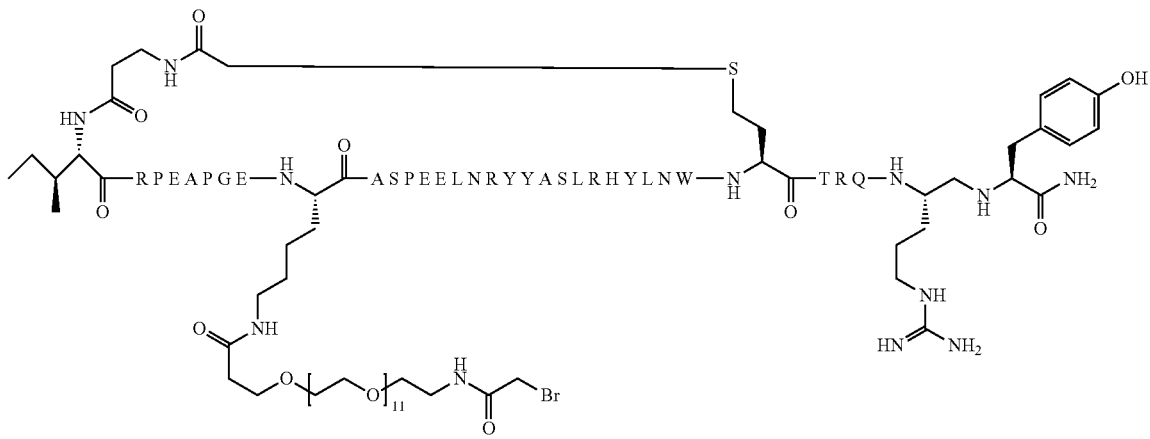
Name: [Cyclo-(βA2-COCH₂-hC31), R4, K(PEG12-AcBr)11, W30, psi-(R35, Y36)]-PYY2-36
SEQ ID NO: 81
Structure:
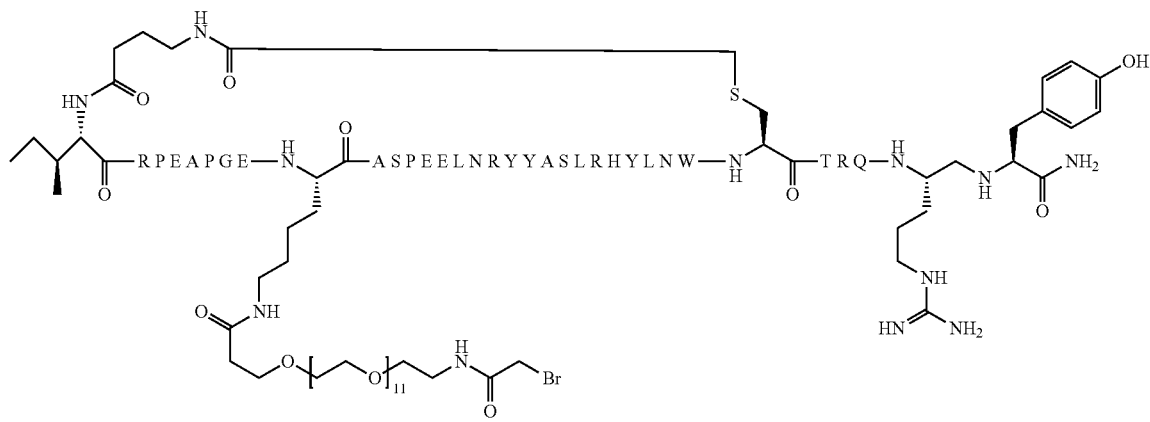
Name: [Cyclo-(3I-COCH₂CH₂CH₂NHCOCH₂-C31), R4, K(PEG12-AcBr)11, W30, psi-(R35, Y36)]-PYY2-36

SEQ ID NO: 82
Structure:
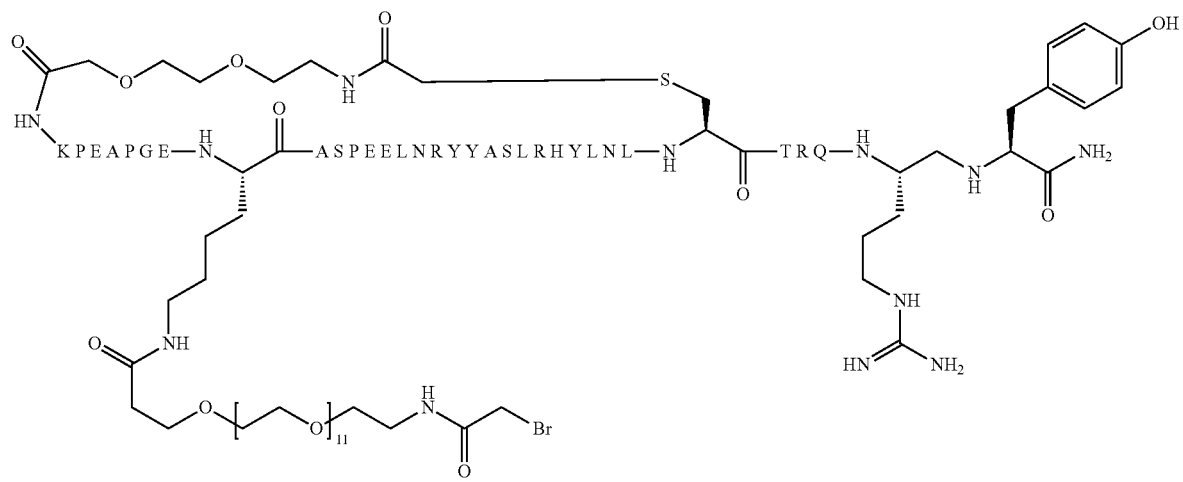
Name: [Cyclo-(K4-OEG-COCH₂-C31), K(PEG12-AcBr)11, psi-(R35, Y36)]-PYY4-36
SEQ ID NO: 83
Structure:
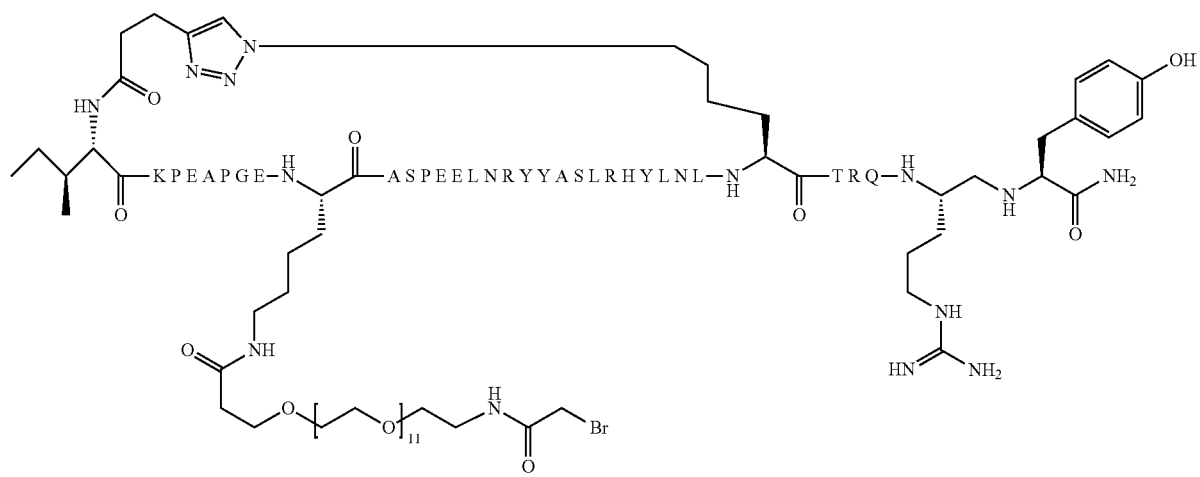
Name: [Cyclo-(I3-COCH₂CH₂triazolylNle31), K(PEG12-AcBr)11, psi-(R35, Y36)]-PYY3-36

SEQ ID NO: 84
Structure:
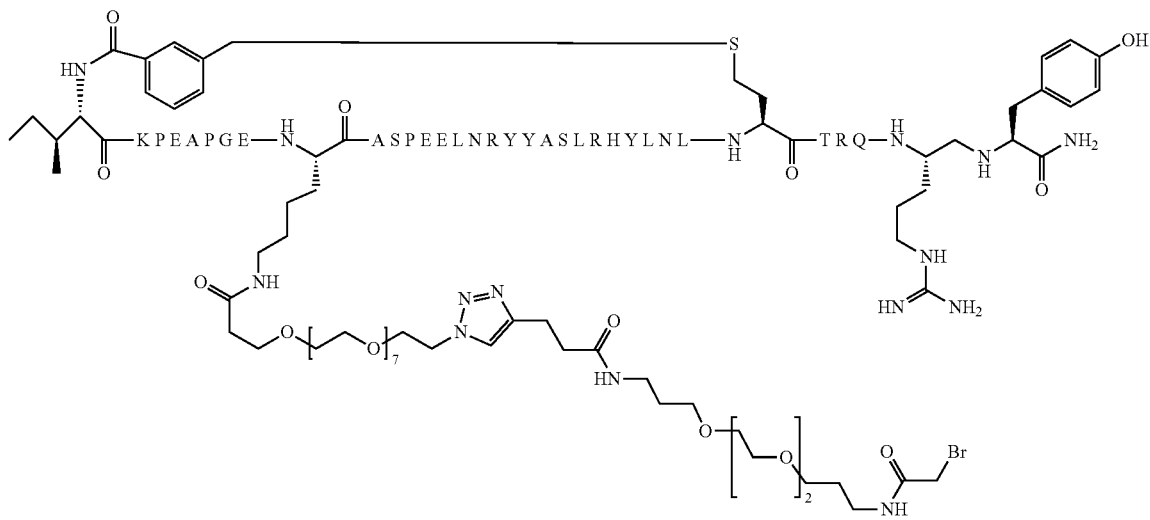
Name: : [Cyclo-(I3-m-CO-benzyl-hC31), K(PEG8-triazolyl-CH₂CH₂CO-PEG4-AcBr)11, psi-(R35, Y36)]-PYY3-36
SEQ ID NO: 85
Structure:
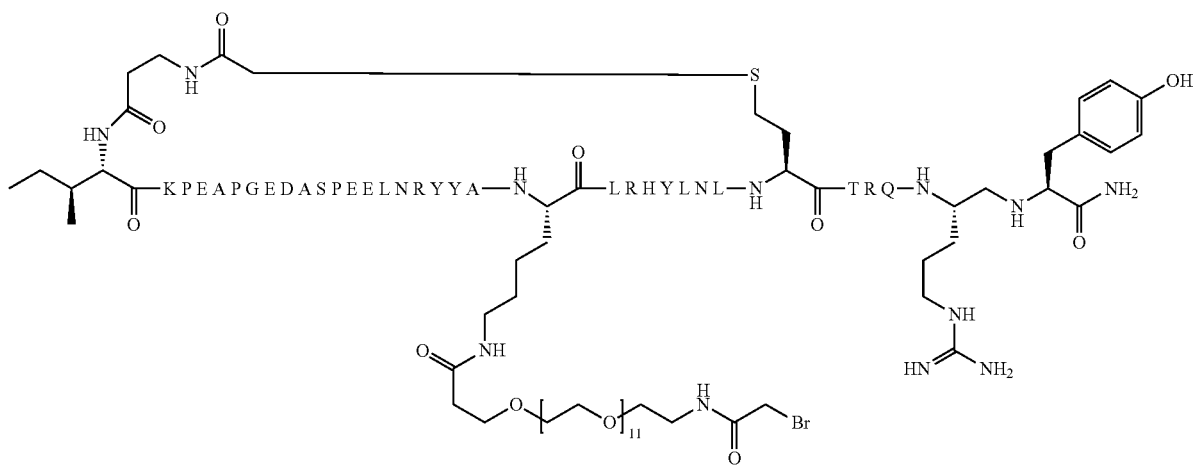
Name: [Cyclo-(βA2-COCH₂-hC31), K(PEG12-AcBr)23, psi-(R35, Y36)]-PYY2-36, SEQ ID NO: 86
Structure:
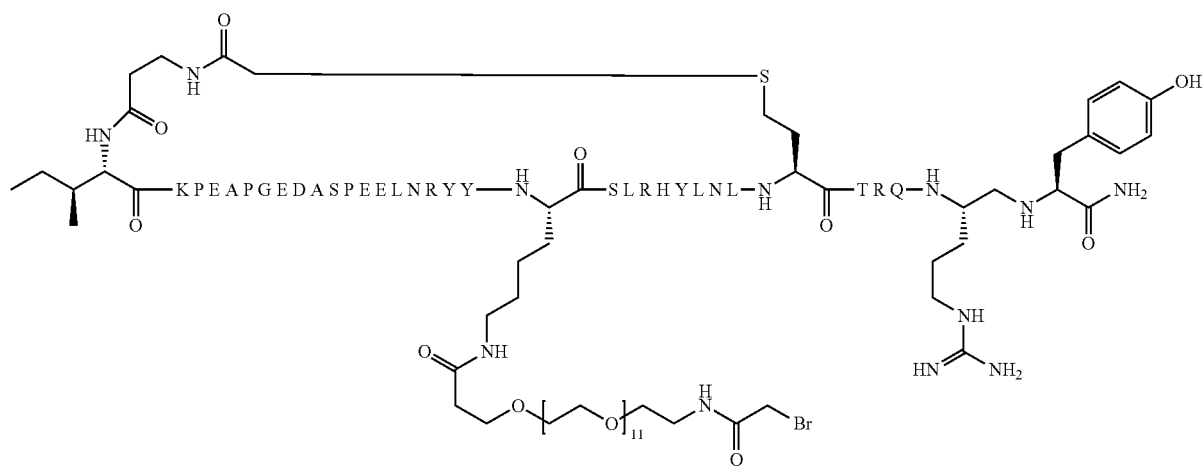
Name: [Cyclo-(βA2-COCH₂-hC31), K(PEG12-AcBr)22, psi-(R35, Y36)]-PYY2-36
SEQ ID NO: 87
Structure:
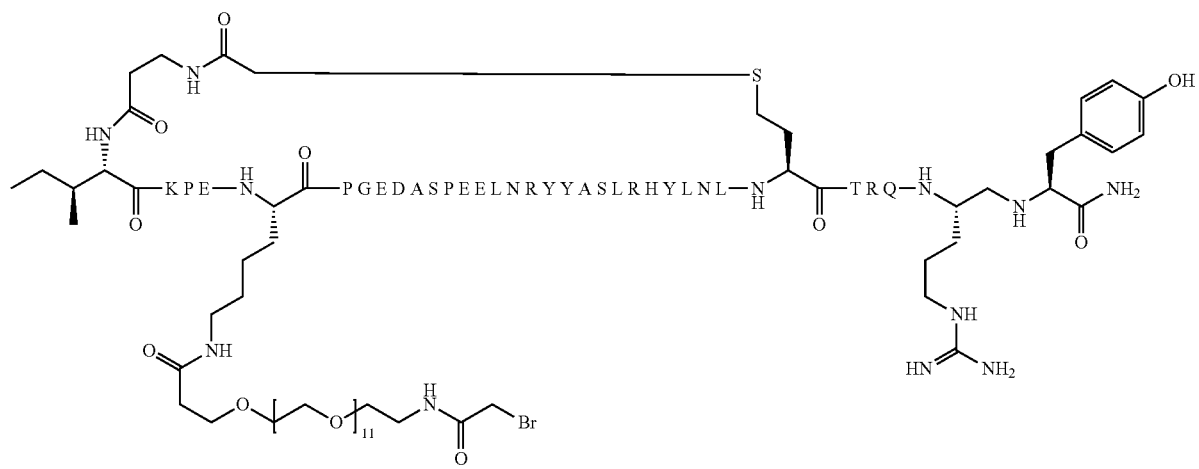
Name: [Cyclo-(βA2-COCH₂-hC31), K(PEG12-AcBr)7, psi-(R35, Y36)]-PYY2-36

SEQ ID NO: 88
Structure:
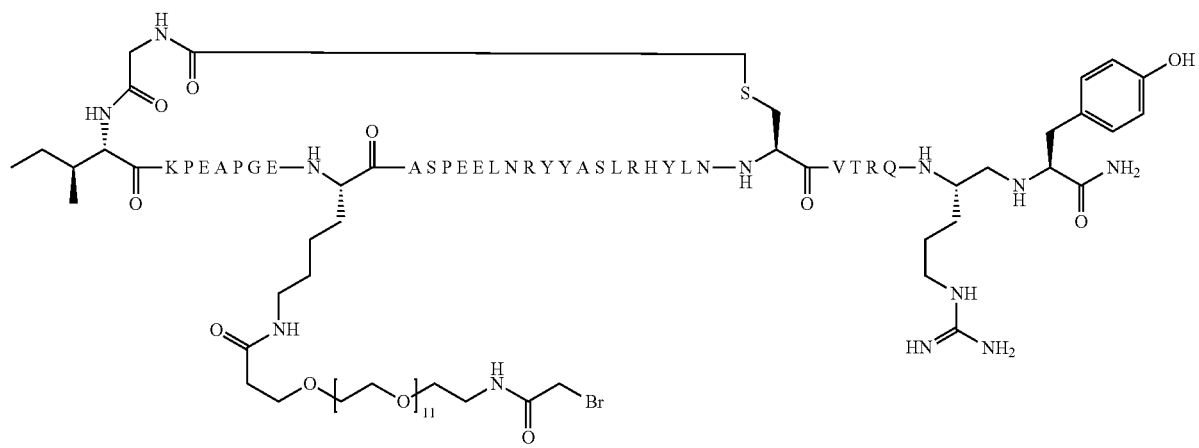
Name: [Cyclo-(G2-COCH$_2$-C30), K(PEG12-AcBr)11, psi-(R35, Y36)]-PYY2-36
SEQ ID NO: 89
Structure:
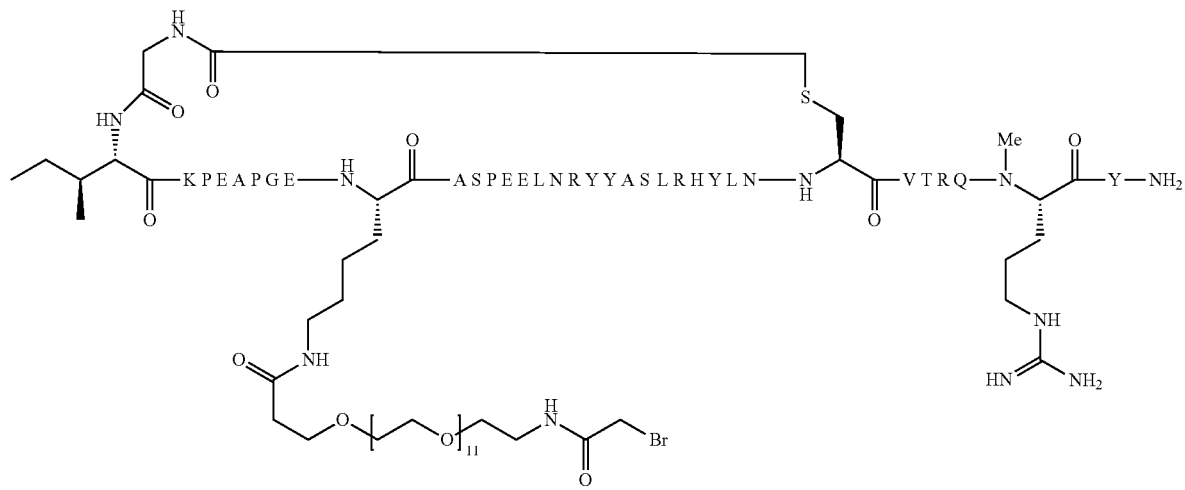
Name: [Cyclo-(G2-COCH$_2$-C30), K(PEG12-AcBr)11, N-Me-R35]-PYY2-36

SEQ ID NO: 90
Structure:
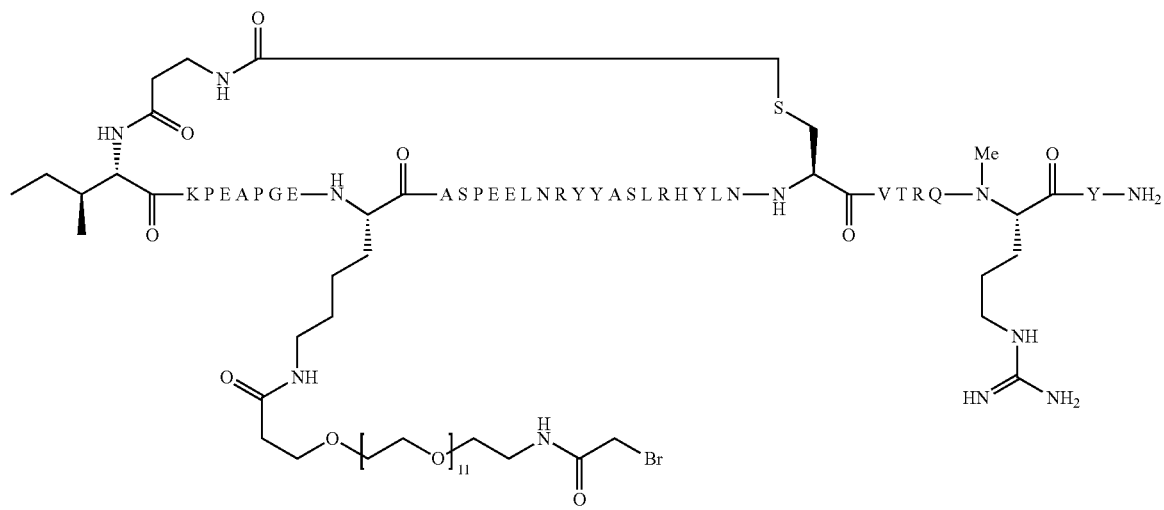
Name: [Cyclo-(βA2-COCH₂-C30), K(PEG12-AcBr)11, N-Me-R35]-PYY2-36
SEQ ID NO: 91
Structure:
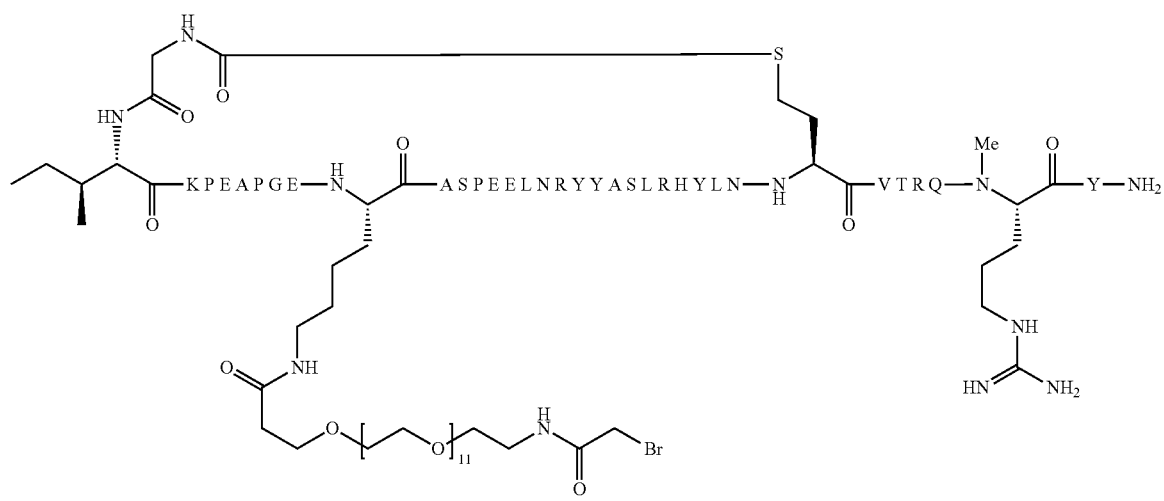
Name: [Cyclo-(G2-COCH₂-hC30), K(PEG12-AcBr)11, N-Me-R35]-PYY2-36

SEQ ID NO: 92
Structure:
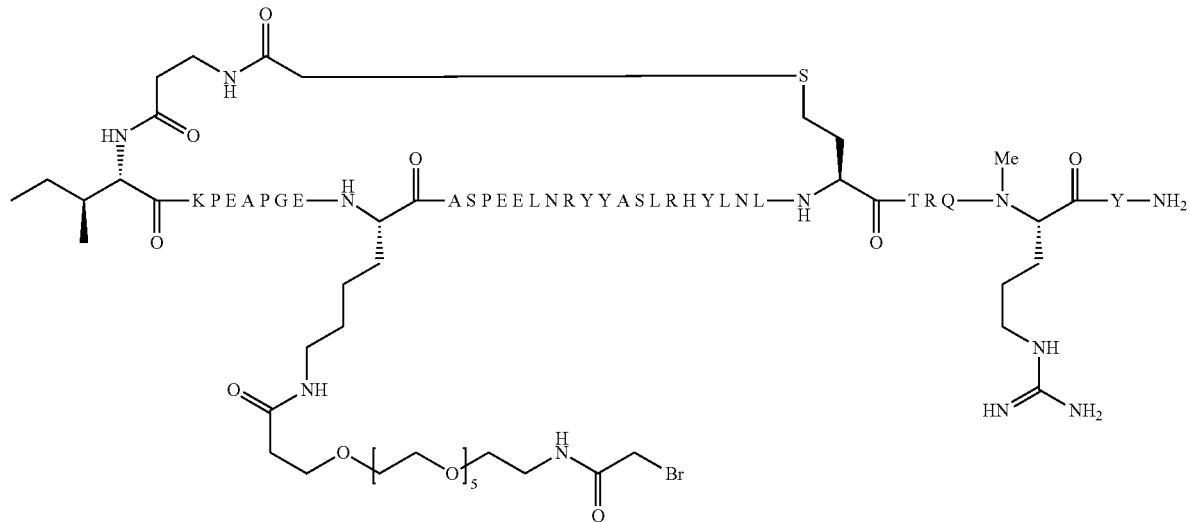
Name: [Cyclo-(βA2-COCH₂-hC31), K(PEG12-AcBr)11, N-Me-R35]-PYY2-36
SEQ ID NO: 93
Structure:
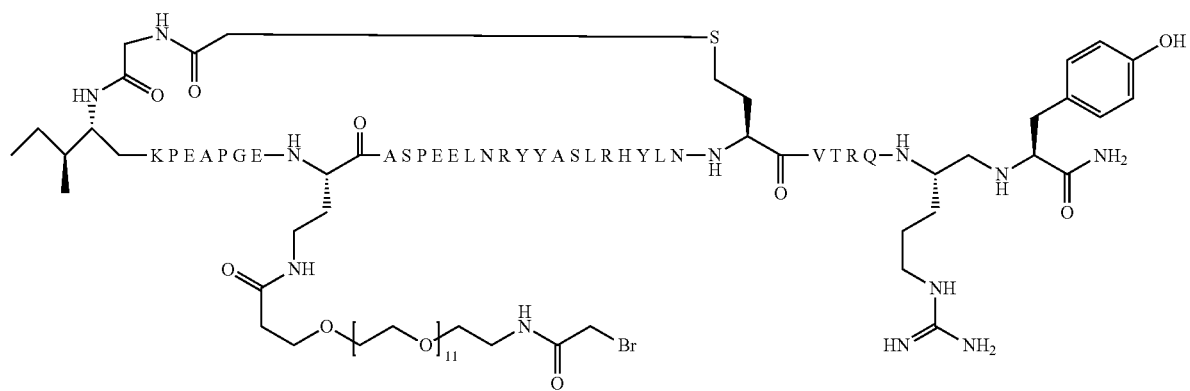
Name: [Cyclo-(G2-COCH₂-hC30), K(PEG12-AcBr11, psi-(R35, Y36)]-PYY2-36
SEQ ID NO: 94
Structure:
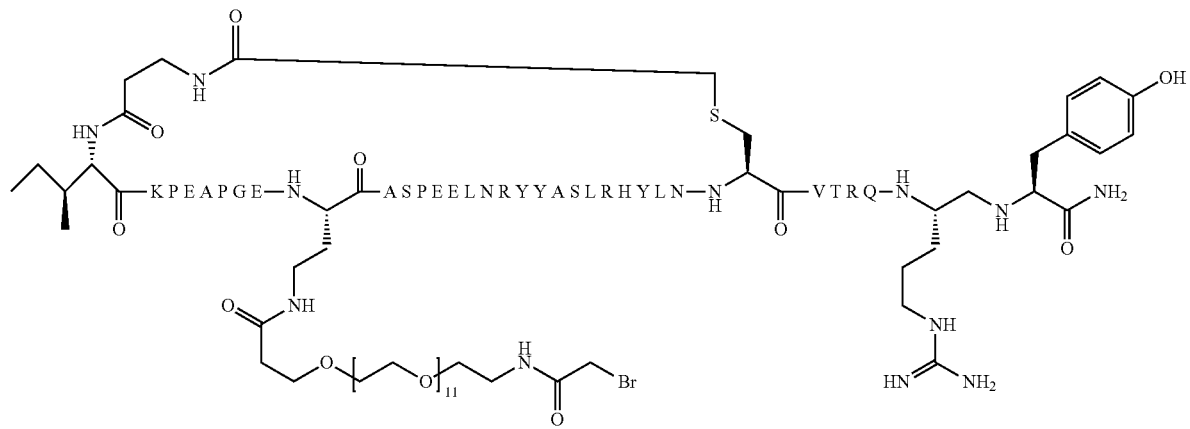
Name: [Cyclo-(βA2-COCH₂-C30), K(PEG12-AcBr)11, psi-(R35, Y36)]-PYY2-36

SEQ ID NO: 95
Structure:
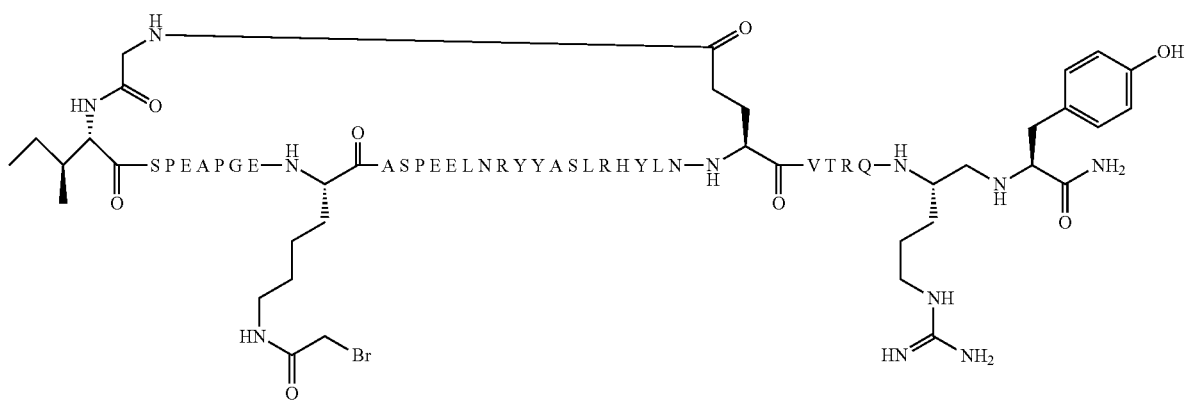
Name: [Cyclo-(G2-E30), S4, K(AcBr)11, psi-(R35, Y36)]-PYY2-36
SEQ ID NO: 96
Structure:
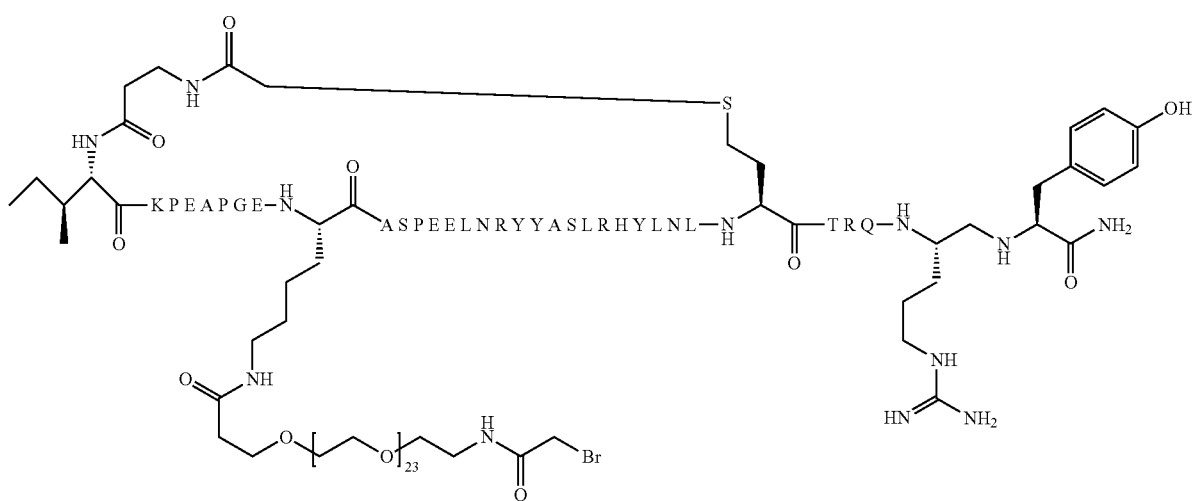
Name: [Cyclo-(βA2-COCH₂-hC31), K(PEG24-AcBr)11, psi-(R35, Y36)]-PYY2-36

SEQ ID NO: 97
Structure:
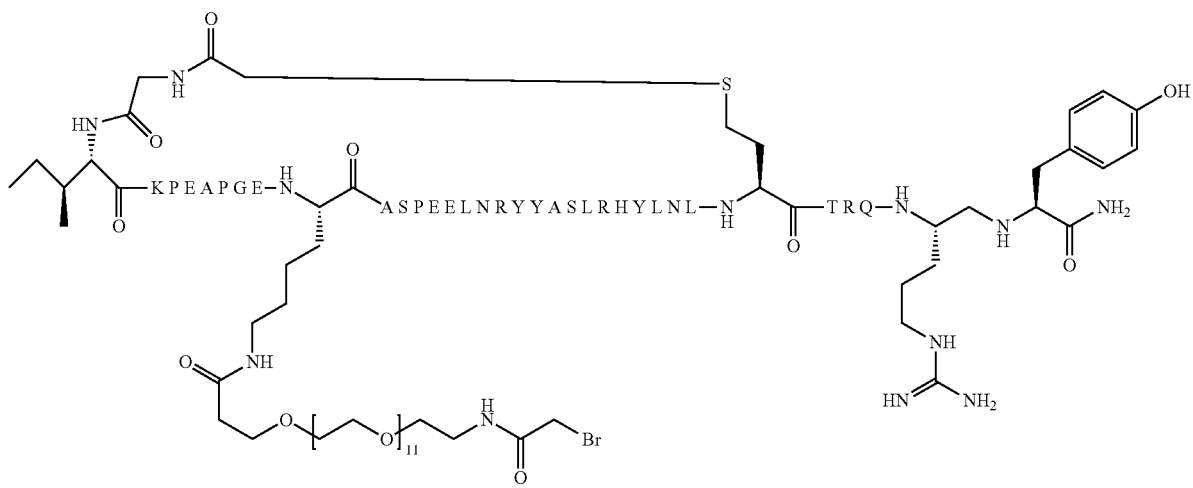
Name: [Cyclo-(G2-Ac-hC31), K(PEG12-AcBr)11, psi-(R35, Y36)]-PYY2-36
SEQ ID NO: 98
Structure:
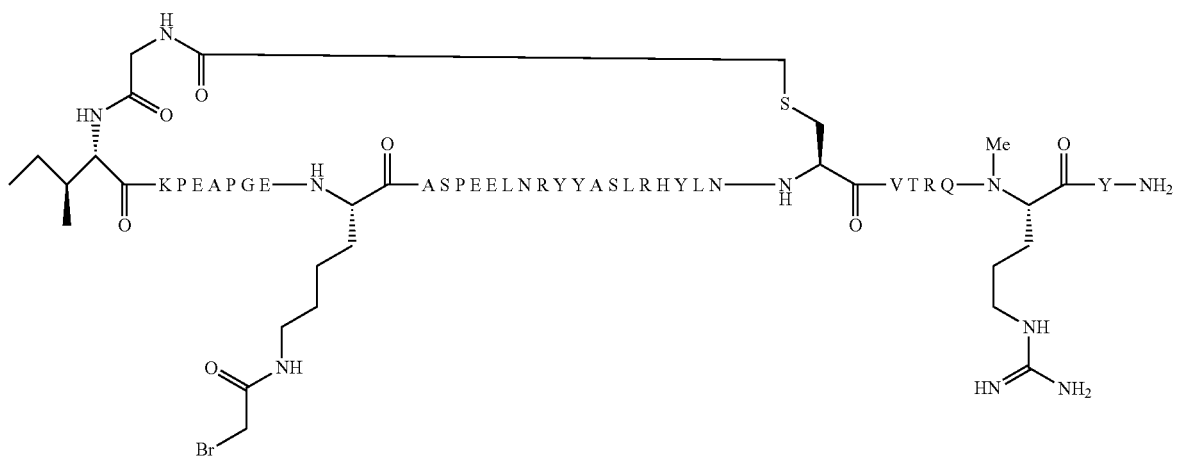
Name: [Cyclo-(G2-COCH2-C30), K(AcBr)11, N-Me-R35]-PYY2-36

SEQ ID NO: 99
Structure:
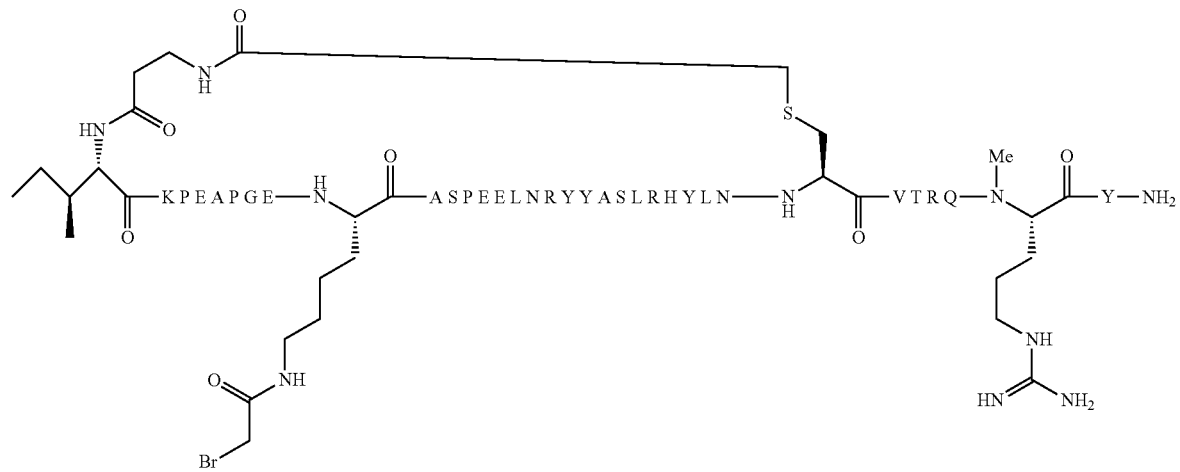
Name: [Cyclo-(βA2-COCH₂-C30), K(AcBr)11, N-Me-R35]-PYY2-36
SEQ ID NO: 100
Structure:
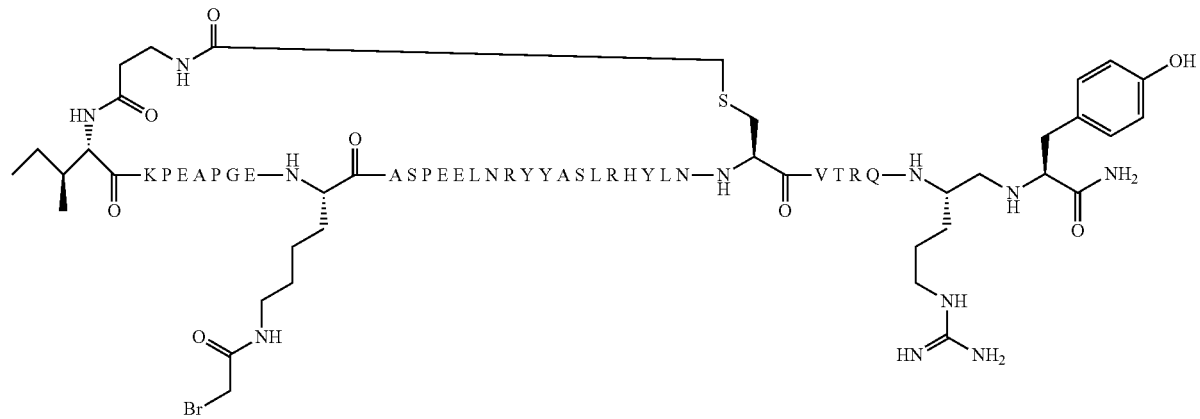
Name: [Cyclo-(βA2-COCH₂-C30), K(AcBr)11, psi-(R35, Y36)]-PYY2-36
SEQ ID NO: 101
Structure:
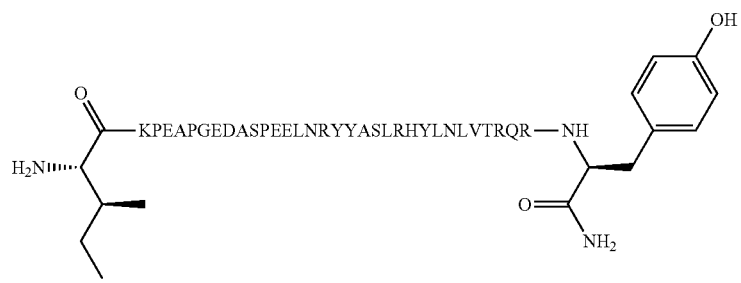
hPYY3-36

SEQ ID NO: 102
Structure:
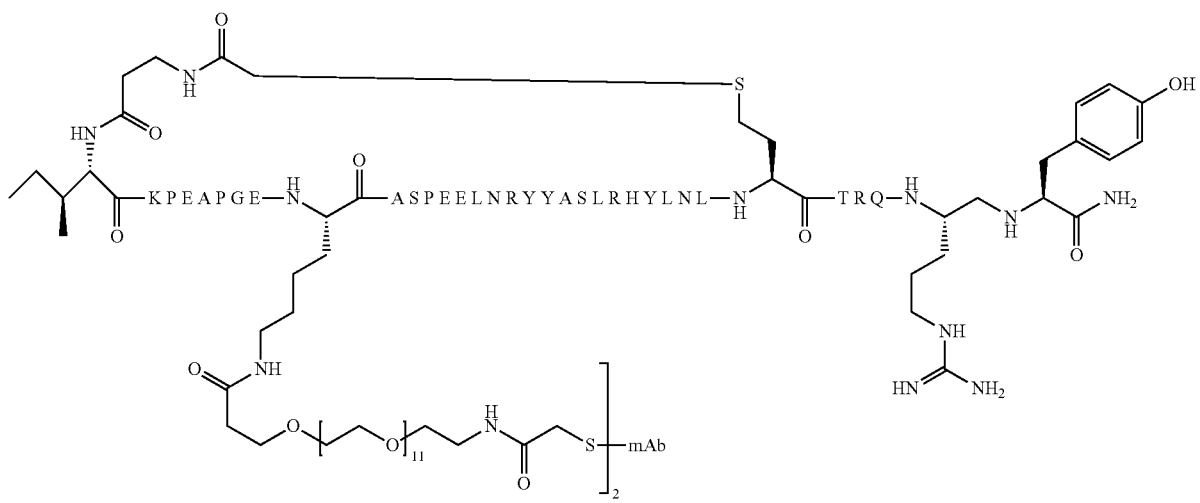
Name: [Cyclo-(βA2-COCH₂-hC31), K(PEG12)11, psi-(R35, 36Y)]-PYY2-36 mAb homodimer conjugate (Compound 1)
SEQ ID NO: 103
Structure:
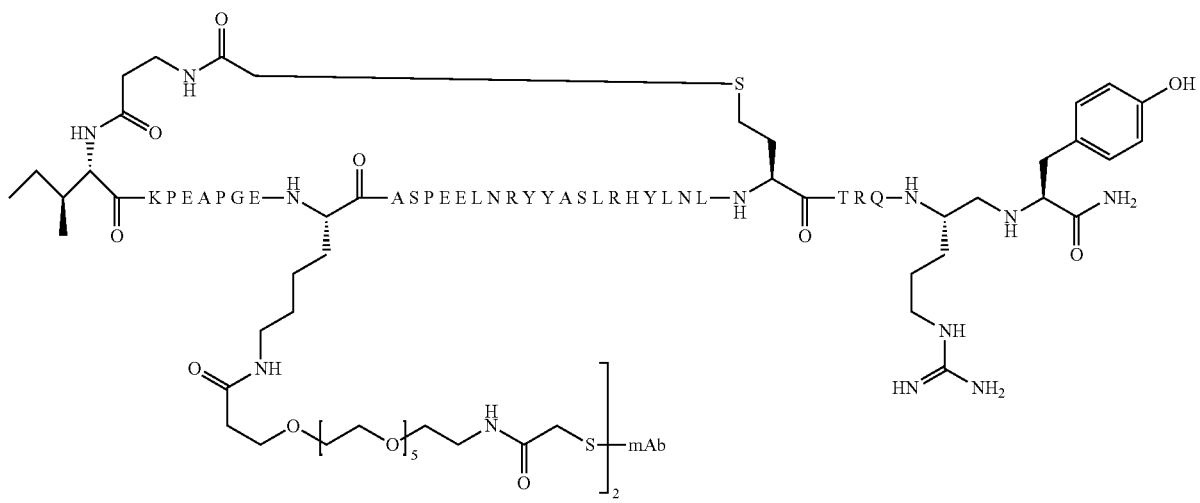
Name: [Cyclo-(βA2-COCH₂-hC31), K(PEG6)11, psi-(R35, Y36)]-PYY2-36 mAb homodimer conjugate (Compound 2)

SEQ ID NO: 104
Structure:
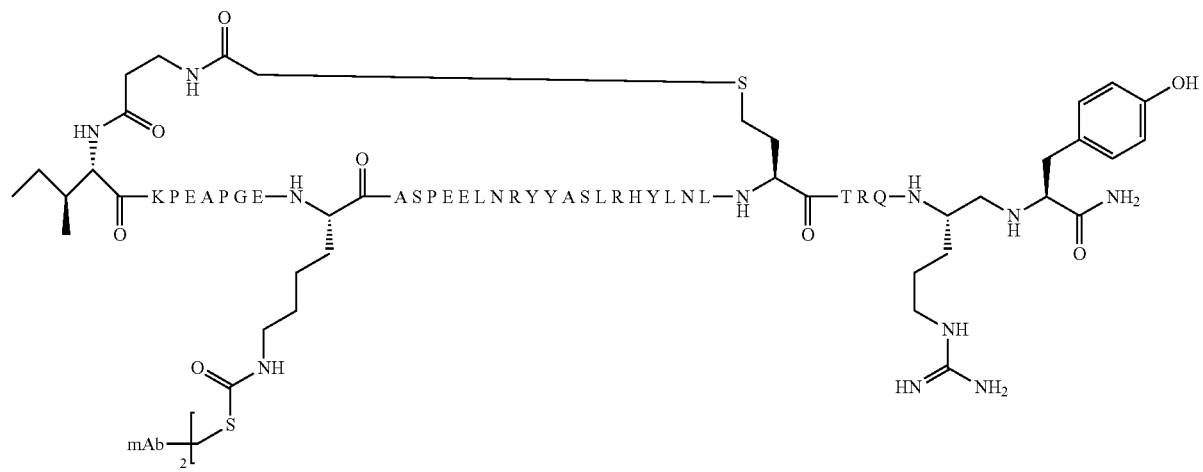
Name: [Cyclo-(βA2-COCH₂-hC31), K11, psi-(R35, Y36)]-PYY2-36 mAb homodimer conjugate (Compound 3)
SEQ ID NO: 105
Structure:
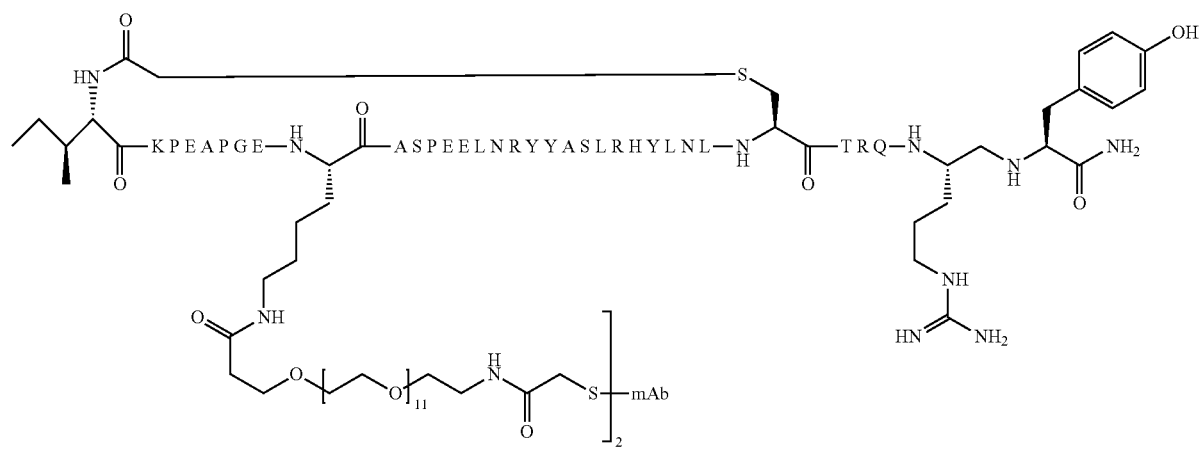
Name: [Cyclo-(I3-COCH₂-C31), K(PEG12)11, psi-(R35, Y36)]-PYY3-36 mAb homodimer conjugate (Compound 4)

-continued
SEQ ID NO: 106
Structure:
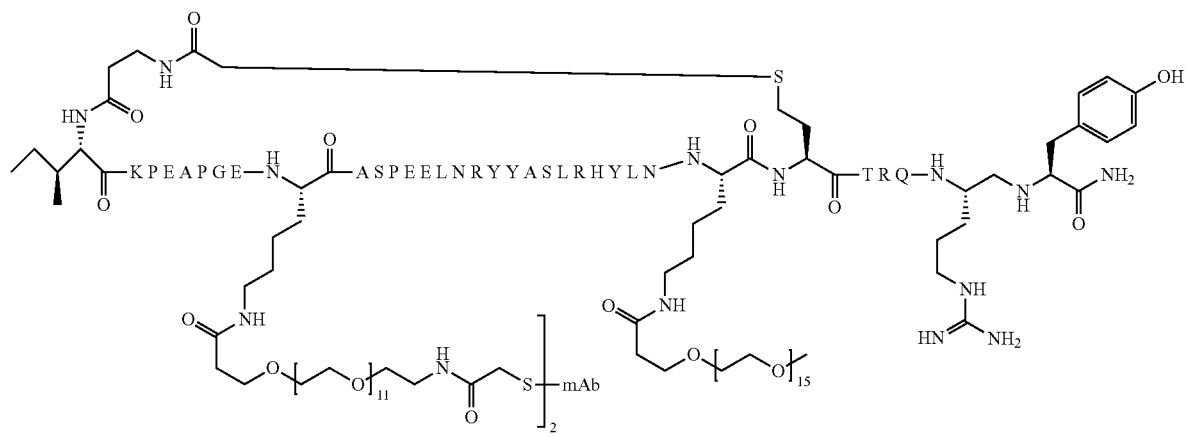
Name: [Cyclo-(βA2-COCH₂-hC31), K(PEG12)11, K(mPEG16)30, psi-(R35, Y36)]-PYY2-36 mAb homodimer conjugate (Compound 5)
SEQ ID NO: 107
Structure:
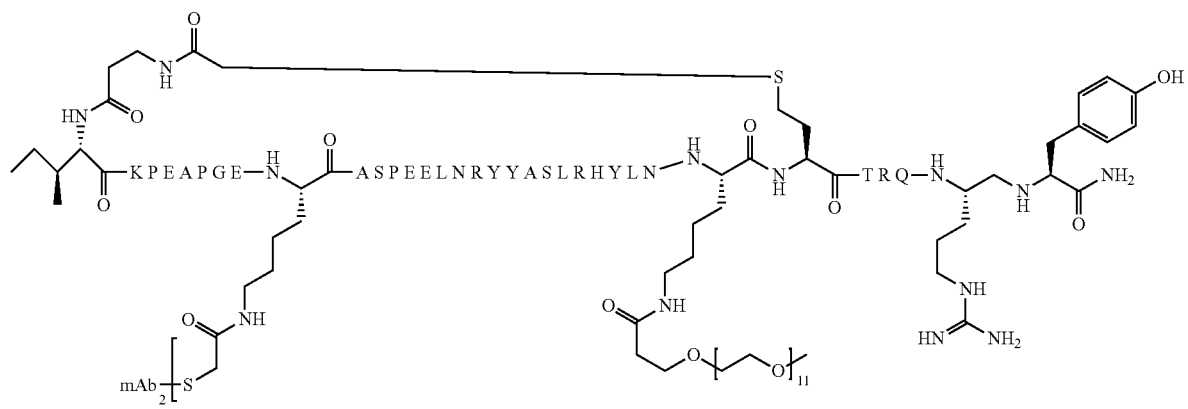
Name: [Cyclo-(βA2-COCH₂-hC31), K11, K(mPEG12)20, psi-(R35, Y36)]-PYY2-36 mAb homodimer conjugate (Compound 6)
SEQ ID NO: 108
Structure:
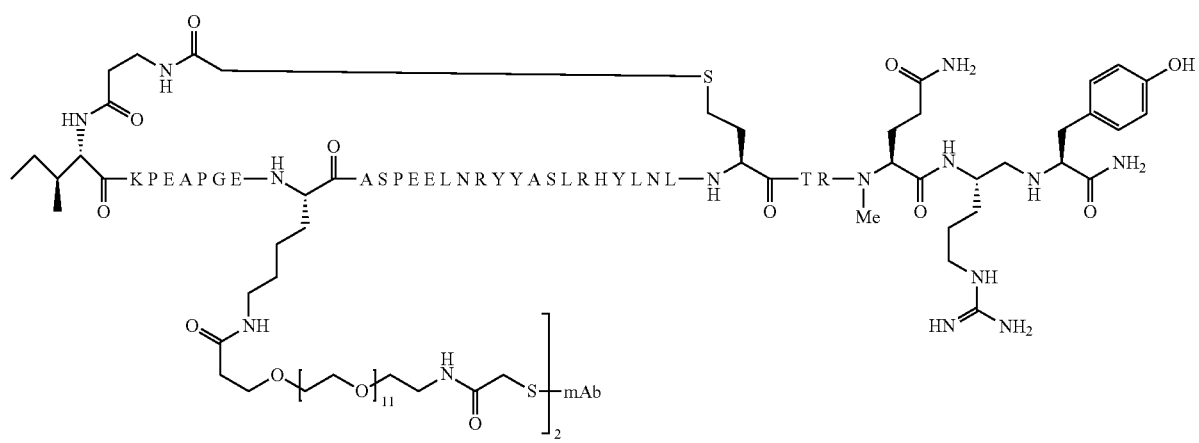
Name: [Cyclo-(βA2-COCH₂-hC31), K(PEG12)11, (N-Me)Q34, psi-(R35, Y36)]-PYY2-36 mAb homodimer conjugate (Compound 7)

SEQ ID NO: 109
Structure:
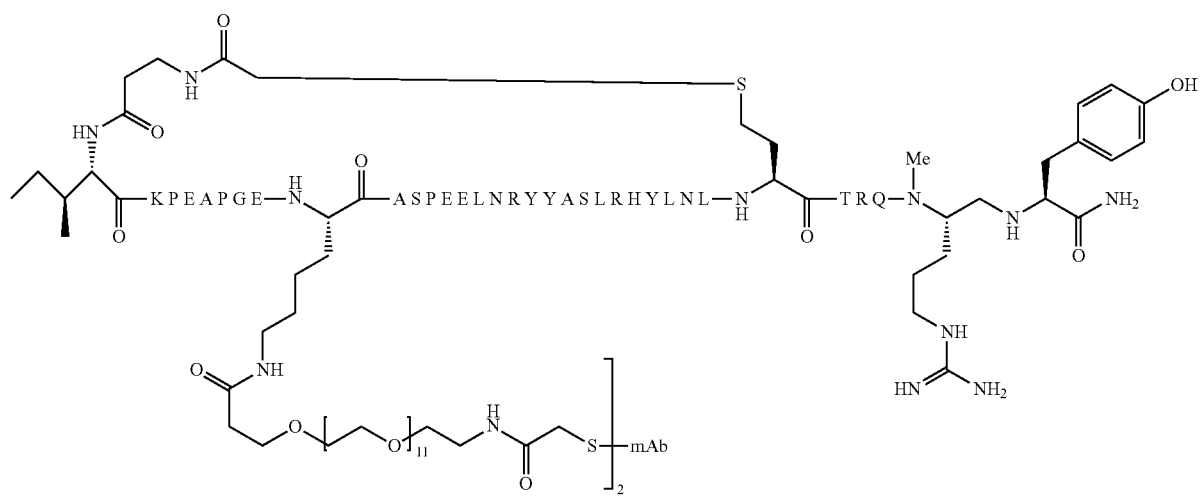
Name: [Cyclo-(βA2-COCH₂-C31), K(PEG12)11, N-Me-R35, psi-(R35, 36Y)]-PYY2-36 mAb homodimer conjugate (Compound 8)
SEQ ID NO: 110
Structure:
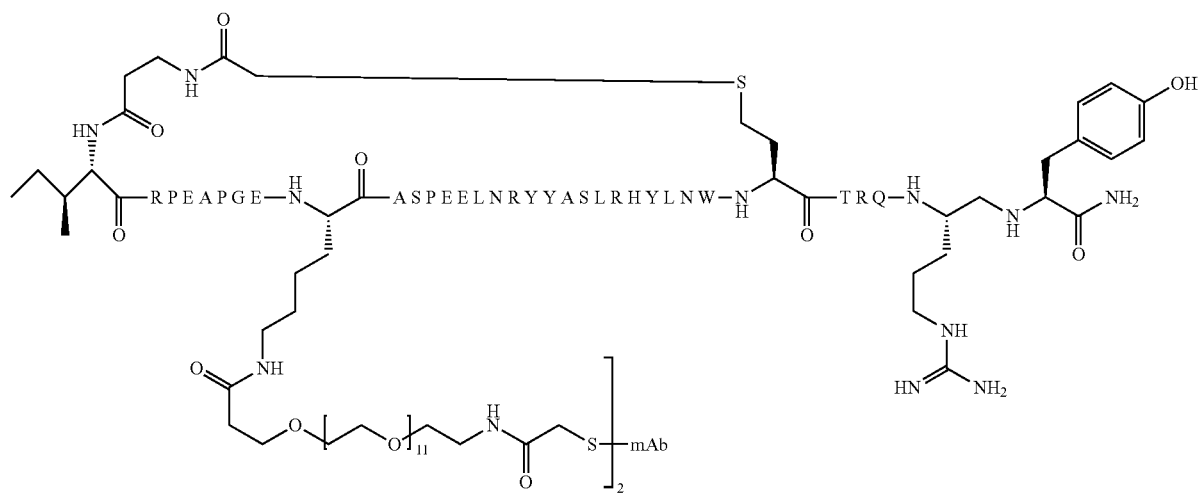
Name: [Cyclo-(βA2-COCH₂-hC31), R4, K(PEG12)11, W30, psi-(R35, Y36)]-PYY2-36 mAb homodimer conjugate (Compound 9)

SEQ ID NO: 111
Structure:
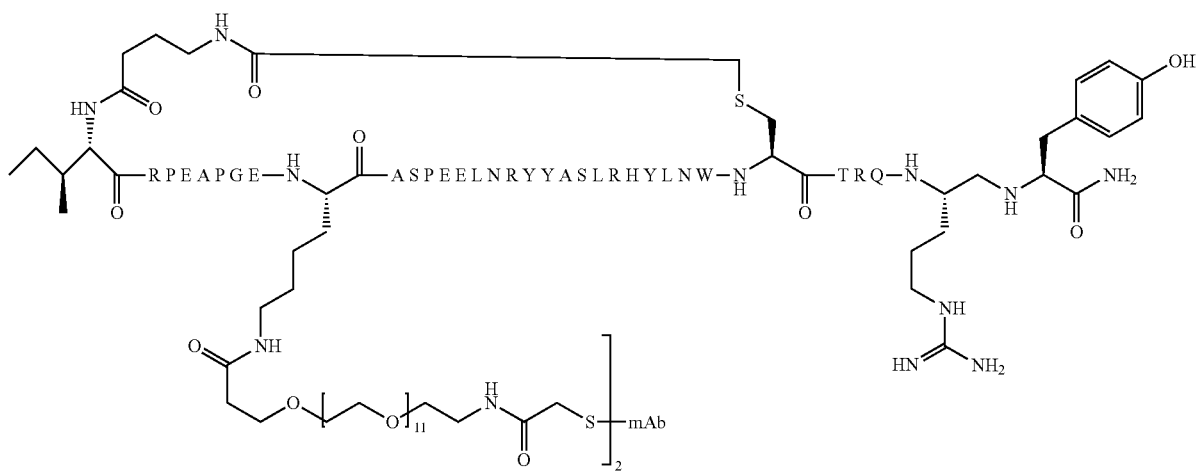
Name: [Cyclo-(3I-COCH₂CH₂CH₂NHCOCH₂-C31), R4, K(PEG12)11, W30, psi-(R35, Y36)]-PYY3-36 mAb homodimer conjugate (Compound 10)
SEQ ID NO: 112
Structure:
Name: [Cyclo-(K4-OEG-COCH₂-C31), K(PEG12)11, psi-(R35, Y36)]-PYY4-36 mAb homodimer conjugate (Compound 11)

SEQ ID NO: 113
Structure
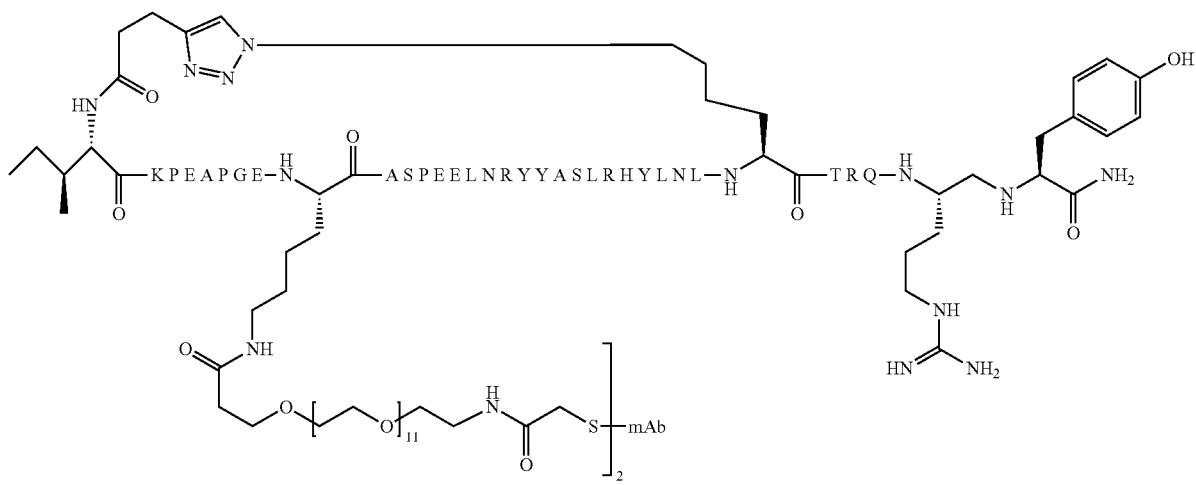
Name: [Cyclo-(I3-COCH$_2$CH$_2$triazolylNle31), K(PEG12)11, psi-(R35, Y36)]-PYY3-36 mAb homodimer conjugate (Compound 12)
SEQ ID NO: 114
Structure:
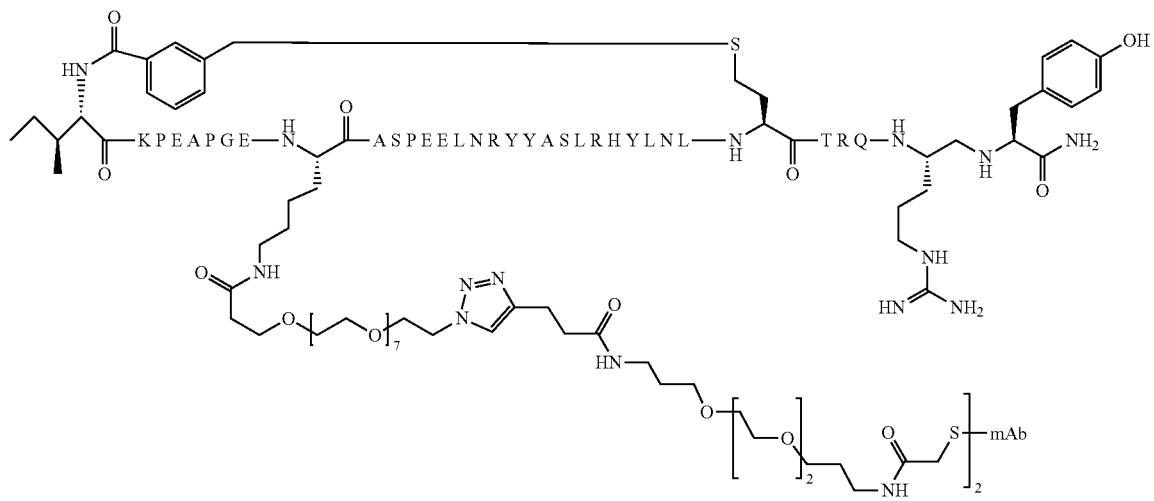
Name: [Cyclo-(I3-m-CO-benzyl-hC31), K(PEG8-triazolyl-CH$_2$CH$_2$CO-PEG4)11, psi-(R35, Y36)]-PYY3-36 mAb homodimer conjugate (Compound 13)

-continued
SEQ ID NO: 115
Structure:
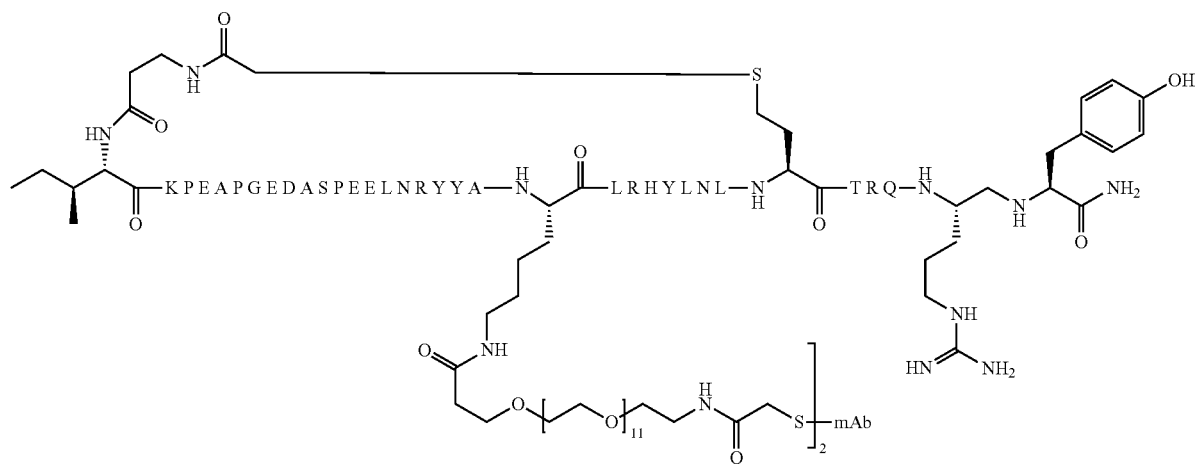
Name: [Cyclo-(βA2-COCH₂-hC31), K(PEG12)23, psi-(R35, Y36)]-PYY2-36 mAb homdimer conjugate (Compound 14)
SEQ ID NO: 116
Structure:
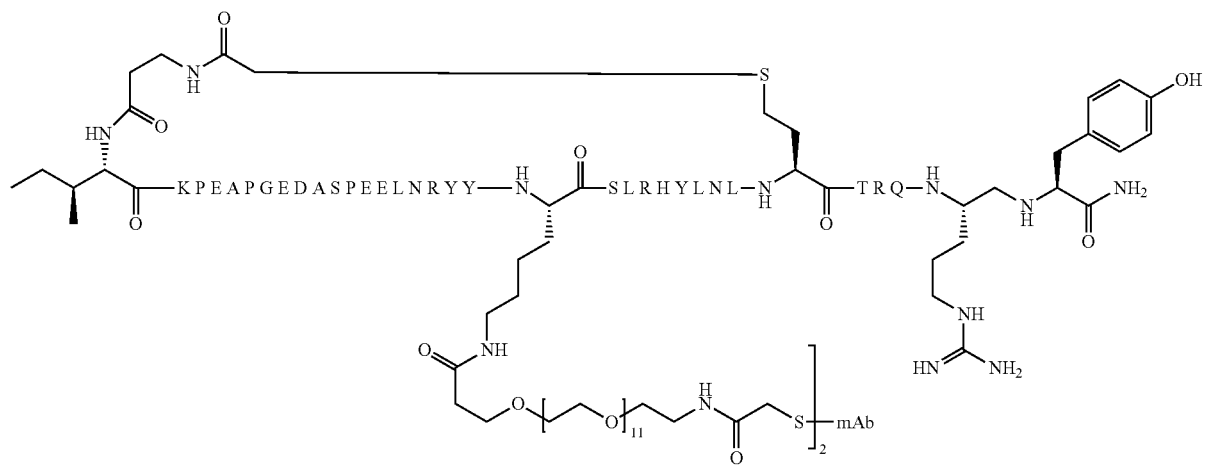
Name: [Cyclo-(βA2-COCH₂-hC31), K(PEG12)22, psi-(R35, Y36)]-PYY2-36 mAb homodimer conjugate (Compound 15)

SEQ ID NO: 117
Structure:
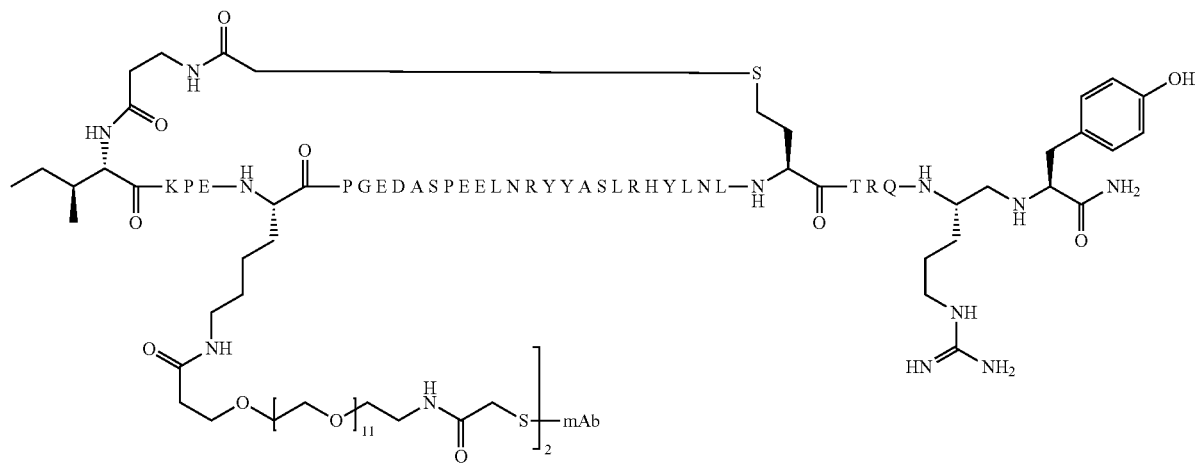
Name: [Cyclo-(βA2-COCH₂-hC31), K(PEG12)7, psi-(R35, Y36)]-PYY2-36 mAb homodimer conjugate (Compound 16)
SEQ ID NO: 118
Structure:
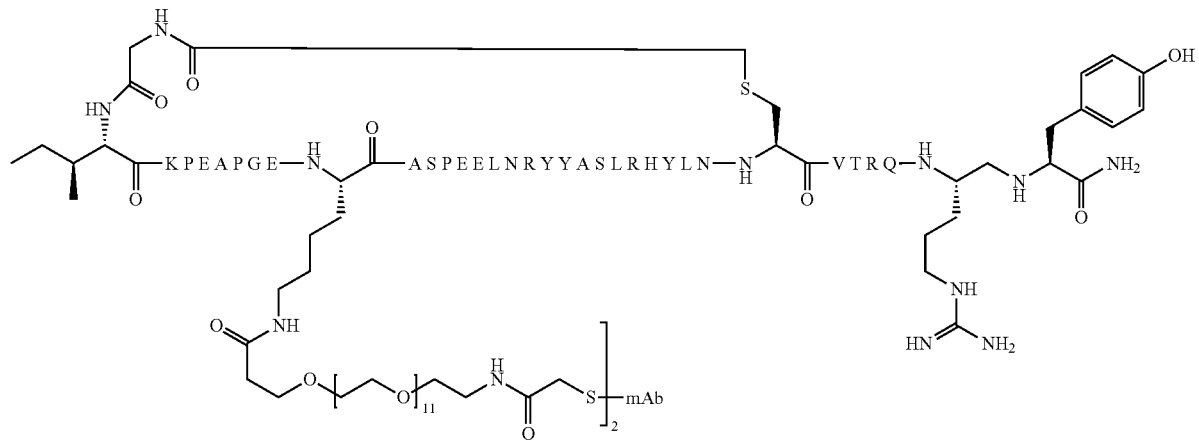
Name: [Cyclo-(G2-COCH₂-C30), K(PEG12-)11, psi-(R35, Y36)]-PYY2-36 mAb homodimer conjugate (Compound 17)

SEQ ID NO: 119
Structure:
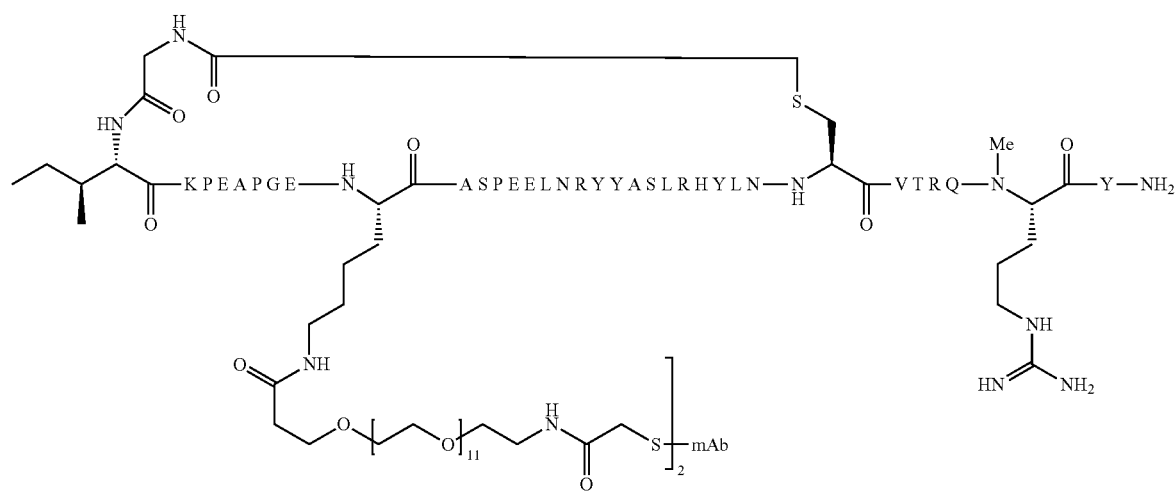
Name: [Cyclo-(G2-COCH$_2$-C30), K(PEG12)11, N-Me-R35]-PYY2-36 mAb homodimer conjugate (Compound 18)
SEQ ID NO: 120
Structure:
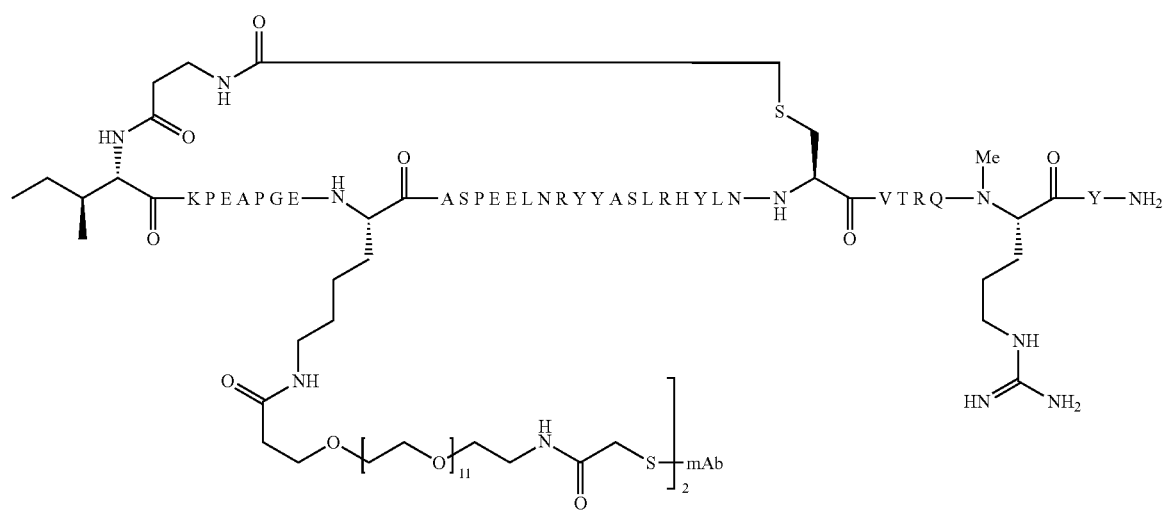
Name: [Cyclo-(βA2-COCH$_2$-C30), K(PEG12)11, N-Me-R35]-PYY2-36 mAb homodimer conjugate (Compound 19)

SEQ ID NO: 121
Structure:
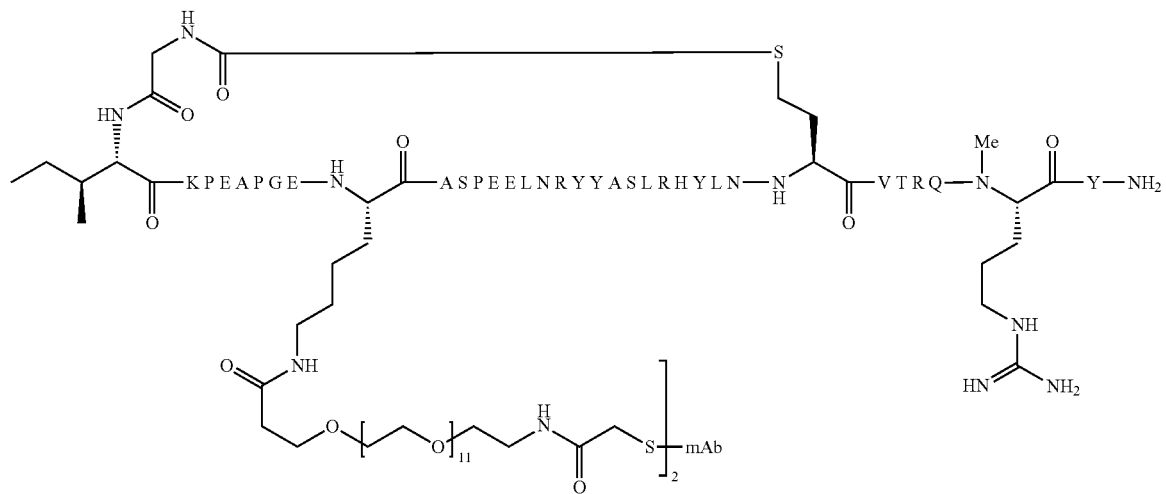
Name: [Cyclo-(G2-COCH₂-hC30), K(PEG12)11, N-Me-R35]-PYY2-36 mAb homodimer conjugate (Compound 20)
SEQ ID NO: 122
Structure:
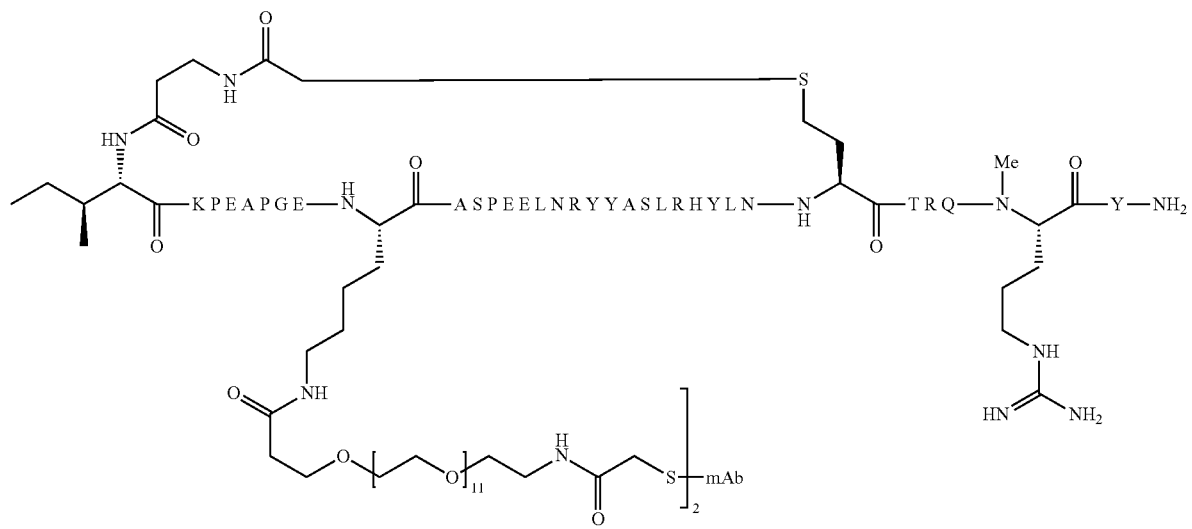
Name: [Cyclo-(βA2-COCH₂-hC31), K(PEG12)11, N-Me-R35]PYY2-36 mAb homodimer conjugate (Compound 21)

SEQ ID NO: 123
Structure:
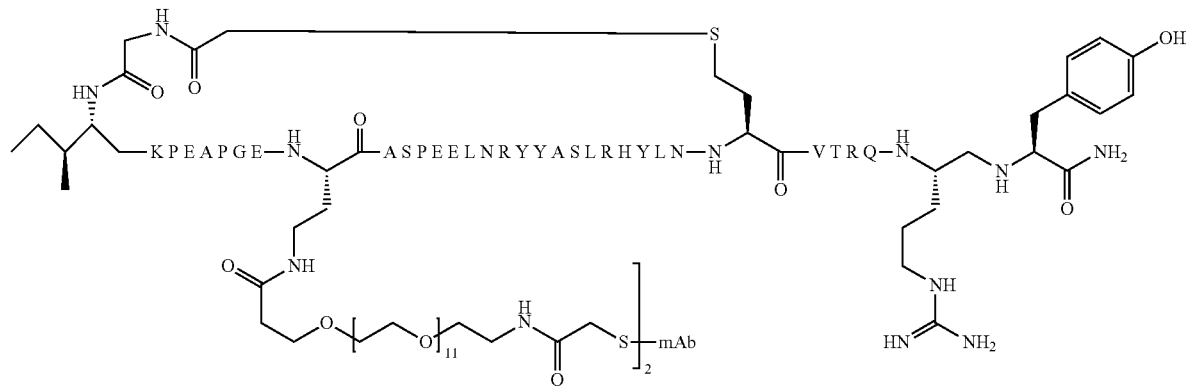
Name: [Cyclo-(G2-COCH₂-hC30), K(PEG12)11, psi-(R35, Y36)]-PYY2-36 mAb homodimer conjugate (Compound 22)
SEQ ID NO: 124
Structure:
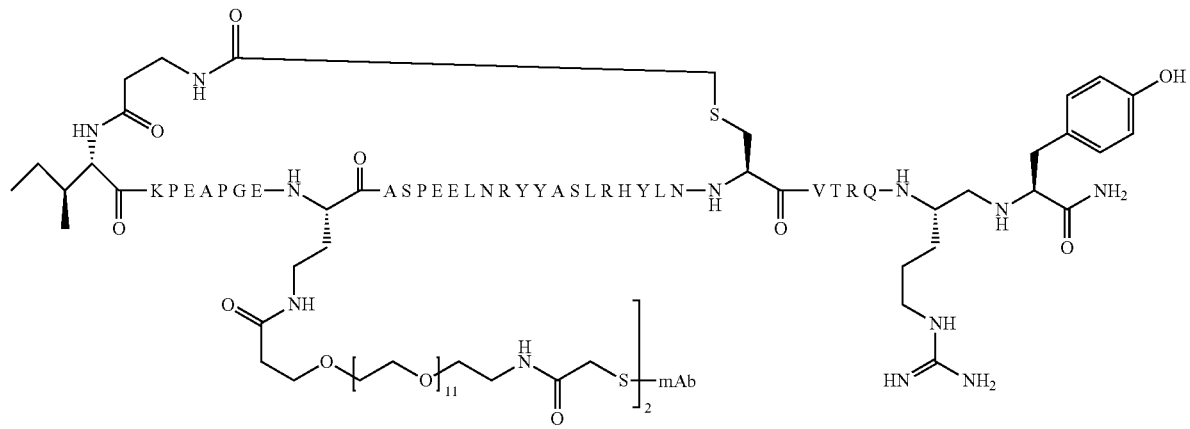
Name: [Cyclo-(βA2-COCH₂-C30), K(PEG12)11, psi-(R35, Y36)]-PYY2-36 mAb homodimer conjugate (Compound 23)
SEQ ID NO: 125
Structure:
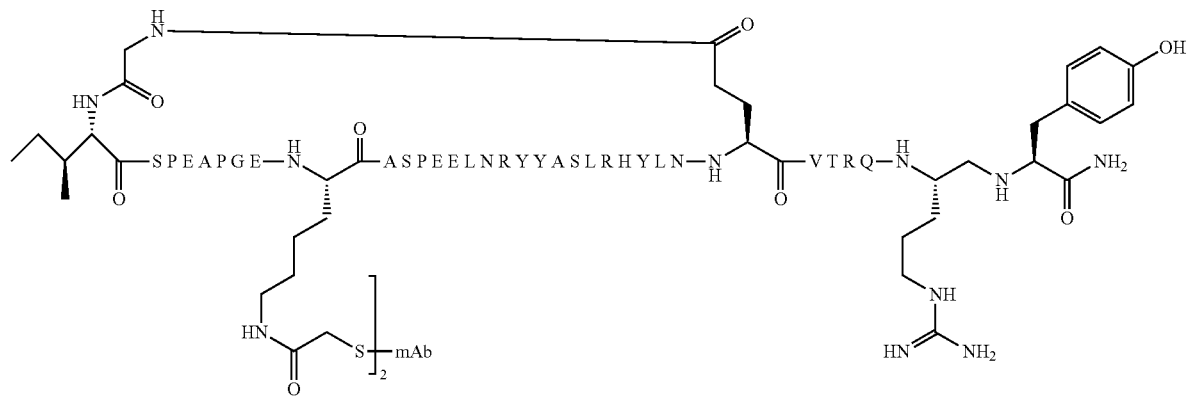
Name: [Cyclo-(G2-E30), S4, K11, psi-(R35, Y36)]-PYY2-36 homodimer conjugate (Compound 24)

SEQ ID NO: 126
Structure:
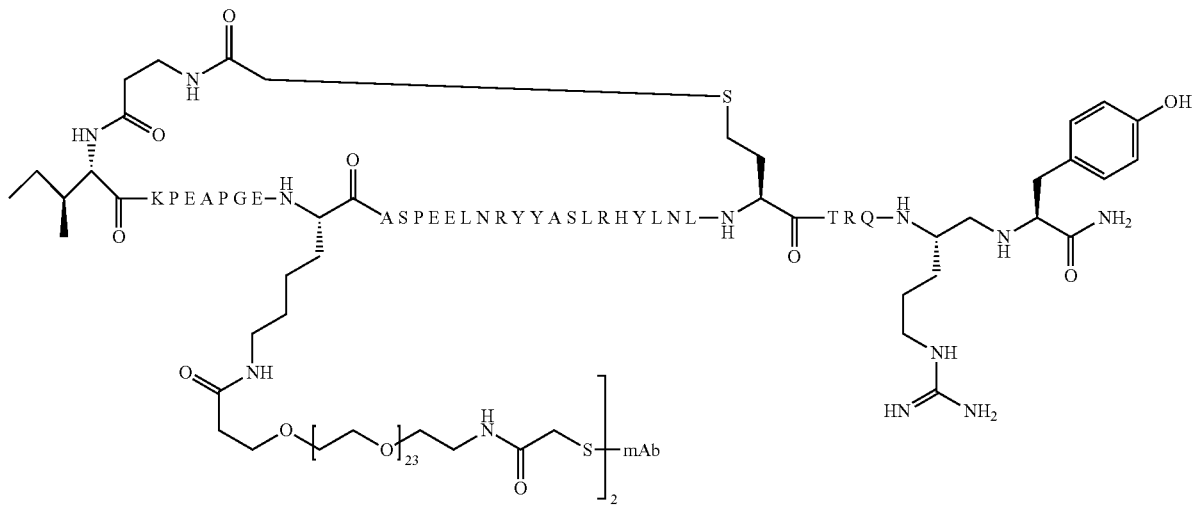
Name: [Cyclo-(βA2-COCH₂-hC31), K(PEG24)11, psi-(R35, Y36)]-PYY2-36 mAb homodimer conjugate (Compound 25)
SEQ ID NO: 127
Structure:
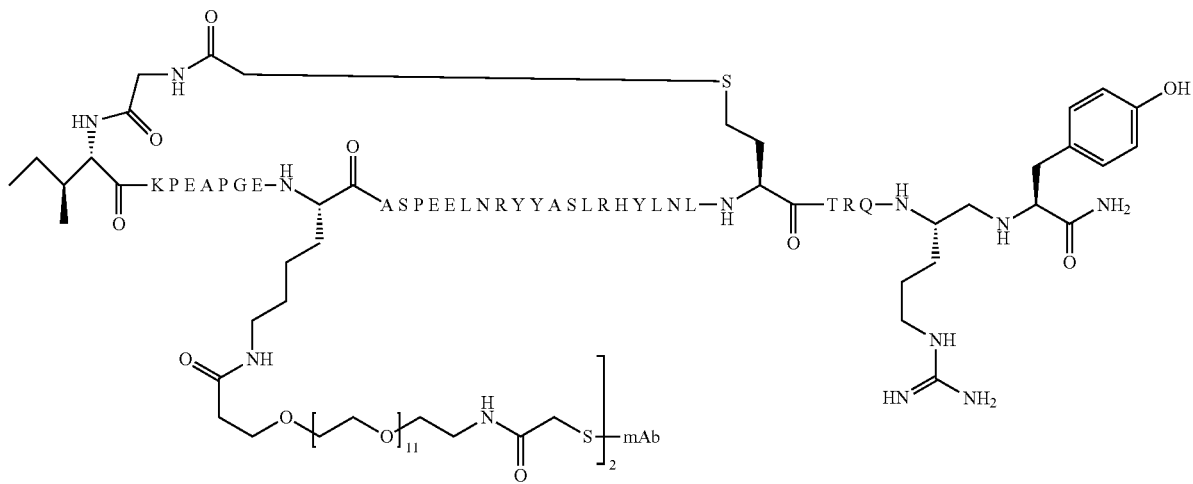
Name: [Cyclo-(G2-Ac-hC31), K(PEG12)11, psi-(R35, Y36)]-PYY2-36 mAb homodimer conjugate (Compound 26)

SEQ ID NO: 147
Structure:
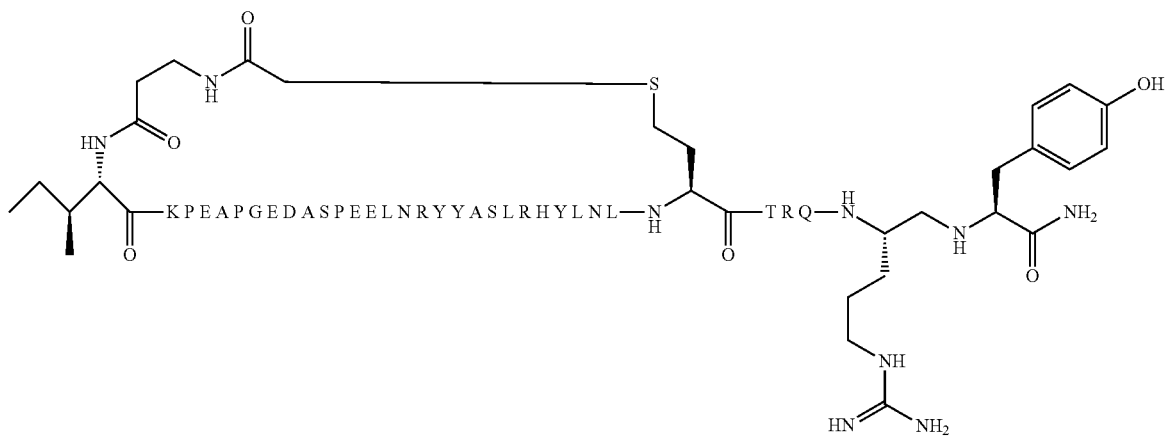
Name: [Cyclo-(βA2-COCH₂-hC31), psi-(R35, Y36)]-PYY2-36
SEQ ID NO: 148
Structure:
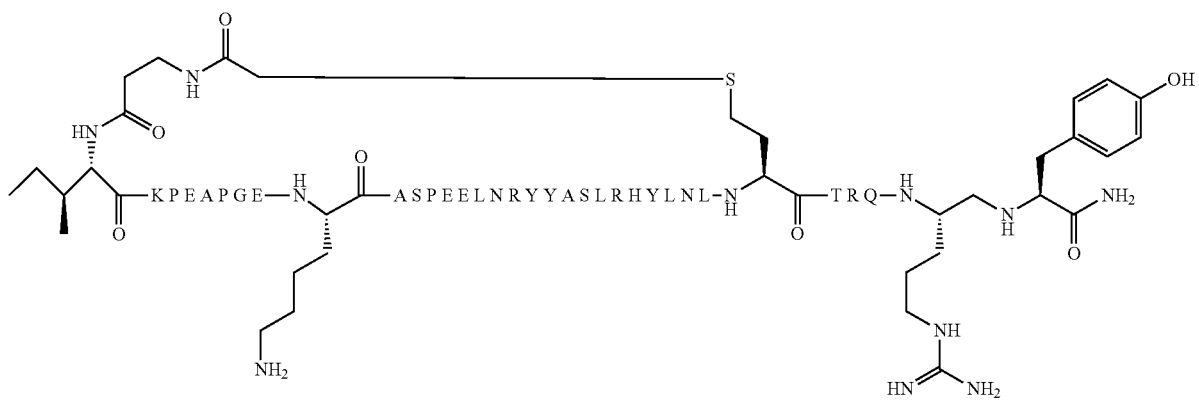
Name: [Cyclo-(βA2-COCH₂-hC31), K11, psi-(R35, Y36)]-PYY2-36
SEQ ID NO: 149
Structure:
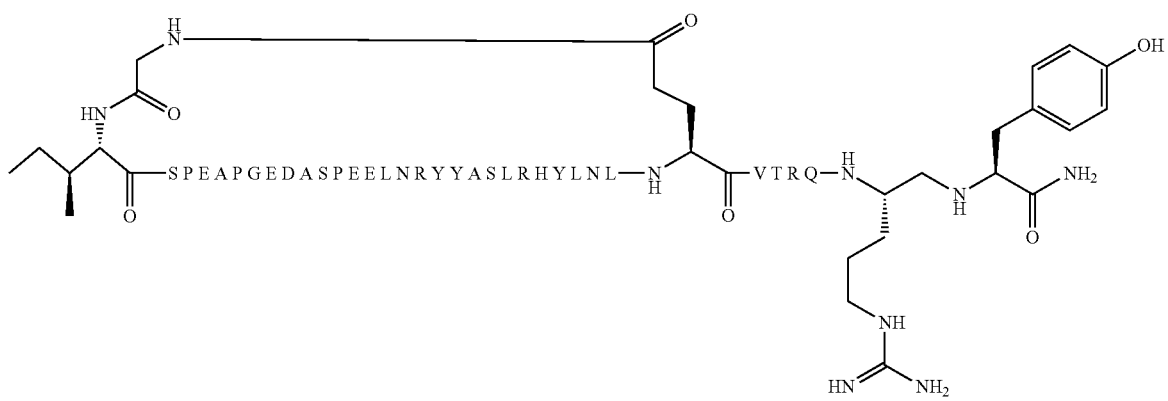
Name: [Cyclo-(G2-E30), S4, psi-(R35, Y36)]-PYY2-36

SEQ ID NO: 150
Structure:
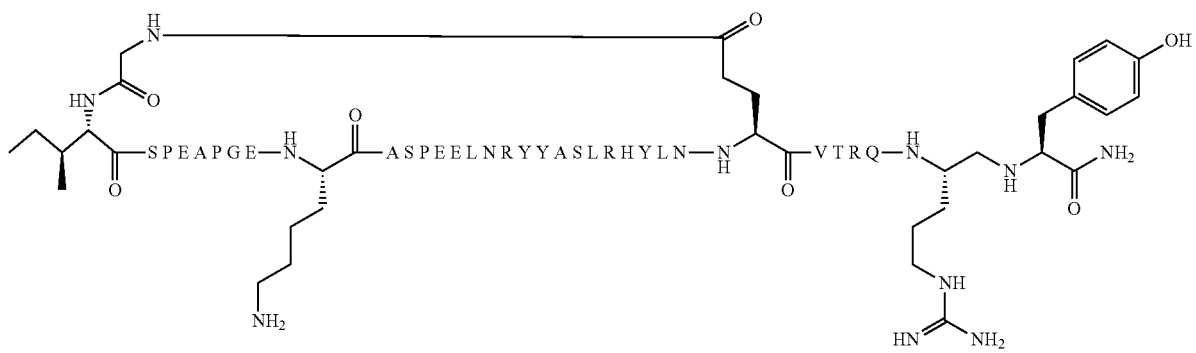
Name: [Cyclo-(G2-E30), S4, K11, psi(R35, Y36)]-PYY2-36
SEQ ID NO: 151
Structure:
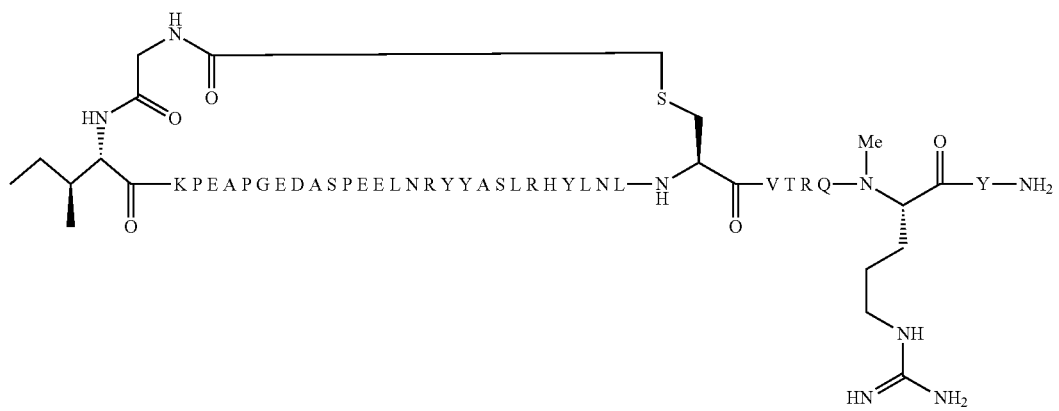
Name: [Cyclo-(G2-COCH₂-C30), N-Me-R35]-PYY2-36
SEQ ID NO: 152
Structure:
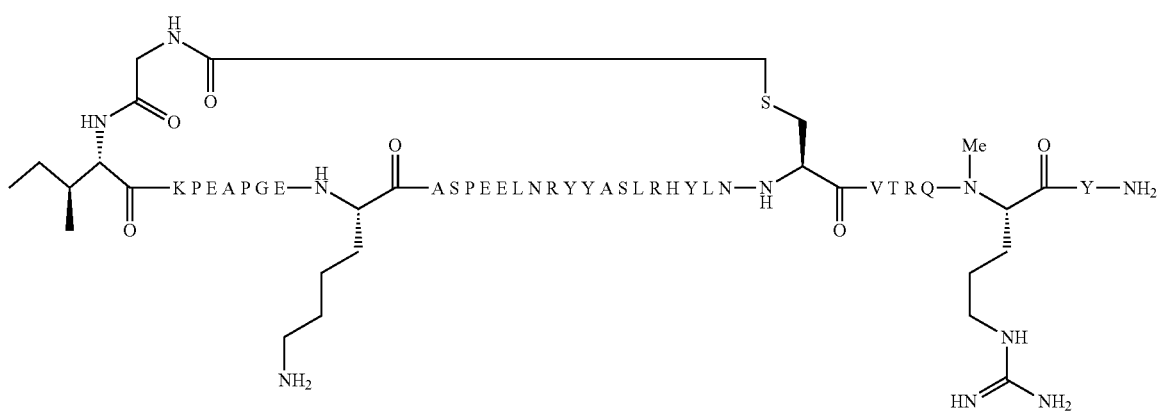
Name: [Cyclo-(G2-COCH₂-C30), K11, N-Me-R35]-PYY2-36

SEQ ID NO: 153
Structure:
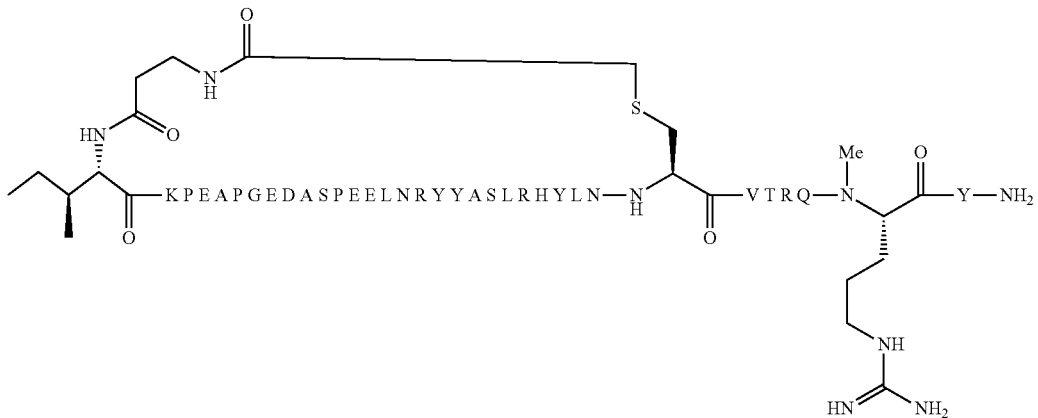
Name: [Cyclo-(βA2-COCH$_2$-C30), N-Me-R35]-PYY2-36
SEQ ID NO: 154
Structure:
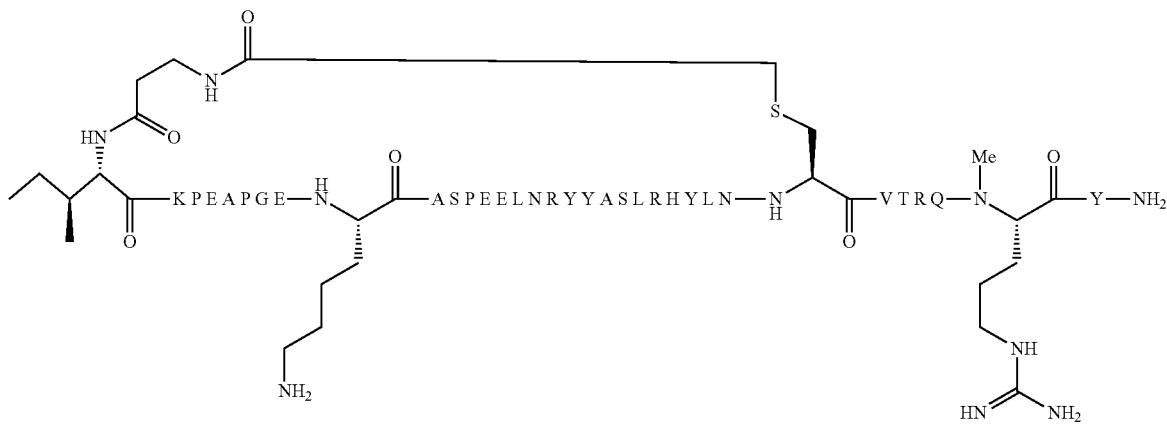
Name: [Cyclo-(βA2-COCH$_2$-C30), K11, N-Me-R35]-PYY2-36
SEQ ID NO: 155
Structure:
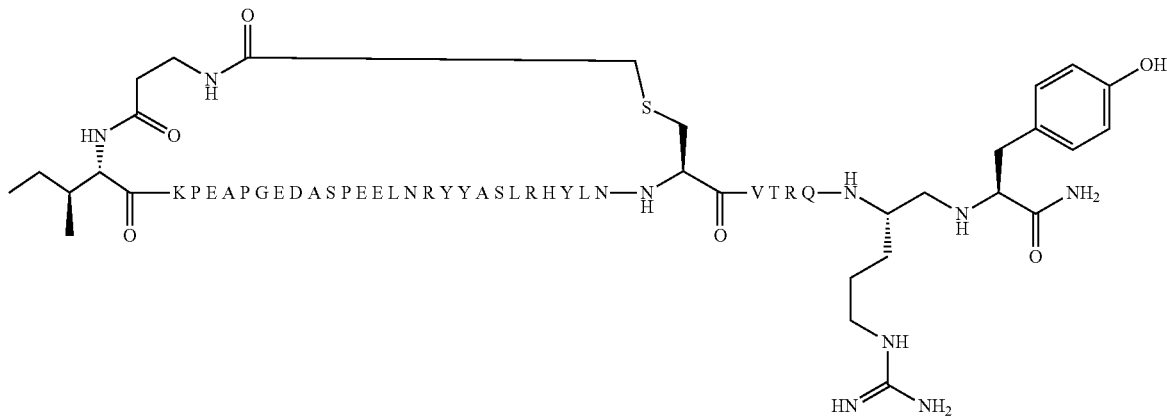
Name: [Cyclo-(βA2-COCH$_2$-C30), psi-(R35, Y36)]-PYY2-36

SEQ ID NO: 156

Structure:

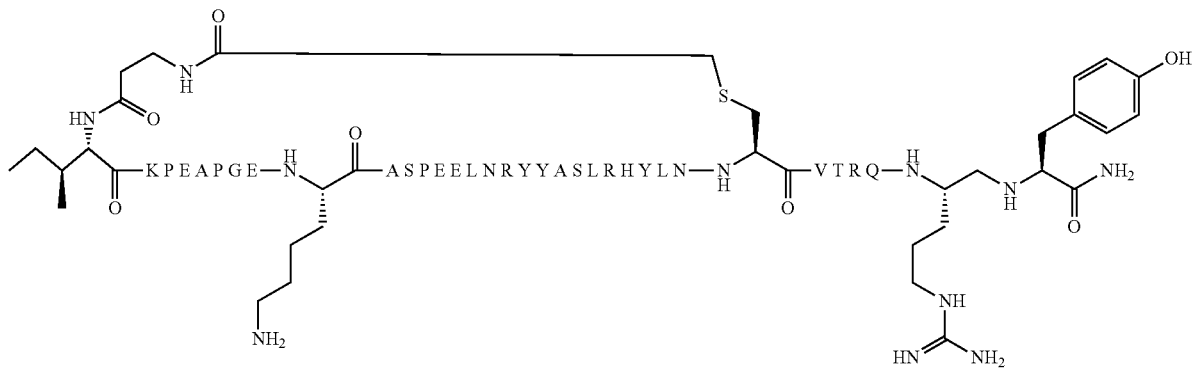

Name: [Cyclo-(βA2-COCH₂-C30), K11, psi(R35, Y36)]-PYY2-36

---

It is claimed:

1. A conjugate comprising a monoclonal antibody or an antigen binding fragment thereof coupled to a cyclic PYY peptide, the monoclonal antibody or the antigen binding fragment thereof comprising a heavy chain complementarity determining region 1 (HCDR1), HCDR2, HCDR3, and a light chain complementarity determining region 1 (LCDR1), LCDR2, and LCDR3, having the polypeptide sequences of SEQ ID NO: 141, 142, 143, 144, 145, and 146, respectively, wherein the cyclic PYY peptide is represented by Formula I or a derivative or pharmaceutically acceptable salt thereof:

Formula I

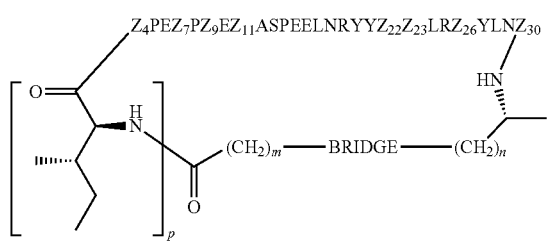

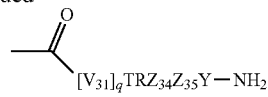

wherein p is 0 or 1;

m is 0, 1, 2, 3, 4, or 5;

n is 1, 2, 3, or 4;

q is 0 or 1; provided that q is 1 only when $Z_{30}$ is absent;

BRIDGE is -Ph-$CH_2$—S—, -triazolyl-, —NHC(O)$CH_2$S—, —$SCH_2$C(O)NH—, —($OCH_2CH_2$)$_2$NHC(O)$CH_2$S, —NHC(O)—, or —$CH_2$S—;

$Z_4$ is K, A, E, S, or R;

$Z_7$ is A or K;

$Z_9$ is G or K;

$Z_{11}$ is D or K;

$Z_{22}$ is A or K;

$Z_{23}$ is S or K;

$Z_{26}$ is A or H;

$Z_{30}$ is L, W, absent, or K;

provided that $Z_{30}$ is absent only when q is 1;

$Z_{34}$ is

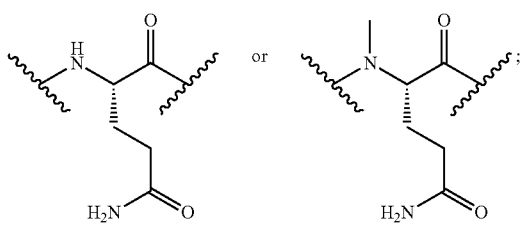 [SMILES: *N[C@@H](CCC(N)=O)C(*)=O ; "or" ; *C(=O)[C@H](CCC(N)=O)N(*)C ; ";"] or $Z_{35}$ is

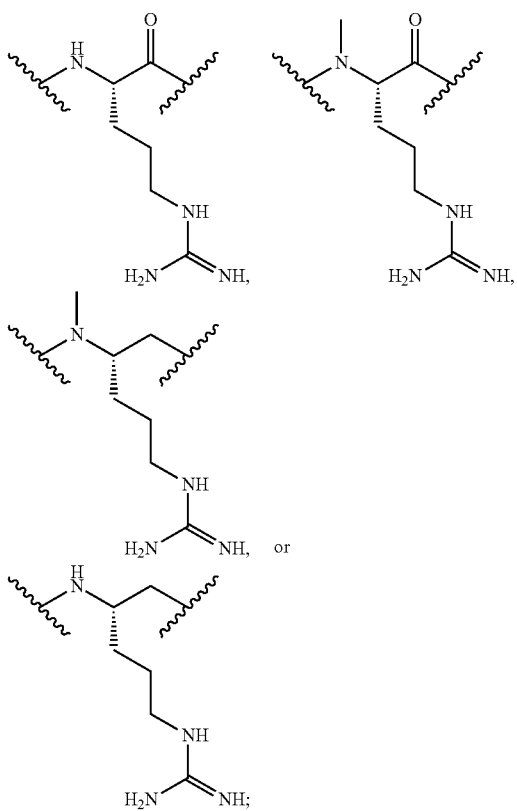

wherein the derivative is the compound of Formula I that is modified by one or more processes selected from the group consisting of amidation, glycosylation, carbamylation, sulfation, phosphorylation, cyclization, lipidation, and pegylation.

2. The conjugate of claim 1, wherein the cyclic PYY peptide is a compound of Formula I or a derivative of the cyclic PYY peptide of Formula I that is modified by one or more processes selected from the group consisting amidation, lipidation, and pegylation, or a pharmaceutically acceptable salt thereof.

3. The conjugate of claim 1, wherein the cyclic PYY peptide is represented by Formula I or the derivative or pharmaceutically acceptable salt thereof, wherein:

p is 0 or 1;
m is 0, 1, 2, 3, 4, or 5;
n is 1, 2, 3, or 4;
q is 0 or 1; provided that q is 1 only when $Z_{30}$ is absent;

BRIDGE is -Ph-$CH_2$-S—, -triazolyl-, —NHC(O)$CH_2$S—, —S$CH_2$C(O)$NH_2$—, —(O$CH_2CH_2$)$_2$NHC(O)$CH_2$S, —NHC(O)—, or —$CH_2$S—;
$Z_4$ is K, A, E, S, or R;
$Z_7$ is A or K, wherein the amino side chain of said K is optionally substituted with

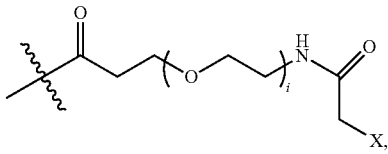

wherein i is an integer of 0 to 24, and X=Br, I or Cl, —C(O)$CH_2$Br, —C(O)$CH_2$I, or —C(O)$CH_2$Cl;
$Z_9$ is G or K, wherein the amino side chain of said K is optionally substituted with

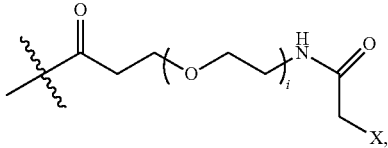

wherein i is an integer of 0 to 24, and X=Br, I or Cl, —C(O)$CH_2$Br, —C(O)$CH_2$I, or —C(O)$CH_2$Cl;
$Z_{11}$ is D or K, wherein the amino side chain of said K is optionally substituted with

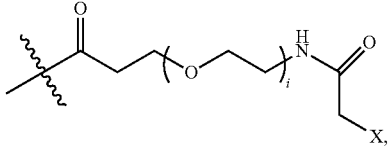

wherein i is an integer of 0 to 24, and X=Br, I or Cl, —C(O)$CH_2$Br, —C(O)$CH_2$I, or —C(O)$CH_2$Cl;
$Z_{22}$ is A or K, wherein the amino side chain of said K is optionally substituted with

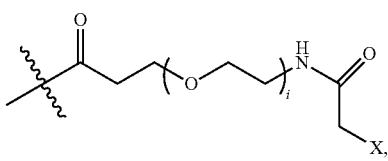

wherein i is an integer of 0 to 24, and X=Br, I or Cl, —C(O)$CH_2$Br, —C(O)$CH_2$I, or —C(O)$CH_2$Cl;
$Z_{23}$ is S or K, wherein the amino side chain of said K is optionally substituted with

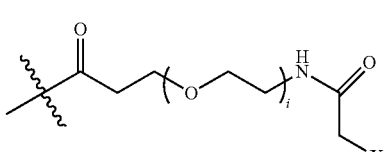

wherein i is an integer of 0 to 24, and X=Br, I or Cl, —C(O)CH₂Br, —C(O)CH₂I, or —C(O)CH₂Cl;

$Z_{26}$ is A or H;

$Z_{30}$ is L or K, wherein the amino side chain of said K is substituted with

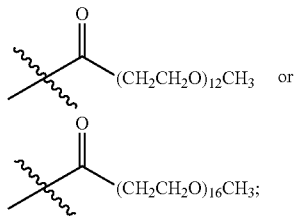

$Z_{34}$ is

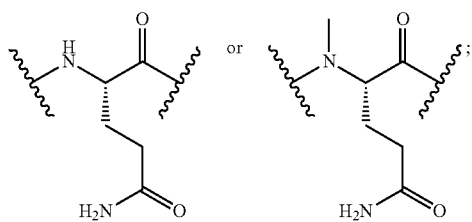

and
$Z_{35}$ is

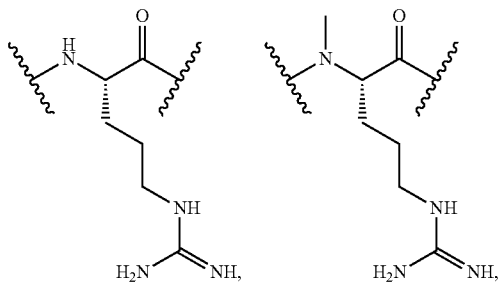

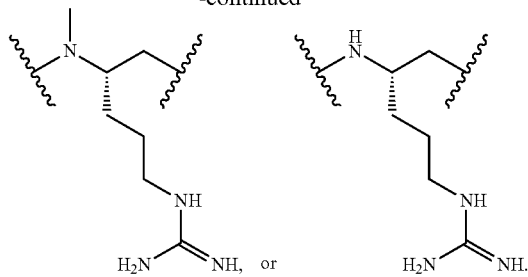

4. The conjugate of claim 1, wherein the cyclic PYY peptide is represented by Formula I or the derivative or pharmaceutically acceptable salt thereof, wherein:

p is 0 or 1;

m is 0, 1, 2, 3, or 5;

n is 1, 2, or 4;

q is 0 or 1; provided that q may be 1 only when $Z_{30}$ is absent;

BRIDGE is -Ph-CH₂—S—, -triazolyl-, —NHC(O)CH₂S—, —(OCH₂CH₂)₂NHC(O)CH₂S, —NHC(O)—, or —CH₂S—;

$Z_4$ is K, A, E, S, or R;

$Z_7$ is A or K, wherein the amino side chain of said K is substituted with

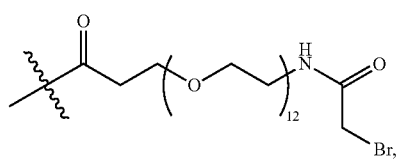

$Z_9$ is G or K, $Z_{11}$ is D or K, wherein the amino side chain of said K is substituted with

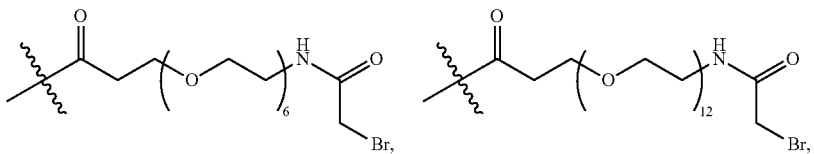

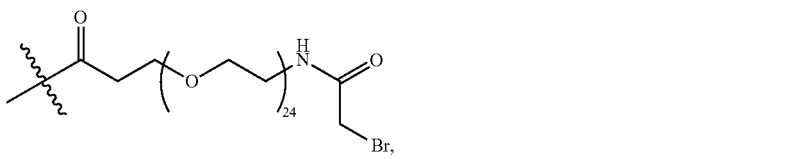

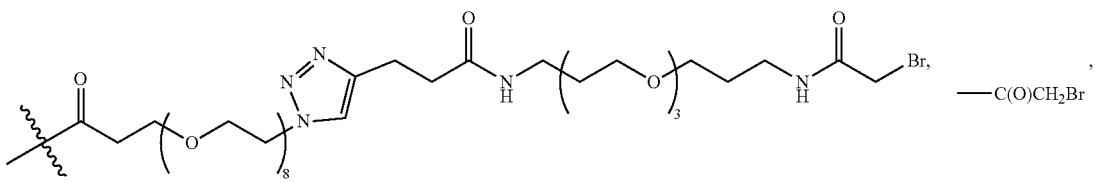

$Z_{22}$ is A or K, wherein the amino side chain of said K is substituted with

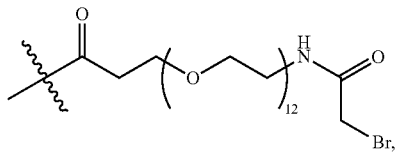

$Z_{23}$ is S or K, wherein the amino side chain of said K is substituted with

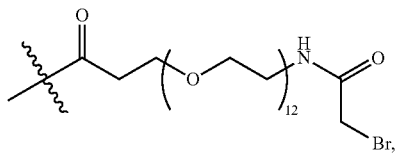

$Z_{26}$ is A or H, $Z_{30}$ is L or K, wherein the amino side chain of said K is substituted with

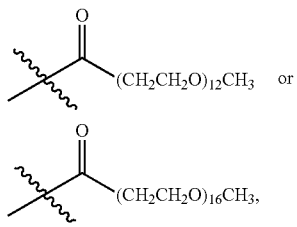

$Z_{34}$ is

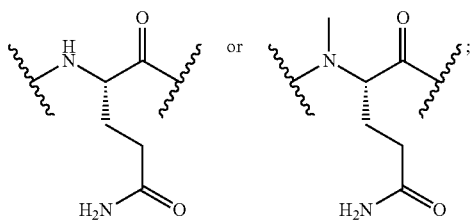 [SMILES: *N[C@@H](CCC(N)=O)C(*)=O ; *C(=O)[C@H](CCC(N)=O)N(*)C]

$Z_{35}$ is

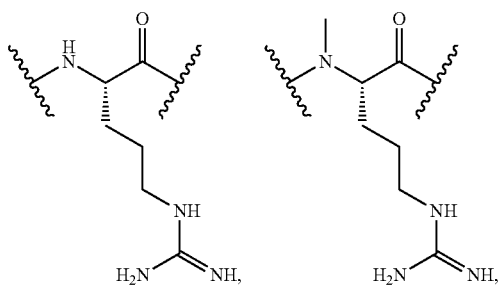

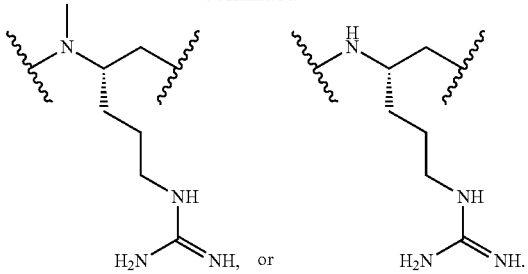

5. The conjugate of claim 1, wherein the cyclic PYY peptide is selected from the group consisting of SEQ ID NOs:1, 73-100, and 147-156, or a pharmaceutically acceptable salt thereof.

6. The conjugate of claim 1, wherein the monoclonal antibody or the antigen binding fragment thereof is covalently linked to the cyclic PYY peptide at a lysine residue of the cyclic PYY peptide via a linker.

7. The conjugate of claim 6, wherein the linker comprises one selected from the group consisting of polyethylene glycol (PEG)8-triazolyl-$CH_2CH_2CO$-PEG4, a PEG chain of 2-24 PEG units, an alkyl chain containing 2-10 carbon atoms, $(Gly_4Ser)_j$ wherein j=1-4, $(AlaPro)_u$ wherein u=1-10, and a bond.

8. The conjugate of claim 7, wherein only one of $Z_7$, $Z_9$, $Z_{11}$, $Z_{22}$ and $Z_{23}$ in Formula I is lysine, and the lysine is covalently linked to an engineered cysteine residue of the monoclonal antibody or the antigen binding fragment thereof via the linker.

9. The conjugate of claim 1, wherein the isolated monoclonal antibody or the antigen binding fragment thereof comprises a heavy chain variable domain (VH) having the polypeptide sequence of SEQ ID NO:137, and a light chain variable domain (VL) having the polypeptide sequence of SEQ ID NO:139.

10. The conjugate of claim 9, further comprising a Fc portion.

11. The conjugate of claim 10, comprising a heavy chain (HC) having the polypeptide sequence of SEQ ID NO:138 and a light chain (LC) having the polypeptide sequence of SEQ ID NO:140.

12. A pharmaceutical composition comprising the conjugate of claim 1 and a pharmaceutically acceptable carrier.

13. A method of modulating Y2 receptor activity in a subject in need thereof, the method comprising administering to the subject in need thereof an effective amount of the pharmaceutical composition of claim 12.

14. A method of reducing food intake in a subject in need thereof, the method comprising administering to the subject in need thereof an effective amount of the pharmaceutical composition of claim 12.

15. The method of claim 14, wherein the pharmaceutical composition is administered via an injection.

16. The method of claim 14, wherein the pharmaceutical composition is administered in a combination with at least one antidiabetic agent.

17. The method of claim 16, wherein said antidiabetic agent is a glucagon-like-peptide-1 receptor modulator.

18. The method of claim 16, wherein the pharmaceutical composition is administered in combination with liraglutide.

19. A kit comprising the conjugate of claim 1, further comprising liraglutide and a device for injection.

20. A method of producing a pharmaceutical composition comprising the conjugate of claim 1, comprising combining the conjugate with a pharmaceutically acceptable carrier to obtain the pharmaceutical composition.

21. A conjugate comprising a monoclonal antibody or an antigen binding fragment thereof coupled to a cyclic PYY peptide, wherein:

the monoclonal antibody or the antigen binding fragment thereof comprises a heavy chain complementarity determining region 1 (HCDR1), HCDR2, HCDR3, and a light chain complementarity determining region 1 (LCDR1), LCDR2, and LCDR3, having the polypeptide sequences of SEQ ID NO: 141, 142, 143, 144, 145, and 146, respectively, the cyclic PYY peptide comprises a polypeptide sequence selected from the group consisting of SEQ ID NOs: 1, 73-100, and 147-156, or a pharmaceutically acceptable salt thereof; and the monoclonal antibody or antigen binding fragment thereof is conjugated to the cyclic PYY peptide at residue 7, 9, 11, 22 or 23 of the cyclic PYY peptide, directly or via a linker.

22. The conjugate of claim 21, wherein the monoclonal antibody or antigen binding fragment thereof comprises a heavy chain variable domain (VH) having the polypeptide sequence of SEQ ID NO:137 and a light chain variable domain (VL) having the polypeptide sequence of SEQ ID NO:139.

23. The conjugate of claim 21, wherein the monoclonal antibody or antigen binding fragment thereof comprises a heavy chain (HC) having the polypeptide sequence of SEQ ID NO:138 and a light chain (LC) having the polypeptide sequence of SEQ ID NO:140.

24. The conjugate of claim 21, wherein the monoclonal antibody or antigen binding fragment thereof is conjugated to the cyclic PYY peptide at lysine residue 11 of the cyclic PYY peptide.

25. A method of producing the conjugate of claim 1, comprising reacting an electrophile, introduced onto a sidechain of the cyclic PYY peptide, with the sulfhydryl group of the cysteine residue of SEQ ID NO:143 of the monoclonal antibody or antigen-binding fragment thereof, thereby creating a covalent linkage between the cyclic PYY peptide and the monoclonal antibody or antigen-binding fragment thereof.

26. The method of claim 25, wherein the electrophile is bromoacetamide or maleimide.

27. The method of claim 25, wherein the sidechain of the cyclic PYY peptide is a sidechain of a lysine residue of the cyclic PYY peptide.

28. A conjugate comprising a monoclonal antibody or an antigen binding fragment thereof coupled to a cyclic PYY peptide, wherein the conjugate comprises the monoclonal antibody or the antigen binding fragment thereof comprising a heavy chain complementarity determining region 1 (HCDR1), HCDR2, HCDR3, and a light chain complementarity determining region 1 (LCDR1), LCDR2, and LCDR3, having the polypeptide sequences of SEQ ID NO: 141, 142, 143, 144, 145, and 146, respectively, and a sequence selected from the group consisting of SEQ ID NOs: 102-127 or a pharmaceutically acceptable salt thereof, wherein mAb represents the monoclonal antibody or the antigen binding fragment thereof, and ]$_2$ represents that 1 or 2 of the cyclic PYY peptides is/are covalently conjugated to the mAb.

* * * * *

```
                        SEQUENCE LISTING

<160> NUMBER OF SEQ ID NOS: 156

<210> SEQ ID NO 1
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein Cys is a homocysteine with a
cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 1

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 2
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
```

```
<221> NAME/KEY: Ile
<222> LOCATION: (1)..(1)
<223> OTHER INFORMATION: Ile with a cyclic modification
<220> FEATURE:
<221> NAME/KEY: Cys
<222> LOCATION: (29)..(29)
<223> OTHER INFORMATION: Cys, wherein Cys is homocysteine with a cyclic
      modification

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 3
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Leu
<222> LOCATION: (29)..(29)
<223> OTHER INFORMATION: Leu, wherien Leu is a norleucine with a cyclic
      modification

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 4
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein cys is a homocysteine with a
      cyclic modification

<400> SEQUENCE: 4

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 5
```

```
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a gamma-Glu-AcVitE chemical
      modification
<220> FEATURE:
<221> NAME/KEY: Cys
<222> LOCATION: (29)..(29)
<223> OTHER INFORMATION: Cys, wherein cys is homocysteine with a cyclic
      modification

<400> SEQUENCE: 5

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 6
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a gamma-Glu-AcVitE chemical
      modification
<220> FEATURE:
<221> NAME/KEY: Leu
<222> LOCATION: (29)..(29)
<223> OTHER INFORMATION: Leu, wherein the leu is norleucine with a
      cyclic modification

<400> SEQUENCE: 6

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Leu Thr Arg Gln
            20                  25                  30

Arg Tyr

<210> SEQ ID NO 7
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (7)..(7)
<223> OTHER INFORMATION: Lys with a gamma-Glu-Pal chemical modification
<220> FEATURE:
<221> NAME/KEY: Cys
```

```
<222> LOCATION: (29)..(29)
<223> OTHER INFORMATION: Cys, wherein cys is homocysteine with a cyclic
      modification

<400> SEQUENCE: 7

Ile Lys Pro Glu Ala Pro Lys Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 8
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein cys is homocysteine with a cyclic
      modification

<400> SEQUENCE: 8

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 9
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Cys
<222> LOCATION: (29)..(29)
<223> OTHER INFORMATION: Cys, wherein cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 9

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr
```

```
<210> SEQ ID NO 10
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-AcVitE chemical
      modification
<220> FEATURE:
<221> NAME/KEY: Cys
<222> LOCATION: (29)..(29)
<223> OTHER INFORMATION: Cys, wherein cys is homocysteine with a cyclic
      modification

<400> SEQUENCE: 10

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Lys Cys Thr Arg
            20                  25                  30

Gln Arg Tyr
        35

<210> SEQ ID NO 11
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-AcVitE chemical
      modification
<220> FEATURE:
<221> NAME/KEY: Cys
<222> LOCATION: (29)..(29)
<223> OTHER INFORMATION: Cys, wherein cys is homocysteine with a cyclic
      modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 11

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Lys Cys Thr Arg
            20                  25                  30

Gln Arg Tyr
        35

<210> SEQ ID NO 12
<211> LENGTH: 34
<212> TYPE: PRT
```

```
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Cys
<222> LOCATION: (29)..(29)
<223> OTHER INFORMATION: Cys, wherein the cys is homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 12

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 13
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 13

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 14
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
```

```
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is homocysteine with a
      cyclic modification
<220> FEATURE:
<221> NAME/KEY: Arg
<222> LOCATION: (33)..(33)
<223> OTHER INFORMATION: Arg with a N-Me-R35 chemical modification

<400> SEQUENCE: 14

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 15
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein cys is homocysteine with a cyclic
      modification

<400> SEQUENCE: 15

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 16
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein the cys is homocysteine with a
      cyclic modification

<400> SEQUENCE: 16
```

-continued

```
Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 17
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification

<400> SEQUENCE: 17

Ile Ala Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 18
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein cys is homocysteine with a cyclic
      modification

<400> SEQUENCE: 18

Ile Glu Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 19
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
```

```
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a N-Me-R35 chemical modification

<400> SEQUENCE: 19

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 20
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a N-Me-R35 the chemical modification

<400> SEQUENCE: 20

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 21
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein cys is a homocysteine with a
``` cyclic modification

<400> SEQUENCE: 21

Ile Ala Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Lys Cys Thr Arg Gln
            20                  25                  30

Arg Tyr

<210> SEQ ID NO 22
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification

<400> SEQUENCE: 22

Ile Glu Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Lys Cys Thr Arg Gln
            20                  25                  30

Arg Tyr

<210> SEQ ID NO 23
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-COC16CO2H chemical
      modification
<220> FEATURE:
<221> NAME/KEY: Cys
<222> LOCATION: (29)..(29)
<223> OTHER INFORMATION: Cys, wherein cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 23

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln

```
                20                  25                  30

Arg Tyr

<210> SEQ ID NO 24
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-COC16CO2H chemical
      modification
<220> FEATURE:
<221> NAME/KEY: Cys
<222> LOCATION: (29)..(29)
<223> OTHER INFORMATION: Cys, wherein cys is homocysteine with a cyclic
      modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 24

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 25
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Stear chemical
      modification
<220> FEATURE:
<221> NAME/KEY: Cys
<222> LOCATION: (29)..(29)
<223> OTHER INFORMATION: Cys, wherein cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 25

Ile Lys Pro Glu Ala Pro Gly Glu Asp Ala Ser Pro Glu Glu Leu Asn
1               5                   10                  15
```

Arg Tyr Tyr Ala Ser Leu Arg His Tyr Leu Asn Lys Cys Thr Arg Gln
            20                  25                  30

Arg Tyr

<210> SEQ ID NO 26
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Arach chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 26

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 27
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-COC16CO2H chemical
      modification
<220> FEATURE:
<221> NAME/KEY: Cys
<222> LOCATION: (29)..(29)
<223> OTHER INFORMATION: Cys, wherein the cys is homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 27

Ile Lys Pro Glu Ala Pro Gly Glu Asp Ala Ser Pro Glu Glu Leu Asn
1               5                   10                  15

```
Arg Tyr Tyr Ala Ser Leu Arg His Tyr Leu Asn Lys Cys Thr Arg Gln
            20                  25                  30

Arg Tyr

<210> SEQ ID NO 28
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 28

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 29
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 29

Lys Pro Glu Ala Pro Gly Glu Asp Ala Ser Pro Glu Glu Leu Asn Arg
1               5                   10                  15
```

Tyr Tyr Ala Ser Leu Arg His Tyr Leu Asn Lys Cys Thr Arg Gln Arg
            20                  25                  30

Tyr

<210> SEQ ID NO 30
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Arg with a psi-(R35, Y36) chemical modification

<400> SEQUENCE: 30

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 31
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-Stear chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 31

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln

Arg Tyr

```
<210> SEQ ID NO 32
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 32
```

Ile Ala Pro Glu Ala Pro Gly Glu Asp Ala Ser Pro Glu Glu Leu Asn
1               5                   10                  15

Arg Tyr Tyr Ala Ser Leu Arg Ala Tyr Leu Asn Lys Cys Thr Arg Gln
            20                  25                  30

Arg Tyr

```
<210> SEQ ID NO 33
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Gln
<222> LOCATION: (32)..(32)
<223> OTHER INFORMATION: Gln with a N-Me-Q34 chemical modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 33
```

Ile Lys Pro Glu Ala Pro Gly Glu Asp Ala Ser Pro Glu Glu Leu Asn

```
1               5                   10                  15
Arg Tyr Tyr Ala Ser Leu Arg His Tyr Leu Asn Lys Cys Thr Arg Gln
            20                  25                  30

Arg Tyr

<210> SEQ ID NO 34
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys with a gamma-Glu-Pal chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 34

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 35
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a N-Me-R35 and a psi-(R35, Y36)
      chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 35

Ile Lys Pro Glu Ala Pro Gly Glu Asp Ala Ser Pro Glu Glu Leu Asn
1               5                   10                  15
```

Arg Tyr Tyr Ala Ser Leu Arg His Tyr Leu Asn Lys Cys Thr Arg Gln
            20                  25                  30

Arg Tyr

<210> SEQ ID NO 36
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (27)..(27)
<223> OTHER INFORMATION: Lys witha gamma-Glu-Pal chemical modification
<220> FEATURE:
<221> NAME/KEY: Cys
<222> LOCATION: (28)..(28)
<223> OTHER INFORMATION: Cys, wherein the cys is a homocysteine with a
      cyclic modification
<220> FEATURE:
<221> NAME/KEY: Arg
<222> LOCATION: (32)..(32)
<223> OTHER INFORMATION: Arg with a N-Me-R35 and a psi-(R35, Y36)
      chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 36

Lys Pro Glu Ala Pro Gly Glu Asp Ala Ser Pro Glu Glu Leu Asn Arg
1               5                   10                  15

Tyr Tyr Ala Ser Leu Arg His Tyr Leu Asn Lys Cys Thr Arg Gln Arg
            20                  25                  30

Tyr

<210> SEQ ID NO 37
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 37

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 38
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a N-Me-R35 and a psi-(R35, Y36)
      chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 38

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 39
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Arach chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 39

Ile Ser Pro Glu Ala Pro Gly Glu Asp Ala Ser Pro Glu Glu Leu Asn
1               5                   10                  15

```
Arg Tyr Tyr Ala Ser Leu Arg His Tyr Leu Asn Lys Cys Thr Arg Gln
            20                  25                  30

Arg Tyr

<210> SEQ ID NO 40
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-Pal chemical
      modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 40

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Leu Thr Arg Gln
            20                  25                  30

Arg Tyr

<210> SEQ ID NO 41
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 41

Ile Lys Pro Glu Ala Pro Gly Glu Asp Ala Ser Pro Glu Glu Leu Asn
1               5                   10                  15
```

Arg Tyr Tyr Ala Ser Leu Arg His Tyr Leu Asn Lys Leu Thr Arg Gln
            20                  25                  30

Arg Tyr

<210> SEQ ID NO 42
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-COC16CO2H chemical
      modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 42

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Leu Thr Arg Gln
            20                  25                  30

Arg Tyr

<210> SEQ ID NO 43
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 43

Ile Lys Pro Glu Ala Pro Gly Glu Asp Ala Ser Pro Glu Glu Leu Asn

```
                1               5                   10                  15
Arg Tyr Tyr Ala Ser Leu Arg His Tyr Leu Asn Lys Cys Thr Arg Gln
            20                  25                  30

Arg Tyr

<210> SEQ ID NO 44
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a (OEG)2-gamma-Glu-COC16CO2H chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 44

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 45
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a COCH2CH2(OCH2CH2)24NH-gamma-Glu-Pal
      chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 45
```

```
Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 46
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 46

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 47
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (5)..(5)
<223> OTHER INFORMATION: Lys with a (OEG)2-gamma-Glu-COC16CO2H chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 47
```

```
Ile Lys Pro Glu Lys Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 48
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (20)..(20)
<223> OTHER INFORMATION: Lys with a (OEG2)-gamma-Glu-COC16CO2H chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 48

Ile Lys Pro Glu Ala Pro Gly Glu Asp Ala Ser Pro Glu Glu Leu Asn
1               5                   10                  15

Arg Tyr Tyr Lys Ser Leu Arg His Tyr Leu Asn Leu Cys Thr Arg Gln
            20                  25                  30

Arg Tyr

<210> SEQ ID NO 49
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-(Pal-16-OH)) chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification
```

<400> SEQUENCE: 49

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 50
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (21)..(21)
<223> OTHER INFORMATION: Lys with a (OEG)2-gamma-Glu-COC16CO2H chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 50

Ile Lys Pro Glu Ala Pro Gly Glu Asp Ala Ser Pro Glu Glu Leu Asn
1               5                   10                  15

Arg Tyr Tyr Ala Lys Leu Arg His Tyr Leu Asn Leu Cys Thr Arg Gln
            20                  25                  30

Arg Tyr

<210> SEQ ID NO 51
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-Pal chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

```
<400> SEQUENCE: 51

Ile Ser Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 52
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a COCH2CH2(OCH2CH2)12NH-gamma-Glu-Pal
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 52

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 53
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a (OEG)4-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification
```

```
<400> SEQUENCE: 53

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 54
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 54

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 55
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (21)..(21)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
```

-continued

<223> OTHER INFORMATION: Tyr with a psi-(R35, Y36) chemical modification

<400> SEQUENCE: 55

Ile Lys Pro Glu Ala Pro Gly Glu Asp Ala Ser Pro Glu Glu Leu Asn
1               5                   10                  15
Arg Tyr Tyr Ala Lys Leu Arg His Tyr Leu Asn Leu Cys Thr Arg Gln
            20                  25                  30
Arg Tyr

<210> SEQ ID NO 56
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-COCH2PH-(4-ClPh) chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 56

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Lys Cys Thr Arg Gln
            20                  25                  30
Arg Tyr

<210> SEQ ID NO 57
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)2PhO-(2,4-Cl2Ph)
      chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:

-continued

```
<221> NAME/KEY: Tyr
<222> LOCATION: (34)..(34)
<223> OTHER INFORMATION: Tyr with a psi-(R35, Y36) chemical modification

<400> SEQUENCE: 57

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 58
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-(4-F-Ph)
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 58

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 59
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (20)..(20)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
```

```
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 59

Ile Lys Pro Glu Ala Pro Gly Glu Asp Ala Ser Pro Glu Glu Leu Asn
1               5                   10                  15

Arg Tyr Tyr Lys Ser Leu Arg His Tyr Leu Asn Leu Cys Thr Arg Gln
            20                  25                  30

Arg Tyr

<210> SEQ ID NO 60
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (5)..(5)
<223> OTHER INFORMATION: Lys with a (OEG)2-gamma-Glu-Pal chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 60

Ile Lys Pro Glu Lys Pro Gly Glu Asp Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 61
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-(4-F3C-Ph)
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
```

```
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 61

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 62
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-CF3 chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 62

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 63
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)13-CF3 chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
```

```
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 63

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Lys Cys Thr Arg Gln
            20                  25                  30
Arg Tyr

<210> SEQ ID NO 64
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with the chemical modification described in
      the specification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 64

Ile Lys Pro Glu Ala Pro Gly Glu Asp Ala Ser Pro Glu Glu Leu Asn
1               5                   10                  15
Arg Tyr Tyr Ala Ser Leu Arg His Tyr Leu Asn Lys Cys Thr Arg Gln
            20                  25                  30
Arg Tyr

<210> SEQ ID NO 65
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)11(CD2)3CD3
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
```

```
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 65

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 66
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-(2,4-(CF3)-Ph
      chemical
      modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 66

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 67
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (28)..(28)
<223> OTHER INFORMATION: Lys with a gamma-Glu-CO(CH2)10-(3,5-(CF3)2-Ph
      chemical modification
<220> FEATURE:
<221> NAME/KEY: Cys
<222> LOCATION: (29)..(29)
<223> OTHER INFORMATION: Cys, wherein the cys is a homocysteine with a
```

-continued

```
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 67

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Lys Cys Thr Arg Gln
            20                  25                  30

Arg Tyr

<210> SEQ ID NO 68
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a (OEG)2-gamma-Glu-COC16CO2H chemical
      modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 68

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Cys Val Thr Arg Gln
            20                  25                  30

Arg Tyr

<210> SEQ ID NO 69
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (30)..(30)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
```

```
<221> NAME/KEY: Tyr
<222> LOCATION: (35)..(35)
<223> OTHER INFORMATION: Tyr with a psi-(R35, Y36) chemical modification

<400> SEQUENCE: 69

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Glu Thr Arg
            20                  25                  30

Gln Arg Tyr
        35

<210> SEQ ID NO 70
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 70

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 71
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 71

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
```

-continued

```
<210> SEQ ID NO 72
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a (OEG)2-gamma-Glu-COC16CO2H chemical
      modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 72

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 73
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG6-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 73

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30
```

Gln Arg Tyr
        35

<210> SEQ ID NO 74
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 74

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 75
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 75

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln

-continued

```
                    20                  25                  30

Arg Tyr

<210> SEQ ID NO 76
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic
      modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Lys
<222> LOCATION: (29)..(29)
<223> OTHER INFORMATION: Lys with a mPEG16 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 76

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Lys Cys Thr Arg
            20                  25                  30

Gln Arg Tyr
        35

<210> SEQ ID NO 77
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Lys
<222> LOCATION: (19)..(19)
<223> OTHER INFORMATION: Lys with a mPEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
```

```
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 77

Ala Ile Lys Pro Glu Ala Pro Gly Glu Lys Ala Ser Pro Glu Leu
1               5                   10                  15

Asn Arg Lys Tyr Ala Ser Leu Arg His Tyr Leu Asn Leu Cys Thr Arg
            20                  25                  30

Gln Arg Tyr
        35

<210> SEQ ID NO 78
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Gln
<222> LOCATION: (33)..(33)
<223> OTHER INFORMATION: Gln with a N-Me-Q34 chemical modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 78

Ala Ile Lys Pro Glu Ala Pro Gly Glu Lys Ala Ser Pro Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 79
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
```

```
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me-R35 and a psi-(R35, Y36)
      chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 79

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 80
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 80

Ala Ile Arg Pro Glu Ala Pro Gly Glu Lys Ala Ser Pro Glu Glu Leu
1               5                   10                  15

Asn Arg Tyr Tyr Ala Ser Leu Arg His Tyr Leu Asn Trp Cys Thr Arg
            20                  25                  30

Gln Arg Tyr
        35

<210> SEQ ID NO 81
<211> LENGTH: 34
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
```

<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 81

Ile Arg Pro Glu Ala Pro Gly Glu Lys Ala Ser Pro Glu Glu Leu Asn
1               5                   10                  15
Arg Tyr Tyr Ala Ser Leu Arg His Tyr Leu Asn Trp Cys Thr Arg Gln
            20                  25                  30
Arg Tyr

<210> SEQ ID NO 82
<211> LENGTH: 33
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (8)..(8)
<223> OTHER INFORMATION: Lys with a PEG12-AcBr chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 82

Lys Pro Glu Ala Pro Gly Glu Lys Ala Ser Pro Glu Glu Leu Asn Arg
1               5                   10                  15
Tyr Tyr Ala Ser Leu Arg His Tyr Leu Asn Leu Cys Thr Arg Gln Arg
            20                  25                  30
Tyr

<210> SEQ ID NO 83
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12-AcBr chemical modification
<220> FEATURE:
<221> NAME/KEY: Leu

```
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 83

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Leu Val Thr Arg
            20                  25                  30

Gln Arg Tyr
        35

<210> SEQ ID NO 84
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG8-triazolyl-CH2CH2CO-PEG4-AcBr
      chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 84

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Val Thr Arg
            20                  25                  30

Gln Arg Tyr
        35

<210> SEQ ID NO 85
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (22)..(22)
```

```
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 85

Ala Ile Lys Pro Glu Ala Pro Gly Glu Asp Ala Ser Pro Glu Glu Leu
1               5                   10                  15
Asn Arg Tyr Tyr Ala Lys Leu Arg His Tyr Leu Asn Leu Cys Val Thr
            20                  25                  30
Arg Gln Arg Tyr
        35

<210> SEQ ID NO 86
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (21)..(21)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 86

Ala Ile Lys Pro Glu Ala Pro Gly Glu Asp Ala Ser Pro Glu Glu Leu
1               5                   10                  15
Asn Arg Tyr Tyr Lys Ser Leu Arg His Tyr Leu Asn Leu Cys Val Thr
            20                  25                  30
Arg Gln Arg Tyr
        35

<210> SEQ ID NO 87
<211> LENGTH: 36
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
```

```
<220> FEATURE:
<221> NAME/KEY: Lys
<222> LOCATION: (6)..(6)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 87

Ala Ile Lys Pro Glu Lys Pro Gly Glu Asp Ala Ser Pro Glu Glu Leu
1               5                   10                  15

Asn Arg Tyr Tyr Ala Ser Leu Arg His Tyr Leu Asn Leu Cys Val Thr
            20                  25                  30

Arg Gln Arg Tyr
            35

<210> SEQ ID NO 88
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 88

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 89
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
```

```
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 89

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 90
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 90

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 91
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys, wherein the cys is a homocysteine with a
```

```
                       cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 91

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 92
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 92

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 93
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
```

```
<221> NAME/KEY: Tyr
<222> LOCATION: (35)..(35)
<223> OTHER INFORMATION: Tyr with a psi-(R35, Y36) chemical modification

<400> SEQUENCE: 93

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 94
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 94

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 95
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
```

```
<221> NAME/KEY: Tyr
<222> LOCATION: (35)..(35)
<223> OTHER INFORMATION: Tyr with a psi-(R35, Y36) chemical modification

<400> SEQUENCE: 95

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 96
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG24-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 96

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 97
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12-AcBr chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
```

```
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 97

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 98
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 98

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 99
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 99
```

```
Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 100
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a AcBr chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 100

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 101
<211> LENGTH: 34
<212> TYPE: PRT
<213> ORGANISM: Homo sapiens

<400> SEQUENCE: 101

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 102
<211> LENGTH: 35
<212> TYPE: PRT
<213> ORGANISM: Artificial Sequence
<220> FEATURE:
<223> OTHER INFORMATION: Conjugate 1
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
```

```
<222> LOCATION: (10)..(10)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 102

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 103
<211> LENGTH: 35
<212> TYPE: PRT
<213> ORGANISM: Artificial Sequence
<220> FEATURE:
<223> OTHER INFORMATION: Conjugate 2
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG6 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 103

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 104
<211> LENGTH: 35
<212> TYPE: PRT
<213> ORGANISM: Artificial Sequence
<220> FEATURE:
<223> OTHER INFORMATION: Conjugate 3
<220> FEATURE:
<221> NAME/KEY: Ala
<222> LOCATION: (1)..(1)
<223> OTHER INFORMATION: Ala, wherein the alanine is a beta-alanine with
```

```
      a cyclic modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 104

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 105
<211> LENGTH: 34
<212> TYPE: PRT
<213> ORGANISM: Artificial Sequence
<220> FEATURE:
<223> OTHER INFORMATION: Conjugate 4
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 105

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Thr Arg Gln
            20                  25                  30

Arg Tyr

<210> SEQ ID NO 106
<211> LENGTH: 35
<212> TYPE: PRT
<213> ORGANISM: Artificial Sequence
<220> FEATURE:
<223> OTHER INFORMATION: Conjugate 5
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
```

<223> OTHER INFORMATION: Lys with a PEG12 chemical modification
<220> FEATURE:
<221> NAME/KEY: Lys
<222> LOCATION: (29)..(29)
<223> OTHER INFORMATION: Lys with a mPEG16 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 106

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Lys Cys Thr Arg
            20                  25                  30

Gln Arg Tyr
        35

<210> SEQ ID NO 107
<211> LENGTH: 35
<212> TYPE: PRT
<213> ORGANISM: Artificial Sequence
<220> FEATURE:
<223> OTHER INFORMATION: Conjugate 6
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (19)..(19)
<223> OTHER INFORMATION: Lys with a mPEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 107

Ala Ile Lys Pro Glu Ala Pro Gly Glu Lys Ala Ser Pro Glu Glu Leu
1               5                   10                  15

Asn Arg Lys Tyr Ala Ser Leu Arg His Tyr Leu Asn Leu Cys Thr Arg
            20                  25                  30

Gln Arg Tyr
        35

<210> SEQ ID NO 108
<211> LENGTH: 35
<212> TYPE: PRT
<213> ORGANISM: Artificial Sequence
<220> FEATURE:
<223> OTHER INFORMATION: Conjugate 7
<220> FEATURE:

```
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Gln
<222> LOCATION: (33)..(33)
<223> OTHER INFORMATION: Gln with a N-Me-Q34 chemical modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 108

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 109
<211> LENGTH: 35
<212> TYPE: PRT
<213> ORGANISM: Artificial Sequence
<220> FEATURE:
<223> OTHER INFORMATION: Conjugate 8
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me-R35 and a psi-(R35, Y36)
      chemical modification
<220> FEATURE:
<221> NAME/KEY: Tyr
<222> LOCATION: (35)..(35)
<223> OTHER INFORMATION: Tyr with a N-Me-R35 and a psi-(R35, Y36)
      chemical modification

<400> SEQUENCE: 109

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35
```

```
<210> SEQ ID NO 110
<211> LENGTH: 35
<212> TYPE: PRT
<213> ORGANISM: Artificial Sequence
<220> FEATURE:
<223> OTHER INFORMATION: Conjugate 9
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 110

Ala Ile Arg Pro Glu Ala Pro Gly Glu Lys Ala Ser Pro Glu Glu Leu
1               5                   10                  15

Asn Arg Tyr Tyr Ala Ser Leu Arg His Tyr Leu Asn Trp Cys Thr Arg
            20                  25                  30

Gln Arg Tyr
        35

<210> SEQ ID NO 111
<211> LENGTH: 34
<212> TYPE: PRT
<213> ORGANISM: Artificial Sequence
<220> FEATURE:
<223> OTHER INFORMATION: Conjugate 10
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 111

Ile Arg Pro Glu Ala Pro Gly Glu Lys Ala Ser Pro Glu Glu Leu Asn
1               5                   10                  15

Arg Tyr Tyr Ala Ser Leu Arg His Tyr Leu Asn Trp Cys Thr Arg Gln
            20                  25                  30

Arg Tyr
```

```
<210> SEQ ID NO 112
<211> LENGTH: 33
<212> TYPE: PRT
<213> ORGANISM: Artificial Sequence
<220> FEATURE:
<223> OTHER INFORMATION: Conjugate 11
<220> FEATURE:
<221> NAME/KEY: Lys
<222> LOCATION: (1)..(1)
<223> OTHER INFORMATION: Lys with a cyclic modification
<220> FEATURE:
<221> NAME/KEY: Lys
<222> LOCATION: (8)..(8)
<223> OTHER INFORMATION: Lys with a PEG12 chemical modification
<220> FEATURE:
<221> NAME/KEY: Cys
<222> LOCATION: (28)..(28)
<223> OTHER INFORMATION: Cys with a cyclic modification
<220> FEATURE:
<221> NAME/KEY: Arg
<222> LOCATION: (32)..(32)
<223> OTHER INFORMATION: Arg with a psi-(R35, Y36) chemical modification
<220> FEATURE:
<221> NAME/KEY: Tyr
<222> LOCATION: (33)..(33)
<223> OTHER INFORMATION: Tyr with a psi-(R35, Y36) chemical modification

<400> SEQUENCE: 112

Lys Pro Glu Ala Pro Gly Glu Lys Ala Ser Pro Glu Glu Leu Asn Arg
1               5                   10                  15

Tyr Tyr Ala Ser Leu Arg His Tyr Leu Asn Leu Cys Thr Arg Gln Arg
            20                  25                  30

Tyr

<210> SEQ ID NO 113
<211> LENGTH: 35
<212> TYPE: PRT
<213> ORGANISM: Artificial Sequence
<220> FEATURE:
<223> OTHER INFORMATION: Conjugate 12
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (9)..(9)
<223> OTHER INFORMATION: Lys with a PEG12 chemical modification
<220> FEATURE:
<221> NAME/KEY: Leu
<222> LOCATION: (29)..(29)
<223> OTHER INFORMATION: Leu, wherein the leu is a norleucine with a
      cyclic modification
<220> FEATURE:
<221> NAME/KEY: Arg
<222> LOCATION: (33)..(33)
<223> OTHER INFORMATION: Arg with a psi-(R35, Y36) chemical modification
<220> FEATURE:
<221> NAME/KEY: Tyr
<222> LOCATION: (34)..(34)
<223> OTHER INFORMATION: Tyr with a psi-(R35, Y36) chemical modification

<400> SEQUENCE: 113

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Leu Val Thr Arg
            20                  25                  30

Gln Arg Tyr
        35
```

```
<210> SEQ ID NO 114
<211> LENGTH: 35
<212> TYPE: PRT
<213> ORGANISM: Artificial Sequence
<220> FEATURE:
<223> OTHER INFORMATION: Conjugate 13
<220> FEATURE:
<221> NAME/KEY: Ile
<222> LOCATION: (1)..(1)
<223> OTHER INFORMATION: Ile with a cyclic modification
<220> FEATURE:
<221> NAME/KEY: Lys
<222> LOCATION: (10)..(10)
<223> OTHER INFORMATION: Lys with a PEG8-triazolyl-CH2CH2CO-PEG4
      chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 114

Ile Lys Pro Glu Ala Pro Gly Glu Lys Ala Ser Pro Glu Glu Leu Asn
1               5                   10                  15

Arg Tyr Tyr Ala Ser Leu Arg His Tyr Leu Asn Leu Cys Val Thr Arg
            20                  25                  30

Gln Arg Tyr
        35

<210> SEQ ID NO 115
<211> LENGTH: 36
<212> TYPE: PRT
<213> ORGANISM: Artificial Sequence
<220> FEATURE:
<223> OTHER INFORMATION: Conjugate 14
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (22)..(22)
<223> OTHER INFORMATION: Lys with a PEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 115

Ala Ile Lys Pro Glu Ala Pro Gly Glu Asp Ala Ser Pro Glu Glu Leu
1               5                   10                  15

Asn Arg Tyr Tyr Ala Lys Leu Arg His Tyr Leu Asn Leu Cys Val Thr
            20                  25                  30
```

Arg Gln Arg Tyr
        35

<210> SEQ ID NO 116
<211> LENGTH: 36
<212> TYPE: PRT
<213> ORGANISM: Artificial Sequence
<220> FEATURE:
<223> OTHER INFORMATION: Conjugate 15
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (21)..(21)
<223> OTHER INFORMATION: Lys with a PEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 116

Ala Ile Lys Pro Glu Ala Pro Gly Glu Asp Ala Ser Pro Glu Glu Leu
1               5                   10                  15

Asn Arg Tyr Tyr Lys Ser Leu Arg His Tyr Leu Asn Leu Cys Val Thr
            20                  25                  30

Arg Gln Arg Tyr
        35

<210> SEQ ID NO 117
<211> LENGTH: 36
<212> TYPE: PRT
<213> ORGANISM: Artificial Sequence
<220> FEATURE:
<223> OTHER INFORMATION: Conjugate 16
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (6)..(6)
<223> OTHER INFORMATION: Lys with a PEG12 chemical modification
<220> FEATURE:
<221> NAME/KEY: Cys
<222> LOCATION: (30)..(30)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 117

Ala Ile Lys Pro Glu Lys Pro Gly Glu Asp Ala Ser Pro Glu Glu Leu
1               5                   10                  15

Asn Arg Tyr Tyr Ala Ser Leu Arg His Tyr Leu Asn Leu Cys Val Thr

```
                    20                  25                  30

Arg Gln Arg Tyr
            35

<210> SEQ ID NO 118
<211> LENGTH: 35
<212> TYPE: PRT
<213> ORGANISM: Artificial Sequence
<220> FEATURE:
<223> OTHER INFORMATION: Conjugate 17
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 118

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
            35

<210> SEQ ID NO 119
<211> LENGTH: 35
<212> TYPE: PRT
<213> ORGANISM: Artificial Sequence
<220> FEATURE:
<223> OTHER INFORMATION: Conjugate 18
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 119

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
            35
```

<210> SEQ ID NO 120
<211> LENGTH: 35
<212> TYPE: PRT
<213> ORGANISM: Artificial Sequence
<220> FEATURE:
<223> OTHER INFORMATION: Conjugate 19
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 120

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 121
<211> LENGTH: 35
<212> TYPE: PRT
<213> ORGANISM: Artificial Sequence
<220> FEATURE:
<223> OTHER INFORMATION: Conjugate 20
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 121

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 122
<211> LENGTH: 35
<212> TYPE: PRT
<213> ORGANISM: Artificial Sequence
<220> FEATURE:
<223> OTHER INFORMATION: Conjugate 21

```
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (30)..(30)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 122

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 123
<211> LENGTH: 35
<212> TYPE: PRT
<213> ORGANISM: Artificial Sequence
<220> FEATURE:
<223> OTHER INFORMATION: Conjugate 22
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 123

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 124
<211> LENGTH: 35
<212> TYPE: PRT
<213> ORGANISM: Artificial Sequence
<220> FEATURE:
<223> OTHER INFORMATION: Conjugate 23
<220> FEATURE:
<221> NAME/KEY: Ala
<222> LOCATION: (1)..(1)
```

```
<223> OTHER INFORMATION: Ala, wherein the alanine is a beta-alanine with
      a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 124

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 125
<211> LENGTH: 35
<212> TYPE: PRT
<213> ORGANISM: Artificial Sequence
<220> FEATURE:
<223> OTHER INFORMATION: Conjugate 24
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 125

Gly Ile Ser Pro Glu Ala Pro Gly Glu Lys Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 126
<211> LENGTH: 35
<212> TYPE: PRT
<213> ORGANISM: Artificial Sequence
<220> FEATURE:
<223> OTHER INFORMATION: Conjugate 25
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
```

```
<222> LOCATION: (10)..(10)
<223> OTHER INFORMATION: Lys with a PEG24 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a pi-(R35, Y36) chemical modification
<220> FEATURE:
<221> NAME/KEY: Tyr
<222> LOCATION: (35)..(35)
<223> OTHER INFORMATION: Tyr with a pi-(R35, Y36) chemical modification

<400> SEQUENCE: 126

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 127
<211> LENGTH: 35
<212> TYPE: PRT
<213> ORGANISM: Artificial Sequence
<220> FEATURE:
<223> OTHER INFORMATION: Conjugate 26
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Lys
<222> LOCATION: (10)..(10)
<223> OTHER INFORMATION: Lys with a PEG12 chemical modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 127

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 128
<211> LENGTH: 107
<212> TYPE: PRT
<213> ORGANISM: Homo sapiens

<400> SEQUENCE: 128

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
                    20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 129
<211> LENGTH: 119
<212> TYPE: PRT
<213> ORGANISM: Homo sapiens

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Asp Gly Ile Tyr Gly Glu Leu Asp Phe Trp Gly Gln Gly
            100                 105                 110

Thr Leu Val Thr Val Ser Ser
        115

<210> SEQ ID NO 130
<211> LENGTH: 10
<212> TYPE: PRT
<213> ORGANISM: Homo sapiens

<400> SEQUENCE: 130

Tyr Asp Gly Ile Tyr Gly Glu Leu Asp Phe
1               5                   10

<210> SEQ ID NO 131
<211> LENGTH: 115
<212> TYPE: PRT
<213> ORGANISM: Artificial Sequence
<220> FEATURE:
<223> OTHER INFORMATION: concatenation of IGHV3-23*01 and IGHJ1*01

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

-continued

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ala Glu Tyr Phe Gln His Trp Gly Gln Gly Thr Leu Val Thr
            100                 105                 110

Val Ser Ser
        115
```

<210> SEQ ID NO 132
<211> LENGTH: 98
<212> TYPE: PRT
<213> ORGANISM: Homo sapiens

<400> SEQUENCE: 132

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys
```

<210> SEQ ID NO 133
<211> LENGTH: 17
<212> TYPE: PRT
<213> ORGANISM: Homo sapiens

<400> SEQUENCE: 133

```
Ala Glu Tyr Phe Gln His Trp Gly Gln Gly Thr Leu Val Thr Val Ser
  1               5                  10                  15

Ser
```

<210> SEQ ID NO 134
<211> LENGTH: 107
<212> TYPE: PRT
<213> ORGANISM: Artificial Sequence
<220> FEATURE:
<223> OTHER INFORMATION: concatenation of IGKV3-11*01 and IGKJ1*01

<400> SEQUENCE: 134

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
```

```
                65                  70                  75                  80
Glu Asp Phe Ala Val Tyr Tyr Cys Gln Gln Arg Ser Asn Trp Pro Trp
                    85                  90                  95

Thr Phe Gly Gln Gly Thr Lys Val Glu Ile Lys
                100                 105

<210> SEQ ID NO 135
<211> LENGTH: 95
<212> TYPE: PRT
<213> ORGANISM: Homo sapiens

<400> SEQUENCE: 135

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 136
<211> LENGTH: 12
<212> TYPE: PRT
<213> ORGANISM: Homo sapiens

<400> SEQUENCE: 136

Trp Thr Phe Gly Gln Gly Thr Lys Val Glu Ile Lys
1               5                   10

<210> SEQ ID NO 137
<211> LENGTH: 119
<212> TYPE: PRT
<213> ORGANISM: Artificial Sequence
<220> FEATURE:
<223> OTHER INFORMATION: MSCB97 VH

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Asp Gly Cys Tyr Gly Glu Leu Asp Phe Trp Gly Gln Gly
                100                 105                 110

Thr Leu Val Thr Val Ser Ser
            115
```

<210> SEQ ID NO 138
<211> LENGTH: 446
<212> TYPE: PRT
<213> ORGANISM: Artificial Sequence
<220> FEATURE:
<223> OTHER INFORMATION: MSCB97 HC

<400> SEQUENCE: 138

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Asp Gly Cys Tyr Gly Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445

<210> SEQ ID NO 139
<211> LENGTH: 107
<212> TYPE: PRT
<213> ORGANISM: Artificial Sequence
<220> FEATURE:
<223> OTHER INFORMATION: MSCB97 VL

<400> SEQUENCE: 139

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 140
<211> LENGTH: 214
<212> TYPE: PRT
<213> ORGANISM: Artificial Sequence
<220> FEATURE:
<223> OTHER INFORMATION: MSCB97 LC

<400> SEQUENCE: 140

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 141
<211> LENGTH: 5
<212> TYPE: PRT
<213> ORGANISM: Artificial Sequence
<220> FEATURE:
<223> OTHER INFORMATION: MSCB97 HCDR1

<400> SEQUENCE: 141

Ser Tyr Ala Met Ser
1               5

<210> SEQ ID NO 142
<211> LENGTH: 17
<212> TYPE: PRT
<213> ORGANISM: Artificial Sequence
<220> FEATURE:
<223> OTHER INFORMATION: MSCB97 HCDR2

<400> SEQUENCE: 142

Ala Ile Ser Gly Ser Gly Gly Ser Thr Tyr Tyr Ala Asp Ser Val Lys
1               5                   10                  15

Gly

<210> SEQ ID NO 143
<211> LENGTH: 10
<212> TYPE: PRT
<213> ORGANISM: Artificial Sequence
<220> FEATURE:
<223> OTHER INFORMATION: MSCB97 HCDR3

<400> SEQUENCE: 143

Tyr Asp Gly Cys Tyr Gly Glu Leu Asp Phe
1               5                   10

<210> SEQ ID NO 144
<211> LENGTH: 11
<212> TYPE: PRT
<213> ORGANISM: Artificial Sequence
<220> FEATURE:
<223> OTHER INFORMATION: MSCB97 LCDR1

<400> SEQUENCE: 144

Arg Ala Ser Gln Ser Val Ser Ser Tyr Leu Ala
1               5                   10

<210> SEQ ID NO 145
<211> LENGTH: 7
<212> TYPE: PRT
<213> ORGANISM: Artificial Sequence
<220> FEATURE:
```

```
<223> OTHER INFORMATION: MSCB97 LCDR2

<400> SEQUENCE: 145

Asp Ala Ser Asn Arg Ala Thr
1               5

<210> SEQ ID NO 146
<211> LENGTH: 9
<212> TYPE: PRT
<213> ORGANISM: Artificial Sequence
<220> FEATURE:
<223> OTHER INFORMATION: MSCB97 LCDR3

<400> SEQUENCE: 146

Gln Gln Arg Ser Asn Trp Pro Leu Thr
1               5

<210> SEQ ID NO 147
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 147

Ala Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 148
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (30)..(30)
<223> OTHER INFORMATION: Cys, wherein the cys is a homocysteine with a
      cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
```

```
<221> NAME/KEY: Tyr
<222> LOCATION: (35)..(35)
<223> OTHER INFORMATION: Tyr with a psi-(R35, Y36) chemical modification

<400> SEQUENCE: 148

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 149
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 149

Gly Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Glu Val Thr Arg
            20                  25                  30

Gln Arg Tyr
        35

<210> SEQ ID NO 150
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Glu
<222> LOCATION: (29)..(29)
<223> OTHER INFORMATION: Glu with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 150

Gly Ile Lys Pro Glu Ala Pro Gly Glu Lys Ala Ser Pro Glu Glu Leu
1               5                   10                  15
```

Asn Arg Tyr Tyr Ala Ser Leu Arg His Tyr Leu Asn Glu Val Thr Arg
            20                  25                  30

Gln Arg Tyr
        35

<210> SEQ ID NO 151
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 151

Gly Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 152
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Gly
<222> LOCATION: (1)..(1)
<223> OTHER INFORMATION: Gly with a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 152

Gly Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 153
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with

```
        a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 153

Ala Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 154
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a N-Me-R35 chemical modification

<400> SEQUENCE: 154

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 155
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 155
```

```
Ala Ile Lys Pro Glu Ala Pro Gly Glu Asp Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35

<210> SEQ ID NO 156
<211> LENGTH: 35
<212> TYPE: PRT
<213> ORGANISM: Artificial Sequence
<220> FEATURE:
<223> OTHER INFORMATION: Cyclic PYY Peptide Compound
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Cys
<222> LOCATION: (29)..(29)
<223> OTHER INFORMATION: Cys with a cyclic modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 156

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Cys Val Thr Arg
            20                  25                  30

Gln Arg Tyr
        35
```